US008476069B2

(12) United States Patent
Zhu et al.

(10) Patent No.: US 8,476,069 B2
(45) Date of Patent: *Jul. 2, 2013

(54) CELLS USEFUL FOR IMMUNO-BASED BOTULINUM TOXIN SEROTYPE A ACTIVITY ASSAYS

(75) Inventors: Hong Zhu, San Diego, CA (US); Joanne Wang, Irvine, CA (US); Birgitte P. S. Jacky, Long Beach, CA (US); D. Dianne Hodges, Tustin, CA (US); Fernandez-Salas Ester, Fullerton, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/339,225

(22) Filed: Dec. 28, 2011

(65) Prior Publication Data
US 2012/0156775 A1   Jun. 21, 2012

Related U.S. Application Data

(62) Division of application No. 12/722,801, filed on Mar. 12, 2010.

(60) Provisional application No. 61/160,199, filed on Mar. 13, 2009.

(51) Int. Cl.
*C12N 15/85*     (2006.01)

(52) U.S. Cl.
USPC ........................................................ 435/325

(58) Field of Classification Search
None
See application file for complete search history.

(56) References Cited

U.S. PATENT DOCUMENTS

| | | | |
|---|---|---|---|
| 5,962,637 | A | 10/1999 | Shone et al. |
| 6,043,042 | A | 3/2000 | Shone et al. |
| 6,337,386 | B1 | 1/2002 | Shone et al. |
| 7,183,066 | B2 | 2/2007 | Fernandez-Salas et al. |
| 7,208,285 | B2 | 4/2007 | Steward |
| 7,332,567 | B2 | 2/2008 | Steward |
| 7,399,607 | B2 | 7/2008 | Williams |
| 7,598,027 | B2 | 10/2009 | Fernandez-Salas et al. |
| 7,645,570 | B2 | 1/2010 | Fernandez-Salas et al. |
| 7,846,722 | B2 | 12/2010 | Williams |
| 8,124,357 | B2 | 2/2012 | Fernandez-Salas et al. |
| 2010/0233741 | A1 | 9/2010 | Wang |
| 2012/0122128 | A1 | 5/2012 | Fernandez-Salas et al. |

FOREIGN PATENT DOCUMENTS

| | | |
|---|---|---|
| WO | WO 95/33850 | 12/1995 |
| WO | WO 2006/042149 | 4/2006 |

OTHER PUBLICATIONS

Shih et al (Oncology Reports: 13: 517-524, 2005).*
Mocellin et al (Ann Surg 2005, vol. 241, pp. 16-26).*
Williamson, L.C., et al., Clostridial Neurotoxins and Substrate Proteolysis in Intact Neurons, J. Biol. Chem. 271(13) : 7694-7699 (1996).
Shimazaki, Y., et al., Phosphorylation of 25-kDa Synaptosome-Associated Protein, J. Biol. Chem. 271(24): 14548-14533 (1996).
Schulte-Baukloh, H., et al., Persistence of the Synaptosomal-Associated Protein-25 Cleavage Product After Intradetrusor Botulinum Toxin A Injections in Patients with Myelomeningocele Showing an Inadequate Response to Treatment, BJU Int. 100(5):1075-1080 (2007).
Rasooly R. and Do, P.M., Development of an In Vitro Assay as an Alternative to the Mouse Bioassay for *Clostridium botulinum* Neurotoxin Type A, App. Environ. Microbiol. 74(14): 4309-4313 (2008).
Nabokina, S., et al., Intracellular Location of SNAP-25 in Human Neutrophils, Biochem Biophys. Res. Comm. 239: 592-597 (1997).
Marini, P., et al., SiMa, a New Neuroblastoma Cell Line Combining Poor Prognostic Cytogenetic Markers with High Adrenergic Differentiation, Cancer Genet. Cytogenet. 112: 161-164 (1999).
Marconi, S., et al., A protein-chip Membrane-Capture Assay for Botulinum Neurotoxin Activity, Toxicol. App. Pharmacol. 233: 439-446 (2008).
Hallis, B., et al., Development of Novel Assays for Botulinum Type A and B Neurotoxins Based on Their Endopeptidase Activities, J. Clin. Microbiol 34(8): 1934-1938 (1996).
Jones R.G.A., et al., Development of Improved SNAP-25 Endopeptidase Immunoassays for Botulinum Type A and E Toxins, J. Immunol. Methods 329: 92-101 (2008).
Garcia-Rodriguez, C., et al., Molecular Evolution of Antibody Cross-Reactivity for Two Subtypes of Type A Botulinum Neurotoxin, Nature Bioltech 25(1): 107-116 (2007).
Foran, P., et al., Botulinum Neurotoxin C1 Cleaves Both Syntaxin and SNAP-25 in Intact and Permeabilized Chromaffin Cells: Correlation With its Blockade of Catecholamine Release, Biochemistry 35: 2630-2636 (1996).
Boyd, R.S., et al., The Effect of Botulinum Neurotoxins on the Release of Insulin from the Insulinoma Cell Lines HIT-5 and RINm5F, J. Biol. Chem. 270(31): 18216-18218 (1995).
Amersdorfer, P., et al., Molecular Characterization of Murine Humoral Immune Response to Botulinum Neurotoxin Type A Binding Domain as Assessed by Using Phage Antibody Libraries, Infect. Immun. 65(9): 3743-3752 (1997).
Masumto, N.; et al.: Involvement of SNAP-25 in TRH-induced Exocytosis in Pituitary GH4Cl Cells, Journal of Endocrinology, vol. 153, No. 1, 1997, pp. R5-R10.
Pellett, Sabine; et al.: A Neuronal Cell-Based Botulinum Neurotoxin Assay for Highly Sensitive and Specific Detection of Neutralizing Serum Antibodies., Febs Letters Oct. 16, 2007 LNKDPUBMED: 17889852, vol. 581, No. 25, pp. 4803-4808.
Yowler, Brian; et al.: Botulinum Neurotoxin A Activity is Dependent Upon The Presence of Specific Gangliosides in Neuroblastoma Cells Expressing Synaptotagmin 1., The Journal of Biological Chemistry Sep. 6, 2002, vol. 277, No. 36, pp. 32815-32819.

* cited by examiner

*Primary Examiner* — Celine Qian
(74) *Attorney, Agent, or Firm* — Kenton Abel; Debra Condino

(57) ABSTRACT

The present specification discloses clonal cell lines susceptible to BoNT/A intoxication, methods of producing such clonal cell lines, and methods of detecting Botulinum toxin serotype A activity using such clonal cell lines.

5 Claims, 9 Drawing Sheets

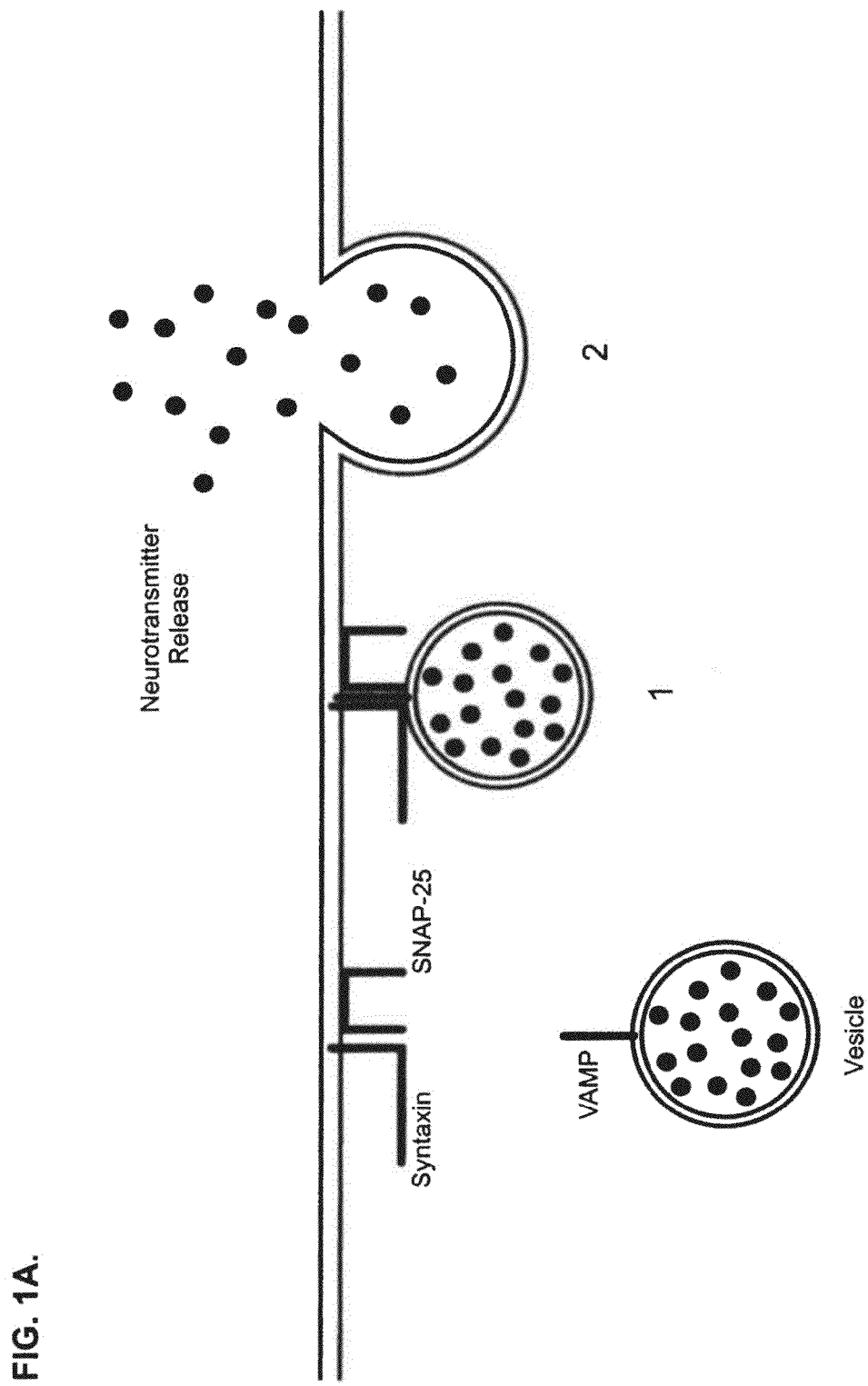

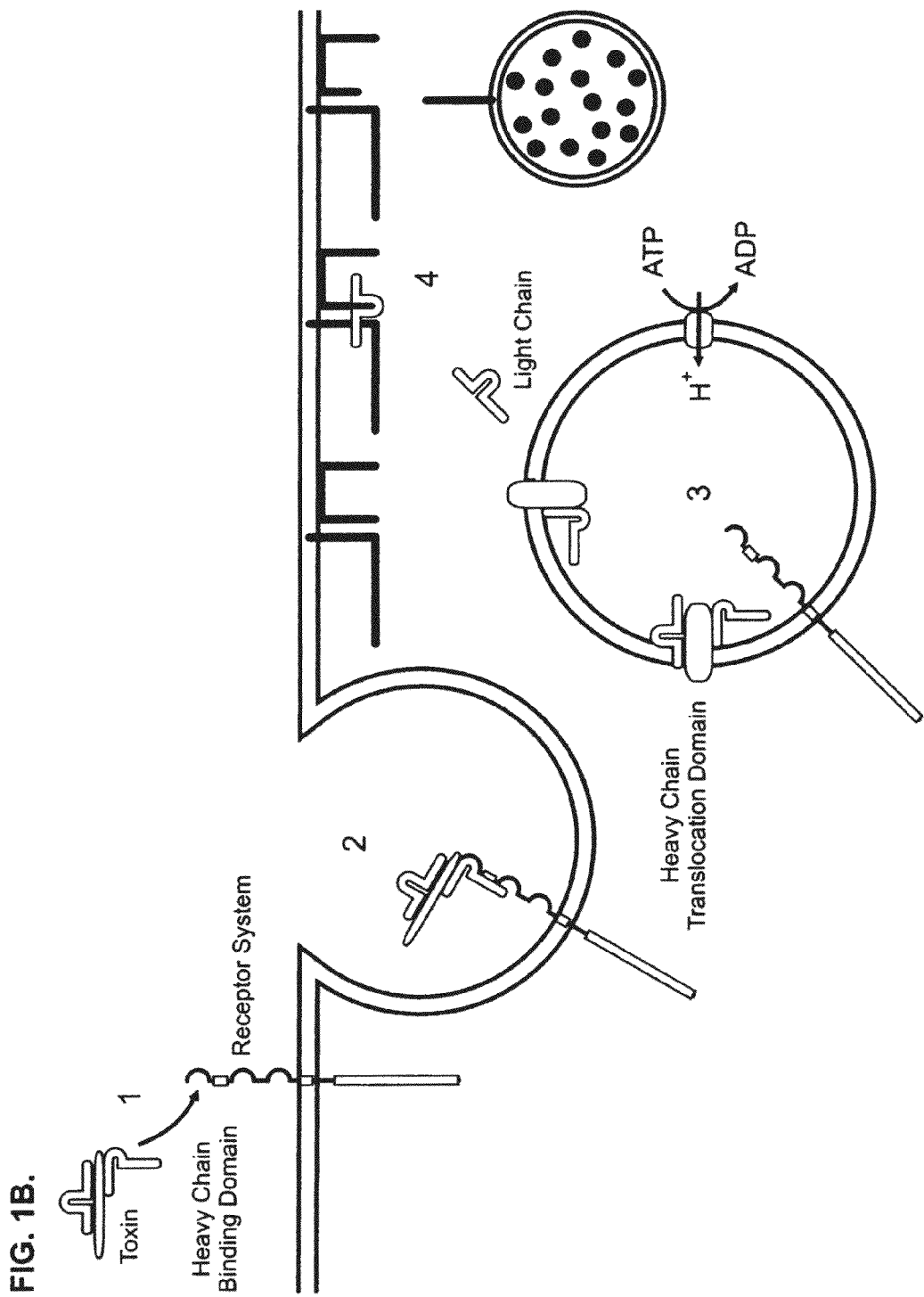

CELLS USEFUL FOR IMMUNO-BASED BOTULINUM TOXIN SEROTYPE A ACTIVITY ASSAYS

This application is a divisional and claims priority pursuant to 35 U.S.C. §120 to U.S. patent application Ser. No. 12/722,801, filed Mar. 12, 2010, which claims priority pursuant to 35 U.S.C. §119(e) to U.S. Provisional Patent Application Ser. No. 61/160,199 filed Mar. 13, 2009, both incorporated entirely by reference.

The sequences disclosed in the present specification are contained in the Sequence Listing submitted with the present specification which is hereby incorporated by reference in its entirety.

The ability of Clostridial toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, Cosmetic and Clinical Applications of Botulinum Toxin (Slack, Inc., 2004). Clostridial toxins commercially available as pharmaceutical compositions include, BoNT/A preparations, such as, e.g., BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A (Biogen-tech Ltd., University, Yantai, Shandong, China); and BoNT/B preparations, such as, e.g., MYOBLOC®/NEUROBLOC® (Solstice Neurosciences, Inc., South San Francisco, Calif.). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder.

At present the mouse $LD_{50}$ bioassay, a lethality test, remains the "gold standard" test used by all pharmaceutical manufacturers to express the potency of their preparations. S. S. Amon et al., JAMA 285: 1059-1070 (2001). In fact, the units on the pharmaceutical preparations' labels are mouse $LD_{50}$ units and the number of animals needed to produce statistically useful $LD_{50}$ data is large. The advantage of the mouse $LD_{50}$ bioassay is that it measures all the steps necessary for botulinum toxin uptake (e.g., toxin binding to a cell surface receptor, internalization of the toxin-receptor complex, light chain translocation into the cytoplasm, light chain cleavage of substrate), instead of merely determining the activity for only part of this intoxication process, such as, e.g., in vitro assays that only measure light chain enzymatic activity. Unfortunately, the mouse $LD_{50}$ bioassay suffers from many drawbacks including high operational cost due to the large numbers of laboratory animals required, a lack of specificity since all BoNT serotypes will cause the same measurable end-point, and the potential for inaccuracy unless large animal groups are used. In addition, animal rights groups have exerted pressure on regulatory agencies in the United States (FDA/NICEATM/ICCVAM) and Europe (MHRA and EDQM), and on pharmaceutical companies manufacturing botulinum neurotoxin products to reduce animal testing and more importantly replace the mouse $LD_{50}$ bioassay for product release. The regulatory agencies are engaging pharmaceutical companies to apply the three "Rs" principle to the potency testing of botulinum neurotoxins: Reduce, Refine, Replace. D. Straughan, Progress in Applying the Three Rs to the Potency Testing of Botulinum Toxin Type A, Altern. Lab. Anim. 34(3): 305-313 (2006). In recent years, several steps have been already taken to reduce and refine the mouse $LD_{50}$ bioassay in order to standardize the protocol and produce more consistent data using fewer animals per assay.

Thus, a simple, reliable, validated and governmental agency acceptable botulinum toxin activity assay that can evaluate the integrity of all the steps necessary in botulinum toxin uptake would be of significant value because such a non-animal based assay would alleviate the need for animal testing and all the disadvantages, costs and ethical concerns associated with this type of animal-based assay. Companion patent application Ester Fernandez-Salas, et al., Immuno-Based Botulinum Toxin Serotype A Activity Assays, U.S. patent application Ser. No. 12/403,531, provides novel compositions, cells, and methods for assaying the activity of a BoNT/A useful for various industries, such as, e.g., the pharmaceutical and food industries. Such compositions, cells, and methods do not use live animals or tissues taken from live animals, but can evaluate all the steps necessary for neurotoxin action, namely, binding and cellular uptake of toxin, translocation into the cell cytosol, and protease activity.

One of the necessary components for the methods disclosed in U.S. patent application Ser. No. 12/403,531 is the use of cells from an established cell line that are susceptible to low levels of BoNT/A intoxication because the amount of BoNT/A contained within a commercially-available pharmaceutical composition is very low. For example, approximately 4-5 ng of a BoNT/A complex is contained in the pharmaceutical composition sold as BOTOX®. Thus, there is a need to identify and create established cell lines comprising cells that are susceptible to BoNT/A intoxication when only very low levels of the neurotoxin is present in the sample. The present specification provides novel cells and cell compositions. that are susceptible to BoNT/A intoxication when only very low amounts of BoNT/A is present and thus allow assaying of commercially-available pharmaceutical composition comprising BoNT/A.

BRIEF DESCRIPTION OF THE DRAWINGS

FIG. 1 shows a schematic of the current paradigm of neurotransmitter release and Clostridial toxin intoxication in a central and peripheral neuron. FIG. 1A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 1B shows a schematic of the intoxication mechanism for tetanus and botulinum toxin activity in a central and peripheral neuron. This intoxication process can be described as comprising four steps: 1) receptor binding, where Clostridial toxin binding to a Clostridial receptor complex and initiates the intoxication process; 2) complex internalization, where after toxin binding, a vesicle containing a toxin/receptor system complex is endocytosed into the cell; 3) light chain translocation, where multiple events are thought to occur, including changes in the internal pH of the vesicle, formation of a channel pore comprising the $H_N$ domain of Clostridial toxin heavy chain, separation of the Clostridial toxin light chain from the heavy chain, and release of the light chain and 4) enzymatic target modification, where the light chain of Clostridial toxin proteolytically cleaves its target SNARE substrates, such as, e.g., SNAP-25, VAMP or Syntaxin, thereby preventing vesicle docking and neurotransmitter release.

FIG. 2 shows volcano plots of genes that are more than 4-fold ($\log_2(4)=2$) up or down regulated in BB10 and H1 cell lines as compared to the 2D6 cell line.

FIG. 3 shows normalized BIAcore SPR curves of 7.8 nM of the antibodies 2E2A6, 1 D3B8, 3C1A5 and 2C9B10 and commercial MC-6050 and MC-6053.

DETAILED DESCRIPTION

Figure 2A:
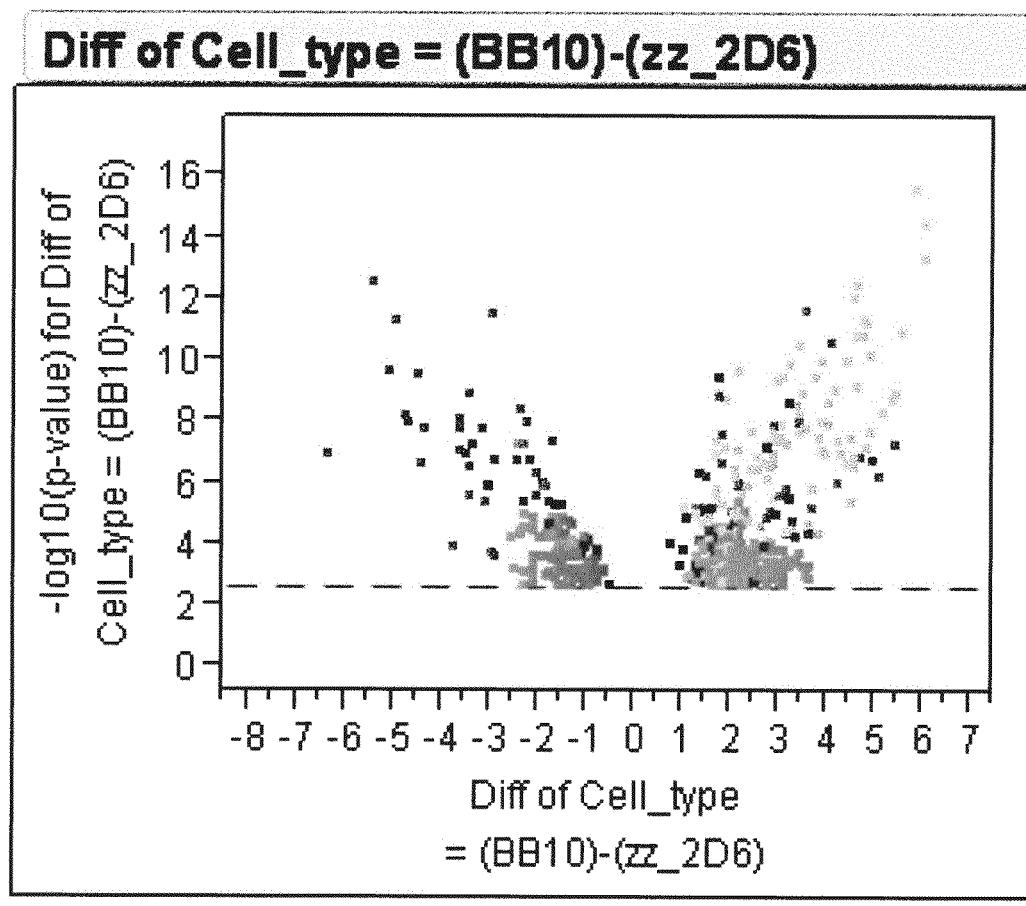
FIG. 2A shows the genes that are up regulated in the BB10 cell line as compared to the 2D6 cell line.
Figure 2B:
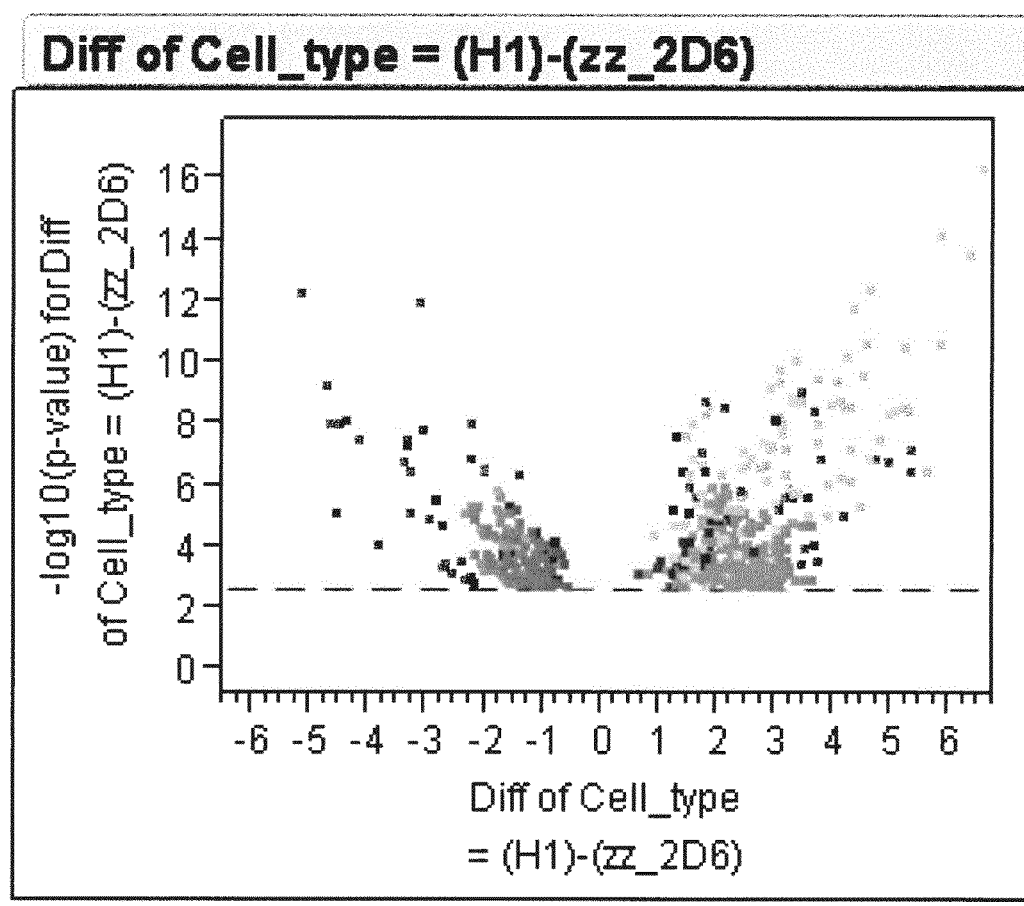
FIG. 2B shows the genes that are up regulated in the H1 cell line as compared to the 2D6 cell line.
Figure 2C:
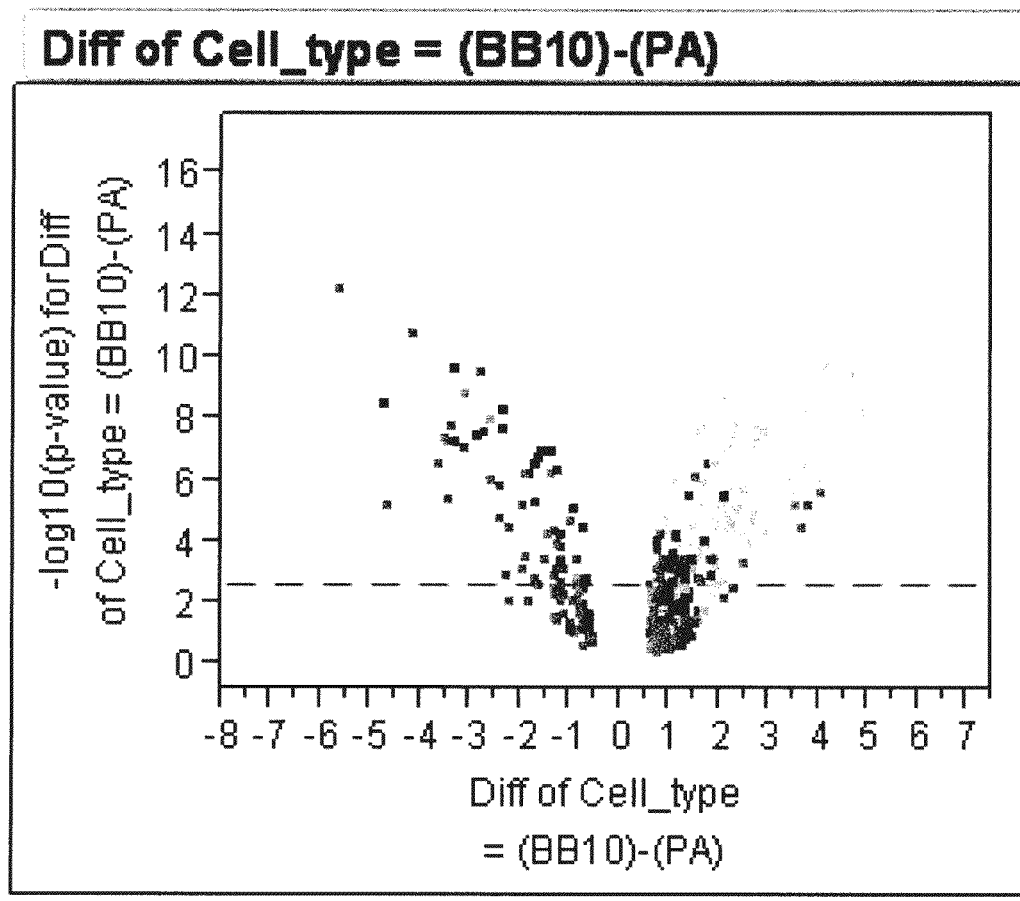
FIG. 2C shows the genes that are up regulated in the BB10 cell line as compared to the parental SiMa cell line (PA).
Figure 2D:
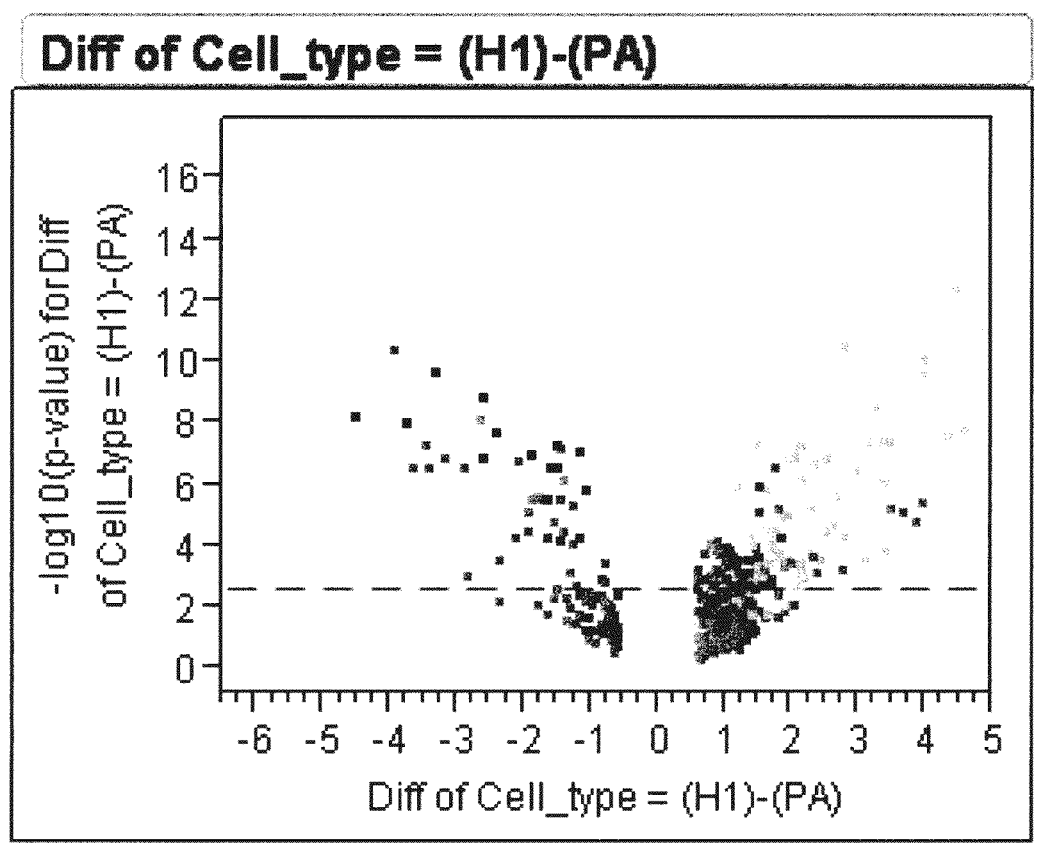
FIG. 2D shows the genes that are up regulated in the H1 cell line as compared to the parental SiMa cell line (PA).
Figure 2E:
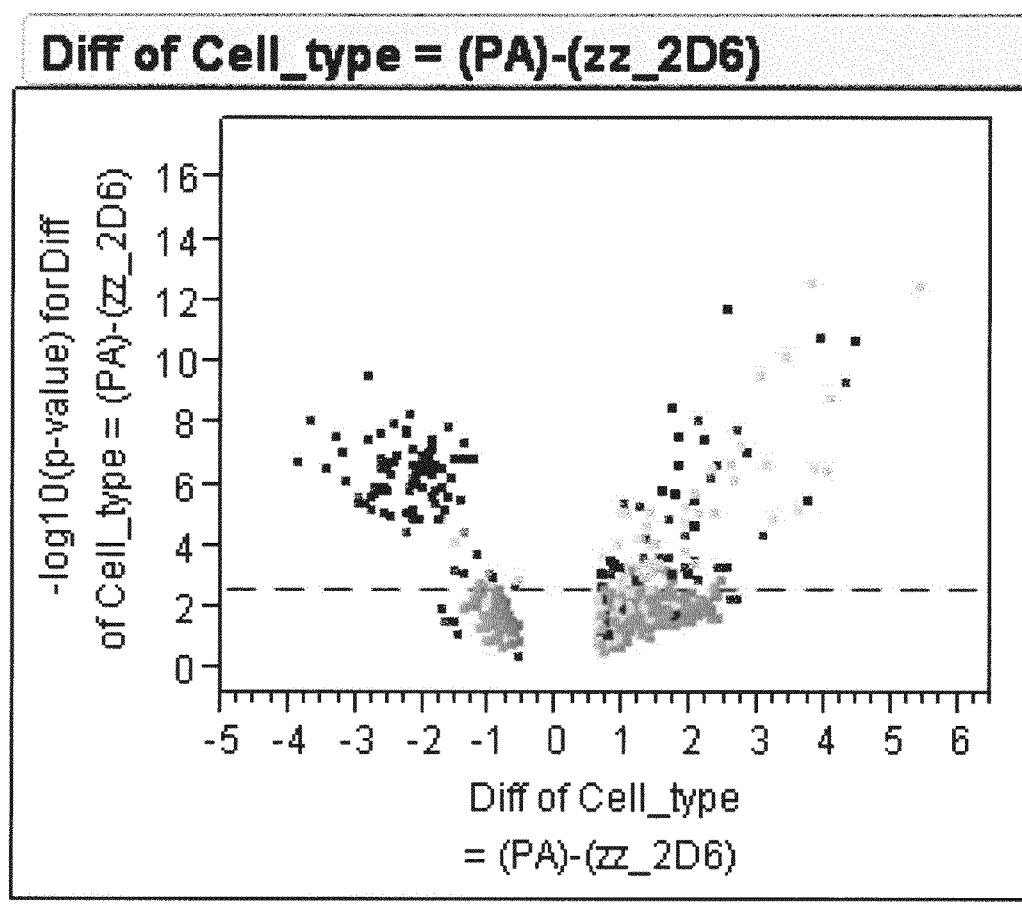
FIG. 2E shows the genes that are up regulated in the parental SiMa cell line (PA) as compared to the 2D6 cell line. Each dot represents a probe set. The dashed line marks the 95% confidence interval, $p \leq 0.05$. Most of the genes that are over expressed in BB10 and H1 compared to 2D6 (A and B) are also over or underexpressed in BB10 compared to PA (C), in H1 compared to PA (D), and in PA compared to 2D6 (E), however a number of them are less than 4-fold over-expressed and/or do not pass the 95% confidence interval.

The present specification provides novel cells and cell compositions that are susceptible to BoNT/A intoxication to allow assaying of BoNT/A and BoNT/A compositions such as, e.g., commercially-available pharmaceutical composition comprising BoNT/A. The cell and cell compositions disclosed in the present specification are useful to conduct methods that can detect picomolar quantities of BoNT/A in a sample, such as the methods disclosed in, e.g., Ester Fernandez-Salas, et al., *Immuno-Based Botulinum Toxin Serotype A Activity Assays*, U.S. patent application Ser. No. 12/403,531, which is hereby incorporated by reference in its entirety. The cells and cell compositions, and their use in methods of detecting BoNT/A activity reduce the need for animal toxicity studies, yet serve to analyze the multiple steps of BoNT/A intoxication, namely, binding and cellular uptake of toxin, translocation into the cell cytosol, and protease activity. As discussed further below, the novel cells and cell compositions of the present specification can be used in assays that analyze crude and bulk samples as well as highly purified di-chain toxins and formulated toxin products and further are amenable to automated high throughput assay formats.

Thus, aspects of the present specification provide a cell composition comprising cells from a clonal cell line that are susceptible to BoNT/A intoxication.

Other aspects of the present specification provide a method of detecting BoNT/A activity using the clonal cell lines disclosed in the present specification. Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct serotypes of botulinum toxins (BoNTs), which have been identified by investigating botulism outbreaks in man (BoNT/A, BoNT/B, BoNT/E and BoNT/F), animals (BoNT/C1 and BoNT/D), or isolated from soil (BoNT/G). While all seven botulinum toxin serotypes have similar structure and biological properties, each also displays heterogeneous characteristics, such as, e.g., different pharmacological properties. In contrast, tetanus toxin (TeNT) is produced by a uniform group of *C. tetani*. Two other species of Clostridia, *C. baratii* and *C. butyricum*, also produce toxins similar to BoNT/F and BoNT/E, respectively.

Clostridial toxins are each translated as a single chain polypeptide of approximately 150 kDa that is subsequently cleaved by proteolytic scission within a disulfide loop by a naturally-occurring protease, such as, e.g., an endogenous Clostridial toxin protease or a naturally-occurring protease produced in the environment. This posttranslational processing yields a di-chain molecule comprising an approximately 50 kDa light chain (LC) and an approximately 100 kDa heavy chain (HC) held together by a single disulfide bond and non-covalent interactions. Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC($H_N$) that facilitates release of the LC from intracellular vesicles into the cytoplasm of the target cell; and 3) a binding domain found within the carboxyl-terminal half of the HC(HO that determines the binding activity and binding specificity of the toxin to the receptor complex located at the surface of the target cell.

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (FIG. 1). The process is initiated when the $H_C$ binding domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate important pH-dependent structural rearrangements that increase hydrophobicity, promote pore formation, and facilitate separation of the heavy and light chains of the toxin. Once separated, the light chain endopeptidase of the toxin is released from the intracellular vesicle into the cytosol where it appears to specifically target core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl terminal region, releasing a nine or twenty six amino acid fragment, respectively, and BoNT/C1 also cleaves SNAP-25 near the carboxy terminus releasing an eight amino acid fragment. The botulinum serotypes BoNT/B, BoNT/D, BoNT/F and BoNT/G, and tetanus toxin, act on the conserved central portion of VAMP, and release the amino terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release,* 82(5) Biochimie. 427-446 (2000); Kathryn Turton et al., *Botulinum and Tetanus Neurotoxins: Structure, Function and Therapeutic Utility,* 27(11) Trends Biochem. Sci. 552-558. (2002); Giovanna Lalli et al., *The Journey of Tetanus and Botulinum Neurotoxins in Neurons,* 11(9) Trends Microbiol. 431-437, (2003).

Aspects of the present disclosure comprise, in part, a cell from an established cell line. As used herein, the term "cell" refers to any eukaryotic cell susceptible to BoNT/A intoxication by a BoNT/A or any eukaryotic cell that can uptake a BoNT/A. The term cell encompasses cells from a variety of organisms, such as, e.g., murine, rat, porcine, bovine, equine, primate and human cells; from a variety of cell types such as, e.g., neuronal and non-neuronal; and can be isolated from or part of a heterogeneous cell population, tissue or organism. As used herein, the term "established cell line" is synonymous with "immortal cell line," or "transformed cell line" and refers to a cell culture of cells selected for indefinite propagation from a cell population derived from an organism, tissue, or organ source. By definition, an established cell line excludes a cell culture of primary cells. As used herein, the term "primary cells" are cells harvested directly from fresh tissues or organs and do not have the potential to propagate indefinitely. An established cell line can comprise a heterogeneous population of cells or a uniform population of cells. An established cell line derived from a single cell is referred to as a clonal cell line. An established cell line can be one whose cells endogenously express all component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Alternatively, an established cell line can be one whose cells have had introduced from an exogenous source at least one component necessary for the cells to undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. Also referred to as a genetically-engineered cell line, cells from such an established cell line may, e.g., express an exogenous FGFR2, an exogenous FGFR3, an exogenous SV2, an exogenous SNAP-25, or any combination thereof. As used herein, the term "established clonal cell line" or "clonal cell line" refers to a cell culture of cells selected from a heterogenous population of cell types comprising an established cell line, which can also be referred to as a parental cell line. Thus, as a non-limiting example, the cells from the A6, A7, A9, A10, A11, B5, B10, C5, C11, C12, D7, D11, E11, F10, H1, H3, H8, H10, 1E3, 2B9, 2E4, 3B8, 3D5, 3G10, 4B5, 4C8, 5F3, AC9, AF4, BB3, BB10, BE3, BF8, CC11, CD6, CE6, CG8, CG10, DC4, DD10, DE7, YF5, and H1 1.4 clonal cell lines were selected from the heterogenous population of cell types comprising the SiMa cell line (or parental SiMa cell line) DSMZ ACC 164.

Aspects of the present disclosure comprise, in part, a cell from an established clonal cell line susceptible to BoNT/A intoxication. As used herein, the terms "cell(s) susceptible to BoNT/A intoxication," "cell(s) susceptible to BoNT/A intoxication by a BoNT/A," or "cell(s) from an established clonal cell line susceptible to BoNT/A intoxication by a BoNT/A" refer to cell(s) that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) susceptible to BoNT/A intoxication must express, or be engineered to express, at least one BoNT/A receptor and at least one SNAP-25 substrate. Non-limiting examples of a cell or cells from an established clonal cell line susceptible to BoNT/A intoxication, include A6, A7, A9, A10, A11, B5, B10, C5, C11, C12, D7, D11, E11, F10, H1, H3, H8, H10, 1E3, 2B9, 2D2, 2D6, 2E4, 3B8, 3D5, 3G10, 4B5, 4C8, 4D3, 5C10, 5F3, AC9, AF4, BB3, BB10, BE3, BF8, CC11, CD6, CE6, CG8, CG10, DC4, DD10, DE7, DFS, YB7, YF5, and H1 1.4 clonal cell lines. As used herein, the terms "cell(s) that can uptake BoNT/A" or "cell(s) comprising an established clonal cell line that can uptake BoNT/A" refer to cells that can undergo the overall cellular mechanism whereby a BoNT/A proteolytically cleaves a SNAP-25 substrate and encompasses the binding of a BoNT/A to a BoNT/A receptor, the internalization of the neurotoxin/receptor complex, the translocation of the BoNT/A light chain from an intracellular vesicle into the cytoplasm and the proteolytic cleavage of a SNAP-25. By definition, cell(s) that can uptake BoNT/A must express, or be engineered to express, at least one BoNT/A receptor and at least one SNAP-25 substrate. Non-limiting examples of a cell or cells from an established clonal cell line that can uptake BoNT/A, include A6, A7, A9, A10, A11, B5, B10, C5, C11, C12, D7, D11, E11, F10, H1, H3, H8, H10, 1E3, 2B9, 2D2, 2D6, 2E4, 3B8, 3D5, 3G10, 4B5, 4C8, 4D3, 5C10, 5F3, AC9, AF4, BB3, BB10, BE3, BF8, CC11, CD6, CE6, CG8, CG10, DC4, DD10, DE7, DFS, YB7, YF5, and H1 1.4 clonal cell lines. Cell lines comprising cell(s) from an established clonal cell line susceptible to BoNT/A intoxication or cell(s) that can uptake BoNT/A are referred to as a "responder cell line."

Aspects of the present disclosure comprise, in part, cells from an established clonal cell line more susceptible to BoNT/A intoxication. As used herein, the terms "cell(s) more susceptible to BoNT/A intoxication," "cell(s) more susceptible to BoNT/A intoxication by a BoNT/A," or "cell(s) from an established clonal cell line more susceptible to BoNT/A intoxication by a BoNT/A" refer to cell(s) that undergo the overall cellular mechanism whereby a BoNT/A proteolytically cleaves a SNAP-25 substrate to a greater degree as compared to a cell(s) comprising a parental SiMa cell line, such as, e.g., parental SiMa cell line DSMZ ACC 164. Non-limiting examples of a cell or cells from an established clonal cell line more susceptible to BoNT/A intoxication, include a cell or cells from a A10, H1, 2E4, 3B8, 3D5, 5F3, AF4, BB3, BB10, DC4, or H1 1.4 clonal cell lines. As used herein, the terms "cell(s) that uptake BoNT/A more" or "cell(s) comprising an established clonal cell line that uptake BoNT/A more" refer to cells that undergo the overall cellular mechanism whereby a BoNT/A proteolytically cleaves a SNAP-25 substrate to a greater degree as compared to a cell(s) comprising a parental SiMa cell line, such as, e.g., parental SiMa cell line DSMZ ACC 164. Non-limiting examples of a cell or cells from an established clonal cell line that can uptake BoNT/A more, include a cell or cells from a A10, H1, 2E4, 3B8, 3D5, 5F3, AF4, BB3, BB10, DC4, or H1 1.4 clonal cell lines. Cell lines comprising cell(s) from an established clonal cell line more susceptible to BoNT/A intoxication or cell(s) that can uptake BoNT/A more are referred to as a "high responder cell line."

Aspects of the present disclosure comprise, in part, cells from an established clonal cell line less susceptible to BoNT/A intoxication. As used herein, the terms "cell(s) less susceptible to BoNT/A intoxication," "cell(s) less susceptible to BoNT/A intoxication by a BoNT/A," or "cell(s) from an established clonal cell line less susceptible to BoNT/A intoxication by a BoNT/A" refer to cell(s) that undergo the overall cellular mechanism whereby a BoNT/A proteolytically cleaves a SNAP-25 substrate to a lesser degree as compared to a cell(s) comprising a parental SiMa cell line, such as, e.g., parental SiMa cell line DSMZ ACC 164. Non-limiting examples of a cell or cells from an established clonal cell line less susceptible to BoNT/A intoxication, include A7, B10, D11, H10, 2D2, 2D6, 4D3, 5C10, DF5, and YB7 clonal cell lines. As used herein, the terms "cell(s) that uptake BoNT/A less" or "cell(s) comprising an established clonal cell line that uptake BoNT/A less" refer to cells that undergo the overall cellular mechanism whereby a BoNT/A proteolytically cleaves a SNAP-25 substrate to a lesser degree as compared to a cell(s) comprising a parental SiMa cell line, such as, e.g., parental SiMa cell line DSMZ ACC 164. Non-limiting examples of a cell or cells from an established clonal cell line that can uptake BoNT/A less, include A7, B10, D11, H10, 2D2, 2D6, 4D3, 5C10, DF5, and YB7 clonal cell lines. Cell lines comprising cell(s) from an established clonal cell line less susceptible to BoNT/A intoxication or cell(s) that can uptake BoNT/A less are referred to as a "low responder cell line."

Aspects of the present disclosure comprise, in part, a cell from an established clonal cell line not susceptible to BoNT/A intoxication. As used herein, the terms "cell(s) not susceptible to BoNT/A intoxication," "cell(s) not susceptible to BoNT/A intoxication by a BoNT/A," or "cell(s) from an established clonal cell line not susceptible to BoNT/A intoxication by a BoNT/A" refer to cell(s) that cannot undergo the overall cellular mechanism whereby a BoNT/A proteolytically cleaves a SNAP-25 substrate. As used herein, the terms "cell(s) that cannot uptake BoNT/A" or "cell(s) comprising an established clonal cell line that cannot uptake BoNT/A" refer to cells that cannot undergo the overall cellular mechanism whereby a BoNT/A proteolytically cleaves a SNAP-25 substrate. Cell lines comprising cell(s) from an established clonal cell line not susceptible to BoNT/A intoxication or cell(s) that cannot uptake BoNT/A are referred to as a "non-responder cell line."

Thus in an embodiment, cells from an established clonal cell line are susceptible to BoNT/A intoxication. In aspects of this embodiment, cells from an established clonal cell line are susceptible to BoNT/A intoxication by, e.g., about 500 pM or less, about 400 pM or less, about 300 pM or less, about 200 pM or less, or about 100 pM or less of a BoNT/A. In other aspects of this embodiment, cells from an established clonal cell line are susceptible to BoNT/A intoxication by, e.g., about 90 pM or less, about 80 pM or less, about 70 pM or less, about 60 pM or less, about 50 pM or less, about 40 pM or less, about 30 pM or less, about 20 pM or less, or about 10 pM or less of a BoNT/A. In still other aspects, cells from an established clonal cell line are susceptible to BoNT/A intoxication by, e.g., about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells from an established clonal cell line are susceptible to BoNT/A intoxication by, e.g., about 0.9 pM or less, about 0.8 pM or less, about 0.7 pM or less, about 0.6 pM or less, about 0.5 pM or less, about 0.4 pM or less, about 0.3 pM or less, about 0.2 pM, or about 0.1 pM or less of a BoNT/A. As used herein, the term "about" when qualifying a value of a stated item, number, percentage, or term refers to a range of plus or minus ten percent of the value of the stated item, percentage, parameter, or term.

In another embodiment, cells comprising an established clonal cell line can uptake a BoNT/A. In aspects of this embodiment, cells comprising an established clonal cell line can uptake, e.g., about 500 pM or less, about 400 pM or less, about 300 pM or less, about 200 pM or less, or about 100 pM or less of a BoNT/A. In other aspects of this embodiment, cells comprising an established clonal cell line possess the ability to uptake about 90 pM or less, about 80 pM or less, about 70 pM or less, about 60 pM or less, about 50 pM or less, about 40 pM or less, about 30 pM or less, about 20 pM or less, or about 10 pM or less of a BoNT/A. In still other aspects, cells comprising an established clonal cell line possess the ability to uptake about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells comprising an established clonal cell line possess the ability to uptake about 0.9 pM or less, about 0.8 pM or less, about 0.7 pM or less, about 0.6 pM or less, about 0.5 pM or less, about 0.4 pM or less, about 0.3 pM or less, about 0.2 pM or less, or about 0.1 pM or less of a BoNT/A. In other aspects, cells comprising an established clonal cell line can uptake BoNT/A from, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

In another embodiment, cells from an established clonal cell line are not susceptible to BoNT/A intoxication. In aspects of this embodiment, cells from an established clonal cell line are not susceptible to BoNT/A intoxication by, e.g., about 500 pM or less, about 400 pM or less, about 300 pM or less, about 200 pM or less, or about 100 pM or less of a BoNT/A. In other aspects of this embodiment, cells from an established clonal cell line are susceptible to BoNT/A intoxication by, e.g., about 90 pM or less, about 80 pM or less, about 70 pM or less, about 60 pM or less, about 50 pM or less, about 40 pM or less, about 30 pM or less, about 20 pM or less A, or about 10 pM or less of a BoNT/A. In still other aspects, cells from an established clonal cell line are not susceptible to BoNT/A intoxication by, e.g., about 9 pM or less, about 8 pM or less, about 7 pM or less, about 6 pM or less, about 5 pM or less, about 4 pM or less, about 3 pM or less, about 2 pM or less, or about 1 pM or less of a BoNT/A. In yet other aspects, cells from an established clonal cell line are not susceptible to BoNT/A intoxication by, e.g., about 0.9 pM or less, about 0.8 pM or less, about 0.7 pM or less, about 0.6 pM or less, about 0.5 pM or less, about 0.4 pM or less, about 0.3 pM or less, about 0.2 pM, or about 0.1 pM or less of a BoNT/A. In other aspects, cells from an established clonal cell line are not susceptible to BoNT/A intoxication from, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

Aspects of the present disclosure comprise, in part, cells from an established clonal cell line susceptible to BoNT/A intoxication that are more stable than cells from a parental SiMa cell line, such as, e.g., parental SiMa cell line DSMZ ACC 164. As used herein, the term "stable" refers to cells from an established clonal cell line for a particular passage number that exhibit a relative $EC_{50}$, sensitivity, efficacy, well-defined upper asymptote, and/or a well-defined dose-response curve for BoNT/A activity that is similar to the values for relative $EC_{50}$, sensitivity, efficacy, well-defined upper asymptote, and/or a well-defined dose-response curve exhibited by cells from a parental SiMa cell line, such as, e.g., parental SiMa cell line DSMZ ACC 164, at the same or similar passage number, where the same assay conditions and the same BoNT/A (or molecule) are used in both assays.

Thus in an embodiment, cells from an established clonal cell line are more stable as compared to a parental SiMa cell line. In an aspect of this embodiment, cells from an established clonal cell line are more stable as compared to the parental SiMa cell line DSMZ ACC 164. In other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to a parental SiMa cell line. In yet other aspects of this embodiment, cells from an established clonal cell line are more stable for, e.g., at least 5 more passages, at least 10 more passages, at least 15 more passages, at least 20 more passages, at least 25 more passages, or at least 30 more passages, as compared to a parental SiMa cell line DSMZ ACC 164.

Aspects of the present disclosure comprise, in part, cells from an established clonal cell line susceptible to BoNT/A intoxication that are stable over a plurality of cell passages. As used herein, the term "stable" refers to cells from an established clonal cell line for a particular passage number that exhibit a relative $EC_{50}$, sensitivity, efficacy, well-defined upper asymptote, and/or a well-defined dose-response curve for BoNT/A activity that is similar to the values for relative $EC_{50}$, sensitivity, efficacy, well-defined upper asymptote, and/or a well-defined dose-response curve exhibited by cells from the same established clonal cell line, but from a prior passage or passages, where the same assay conditions and the same BoNT/A (or molecule) are used in both assays.

Cells from an established cell line disclosed in the present specification can exhibit consistent sensitivity to BoNT/A activity over a plurality of cell passages. As used herein, the term "sensitivity to BoNT/A activity" refers to the lowest dose that an assay can measure consistently above the signal detected by a non-treatment control or background signal.

Thus, in an embodiment, cells from the established clonal cell line exhibit a sensitivity for BoNT/A activity for any given passages that is e.g., 100 pM or less, about 80 pM or less, about 70 pM or less, about 60 pM or less, about 50 pM or less, about 40 pM or less, about 30 pM or less, about 20 pM or less, about 10 pM or less, about 1 pM or less, about 0.9 pM or less, about 0.8 pM or less, about 0.7 pM or less, about 0.6 pM or less, about 0.5 pM or less, about 0.4 pM or less, about 0.3 pM or less, about 0.2 pM or less, or about 0.1 pM or less of a BoNT/A. In aspects of this embodiment, cells from the established clonal cell line exhibit a sensitivity for BoNT/A activity for any given passages that is, e.g., about 0.01 pM to about 100 pM, about 0.01 pM to about 75 pM, about 0.01 pM to about 50 pM, about 0.01 pM to about 25 pM, about 0.01 pM to about 20 pM, about 0.01 pM to about 15 pM, about 0.01 pM to about 10 pM, about 0.01 pM to about 5 pM, about 0.001 pM to about 100 pM, about 0.001 pM to about 75 pM, about 0.001 pM to about 50 pM, about 0.001 pM to about 25 pM, about 0.001 pM to about 20 pM, about 0.001 pM to about 15 pM, about 0.001 pM to about 10 pM, or about 0.001 pM to about 5 pM of BoNT/A.

In another embodiment, cells from the established clonal cell line exhibit a sensitivity for BoNT/A activity that is about 100 pM or less, about 75 pM or less, about 50 pM or less, about 25 pM or less, less about 20 pM or less, about 15 pM or less, about 10 pM or less, or about 1 pM or less for, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from the established clonal cell line exhibit a sensitivity for BoNT/A activity that is about 100 pM or less, about 75 pM or less, about 50 pM or less, about 25 pM or less, less about 20 pM or less, about 15 pM or less, about 10 pM or less, or about 1 pM or less for, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative efficacy of BoNT/A uptake, BoNT/A activity, or BoNT/A intoxication over a plurality of cell passages. As used herein, the term "relative efficacy" refers to how well the upper asymptote for the BoNT/A activity detected in the current assay run compares to the upper asymptote for the BoNT/A activity detected in a reference standard, a reference molecule, or a reference passage number used on that assay. As used herein, the term "signal to noise ratio for the upper asymptote" refers to the signal detected in an assay at the upper limit of detection divided by the signal detected by a non-treatment control or background signal. The upper limit of detection is the highest dose that an assay can measure consistently before saturation of the signal occurs.

Thus, in an embodiment, cells from an established cell line disclosed in the present specification can exhibit a well defined upper asymptote over a plurality of cell passages and maintain a signal to noise ratio that is consistent and adequate for the assay. In aspects of this embodiment, cells from an established cell line disclosed in the present specification must have a signal to noise ratio for the upper asymptote for BoNT/A activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification must have a signal to noise ratio for the upper asymptote for BoNT/A activity of, e.g., at least 3:1, at least 4:1, at least 5:1, at least 6:1, at least 7:1, at least 8:1, at least 9:1, at least 10:1, at least 15:1, at least 20:1, at least 25:1, at least 30:1, at least 35:1, at least 40:1, at least 45:1, at least 50:1, at least 60:1, at least 70:1, at least 80:1, at least 90:1, or at least 100:1, at least 150:1, at least 200:1, at least 250:1, at least 300:1, at least 350:1, at least 400:1, at least 450:1, at least 500:1, at least 550:1, or at least 600:1, over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a well defined dose-response curve for BoNT/A activity over a plurality of cell passages. As used herein, the term "dose-response curve" refers to the how well the raw data fits the statistical model of choice for that assay. As a non-limiting example, a sigmoidal curve with a four parameter logistics fit is a dose-response curve for an enzymatic activity assay, such as, e.g., a potency assay. As another non-limiting example, a ligand binding with one site saturation fit is a dose-response curve for a ligand/antibody binding assay. Thus, in an embodiment, cells from an established cell line disclosed in the present specification exhibit a well defined dose-response curve for BoNT/A activity over a plurality of cell passages. In aspects of this embodiment, cells from an established cell line disclosed in the present specification exhibit a well defined dose-response curve for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established cell line disclosed in the present specification exhibit a well defined dose-response curve for BoNT/A activity over, e.g., about 15 to about 60 passages, about 20 to about 60 passages, about 25 to about 60 passages, about 30 to about 60 passages, about 35 to about 60 passages, about 40 to about 60 passages, about 45 to about 60 passages, about 50 to about 60 passages, about 15 to about 50 passages, about 20 to about 50 passages, about 25 to about 50 passages, about 30 to about 50 passages, about 35 to about 50 passages, about 40 to about 50 passages, about 15 to about 40 passages, about 20 to about 40 passages, about 25 to about 40 passages, or about 30 to about 40 passages.

Cells from an established cell line disclosed in the present specification can exhibit a consistent relative $EC_{50}$ value for BoNT/A activity over a plurality of cell passages. As used herein, the term "relative $EC_{50}$" or "relative $EC_{50}$ value" refers to an $EC_{50}$ value of BoNT/A activity that is normalized against the $EC_{50}$ calculated for a reference standard, a reference molecule, or a reference passage number used on that assay.

Thus, in an embodiment, cells from an established clonal cell line exhibit a consistent relative $EC_{50}$ for BoNT/A activity over a plurality of cell passages. In aspects of this embodiment, cells from an established clonal cell line exhibit a consistent relative $EC_{50}$ for BoNT/A activity that is, e.g., about ±10%, about ±20%, about ±30%, about ±40%, about ±50%, about 60%, about 70%, or about ±75%, the relative $EC_{50}$ for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages. In other aspects of this embodiment, cells from an established clonal cell line exhibit a relative $EC_{50}$ for BoNT/A activity that is, e.g., about ±10% to about 75%, about ±10% to about 70%, about ±10% to about 60%, about ±10% to about 50%, about ±10% to about 40%, about ±10% to about 30%, or about ±10% to about 20% the relative $EC_{50}$ for BoNT/A activity over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, or 50 or more cell passages.

Aspects of the present disclosure comprise, in part, cells from an established clonal cell line susceptible to BoNT/A intoxication that exhibit at least a 1.5-fold difference in gene expression levels of one or more genes listed in Tables 5, 6, 7, or 8 as compared to the expression levels of these genes in cells from the 2D6 cell line. In other aspects of this embodiment, cells from an established clonal cell line susceptible to BoNT/A intoxication exhibit a difference in gene expression levels of one or more genes listed in Tables 5, 6, 7, or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the 2D6 cell line. In other aspects of this embodiment, cells from an established clonal cell line susceptible to BoNT/A intoxication exhibit a difference in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5, 6, 7, or 8 as compared to the expression levels of these genes in cells from the 2D6 cell line. In yet other aspects, cells from an established clonal cell line susceptible to BoNT/A intoxication exhibit a difference in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5, 6, 7, or 8 as compared to the expression levels of these genes in cells from the 2D6 cell line. The log ratio in Tables 5, 6, 7, and 8 represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

In an embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line. In aspects of this embodiment, cells from an established clonal cell line susceptible to BoNT/A intoxication exhibit an increase in gene expression levels of one or more genes listed in Tables 5 or 7 of, e.g., at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the 2D6 cell line. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5 or 7 as compared to the expression levels of these genes in cells from the 2D6 cell line. In yet other aspects, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5 or 7 as compared to the expression levels of these genes in cells from the 2D6 cell line.

In an embodiment, cells from an established clonal cell line susceptible to BoNT/A intoxication exhibit at least a 1.5-fold increase in gene expression levels of one or more genes selected from A2BP1, ACO1, ACOT7, ACOT9, ACTL6A, ACTL6B, ADRBK2, AGPS, AIDA, AKAP13, ALCAM, ALDH7A1, AMOTL1, ANAPC7, ANKRD13A, ANKRD54, ANKS1B, ANLN, ANP32E, ANXA6, APAF1, APBB2, APOO, ARF3, ARHGAP11A, ARHGAP24, ARHGAP27, ARHGAP6, ARHGEF3, ARHGEF6, ARL13B, ARL6, ARL61P1, ASCL1, ASF1A, ASF1B, ASXL3, ATAD2, ATP6V1A, AURKA, AURKB, BARD1, BASP1, BAX, BCL11A, BCR, BNC2, BOK, BRCA1, BRCA2, BRD4, BR13BP, BRIP1, BTBD3, BTG3, BUB1, BUB1B, BUB3, BVES, C10ORF58, C10ORF78, C11ORF75, C12ORF48, C12ORF49, C14ORF106, C14ORF143, C15ORF23, C15ORF42, C18ORF54, C1ORF112, C1ORF183, C1ORF43, C1QL1, C20ORF108, C20ORF20, C20ORF7, C20ORF72, C22ORF28, C22ORF29, C22ORF39, C3ORF14, C3ORF70, C4ORF46, C4ORF49, C5ORF32, C6ORF115, C9ORF100, CARHSP1, CBLB, CBWD1, CBX5, CCDC109B, CCDC117, CCDC15, CCDC21, CCDC3, CCDC34, CCDC52, CCDC86, CCDC99, CCNB1, CCNE2, CCNF, CCNYL1, CD24, CD47, CD9, CDC2, CDC25B, CDC42EP4, CDC45L, CDC5L, CDC6, CDCA2, CDCA4, CDCA5, CDCA7, CDCA8, CDH2, CDK2, CDK2AP1, CDK6, CDKAL1, CDKN2C, CDKN2D, CDO1, CDS2, CECR5, CELSR3, CENPF, CENPH), CENPI, CENPJ, CENPK, CENPL, CENPM, CENPN, CENPO, CEP135, CEP152, CEP55, CEP78, CEP97, CHAF1A, CHD6, CHEK1, CHEK2, CHMP4B, CHRNA3, CHRNA7, CHST15, CIT, CKAP2, CKAP2L, CKLF, CKS1B, CLDND1, CLSTN2, CMTM7, CNN3, CNOT4, CNP, CNTN1, CNTN4, COBLL1, COQ3, CPNE4, CPT1A, CPVL, CRISPLD1, CRTAC1, CRYBG3, CRYZ, CSE1L, CSRP2, CSRP2BP, CSTF1, CTDSPL2, CTNNBL1, CTSL2, CUGBP2, CXCR4, CYTSA, DACT1, DAZ1, DBF4B, DBH, DCLRE1B, DCPS, DDAH2, DDT, DEK, DENR, DEPDC1, DEPDC1B, DERA, DGCR14, DGKE, DHX15, DHX35, DIAPH1, DIAPH3, DKFZP434L187, DLEU2, DLGAP5, DLL3, DLX6, DNA2, DNM3, DNMT3B, DOCK10, DOK4, DOK5, DPF1, DPYD, DPYSL3, DRAM1, DRG1, DSCC1, DSN1, DTL, DTNBP1, DTYMK, DVL2, DYNLT3, DYRK4, E2F1, E2F2, E2F7, E2F8, EAF2, EBF1, ECT2, EFNA5, EFNB2, ELAVL4, ELOVL7, EME1, EMILIN2, EMILIN3, EML1, ENC1, EPB41L5, EPOR, ERCC6L, ESCO2, ESF1, ESPL1, ETS1, ETV1, EXO1, EX005, EXOSC6, EXPH5, EZH2, FAM101B, FAM105A, FAM110A, FAM114A1, FAM118A, FAM120C, FAM129B, FAM13A, FAM162B, FAM181B, FAM19A4, FAM19A5, FAM54A, FAM64A, FAM7A3, FAM83D, FANCG, FANCI, FANCL, FANCM, FARP1, FAT1, FBLN1, FBN1, FBP1, FBXO43, FBXO5, FEN1, FGFR2, FH, FIGNL1, FKBP5, FNDC5, FOXD1, FOXN3, FRMD6, FRZB, FSTL1, FZD2, FZD5, FZD8, G2E3, GABBR2, GAP43, GAP43, GAS2L3, GATM, GEMIN4, GFPT2, GFRA1, GFRA2, GGCX, GINS1, GINS3, GJC1, GLDC, GMNN, GNAI1, GNASAS, GNB4, GNG11, GNG12, GNG4, GPAM, GPN3, GPR125, GPR161, GPSM2, GPX3, GRP, GSG2, GSS, GSTCD, GTSE1, GTSF1, GXYLT1, H1F0, H2AFX, HAT1, HAUS6, HDAC8, HEG1, HES6, HGF, HIC2, HMG4L, HMGB1, HMGB2, HMGB3, HMGXB4, HMMR, HOOK3, HPS4, HRH3, HS3ST2, HS6ST2, HSPB11, HTATSF1, IDH2, IF127L1, IQGAP1, ITGA6, ITGAV, ITGB5, ITPRIP, JARID2, KCNG3, KCNJ8, KCNN1, KCTD12, KDELC2, KHDRBS3, KIAA0101, KIAA0406, KIAA1211, KIAA1524, KIF11, KIF14, KIF16B, KIF18A, KIF23, KIFC1, KLF7, KLHL13, KLHL5, KNTC1, KPNA2, LBH, LGR5, LHFPL2, LIFR, LIG3, LMF2, LMNB1, LOC100127983, LOCI 00128844, LOC100288551, LOC340109, LOC344595, LOC440288, LOC642597, LOC728052, LPAR1, LRFN2, LRRC1, LSM4, LUM, MAB21L1, MAB21L2, MAGEH1, MAN1A1, MAN2A1, MAOA, MAP3K13, MAPK11, MAPK12, MAPKAPK3, MASTL, MBD2, MCAM, MCM10, MCM3, MCM4, MCM5, MCM6, MCM7, MCM8, MDC1, MDM1, MED20, MEIS1, MEIS2, MELK, MEST, MFAP2, MGAT5B, MINA, MK167, MKL1, MLF11P, MMD, MNS1, MPHOSPH9, MPP5, MPPED2, MRC2, MRPL35, MRPL49, MRS2, MSN, MTF2, MTHFD1, MTUS1, MVK, MYBL1, MYBL2, MYD88, MYO1B, MYO6, MYST1, NAAA, NAGA, NANP, NARG1, NASP, NAT11, NAT13, NCAPD3, NCAPG, NCAPG2, NCAPH, NCAPH2, NDN, NEDD1, NEDD9, NEIL3, NELL2, NFIB, NOC4L, NOS1, NR3C1, NRG3, NRM, NRXN1, NSMCE4A, NTAN1, NUCKS1, NUDT1, NUF2, NUP107, NUP37, NUP43, NUP50, NUP93, NUSAP1, NXPH1, NXT2, ODZ3, ODZ4, OIP5, ORC1L, ORC6L, OSBPL3, PAICS, PANK2, PARP3, PASK, PBK, PCDH17, PCDH8, PCGF5, PCNA, PDCL, PDE5A, PDLIM5, PDRG1, PEG3, PELI2, PELO, PEX13, PEX26, PFKFB3, PGAM5, PGM2, PHF19, PHF20, PHF21B, PHF5A, PHLPP1, PHYHIPL, PI4KA, PIP4K2A, PIR, PKMYT1, PLCL2, PLD5, PLEKHF2, PLK2, PLK4, PLS3, PLXNA2, PLXNA4, PLXNB2, PM20D2, POLA1, POLA2, POLE, POLE2, POLQ, POSTN, PPAP2B, PPAT, PPIF, PPIL5, PPM1F, PPP1R13B, PPP1R3c, PPP2R2B, PPP3CB, PRIM1, PRIM2, PRLHR, PRPS1, PRSS12, PSMA7, PSMC31P, PSMD5, PSMD9, PSRC1, PTER, PTGES2, PTGFRN, PTGR1, PTPRE, PTPRG, PTPRK, PTPRM, PTTG1, PVRL3, PXMP4, PXN, RAB35, RAB3B, RAD18, RAD51, RAD51C, RALY, RAN, RANBP1, RANGAP1, RASEF, RBBP7, RBBP9, RBL1, RBPMS, RBX1, RECQL4, REEP1, RELB, RELL1, REXO2, RFC1, RFC2, RFC3, RFC4, RFC5, RGMA, RGS5, RILPL2, RIMBP2, RMI1, RNASEH2A, RNF182, RNF26, RNF34, RPA1, RPP30, RRM1, RRM2, RRP7A, RSRC1, S1PR3, SALL4, SAP30, SASS6, SBF2, SCD5, SCML1, SCML2, SDC1, SEC23A, SEC61A2, SELM, SEMA6A, SEMA6D, SESN3, SEZ6L, SF11, SFRP1, SGOL2, SH3D19, SHCBP1, SHMT1, SHOX2, SIM1, SIVA1, SKA1, SKA2, SKA3, SKP2, SLC25A10, SLC26A2, SLC2A4RG, SLC2A8, SLC43A3, SLC44A5, SLC7A2, SLC8A1, SLCO3A1, SLIT3, SLITRK5, SLK, SLMO2, SMC1A, SMC2, SMC4, SMC6, SMO, SMYD5, SNAI2, SNAP29, SNCAIP, SNRPD3, SNX18, SNX5, SORD, SOX4, SPAG6, SPARC, SPATS2L, SPC24, SPC25, SPOCK1, SPSB4, SRGAP1, SRRD, SRRM4, SSH2, ST8SIA1, ST8SIA2, ST8SIA4, STARD4, STIL, STK17A, STMN3, STOM, STON2, STRA6, SUSD5, SUV39H1, SVIP, SYN2, SYNE2, SYNM, SYT17, SYTL4, TBC1D1, TBX3, TCF19, TCF7L2, TCFL5, TDRKH, TEAD3, TESC, TFDP1, TFDP2, TFPI2, TH1L, THOC4, TIFA, TIMP3, TLE3, TLE4, TMCC3, TMEM107, TMEM132C, TMEM151B, TMEM170B, TMEM178, TMEM194A, TMEM38B, TMEM48, TMEM56, TMEM98, TMPO, TMSB15B, TNFAIP8, TOB2, TOMM34, TPBG, TPTE, TPX2, TRIM29, TRIM36, TRIM68, TRIM9, TRIP13, TROAP, TSHZ3, TSPAN14, TSPAN4, TSPAN5, TTC28, TTC9, TUBA1B, TUBB, TWIST1, TXNRD1, TYMS, TYRO3, UBE2C, UBE2L3, UBE2V1, UBE3B, UCK1, UCP2, UFD1L, UHRF1, UNC119B, UNG, UQCC, USP1, USP48, UTP18, VAPB, VAV3, VPS29, VSTM2L, WDHD1, WDR51A, WDR53, WDR62, WDR67, WEE1, WEE1, WHSC1, WRAP53, WWC3, XRCC4, XRCC6, ZAK, ZFHX4, ZFP82, ZGPAT, ZNF215, ZNF217, ZNF238, ZNF253, ZNF280B, ZNF367, ZNF43, ZNF443, ZNF503, ZNF521, ZNF560, ZNF608, ZNF626, ZNF681, ZNF71, ZNF823, ZNF85, ZNF92, ZNF93, and/or ZWINT, as compared to the expression levels of these genes in cells from the 2D6 cell line.

In an aspect of this embodiment, cells from an established clonal cell line susceptible to BoNT/A intoxication exhibit at least a 1.5-fold increase in gene expression levels of one or more genes selected from A2BP1, ACOT9, ALCAM, ANLN, ARHGAP24, ARHGAP6, ARHGEF3, ARHGEF6, ASCL1, ASF1B, ATAD2, AURKA, AURKB, BARD1, BASP1, BNC2, BRCA2, BRIP1, BTG3, BUB1, BUB1B, BYES, C11ORF75, C12ORF48, C14ORF106, C15ORF42, C18ORF54, C1ORF112, C3ORF70, C4ORF49, CCDC109B, CCDC3, CCNB1, CCNE2, CD9, CDC2, CDC25B, CDC45L, CDC6, CDCA2, CDCA5, CDCA8, CDK2, CDKN2D, CENPF, CENPI, CENPL, CENPN, CEP55, CHEK1, CHEK2, CHRNA7, CIT, CKAP2L, CLSTN2, CNTN1, CNTN4, CPVL, CRYBG3, CSRP2, CTSL2, CUGBP2, CXCR4, DAZ1, DEPDC1, DEPDC1B, DIAPH3, DLGAP5, DNA2, DOK5, DPYD, DPYSL3, DSCC1, DSN1, DTL, DYNLT3, E2F1, E2F2, E2F7, E2F8, ECT2, EFNB2, ELOVL7, EME1, EMILIN2, EMILIN3, EML1, ENC1, ERCC6L, ESCO2, ESPL1, ETV1, EXO1, EXPH5, FAM101B, FAM114A1, FAM54A, FAM64A, FAM7A3, FAM83D, FANCI, FAT1, FBLN1, FBP1, FBXO43, FGFR2, FNDC5, FOXD1, FRMD6, FRZB, FZD5, GAS2L3, GFRA2, GINS1, GINS3, GNAI1, GNB4, GNG11, GNG12, GPSM2, GRP, GTSE1, GTSF1, HGF, HMMR, HS3ST2, ITGA6, ITPRIP, KCNG3, KCTD12, KDELC2, KIAA0101, KIAA1524, KIF11, KIF14, KIF18A, KIF23, KIFC1, LOC340109, LOC642597, LOC728052, LOC728052, LPAR1, LUM, MAB21L1, MAB21L2, MAOA, MCM10, MCM5, MELK, MINA, MKI67, MLF1IP, MPPED2, MRC2, MSN, MYBL1, MYBL2, MYO6, NCAPG, NCAPH, NDN, NEDD9, NEIL3, NR3C1, NRXN1, NUF2, NUSAP1, OIP5, ORC1L, OSBPL3, PBK, PCGF5, PDE5A, PEG3, PELO, PFKFB3, PHLPP1, PLD5, PLK2, PLK4, PLS3, POLA2, POLE2, POLQ, PPAP2B, PPP1R3C, PRLHR, PRSS12, PSRC1, PTGR1, PTPRE, PTPRK, PTPRM, PTTG1, PVRL3, RAD51, RBL1, RBPMS, RELL1, RFC5, RGMA, RGS5, RNF182, RRM2, S1PR3, SGOL2, SHCBP1, SHOX2, SIM1, SKA1, SLC43A3, SLC44A5, SLC7A2, SLITRK5, SMC2, SMC6, SPAG6, SPARC, SPC24, SPC25, ST8SIA4, STK17A, SUSD5, SYN2, SYNM, SYT17, TCF19, TESC, TFDP2, TFPI2, TIMP3, TLE3, TMEM132C, TMEM178, TNFAIP8, TPBG, TPTE, TPX2, TRIM29, TRIM36, TRIM68, TROAP, TWIST1, TYMS, UBE2C, UBE3B, UHRF1, WDHD1, WDR51A, WDR67, WEE1, ZFP82, ZNF367, ZNF521, and/ or ZWINT, as compared to the expression levels of these genes in cells from the 2D6 cell line.

In another aspect of this embodiment, cells from an established clonal cell line susceptible to BoNT/A intoxication exhibit at least a 1.5-fold increase in gene expression levels of one or more genes selected from A2BP1, ALCAM, ANLN, ARHGAP24, ARHGAP6, ASCL1, ASF1B, ATAD2, AURKA, AURKB, BARD1, BASP1, BNC2, BRIP1, BUB1, BYES, C11ORF75, C12ORF48, C14ORF106, C18ORF54, C3ORF70, CCDC109B, CCDC3, CD9, CDC2, CDC45L, CDCA2, CDCA8, CDK2, CENPL, CEP55, CHEK2, CHRNA7, CKAP2L, CNTN1, CRYBG3, CUGBP2, CXCR4, DAZ1, DEPDC1, DIAPH3, DLGAP5, DOK5, DPYD, DTL, DYNLT3, E2F1, E2F7, E2F8, EFNB2, ELOVL7, EMILIN2, EML1, ENC1, ESPL1, ETV1, EXO1, EXPH5, FAM54A, FAM64A, FAM7A3, FAM83D, FANCI, FAT1, FBLN1, FBXO43, FGFR2, FZD5, GNAI1, GNB4, GNG11, GNG12, GPSM2, GRP, GTSE1, GTSF1, HGF, HMMR, ITGA6, ITPRIP, KCTD12, KDELC2, KIF11, KIF14, KIF18A, KIF23, KIFC1, LOC340109, LOC728052, LPAR1, LUM, MAB21L1, MAB21L2, MAOA, MCM10, MELK, MINA, MKI67, MSN, MYBL1, NCAPH, NDN, NEDD9, NEIL3, NRXN1, NUF2, NUSAP1, OIP5, ORC1L, OSBPL3, PBK, PCGF5, PEG3, PEG3, PHLPP1, PLD5, PLK2, PLK4, PLS3, POLE2, PPAP2B, PPP1R3c, PRLHR, PRSS12, PTPRE, PTPRK, PTPRM, RBPMS, RELL1, RGS5, RNF182, RRM2, S1PR3, SGOL2, SHCBP1, SHOX2, SIM1, SLC43A3, SLC44A5, SLC7A2, SLITRK5, SMC6, SPAG6, SPARC, SPC24, SPC25, ST8SIA4, STK17A, SYT17, TFPI2, TIMP3, TMEM132C, TMEM178, TPBG, TPTE, TPX2, TRIM36, TWIST1, UBE3B, and/or ZNF367, as compared to the expression levels of these genes in cells from the 2D6 cell line.

In yet another aspect of this embodiment, cells from an established clonal cell line susceptible to BoNT/A intoxication exhibit at least a 1.5-fold increase in gene expression levels of one or more genes selected from A2BP1, ARHGAP24, ARHGAP6, ASCL1, ASF1B, ATAD2, AURKA, BARD1, BASP1, BNC2, BUB1, BYES, C11ORF75, CCDC3, CHEK2, CHRNA7, CKAP2L, CNTN1, CRYBG3, CUGBP2, CUGBP2, CXCR4, DAZ1, DEPDC1, DIAPH3, DLGAP5, DOK5, DPYD, DTL, DYNLT3, E2F8, EFNB2, ELOVL7, ENC1, EXPH5, FAM7A3, FANCI, FAT1, FBLN1, FGFR2, GNAI1, GNB4, GNG11, GNG12, GRP, GTSE1, GTSF1, HMMR, ITGA6, ITPRIP, KCTD12, KDELC2, LOC728052, LPAR1, LUM, MAB21L1, MAB21L2, MAOA, MCM10, MELK, MINA, MKI67, MSN, MYBL1, NDN, NEDD9, NRXN1, OSBPL3, PEG3, PLK2, PLS3, PRLHR, PRSS12, PTPRK, PTPRM, RBPMS, RGS5, RNF182, RRM2, SGOL2, SIM1, SLC43A3, SLC44A5, SLC7A2, SMC6, SPAG6, SPARC, STK17A, TFPI2, TIMP3, TMEM132C, TMEM178, and/or TPTE, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ADAMTS9, ATAD2, C11ORF82, CDC45L, CNTN1, CNTN4, Cyclin A, Cyclin E, E2F1, E2F2, E2F7, ELOVL7, EME1, FGFR, FGFR2, KIAA1524, MELK, MYBL1, MYBL2, NDC80, NDN, ORC1L, PLS3, PRIMA1, RAD54L, RBL1, RBPMS, RRM2, S1PR3, SCLY, SLC1A3, SPC24, SPC25, ST8SIA4, TFDP1, TFP12, TK1, TMEM35, TTK, TWIST1, TYMS, TYK, and/or ZWINT, as compared to the expression levels of these genes in cells from the 2D6 cell line.

In yet another embodiment, cells from an established clonal cell line susceptible to BoNT/A intoxication exhibit at least a 1.5-fold increase in gene expression levels of one or more genes selected from AURKB, BIRC5, BRCA1, BRCA2, BRIP1, BUB1B, CD9, DLGAP3, DYNLT3, ENC1, FBLN1, FOXM1, Gβγ, GNAI1, GNG11, GNG12, GPSM2, GUCY1B3, HGF, ITGA6, JNK, KCNJ5, KIF18A, KITLG, MMD, MSN, MYRIP, NEK2, NR3C1, NXPH1, OSBPL3, PKMYT1, PTPRM, RAD51, RAD51AP1, SLC7A2, SLC43A3, SMC6, SNAI2, SNCAIP, SSH2, STK17A, SYNPO2, TOP2A, TPTE, TRAF4, TSPAN, TSPAN4, UBE3, UBE3B, and/or VAV3, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from ALCAM, AURKA, CHEK, CIT, CSRP2, E2F, ECT2, EFNB2, ERK, ESPL1, GNAI, GPR161, HMMR, KIF4A, KIF14, KIF15, KIF22, KIF23, KIFC1, LPAR1, MK167, OIP5, PHLPP, PP1/PP2A, PPP1R3c, PRC1, PTTG1, RACGAP, RB, RGSS, SDC2, and/or TPX2, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ASCL1, HES6, MAPK, NMU, PEG3, PTPRK, PRLHR, PTPRK, SGOL2, SPARC, and/or ZNF217, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from ASF1B, BASP1, CHAF1A, NCAPH, PBK, PRAME, SMC2, UHRF1, and/or VRK1, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from C14ORF106, CEP72, KIF20A, PCNA, PEX13, PFCS, POLQ, SPAGS, SYTL4, TROAP, and/or WDR51A, as compared to the expression levels of these genes in cells from the 2D6 cell line. In a further embodiment, cells from an established clonal cell line susceptible to BoNT/A intoxication exhibit at least a 1.5-fold increase in gene expression levels of one or more genes selected from ANLN, ARHGAP24, ASPM, BUB1, CCDC99, CEP55, CKAP2, DRAM, E2F8, PLXNA2, SLC16A10, UBE2C, UBE2S, and/or WDHD1, as compared to the expression levels of these genes in cells from the 2D6 cell line.

In another embodiment, cells from an established clonal cell line susceptible to BoNT/A intoxication exhibit at least a 1.5-fold increase in gene expression levels of one or more genes selected from ARHGEF3, CTSL2, DIAPH3, FBP1, KIF2C, KIF11, PFKFB3, and/or PLK4, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from ARHGEF3, CTSL2, DIAPH3, FBP1, KIF2C, KIF11, PFKFB3, and/or PLK4, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from FNDCS, HSPC159, MAB21L2, SLITRKS, SYN2, and/or ZNF367, as compared to the expression levels of these genes in cells from the 2D6 cell line. In a further another embodiment, cells from an established clonal cell line susceptible to BoNT/A intoxication exhibit at least a 1.5-fold increase in gene expression levels of one or more genes selected from EXO1, KCTD12, MYO6, PHEBL1, SHCBP1, TPBG, and/or TUBB6, as compared to the expression levels of these genes in cells from the 2D6 cell line. In yet another embodiment, cells from an established clonal cell line susceptible to BoNT/A intoxication exhibit at least a 1.5-fold increase in gene expression levels of one or more genes selected from BTG3, GABRAS, TR1P10, and/or ZNF521, as compared to the expression levels of these genes in cells from the 2D6 cell line. In still another embodiment, cells from an established clonal cell line susceptible to BoNT/A intoxication exhibit at least a 1.5-fold increase in gene expression levels of one or more genes selected from BNC2, DPYD, EMILIN2, PPILS, and/or TACC3, as compared to the expression levels of these genes in cells from the 2D6 cell line.

In another embodiment, cells from an established clonal cell line susceptible to BoNT/A intoxication exhibit at least a 1.5-fold difference in gene expression levels of one or more genes listed in Tables 14 or 16 as compared to the expression levels levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOKS, DPYD, DYNLT3, EMILIN2, ETV1, FAM101B, FBLN1, FGFR2, FNDCS, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3c, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, BASP1, BYES, C11ORF75, CDCA7L, CNTN1, CUGBP2, DOKS, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the 2D6 cell line. In yet another aspect of this embodiment, cells from an established clonal cell line susceptible to BoNT/A intoxication exhibit at least a 1.5-fold increase in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the 2D6 cell line.

In yet another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3c, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOKS, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from ADAMTS9, ASCL1, DOKS, GNB4, GNG11, MSN, PEG3, PLK2, SPARC, TFPI2, and/or TPTE, as compared to the expression levels of these genes in cells from the 2D6 cell line.

In still another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDCS, GTSE1, MAOA, MINA, MYO6, MYRIP, PLK2, PRLHR, PVRL3, RBPMS, SGOL2, SMC2, TFP12, TMEM178, and/or ZNF521, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from the 2D6 cell line. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from the 2D6 cell line.

In a further embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from the 2D6 cell line. In an aspect of this embodiment, cells from an established clonal cell line susceptible to BoNT/A intoxication exhibit at least a 1.5-fold increase in gene expression levels of one or more genes selected from MAB21L2 and/or PRSS12, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from a 2D6 cell line. In other aspects of this embodiment, cells from an established clonal cell line susceptible to BoNT/A intoxication exhibit a decrease in gene expression levels of one or more genes listed in Tables 6 or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a 2D6 cell line. In other aspects of this embodiment, cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 6 or 8 as compared to the expression levels of these genes in cells from the 2D6 cell line. In yet other aspects of this embodiment, cells from an established clonal cell line susceptible to BoNT/A intoxication exhibit an decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 6 or 8 as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from AATK, ABCA2, ABCCS, ABCC8, ABR, ABTB1, ACOT1, ACRBP, ACRV1, ACYP2, ADARB1, ADCY1, ADM, AFF1, AGAP4, AGPAT3, AGXT2L2, AHI1, AKAP9, AKIRIN1, AKT2, AMH, ANK2, ANK3, ANKHD1, ANKRD17, ANKRD50, ANKS1A, AQP1, ARF1, ARHGAP1, ARHGAP23, ARL17A, ASAM, ASPHD1, ATP2B3, ATP2B3, ATP6V0A1, ATP8B2, ATP9A, BACE1, BACH2, BLZF1, BPTF, BRUNOL4, BRUNOL5, BRWD1, BRWD2, BTBD18, BTN3A3, BZRAP1, C14ORF159, C15ORF24, C15ORF57, C16ORF52, C17ORF28, C1ORF21, C1ORF21, C1ORF50, C21ORF57, C21ORF59, C21ORF66, C2CD2, C2CD4A, C2ORF60, C2ORF68, C3ORF23, C4ORF41, C5ORF42, C6ORF154, C6ORF52, C7ORF28B, C7ORF54, C9ORF150, C9ORF68, CACNA1D, CALY, CAMK2B, CAMK2N2, CAP2, CAPN2, CARTPT, CBS, CCDC104, CCDC50, CCDC76, CD151, CD163L1, CD302, CDC42EP1, CDH10, CDH12, CDKN1C, CDKN2A, CDS1, CFCl, CHDS, CLCN3, CLDN12, CLIP4, CLMN, CNGA3, CNNM1, CNOT6L, COL6A1, COPA, CPNE8, CRKRS, CRTC1, CRYGS, CSTB, CTSK, CUL4A, CYGB, CYLD, CYP2E1, CYP3A5, CYTL1, D4S234E, DCLK1, DCTD, DEPDC6, DHX36, DIP2A, DIS3, DKFZP547G183, DNAJC22, DTNA, DTWD1, DUSP16, DUSP5, DVL3, EFNB3, EIF3C, ELFN2, ENOSF1, ERAP1, ERBB2, ERBB4, ERMAP, ETFDH, EXOSC6, FADS3, FAM120AOS, FAM150B, FAM165B, FAM184B, FAM30A, FAM46A, FAM66C, FAT4, FBRSL1, FBXW7, FGD5, FGF13, FLJ33630, FNBP1, FOXO6, FUBP3, GAL, GAL, GLT25D2, GNAS, GOLGA8A, GPR123, GPX7, GRIA2, GRIP2, GRM5, GUCY1A3, H2AFY, HCG 1776018, HCG 2022304, HCN4, HEATR1, HELQ, HERC4, HERPUD2, HEXDC, HGSNAT, H1ST1H2AC, H1ST1H2AE, HIST1H2BD, HIST1H2BK, HIST1H31, HIST2H2BE, HIVEP3, HNRNPM, HNRNPR, HPCAL1, HPCAL4, HSPD1, IER3, IL10RB, IL17B, INTU, JMY, KAT2B, KATNB1, KBTBD11, KCNMA1, KCNQ2, KCNS2, KCTD13, KHDC1, KIAA0125, KIAA1370, KIAA1598, KIF1A, KIF5C, KIF5C, KISS1R, KLHDC1, LCORL, LGALS3BP, LOC100130097, LOC100130360, LOC100130522, LOC100272228, LOC284408, LOC399491, LOC401320, LOC641298, LOC642852, LOC90110, LOC94431, LONRF2, LRP2BP, LRRC37A2, LRRFIP1, LTBP3, LYPLAL1, LYRM5, MAP3K5, MAP7, MAP9, MCM3AP, MCM3APAS, MCTP1, MEOX2, METTL3, MFSD4, MGAT4A, MLXIP, MRPL1, MRPS33, MST1, MUC20, MXD1, MZF1, NAMPT, NAP1L3, NBPF1, NBPF10, NCOA7, NCRNA00171, NCRNA00182, NDRG1, NDUFA4L2, NDUFV3, NEBL, NELF, NHEDC2, NHEG1, NIPAL2, NIPAL3, NLRX1, NOL3, NSMAF, NUDT19, NUP153, NUP54, OLFM3, OR7D2, OSBP, PABPC1L, PABPC4, PACRGL, PAM, PAPPA, PAQR6, PARP12, PCBD2, PCNXL2, PDCD6, PDE4C, PDE9A, PDGFRB, PDIA2, PGAP1, PHF17, PHKA1, PHKA2, PHLDA2, PIGH, PION, PKD1, PLA2G4C, PLCB4, PLEKHH1, PLP2, PLRG1, PLXNC1, PNCK, PNMA3, POFUT2, POGK, PPAPDC1A, PPAPDC1B, PPID, PPIE, PPM1K, PPP1R2, PPP2R2C, PPT1, PRKACB, PRPH, PSMB7, PTCD1, PTGER2, PTGS1, PTN, PTPRD, PTPRN, RAB11FIP3, RAB6B, RAF1, RGAG4, RGS11, RGS8, RHBDL1, RHOQ, RHOU, RLF, RNASET2, RNF13, RNF149, RNF165, RNF207, RNF41, RPL37, RSL1D1, RUNDC3A, S100A6, SCMH1, SCN2A, SERP1, SETX, SFRS18, SFXN3, SGK3, SH3BP5, SH3GL2, SH3YL1, SHC2, SHC4, SIGIRR, SIK1, SLC12A7, SLC1A2, SLC1A6, SLC22A17, SLC35F3, SLC38A5, SLCO1A2, SMAGP, SMAP2, SNCA, SOBP, SORCS1, SORL1, SPINT2, SPIRE2, SPOCK2, SRR, ST8SIA3, STAR, STEAP3, STOX2, STX3, SYNJ1, SYT13, SYT5, TAF10, TANC2, TCEA1, THBS2, THSD4, TIMP1, TM2D1, TMEM111, TMEM151A, TMEM184C, TMEM41B, TMEM43, TMEM5, TMEM59L, TMIE, TNFRSF25, TNFRSF25, TOX4, TP53BP1, TPM3, TRA2A, TRIM33, TRIM73, TRIMS, TRIT1, TSR1, TTC17, TTC3, TTC39C, TUSC3, TXLNB, U2AF1, UBE2D3, UBE2G2, UBN2, UBXN6, UCN, UGP2, UNC80, UNQ1887, USP36, USPL1, VN1R1, VPS13C, VPS53, VPS8, WDFY3, WDR27, WDR85, WSB1, YJEFN3, YLPM1, ZDHHC11, ZER1, ZG16B, ZNF275, ZNF440, ZNF573, ZNF641, ZNF662, ZNF785, and/or ZNF814, as compared to the expression levels of these genes in cells from the 2D6 cell line.

In an aspect of this embodiment, cells from an established clonal cell line susceptible to BoNT/A intoxication exhibit at least a 1.5-fold decrease in gene expression levels of one or more genes selected from ACOT1, ADARB1, ADM, ANK2, AQP1, ASAM, C2CD4A, C3ORF23, CACNA1D, CAMK2B, CAP2, CARTPT, CD163L1, CDC42EP1, CDH10, CDKN1C, CDKN2A, CFC1, CLMN, CPNE8, CYGB, CYP2E1, CYTL1, DNAJC22, DUSP5, ENOSF1, ERAP1, FGF13, FOXO6, GAL, GNAS, GPX7, GRIA2, GRM5, HCG 1776018, H1ST1H2AC, HIST1H2BD, HIST1H2BK, HIST2H2BE, IL17B, KIAA0125, KIAA1598, KISS1R, LRP2BP, MEOX2, NCRNA00182, NDRG1, NDUFA4L2, NIPAL2, NUDT19, PDE4C, PHKA2, PHLDA2, PTGER2, RGS11, S100A6, SCN2A, SHC4, SIGIRR, SLC1A2, SLC1A6, SLC35F3, SLC38A5, SORCS1, SYT13, SYT5, THBS2, TIMP1, and/or TMEM111, as compared to the expression levels of these genes in cells from the 2D6 cell line.

In another aspect of this embodiment, cells from an established clonal cell line susceptible to BoNT/A intoxication exhibit at least a 1.5-fold decrease in gene expression levels of one or more genes selected from ACOT1, ADARB1, ANK2, AQP1, C3ORF23, CAP2, CARTPT, CD163L1, CDC42EP1, CDKN2A, CFC1, CPNE8, CYGB, CYP2E1, CYTL1, FGF13, FOXO6, GNAS, GRIA2, GRM5, H1ST1H2AC, IL17B, KIAA0125, KIAA1598, KISS1R, MEOX2, NDRG1, NDUFA4L2, NIPAL2, PDE4C, PHKA2, RGS11, SCN2A, SLC1A2, SLC35F3, SLC38A5, SYT13, and/or THBS2, as compared to the expression levels of these genes in cells from the 2D6 cell line.

In yet another aspect of this embodiment, cells from an established clonal cell line susceptible to BoNT/A intoxication exhibit at least a 1.5-fold decrease in gene expression levels of one or more genes selected from AQP1, CAP2, CARTPT, CD163L1, CDC42EP1, CFC1, CPNE8, CYGB, CYP2E1, CYTL1, FGF13, GNAS, GRIA2, GRM5, H1ST1H2AC, IL17B, KIAA0125, MEOX2, NDUFA4L2, PDE4C, PHKA2, RGS11, SLC1A2, SLC35F3, SLC38A5, and/or SYT13, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ANXA2, AQP1, ARHGAP9, CDH10, CDKN2A, CHPT1, CNTN2, ERAP1, and/or RGS11, as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from ABCC8, AELIM3, CAP2, IL17B, MEF2A, NEEBL, PHC, S100A6, SLC1A6, SMAD1, SMADS, SMAD8, SYT13, and/or SYTL1, as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from CSTB, GPCR, GRIMS, KISSR, SCN2A, SLC1A2, and/or THBS2, as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ADARB1, ADM, PTPPH, and/or SLCO1A2, as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from CNGA3, HIST1H3E, and/or PTGS1, as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from HIST1H2BD and/or OSCAR as compared to the expression levels of these genes in cells from the 2D6 cell line. In a further embodiment, cells from an established clonal cell line susceptible to BoNT/A intoxication exhibit at least a 1.5-fold decrease in gene expression levels of one or more genes selected from CALY as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from COL5A1 and/or MICAL2 as compared to the expression levels of these genes in cells from the 2D6 cell line. In yet another embodiment, cells from an established clonal cell line susceptible to BoNT/A intoxication exhibit at least a 1.5-fold decrease in gene expression levels of one or more genes selected from OLFML2A and/or SIGIRR as compared to the expression levels of these genes in cells from the 2D6 cell line. In still another embodiment, cells from an established clonal cell line susceptible to BoNT/A intoxication exhibit at least a 1.5-fold decrease in gene expression levels of one or more genes selected from HPCAL1 and/or LPAR5 as compared to the expression levels of these genes in cells from the 2D6 cell line. In a further embodiment, cells from an established clonal cell line susceptible to BoNT/A intoxication exhibit at least a 1.5-fold decrease in gene expression levels of one or more genes selected from HTR1E and/or SORCS1 as compared to the expression levels of these genes in cells from the 2D6 cell line.

In another embodiment, cells from an established clonal cell line susceptible to BoNT/A intoxication exhibit at least a 1.5-fold decrease in gene expression levels of one or more genes selected from ANK2, CPNE8, CREBS, IL17B, KIAA0125, LOC100289109, LOC144571, NPAS4, SLC1A2, SORCS1, THBS2, and/or ZNF814, as compared to the expression levels of these genes in cells from the 2D6 cell line.

Aspects of the present disclosure comprise, in part, cells from an established clonal cell line susceptible to BoNT/A intoxication that exhibit at least a 1.5-fold difference in gene expression levels of one or more genes listed in Tables 9, 10, 11, or 12 as compared to the expression levels of these genes in cells from a parental SiMa cell line. In aspects of this embodiment, cells from an established clonal cell line susceptible to BoNT/A intoxication exhibit at least a 1.5-fold difference in gene expression levels of one or more genes listed in Tables 9, 10, 11, or 12 as compared to the expression levels of these genes in cells from the parental SiMa cell line DSMZ ACC 164. In other aspects of this embodiment, cells from an established clonal cell line susceptible to BoNT/A intoxication exhibit a difference in gene expression levels of one or more genes listed in Tables 9, 10, 11, or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the parental SiMa cell line DSMZ ACC 164. In yet other aspects of this embodiment, cells from an established clonal cell line susceptible to BoNT/A intoxication exhibit a difference in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 9, 10, 11, or 12 as compared to the expression levels of these genes in cells from the parental SiMa cell line DSMZ ACC 164. In still other aspects of this embodiment, cells from an established clonal cell line susceptible to BoNT/A intoxication exhibit a difference in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 9, 10, 11, or 12 as compared to the expression levels of these genes in cells from the parental SiMa cell line DSMZ ACC 164. The log ratio in Tables 9, 10, 11, or 12 represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

In an embodiment, cells from an established clonal cell line susceptible to BoNT/A intoxication exhibit at least a 1.5-fold difference in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDC5, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3c, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold difference in gene expression levels of one or more genes selected from ADAMTS9, ARHGAP24, ASCL1, BARD1, BASP1, BYES, C11ORF75, CDCA7L, CNTN1, CUGBP2, DOKS, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the parental SiMa cell line DSMZ ACC 164. In yet another aspect of this embodiment, cells from an established clonal cell line susceptible to BoNT/A intoxication exhibit at least a 1.5-fold difference in gene expression levels of one or more genes selected from ADAMTS9, ASCL1, BASP1, DOKS, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 9 or 11 as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of one or more genes listed in Tables 9 or 11 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 9 or 11 as compared to the expression levels of these genes in cells from the parental SiMa cell line DSMZ ACC 164. In yet other aspects of this embodiment, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 9 or 11 as compared to the expression levels of these genes in cells from the parental SiMa cell line DSMZ ACC 164.

In an embodiment, cells from an established clonal cell line susceptible to BoNT/A intoxication exhibit at least a 1.5-fold increase in gene expression levels of one or more genes selected from A2BP1, ADRM1, AFF4, AGAP4, ALCAM, ANAPC7, ANKRD13D, ANKRD28, APIS, ARF1, ARHGAP6, ARHGEF10, ARHGEF6, ARL17A, ASCL1, ASXL1, ASXL3, ATF71P, B3GALNT2, BASP1, BLCAP, BNC2, C10ORF58, C12ORF49, C12ORF51, C1ORF43, C20ORF117, C20ORF7, CADM1, CADPS, CALCB, CAPN1, CAPRIN2, CBLB, CBLN2, CBWD1, CCDC150, CCDC3, CD9, CDC25B, CFDP1, CHRNA7, CIAPIN1, CLASP2, CNOT7, CPVL, CRYBG3, CSE1L, CTTNBP2NL, CUGBP2, CXCR4, DACT1, DAZ1, DBH, DCAF8, DENR, DHX35, DKFZP434L187, DLEU2, DLL1, DLL3, DYNC2H1, EAF2, EFNAS, EIF3B, EIF3C, ELOVL7, EML1, EML4, ENC1, EVL, EXOSC6, EXPHS, EZH2, FAM178A, FAM181B, FAM19A4, FAM7A3, FLJ10213, FUBP3, FUS, FZDS, GAP43, GFM1, GFRA2, GGA2, GNAI1, GNAS, GNB4, GNG11, GOLGA4, GPR125, GRM8, GRP, GSPT1, GSS, GSTCD, GULP1, HAUS2, HEG1, HNRNPL, HNRNPM, HOXA7, HOXD4, ID2, IDH3B, ILIA, INSM1, IREB2, ITGA6, ITGBS, KCTD12, KDELC2, KHDRBS3, KIAA0907, KIAA1267, KIF16B, KLC1, KLHL13, LBH, LMO4, LOC100128844, LOC340109, LOC641298, LOC647190, LOC728052, LOC728153, LRPPRC, LRRFIP2, LSM3, LUM, MAB21L1, MAB21L2, MAN2A1, MAOA, MARS, MDN1, MED13L, MED22, MGC24103, MINA, MKLN1, MLEC, MMD, MORF4L2, MPZL1, MSH6, MS12, MSN, MTMR9, MYO1B, MYO6, N4BP2, NAAA, NDUFS8, NEDD9, NFIB, NKTR, NLN, NOS1, NR2C1, NUFIP2, NUPL1, OSBPL3, PAPD4, PCBP2, PCDH9, PCGFS, PCNX, PDLIMS, PDZRN3, PELI2, PFKFB3, PGP, PHF20, PLK2, PLXNA2, PLXNA4, PM20D2, POLE, POLQ, PPP2R2A, PPP2R3c, PRDX2, PSMA7, PSME4, PTGFRN, PTK2, PTPN1, PTPRE, PTPRG, QKI, RAB12, RAB35, RAB3GAP2, RAD23B, RAF1, RALGAPA1, RAN, RASEF, RBL1, RDH11, RELL1, REPS1, RGS5, RIMBP2, RNF182, RNF34, RNPEP, ROBO2, RPAIN, RPL35A, RPRD1A, S1PR3, SALL4, SBNO1, SCARB2, SDHA, SEMA6A, SEZ6L, SF1, SFRS8, SIM1, SIRT2, SKIL, SLC20A1, SLC44A5, SLC7A2, SLCO3A1, SLITRK5, SMAD4, SMARCC2, SMC3, SNRPB2, SNRPN, SNX5, SOX2, SPAG6, SPAG9, SPATS2L, SPON1, SR140, SSBP2, ST8SIA1, STMN3, STRA6, SYNCRIP, SYTL3, TAF15, TCF7L2, TDG, TERT, TFPI2, TGFBR1, TH1L, THOC4, TIMP3, TLE3, TMEM132C, TMEM178, TMEM181, TNRC6A, TPBG, TRA2A, TRIM29, TRIM36, TSHZ3, TXNRD1, U2AF1, UBE2O, UBE2V1, UBE2Z, UBXN2A, UCHL1, USP25, USP32, USP34, VPS29, XPO1, XPO7, ZFAND6, ZFHX4, ZFYVE16, ZGPAT, ZNF217, ZNF451, ZNF503, and/or ZNF664, as compared to the expression levels of these genes in cells from the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, ASCL1, BNC2, CBLN2, CCDC150, CCDC3, CHRNA7, CRYBG3, CUGBP2, CXCR4, DAZ1, DKFZP434L187, DLL1, EFNA5, ELOVL7, EML1, EML4, ENC1, EXPH5, FAM7A3, FZD5, GFRA2, GNAI1, GNB4, GNG11, GRP, ID2, ITGA6, KCTD12, LOC100128844, LOC340109, LOC728052, LUM, MAB21L1, MAB21L2, MAOA, MGC24103, MSN, NEDD9, NFIB, OSBPL3, PAPD4, PCDH9, PDZRN3, PLK2, POLQ, PTGFRN, PTPRE, PTPRG, RAD23B, RGS5, RNF182, ROBO2, SIM1, SLC20A1, SLC44A5, SLITRK5, SPAG6, SPAG9, SR140, TFPI2, TIMP3, TMEM132C, TPBG, TRIM29, TRIM36, and/or ZFAND6, as compared to the expression levels of these genes in cells from the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, CBLN2, CCDC3, CHRNA7, CRYBG3, CUGBP2, CXCR4, DAZ1, ELOVL7, EML1, EXPH5, FAM7A3, GNB4, GNG11, GRP, ITGA6, KCTD12, LOC340109, LUM, MAB21L1, MAB21L2, MGC24103, PCDH9, PLK2, POLQ, PTPRE, RGS5, RNF182, ROBO2, SIM1, SLC44A5, SLITRK5, SPAG6, TIMP3, and/or TMEM132C, as compared to the expression levels of these genes in cells from the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from CBLN2, CCDC3, CHRNA7, CRYBG3, CXCR4, DAZ1, EXPH5, FAM7A3, GNB4, GRP, KCTD12, LUM, MGC24103, PCDH9, PLK2, POLQ, PTPRE, RGS5, ROBO2, SIM1, SLITRK5, TIMP3, and/or TMEM132C, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 14 or 16 as compared to the expression levels of these genes in cells from the parental SiMa cell line DSMZ ACC 164. In aspects of this embodiment, cells from an established clonal cell line susceptible to BoNT/A intoxication exhibit at least a 1.5-fold increase in gene expression levels of one or more genes listed in Tables 14 or 16 as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of one or more genes listed in Tables 14 or 16 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from a parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 14 or 16 as compared to the expression levels of these genes in cells from the parental SiMa cell line DSMZ ACC 164. In yet other aspects of this embodiment, cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 14 or 16 as compared to the expression levels of these genes in cells from the parental SiMa cell line DSMZ ACC 164.

In aspects of this embodiment, cells from an established clonal cell line susceptible to BoNT/A intoxication exhibit at least a 1.5-fold increase in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOK5, DPYD, DYNLT3, EMILIN2, ETV1, FAM101B, FBLN1, FGFR2, FNDCS, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3c, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, BASP1, BYES, C11ORF75, CDCA7L, CNTN1, CUGBP2, DOKS, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from the parental SiMa cell line DSMZ ACC 164. In yet another aspect of this embodiment, cells from an established clonal cell line susceptible to BoNT/A intoxication exhibit at least a 1.5-fold increase in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from the parental SiMa cell line DSMZ ACC 164.

In yet another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3c, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOK5, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ASCL1, DOK5, GNB4, GNG11, MSN, PEG3, PLK2, SPARC, TFPI2, and/or TPTE, as compared to the expression levels of these genes in cells from the parental SiMa cell line DSMZ ACC 164.

In still another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDCS, GTSE1, MAOA, MINA, MYO6, MYRIP, PLK2, PRLHR, PVRL3, RBPMS, SGOL2, SMC2, TFP12, TMEM178, and/or ZNF521, as compared to the expression level of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from the parental SiMa cell line DSMZ ACC 164.

In a further embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from MAB21 L2 and/or PRSS12, as compared to the expression levels of these genes in cells from the parental SiMa cell line DSMZ ACC 164.

In another embodiment, cells from an established clonal cell line susceptible to BoNT/A intoxication exhibit at least a 1.5-fold decrease in gene expression levels of one or more genes listed in Tables 10 or 12 as compared to the expression levels of these genes in cells from a parental SiMa cell line. In aspects of this embodiment, cells from an established clonal cell line susceptible to BoNT/A intoxication exhibit at least a 1.5-fold decrease in gene expression levels of one or more genes listed in Tables 10 or 12 as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of one or more genes listed in Tables 10 or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from the parental SiMa cell line DSMZ ACC 164. In other aspects cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 10 or 12 as compared to the expression levels of these genes in cells from the parental SiMa cell line DSMZ ACC 164. In yet other aspects cells from an established clonal cell line susceptible to BoNT/A intoxication exhibit an decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 10 or 12 as compared to the expression levels of these genes in cells from the parental SiMa cell line DSMZ ACC 164.

In an embodiment, cells from an established clonal cell line susceptible to BoNT/A intoxication exhibit at least a 1.5-fold decrease in gene expression levels of one or more genes selected from 1-Mar, ABCG1, ABTB1, ACOT1, ACSL1, ACVR1, ACVR2A, ACYP2, ADAMTS1, ADAMTS3, ADAMTSL1, ADARB1, ADCY1, ADD2, ADO, AFF3, AKAP12, ALDH1A2, ALKBH1, ALLC, AMN1, ANKH, ANKRA2, ANKRD50, ANXAS, AP3B2, ARMC10, ARMCXS, ASAM, ASB13, ASPHD1, ATGS, ATL3, ATP2B3, ATP2C1, ATRNL1, B3GALTL, BACE1, BACE2, BBS10, BBS7, BCAP29, BCL2, BCORL1, BRUNOL4, BRUNOL6, BRWD1, BTN3A3, C1 OORF10, C10ORF104, C11ORF57, C11ORF70, C14ORF167, C15ORF39, C16ORF52, C17ORF69, C18ORF18, C1GALT1C1, C1ORF21, C1ORF25, C1ORF97, C1 RL, C21ORF57, C2CD2, C2CD4A, C2ORF67, C2ORF68, C3ORF23, C4ORF12, C4ORF39, C4ORF41, C5ORF42, C6ORF120, C9ORF150, CADM2, CAMK2D, CAMK2N1, CAMK2N2, CAP2, CAPN2, CARTPT, CCDC126, CCDC40, CCDC50, CCNY, CD248, CD302, CDC2L6, CDC37L1, CDC42EP3, CDH12, CDKN1C, CDKN2A, CDS1, CFC1, CHMP1B, CLCN3, CLDN12, CLMN, CLN8, CNGA3, CNNM1, CNOT6L, COL27A1, COL5A1, COL6A1, COL6A2, COL6A3, COX18, COX5B, CRYGD, CRYZL1, CTPS2, CTSC, CYB5R2, CYGB, CYLD, CYP2E1, CYP2U1, CYTL1, CYYR1, D4S234E, DAB1, DBT, DCAF10, DCLK1, DCTD, DDAH1, DHRSX, DISP1, DKFZP43410714, DKK1, DNAJC12, DNAJC24, DNASE1L1, DNER, DOPEY2, DRAM2, DSCAM, DSCR3, DTX3L, DUSP16, DUSP22, ECEL1, ECHDC3, EEF1D, EEF2K, EFEMP2, EFNB3, EMID1, ENOX2, ERAP1, ERBB2, ERBB4, ETFDH, ETS2, EYA1, FAM13C, FAM162B, FAM165B, FAM172A, FAM175A, FAM190A, FAM26F, FAM46A, FAM49A, FAM71E1, FAM76A, FAM85A, FBXL5, FBXW7, FCRLB, FGD5, FGF1, FGF13, FGF19, FGF3, FGF7, FIP1L1, FKTN, FLJ10038, FLJ35220, FLJ35390, FLJ37798, FLJ39051, FOXO6, FSTL1, FUCA2, GAL, GART, GAS5, GDPD5, GLCE, GLI2, GLIS1, GLIS3, GLT25D2, GNA14, GNAS, GPR123, GPX7, GRM5, GTF2H5, GUCY1A3, H2AFJ, HCG 1776018, HDAC4, HEBP2, HELQ, HERPUD2, HHLA3, H1ST1H2AC, HIST1H2BD, HIST1H2BK, HIST2H2BE, HMGCLL1, HNRNPR, HPCAL1, HPDL, HPS3, HSBP1L1, HSPA1A, HTATIP2, ICAM2, IFNAR1, IGFBP5, IGFBP7, IGSF5, IL10RB, IL13RA2, IL17D, IL20RA, IL7, IMMP2L, INSR, IRS1, ITGB1BP1, JMY, JRKL, KAT2B, KBTBD11, KCMF1, KCNMA1, KCNQ2, KCNQ5, KCTD18, KDM1A, KDSR, KHDC1, KIAA1109, KIAA1324, KIAA1598, KIAA1804, KIRREL3, KLHDC1, KRCC1, LGALS3, LGALS3BP, LIFR, LINGO1, LIPT1, LMAN2L, LMCD1, LOC100129195, LOC100129884, LOC100130522, LOC100130856, LOC100132167, LOC100216479, LOC100272217, LOC100287039, LOC151146, LOC153682, LOC220930, LOC254128, LOC255167, LOC283588, LOC285286, LOC285550, LOC285878, LOC286052, LOC339290, LOC401321, LOC645513, LOC80154, LOC90246, LOC93622, LOC94431, LPAR3, LPHN2, LRCH2, LRP2BP, LYRM1, LYRM5, MAGI2, MANSC1, MAP3K13, MAP3K5, MAP9, MAPKAP1, MBD5, MBLAC2, MBNL1, MCTP1, MED6, MEGF11, MEOX2, MET, METT5D1, MFSD4, MFSD6, MFSD9, MGAT4A, MORC3, MREG, MRPS18C, MRPS33, MST1, MTMR3, MTUS2, MXRA7, N4BP3, NAP1L3, NCAM1, NCAM2, NCOA7, NCRNA00081, NCRNA00117, NCRNA00171, NDUFA4L2, NDUFV3, NEAT1, NEBL, NEIL2, NETO1, NFATC4, NHEDC2, NIPAL3, NLRX1, NNAT, NOTCH4, NPW, NPY, NR1H3, NR2F1, NT5E, NUDT19, NUDT6, OGFRL1, OLFM3, OMA1, OPRM1, OPTN, P4HTM, PABPC4L, PABPC5, PAK1, PAM, PAPOLG, PAPPA, PBX1, PCDHB10, PCDHB16, PCNX, PCNXL2, PDCD2, PDE4DIP, PDGFRB, PEX12, PEX6, PHKA1, PHLDB3, PIBF1, PID1, PIGH, PIGP, PIK3CB, PIWIL2, PKNOX1, PKNOX2, PLA2G12A, PLCB1, PLEKHA2, PLEKHA3, PLIN2, PLRG1, POLR3GL, POU6F1, PPAPDC1A, PPDX, PPP1R14A, PPP2R5c, PPP3CA, PRAME, PRKACB, PRMT2, PRPH, PSD3, PSTK, PTGER2, PTGES, PTN, PTP4A3, PTPRD, PTPRN2, PTPRR, QPCT, RAB4A, RAB6B, RAC2, RAI2, RCAN1, RCC1, RDH13, RFPL1S, RG9MTD2, RGAG4, RHBDD1, RHBDF2, RHOU, RNF13, RNF41, RNLS, RPL31, RPL37, RPRD1A, RRN3, RSL1D1, RSPH3, SAP30, SAV1, SCG5, SCN5A, SERTAD4, SGMS1, SH3BGR, SH3GL2, SH3 KBP1, SH3YL1, SIAE, SIGIRR, SIK1, SIK3, SIX2, SLC12A7, SLC16A14, SLC22A17, SLC22A5, SLC25Al2, SLC25A4, SLC35F3, SLC6A15, SLIT1, SMARCA2, SMEK2, SNAP91, SNCA, SOCS5, SORCS2, SPATA17, SPATA7, SPIN3, SPINT1, SPINT2, SPOCK2, SPRED1, SSPN, ST8SIA3, STAC2, STAR, STEAP3, STOX2, STX12, STXBP5L, SUCLG2, SYNJ1, SYNPR, SYT13, TAF12, TAF1B, TBC1D12, TBC1D15, TCEAL2, TEX264, THAP2, TM2D1, TMCC1, TMEM182, TMEM184C, TMEM196, TMEM45B, TMEM5, TMEM59L, TMEM65, TMIE, TNC, TNFRSF10D, TNFSF4, TOX, TRAPPC9, TRHDE, TRIM61, TRIM69, TSPAN7, TSPAN9, TTC23, TTC39C, TUSC3, TXLNB, UBE2D3, UBE2W, UCN, UNC5A, UTP23, VPS37A, VSTM2A, WASF3, WDFY3, WDTC1, XPR1, XYLT1, ZBTB41, ZC3H12B, ZNF148, ZNF185, ZNF22, ZNF23, ZNF25, ZNF250, ZNF280D, ZNF285A, ZNF295, ZNF346, ZNF528, ZNF585A, ZNF610, ZNF641, ZNF662, ZNF677, and/or ZNF862, as compared to the expression levels of these genes in cells from the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from ACOT1, ADARB1, ASAM, BACE2, C11ORF70, C2CD4A, C3ORF23, CADM2, CAP2, CARTPT, CDKN1C, CFC1, CNGA3, COL5A1, CYGB, CYP2E1, CYTL1, DSCAM, ECEL1, ECHDC3, FAM26F, FAM49A, FGF1, FGF13, FGF19, FLJ39051, FUCA2, GAL, GPX7, GRM5, HCG 1776018, HHLA3, H1ST1H2AC, HIST1H2BD, HSPA1A, HTATIP2, ICAM2, IGFBP5, IGFBP7, IL13RA2, KCNMA1, KCNQ5, KIAA1598, KRCC1, LMCD1, LOC100216479, LOC254128, LOC339290, LPAR3, MEGF11, MEOX2, NCAM2, NDUFA4L2, NEAT1, NNAT, NPW, NPY, PABPC4L, PAPPA, PID1, PPAPDC1A, PRAME, PRKACB, PTGER2, PTN, PTP4A3, RAC2, SLC35F3, SYT13, TCEAL2, THAP2, TMIE, TNFRSF10D, TRHDE, TXLNB, and/or ZNF662, as compared to the expression levels of these genes in cells from the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from ACOT1, ASAM, BACE2, C11ORF70, C2CD4A, C3ORF23, CADM2, CAP2, CARTPT, CFC1, CNGA3, CYGB, CYP2E1, CYTL1, DSCAM, ECEL1, ECHDC3, FGF1, FGF13, FUCA2, GAL, GPX7, HSPA1A, HTATIP2, ICAM2, IGFBP5, IGFBP7, KIAA1598, KRCC1, LMCD1, LOC100216479, LOC254128, LOC339290, LPAR3, MEOX2, NDUFA4L2, NEAT1, NNAT, NPW, NPY, PAPPA, PID1, PPAPDC1A, PRAME, PTN, SLC35F3, SYT13, TCEAL2, TMIE, TNFRSF10D, TRHDE, and/or ZNF662, as compared to the expression levels of these genes in cells from the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from C11ORF70, CADM2, CAP2, CARTPT, CNGA3, CYGB, CYP2E1, CYTL1, DSCAM, FGF13, FUCA2, GAL, HSPA1A, HTATIP2, ICAM2, IGFBP5, IGFBP7, LMCD1, LOC100216479, MEOX2, NDUFA4L2, NEAT1, NNAT, NPW, PID1, PRAME, SLC35F3, SYT13, TCEAL2, TMIE, TNFRSF10D, and/or ZNF662, as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line, and at least a 1.5-fold increase in gene expression levels of one or more genes listed in in Tables 9 or 11 as compared to the expression levels of these genes in cells from a parental SiMa cell line. In aspects of this embodiment, cells from an established clonal cell line susceptible to BoNT/A intoxication exhibit at least a 1.5-fold increase in gene expression levels of one or more genes listed in Tables 5 or 7 as compared to the expression levels of these genes in cells from the 2D6 cell line, and at least a 1.5-fold increase in gene expression levels of one or more genes listed in in Tables 9 or 11 as compared to the expression levels of these genes in cells from the parental SiMa cell line DSMZ ACC 164. In other aspects of this embodiment, cells from an established clonal cell line susceptible to BoNT/A intoxication exhibit an increase in gene expression levels of one or more genes listed in Tables 5 or 7 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the 2D6 cell line, and exhibit an increase in gene expression levels of one or more genes listed in Tables 9 or 11 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 5 or 7 as compared to the expression levels of these genes in cells from the 2D6 cell line, and listed in Tables 9 or 11 as compared to the expression levels of these genes in cells from the parental SiMa cell line DSMZ ACC 164. In yet other aspects cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 5 or 7 as compared to the expression levels of these genes in cells from the 2D6 cell line, and listed in Tables 9 or 11 as compared to the expression levels of these genes in cells from the parental SiMa cell line DSMZ ACC 164.

In another embodiment, cells from an established clonal cell line susceptible to BoNT/A intoxication exhibit at least a 1.5-fold increase in gene expression levels of one or more genes selected from A2BP1, ALCAM, ANAPC7, ARF1, ARHGAP6, ARHGEF6, ARL17A, ASCL1, ASXL3, BASP1, BNC2, C10ORF58, C12ORF49, C1ORF43, C2ORF7, CBLB, CBWD1, CCDC3, CD9, CDC25B, CHRNA7, CPVL, CRYBG3, CSE1L, CUGBP2, CXCR4, DACT1, DAZ1, DBH, DHX35, DKFZP434L187, DLEU2, DLL3, EAF2, EFNA5, EIF3C, ELOVL7, EML1, ENC1, EXOSC6, EXPH5, EZH2, FAM181B, FAM19A4, FAM7A3, FUBP3, FZD5, GAP43, GFRA2, GNAI1, GNB4, GNG11, GPR125, GRP, GSS, ITGA6, ITGA6, ITGB5, KCTD12, KDELC2, KHDRBS3, KIF16B, KLHL13, LBH, LOC100128844, LOC340109, LOC641298, LOC728052, LUM, MAB21L1, MAN2A1, MAOA, MINA, MMD, MSN, MYO1B, MYO6, NAAA, NEDD9, NOS1, OSBPL3, PCGF5, PELI2, PFKFB3, PHF20, PLK2, PLS3, PLXNA2, PLXNA4, PM20D2, POLE, PSMA7, PTGFRN, PTPRE, PTPRG, RAB35, RAF1, RAN, RASEF, RBL1, RELL1, RGS5, RIMBP2, RNF182, RNF34, S1PR3, SALL4, SEMA6A, SEZ6L, SIM1, SLC44A5, SLC7A2, SLCO3A1, SLITRK5, SPAG6, SPATS2L, ST8SIA1, STMN3, STRA6, TCF7L2, TFPI2, TH1L, THOC4, TIMP3, TLE3, TMEM132C, TMEM178, TPBG, TRA2A, TRIM29, TRIM36, TSHZ3, TXNRD1, U2AF1, UBE2V1, VPS29, ZFHX4, ZGPAT, ZNF217, and/or ZNF503, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, ASCL1, BNC2, CCDC3, CHRNA7, CRYBG3, CUGBP2, CXCR4, DAZ1, EFNA5, ELOVL7, EML1, ENC1, EXPH5, FAM7A3, FZD5, GFRA2, GNAI1, GNB4, GNG11, GRP, ITGA6, KCTD12, LOC100128844, LOC340109, LOC728052, LUM, MAB21L1, MAB21L2, MAOA, MSN, NEDD9, OSBPL3, PLK2, PTGFRN, PTPRE, RGS5, RNF182, SIM1, SLC44A5, SLITRK5, SPAG6, TFPI2, TIMP3, TMEM132C, TPBG, TRIM29, and/or TRIM36, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ALCAM, ARHGAP6, ARHGEF6, CCDC3, CHRNA7, CRYBG3, CUGBP2, CXCR4, DAZ1, ELOVL7, EML1, EXPH5, FAM7A3, GNB4, GNG11, GRP, ITGA6, KCTD12, LOC340109, LUM, MAB21L1, MAB21L2, PLK2, PTPRE, RGS5, RNF182, SIM1, SLC44A5, SLITRK5, SPAG6, TIMP3, and/or TMEM132C, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from CCDC3, CHRNA7, CRYBG3, CXCR4, DAZ1, EXPH5, FAM7A3, GNB4, GRP, KCTD12, LUM, PLK2, PTPRE, RGS5, SIM1, SLITRK5, TIMP3, and/or TMEM132C, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold increase in gene expression levels of one or more genes selected from A2BP1, ALCAM, ARF1, ARL17A, ASCL1, BASP1, CD9, CUGBP2, EAF2, EIF3C, FAM181B, FUBP3, GNAI1, GNB4, GNG11, KDELC2, KHDRBS3, KLHL13, LOC641298, LOC728052, MAB21L2, MAOA, MINA, MSN, MYO6, PLK2, PLS3, RAF1, RELL1, RNF182, SEZ6L, SEZ6L, SIM1, SLC44A5, SLC7A2, SLCO3A1, SLITRK5, SPATS2L, TCF7L2, TFPI2, TMEM178, TRA2A, U2AF1, and/or ZNF217, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold increase in gene expression levels of one or more genes selected from A2BP1, ALCAM, ARF1, ASCL1, BASP1, CD9, CUGBP2, EIF3C, FUBP3, GNAI1, GNB4, GNG11, KDELC2, KHDRBS3, LOC641298, LOC728052, MAB21L2, MAOA, MINA, MSN, MYO6, PLK2, PLS3, RELL1, RNF182, SIM1, SLC44A5, SLC7A2, SLCO3A1, SLITRK5, TCF7L2, TFPI2, TMEM178, TRA2A, and/or ZNF217, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold increase in gene expression levels of one or more genes selected from ASCL1, CUGBP2, GNAI1, GNB4, GNG11, LOC728052, MAB21L2, MAOA, MSN, PLK2, RNF182, SIM1, SLC44A5, SLITRK5, and/or TFPI2, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold increase in gene expression levels of one or more genes selected from GNB4, GNG11, PLK2, RNF182, SIM1, SLC44A5, and/or SLITRK5, as compared to the expression levels of these genes in cells from both the 2D6 cell line and the parental SiMa cell line DSMZ ACC 164.

In still another aspect of this embodiment, cells from an established clonal cell line susceptible to BoNT/A intoxication exhibit at least a 1.5-fold increase in gene expression levels of one or more genes selected from GNB4, PLK2, SIM1, and/or SLITRK5, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from the 2D6 cell line, and at least a 1.5-fold decrease in gene expression levels of one or more genes listed in in Tables 10 or 12 as compared to the expression levels of these genes in cells from a parental SiMa cell line. In aspects of this embodiment, cells from an established clonal cell line susceptible to BoNT/A intoxication exhibit at least a 1.5-fold decrease in gene expression levels of one or more genes listed in Tables 6 or 8 as compared to the expression levels of these genes in cells from the 2D6 cell line, and at least a 1.5-fold decrease in gene expression levels of one or more genes listed in in Tables 10 or 12 as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of one or more genes listed in Tables 6 or 8 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the 2D6 cell line, and a decrease in gene expression levels of one or more genes listed in Tables 10 or 12 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least 7.0-fold, or at least 8.0-fold as compared to the expression levels of these genes in cells from the parental SiMa cell line DSMZ ACC 164. In other aspects of this embodiment, cells from an established clonal cell line susceptible to BoNT/A intoxication exhibit a decrease in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 6 or 8 as compared to the expression levels of these genes in cells from the 2D6 cell line, and listed in Tables 10 or 12 as compared to the expression levels of these genes in cells from the parental SiMa cell line DSMZ ACC 164. In yet other aspects cells from an established clonal cell line susceptible to BoNT/A intoxication exhibit a decrease in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 6 or 8 as compared to the expression levels of these genes in cells from the 2D6 cell line, and listed in Tables 10 or 12 as compared to the expression levels of these genes in cells from the parental SiMa cell line DSMZ ACC 164.

In an embodiment, cells from an established clonal cell line susceptible to BoNT/A intoxication exhibit at least a 1.5-fold decrease in gene expression levels of one or more genes selected from ABTB1, ACOT1, ACYP2, ADARB1, ADCY1, ANKRD50, ASAM, ASPHD1, ATP2B3, BACE1, BRUNOL4, BRWD1, BTN3A3, C16ORF52, C1ORF21, C21ORF57, C2CD2, C2CD4A, C3ORF23, C9ORF150, CAMK2N2, CAP2, CAPN2, CARTPT, CD302, CDH12, CDKN2A, CDS1, CFC1, CLCN3, CLDN12, CLMN, CNGA3, CNNM1, CNOT6L, COL6A1, CYGB, CYLD, CYP2E1, CYTL1, D4S234E, DCLK1, DCTD, DUSP16, EFNB3, ERAP1, ERBB2, ERBB4, ETFDH, FAM162B, FAM165B, FAM46A, FBXW7, FGD5, FGF13, FOXO6, FSTL1, GAL, GLT25D2, GNAS, GPR123, GPX7, GRM5, GUCY1A3, HCG 1776018, HELQ, HERPUD2, H1ST1H2AC, HIST1H2BD, HIST1H2BK, HIST2H2BE, HNRNPR, HPCAL1, IL10RB, JMY, KAT2B, KBTBD11, KCNMA1, KCNQ2, KHDC1, KIAA1598, KLHDC1, LGALS3BP, LIFR, LOCI 00130522, LOC94431, LRP2BP, LYRM5, MAP3K5, MAP9, MCTP1, MEOX2, MFSD4, MGAT4A, MRPS33, MST1, NAP1L3, NCOA7, NCRNA00171, NDUFA4L2, NDUFV3, NEBL, NHEDC2, NIPAL3, NLRX1, NUDT19, OLFM3, PAM, PAPPA, PCNXL2, PDGFRB, PHKA1, PIGH, PLRG1, PLRG1, PPAPDC1A, PRKACB, PRPH, PTGER2, PTN, PTPRD, RAB6B, RGAG4, RHOU, RNF13, RNF41, RSL1D1, SH3GL2, SH3YL1, SIGIRR, SIK1, SLC12A7, SLC22A17, SLC35F3, SNCA, SPINT2, SPOCK2, ST8SIA3, STAR, STEAP3, STOX2, SYNJ1, SYT13, TM2D1, TMEM184C, TMEM5, TMEM59L, TMIE, TTC39C, TUSC3, TXLNB, UCN, WDFY3, WDFY3, ZNF641, and/or ZNF662, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from ACOT1, ADARB1, ASAM, C2CD4A, C3ORF23, CAP2, CARTPT, CFC1, CNGA3, CYGB, CYP2E1, CYTL1, FGF13, GAL, GPX7, GRM5, HCG 1776018, H1ST1H2AC, HIST1H2BD, KCNMA1, KIAA1598, MEOX2, NDUFA4L2, PPAPDC1A, PRKACB, PTGER2, PTN, SLC35F3, SYT13, TMIE, TXLNB, and/or ZNF662, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from ACOT1, ASAM, C2CD4A, C3ORF23, CAP2, CARTPT, CFC1, CNGA3, CYGB, CYP2E1, CYTL1, FGF13, GAL, GPX7, KIAA1598, MEOX2, NDUFA4L2, PPAPDC1A, PTN, SLC35F3, SYT13, TMIE, and/or ZNF662, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from CAP2, CARTPT, CNGA3, CYGB, CYP2E1, CYTL1, FGF13, GAL, MEOX2, NDUFA4L2, SLC35F3, SYT13, TMIE, and/or ZNF662, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold decrease in gene expression levels of one or more genes selected from CAP2, CDKN2A, CNGA3, FAM162B, FGF13, FOXO6, FSTL1, KCNMA1, KHDC1, LIFR, MCTP1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In an aspect of this embodiment, cells from an established clonal cell line susceptible to BoNT/A intoxication exhibit at least a 1.5-fold decrease in gene expression levels of one or more genes selected from CAP2, CDKN2A, CNGA3, FGF13, FOXO6, FSTL1, KCNMA1, KHDC1, MCTP1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In another aspect of this embodiment, cells from an established clonal cell line susceptible to BoNT/A intoxication exhibit at least a 1.5-fold decrease in gene expression levels of one or more genes selected from CNGA3, FGF13, KCNMA1, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In yet another aspect of this embodiment, cells from an established clonal cell line susceptible to BoNT/A intoxication exhibit at least a 1.5-fold decrease in gene expression levels of one or more genes selected from CNGA3, FGF13, MEOX2, PPAPDC1A, PTN, SYT13, TMIE, and/or ZNF662, as compared to the expression levels of these genes in cells from both the 2D6 cell line and the parental SiMa cell line DSMZ ACC 164.

In still another aspect of this embodiment, cells from an established clonal cell line susceptible to BoNT/A intoxication exhibit at least a 1.5-fold decrease in gene expression levels of one or more genes selected from CNGA3, FGF13, MEOX2, SYT13, TMIE, and/or ZNF662, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold difference in gene expression levels of one or more genes listed in Tables 14 or 16 as compared to the expression levels of these genes in cells from both the 2D6 cell line and the parental SiMa cell line DSMZ ACC 164. In aspects of this embodiment, cells from an established clonal cell line susceptible to BoNT/A intoxication exhibit at least a 1.5-fold difference in gene expression levels of one or more genes listed in Tables 14 or 16 as compared to the expression levels of these genes in cells from both the 2D6 cell line and the parental SiMa cell line DSMZ ACC 164. In other aspects of this embodiment, cells from an established clonal cell line susceptible to BoNT/A intoxication exhibit a difference in gene expression levels of one or more genes listed in Tables 14 or 16 of, e.g., at least a 1.5-fold, at least a 2.0-fold, at least a 2.5-fold, at least a 3.0-fold, at least a 3.5-fold, at least a 4.0-fold, at least a 4.5-fold, at least a 5.0-fold, at least a 5.5-fold, at least a 6.0-fold, at least a 7.0-fold, or at least a 8.0-fold as compared to the expression levels of these genes in cells from both the 2D6 cell line and the parental SiMa cell line DSMZ ACC 164. In other aspects of this embodiment, cells from an established clonal cell line susceptible to BoNT/A intoxication exhibit an increase in gene expression levels of, e.g., 2 or more genes, 3 or more genes, 4 or more genes, 5 or more genes, 6 or more genes, 7 or more genes, 8 or more genes, 9 or more genes, 10 or more genes, 20 or more genes, 30 or more genes, 40 or more genes, 50 or more genes, 60 or more genes, 70 or more genes, 80 or more genes, 90 or more genes, or 100 or more genes listed in Tables 14 or 16 as compared to the expression levels of these genes in cells from both the 2D6 cell line and the parental SiMa cell line DSMZ ACC 164. In yet other aspects cells from an established clonal cell line susceptible to BoNT/A intoxication exhibit an increase in gene expression levels of, e.g., about 5 genes to about 100 genes, about 10 genes to about 100 genes, about 15 genes to about 100 genes, about 20 genes to about 100 genes, about 25 genes to about 100 genes, about 5 genes to about 75 genes, about 10 genes to about 75 genes, about 15 genes to about 75 genes, about 20 genes to about 75 genes, about 25 genes to about 75 genes, about 5 genes to about 50 genes, about 10 genes to about 50 genes, about 15 genes to about 50 genes, about 20 genes to about 50 genes, or about 25 genes to about 50 genes listed in Tables 14 or 16 as compared to the expression levels of these genes in cells from both the 2D6 cell line and the parental SiMa cell line DSMZ ACC 164.

In an embodiment, cells from an established clonal cell line susceptible to BoNT/A intoxication exhibit at least a 1.5-fold difference in gene expression levels of one or more genes selected from ACOT9, ADAMTS9, ARHGAP24, ARHGEF3, ASCL1, BARD1, BASP1, C3ORF70, C11ORF75, CCDC109B, CD9, CDCA7L, CDK2, CENPL, CLSTN2, CNTN1, CSRP2, CTSL2, CUGBP2, DEPDC1, DIAPH3, DOKS, DPYD, DYNLT3, EMILIN2, ETV1, FAM101B, FBLN1, FGFR2, FNDCS, GNAI1, GNB4, GNG11, GNG12, GPR177, GTSE1, HGF, KITLG, LPAR1, MAB21L2, MAOA, MCM10, MINA, MSN, MYO6, MYRIP, PAG1, PEG3, PLK2, POLA2, PPP1R3c, PRLHR, PRSS12, PTGR1, PTPRK, PVRL3, RAB32, RBPMS, SDC2, SGOL2, SLC43A3, SLC7A2, SMC2, SMC6, SPARC, SPC25, ST8SIA4, TCF7L1, TFPI2, TMEM35, TMEM178, TNFAIP8, TPTE, TRIP10, TWIST1, and/or ZNF521, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold difference in gene expression levels of one or more genes selected from ADAMTS9, ARHGAP24, ASCL1, BARD1, BASP1, BYES, C11ORF75, CDCA7L, CNTN1, CUGBP2, DOKS, DPYD, DYNLT3, FBLN1, FGFR2, GNAI1, GNB4, GNG11, GNG12, GTSE1, GTSF1, ITPRIP, KDELC2, LOC728052, LPAR1, MAB21L2, MAOA, MINA, MSN, PEG3, PLK2, PRLHR, PRSS12, PTPRK, RBPMS, RNF182, SGOL2, SLC43A3, SLC44A5, SLC7A2, SMC6, SPARC, TFPI2, TMEM178, and/or TPTE, as compared to the expression levels of these genes in cells from both the 2D6 cell line and the parental SiMa cell line DSMZ ACC 164. In yet another aspect of this embodiment, cells from an established clonal cell line susceptible to BoNT/A intoxication exhibit at least a 1.5-fold difference in gene expression levels of one or more genes selected from ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and/or TPTE, as compared to the expression levels of these genes in cells from both the 2D6 cell line and the parental SiMa cell line DSMZ ACC 164.

In another embodiment, cells from an established clonal cell line susceptible to BoNT/A intoxication exhibit at least a 1.5-fold increase in gene expression levels of one or more genes selected from ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3c, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and/or TWIST1, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from ADAMTS9, ARHGAP24, ASCL1, BARD1, DOKS, DYNLT3, FBLN1, FGFR2, GNAI1, GNB4, GNG11, GNG12, LPAR1, MSN, PEG3, PLK2, PTPRK, SLC43A3, SLC7A2, SMC6, SPARC, TFPI2, and/or TPTE, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from ADAMTS9, ASCL1, DOKS, GNB4, GNG11, MSN, PEG3, PLK2, SPARC, TFPI2, and/or TPTE, as compared to the expression levels of these genes in cells from both the 2D6 cell line and the parental SiMa cell line DSMZ ACC 164.

In yet another embodiment, cells from an established clonal cell line susceptible to BoNT/A intoxication exhibit at least a 1.5-fold increase in gene expression levels of one or more genes selected from ACOT9, BASP1, C11ORF75, CCDC109B, CDCA7L, CLSTN2, CNTN1, CUGBP2, DEPDC1, DPYD, FAM101B, FNDCS, GTSE1, MAOA, MINA, MYO6, MYRIP, PLK2, PRLHR, PVRL3, RBPMS, SGOL2, SMC2, TFP12, TMEM178, and/or ZNF521, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from BASP1, C11ORF75, CDCA7L, CNTN1, CUGBP2, DPYD, GTSE1, MAOA, MINA, PLK2, PRLHR, RBPMS, SGOL2, TFPI2, and/or TMEM178, as compared to the expression levels of these genes in cells from both the 2D6 cell line and the parental SiMa cell line DSMZ ACC 164. In another aspect of this embodiment, cells from an established clonal cell line susceptible to BoNT/A intoxication exhibit at least a 1.5-fold increase in gene expression levels of one or more genes selected from BASP1, DPYD, MAOA, MINA, PLK2, and/or TFPI2, as compared to the expression levels of these genes in cells from both the 2D6 cell line and the parental SiMa cell line DSMZ ACC 164.

In a still another embodiment, cells from an established clonal cell line susceptible to BoNT/A intoxication exhibit at least a 1.5-fold increase in gene expression levels of one or more genes selected from C3ORF70, MAB21L2, PRSS12, CENPL, GPR177, and/or PTGR1, as compared to the expression levels of these genes in cells from both the 2D6 cell line and the parental SiMa cell line DSMZ ACC 164. In an aspect of this embodiment, cells from an established clonal cell line susceptible to BoNT/A intoxication exhibit at least a 1.5-fold increase in gene expression levels of one or more genes selected from MAB21L2 and/or PRSS12, as compared to the expression levels of these genes in cells from both the 2D6 cell line and the parental SiMa cell line DSMZ ACC 164.

Aspects of the present disclosure comprise, in part, cells from an established clonal cell line susceptible to BoNT/A intoxication that exhibit an equivalent or lower $EC_{50}$ for BoNT/A activity relative to the $EC_{50}$ for BoNT/A activity of cells from a parental SiMa cell line. In an aspect of this embodiment, cells from an established clonal cell line susceptible to BoNT/A intoxication exhibit an equivalent or lower $EC_{50}$ for BoNT/A activity relative to the $EC_{50}$ for BoNT/A activity of cells from the parental SiMa cell line DSMZ ACC 164. In an aspect of this embodiment, cells from an established clonal cell line susceptible to BoNT/A intoxication exhibit an equivalent $EC_{50}$ for BoNT/A activity relative to the $EC_{50}$ for BoNT/A activity of cells from the parental SiMa cell line DSMZ ACC 164. In aspects of this embodiment, cells from an established clonal cell line susceptible to BoNT/A intoxication exhibit a lower $EC_{50}$ for BoNT/A activity of, e.g., at least 10%, at least 20%, at least 30%, at least 40%, at least 50%, at least 60%, at least 70%, at least 80%, at least 90%, or at least 100% relative to the $EC_{50}$ for BoNT/A activity of cells from the parental SiMa cell line DSMZ ACC 164. In other aspects of this embodiment, cells from an established clonal cell line susceptible to BoNT/A intoxication exhibit a lower $EC_{50}$ for BoNT/A activity of, e.g., at least 110%, at least 120%, at least 130%, at least 140%, at least 150%, at least 160%, at least 170%, at least 180%, at least 190%, or at least 200% relative to the $EC_{50}$ for BoNT/A activity of cells from the parental SiMa cell line DSMZ ACC 164. In yet other aspects of this embodiment, cells from an established clonal cell line susceptible to BoNT/A intoxication exhibit a lower $EC_{50}$ for BoNT/A activity of, e.g., at least 225%, at least 250%, at least 275%, at least 300%, at least 325%, at least 350%, at least 375%, at least 400%, at least 425%, at least 450%, at least 475%, or at least 500% relative to the $EC_{50}$ for BoNT/A activity of cells from the parental SiMa cell line DSMZ ACC 164. In still other aspects of this embodiment, cells from an established clonal cell line susceptible to BoNT/A intoxication exhibit an $EC_{50}$ for BoNT/A activity of, e.g., 10 pM or less, 9 pM or less, 8 pM or less, 7 pM or less, 6 pM or less, 5 pM or less, 4 pM or less, 3.0 pM or less, 2.9 pM or less, 2.8 pM or less, 2.7 pM or less, 2.6 pM or less, 2.5 pM or less, 2.4 pM or less, 2.3 pM or less, 2.2 pM or less, 2.1 pM or less, 2.0 pM or less, 1.9 pM or less, 1.8 pM or less, 1.7 pM or less, 1.6 pM or less, 1.5 pM or less, 1.4 pM or less, 1.3 pM or less, 1.2 pM or less, 1.1 pM or less, 1.0 pM or less, 0.9 pM or less, 0.8 pM or less, 0.7 pM or less, 0.6 pM or less, 0.5 pM or less, 0.4 pM or less, 0.3 pM or less, 0.2 pM or less, or 0.1 pM or less.

Aspects of the present disclosure comprise, in part, a BoNT/A. As used herein, the term "BoNT/A" is synonymous with "botulinum neurotoxin serotype A" or "botulinum neurotoxin type A" and refers to both a naturally-occurring BoNT/A or a non-naturally occurring BoNT/As thereof, and includes BoNT/A complex comprising the about 150 kDa BoNT/A neurotoxin and associated non-toxin associated proteins (NAPs), as well as the about 150 kDa BoNT/A neurotoxin alone. Non-limiting examples of BoNT/A complexes include, e.g., the 900-kDa BoNT/A complex, the 500-kDa BoNT/A complex, the 300-kDa BoNT/A complex. Non-limiting examples of the about 150 kDa BoNT/A neurotoxin include, e.g., SEQ ID NO: 1, SEQ ID NO: 2, SEQ ID NO: 3, SEQ ID NO: 4.

As used herein, the term "naturally occurring BoNT/A" refers to any BoNT/A produced by a naturally-occurring process, including, without limitation, BoNT/A isoforms produced from a post-translational modification, an alternatively-spliced transcript, or a spontaneous mutation, and BoNT/A subtypes, such as, e.g., a BoNT/A1 subtype, BoNT/A2 subtype, BoNT/A3 subtype, BoNT/A4 subtype, and BoNT/A5 subtype. A naturally occurring BoNT/A includes, without limitation, SEQ ID NO: 1, SEQ ID NO: 2, SEQ ID NO: 3, SEQ ID NO: 4, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 amino acids from SEQ ID NO: 1, SEQ ID NO: 2, SEQ ID NO: 3, or SEQ ID NO: 4. Commercially available pharmaceutical compositions of a naturally-occurring BoNT/A includes, without limitation, BOTOX® (Allergan, Inc., Irvine, Calif.), DYSPORT®/RELOXIN®, (Ipsen Ltd., Slough, England), PURTOX® (Mentor Corp., Santa Barbara, Calif.), XEOMIN® (Merz Pharmaceuticals, GmbH., Frankfurt, Germany), NEURONOX® (Medy-Tox, Inc., Ochang-myeon, South Korea), BTX-A. As used herein, the term "non-naturally occurring BoNT/A" refers to any BoNT/A whose structure was modified with the aid of human manipulation, including, without limitation, a BoNT/A with an altered amino acid sequence produced by genetic engineering using random mutagenesis or rational design and a BoNT/A produced by in vitro chemical synthesis. Non-limiting examples of non-naturally occurring BoNT/As are described in, e.g., Steward, L. E. et al., *Post-translational Modifications and Clostridial Neurotoxins*, U.S. Pat. No. 7,223,577; Dolly, J. O. et al., *Activatable Clostridial Toxins*, U.S. Pat. No. 7,419,676; Steward, L. E. et al., *Clostridial Neurotoxin Compositions and Modified Clostridial Neurotoxins*, US 2004/0220386; Steward, L. E. et al., *Modified Clostridial Toxins With Enhanced Targeting Capabilities For Endogenous Clostridial Toxin Receptor Systems*, U.S. Patent Publication No. 2008/0096248; Steward, L. E. et al., *Modified Clostridial Toxins With Altered Targeting Capabilities For Clostridial Toxin Target Cells*, U.S. Patent Publication No. 2008/0161543; Steward, L. E. et al., *Modified Clostridial Toxins With Enhanced Translocation Capabilities*

*and Altered Targeting Activity For Clostridial Toxin Target Cells*, U.S. Patent Publication No. 2008/0241881, each of which is hereby incorporated by reference in its entirety.

Thus in an embodiment, the BoNT/A activity being detected is from a naturally occurring BoNT/A. In aspects of this embodiment, the BoNT/A activity being detected is from a BoNT/A isoform or a BoNT/A subtype. In aspects of this embodiment, the BoNT/A activity being detected is from the BoNT/A of SEQ ID NO: 1, SEQ ID NO: 2, SEQ ID NO: 3, or SEQ ID NO: 4. In other aspects of this embodiment, the BoNT/A activity being detected is from a BoNT/A having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from BOTOX®, DYSPORT®/RELOXIN®, PURTOX®, XEOMIN®, NEURONOX®, or BTX-A.

In another embodiment, the BoNT/A activity being detected is from a non-naturally occurring BoNT/A. In other aspects of this embodiment, the BoNT/A activity being detected is from a non-naturally occurring BoNT/A variant having, e.g., at least 70%, at least 75%, at least 80%, at least 85%, at least 90%, or at least 95% amino acid identity with SEQ ID NO: 1, SEQ ID NO: 2, SEQ ID NO: 3, or SEQ ID NO: 4. In other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 1, SEQ ID NO: 2, SEQ ID NO: 3, or SEQ ID NO: 4. In yet other aspects of this embodiment, the BoNT/A activity being detected is from a non-naturally occurring BoNT/A variant having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 1, SEQ ID NO: 2, SEQ ID NO: 3, or SEQ ID NO: 4.

Aspects of the present disclosure comprise, in part, a SNAP-25. As used herein, the term "SNAP-25" refers to a naturally-occurring SNAP-25 or a non-naturally occurring SNAP-25 which is preferentially cleaved by a BoNT/A. As used herein, the term "preferentially cleaved" refers to that the cleavage rate of a BoNT/A substrate by a BoNT/A that is at least one order of magnitude higher than the cleavage rate of any other substrate by BoNT/A. In aspects of this embodiment, the cleavage rate of a BoNT/A substrate by a BoNT/A that is at least two orders of magnitude higher, at least three orders of magnitude higher, at least four orders of magnitude higher, or at least five orders of magnitude higher than the cleavage rate of any other substrate by BoNT/A.

As used herein, the term "naturally occurring SNAP-25" refers to any SNAP-25 produced by a naturally-occurring process, including, without limitation, SNAP-25 isoforms produced from a post-translational modification, an alternatively-spliced transcript, or a spontaneous mutation, and SNAP-25 subtypes. A naturally occurring SNAP-25 includes, without limitation, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

As used herein, the term "non-naturally occurring SNAP-25" refers to any SNAP-25 whose structure was modified with the aid of human manipulation, including, without limitation, a SNAP-25 produced by genetic engineering using random mutagenesis or rational design and a SNAP-25 produced by in vitro chemical synthesis. Non-limiting examples of non-naturally occurring SNAP-25s are described in, e.g., Steward, L. E. et al., *FRET Protease Assays for Clostridial Toxins*, U.S. Pat. No. 7,332,567; Fernandez-Salas et al., *Lipohilic Dye-based FRET Assays for Clostridial Toxin Activity*, U.S. Patent Publication 2008/0160561, each of which is hereby incorporated by reference in its entirety. A non-naturally occurring SNAP-25 may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Thus in an embodiment, a SNAP-25 is a naturally occurring SNAP-25. In aspects of this embodiment, the SNAP-25 is a SNAP-25 isoform or a SNAP-25 subtype. In aspects of this embodiment, the naturally occurring SNAP-25 is the naturally occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, the SNAP-25 is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, a SNAP-25 is a non-naturally occurring SNAP-25. In other aspects of this embodiment, the SNAP-25 is a non-naturally occurring SNAP-25 having, e.g., at least 70%, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, the SNAP-25 is a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

A SNAP-25 can be an endogenous SNAP-25 or an exogenous SNAP-25. As used herein, the term "endogenous SNAP-25" refers to a SNAP-25 naturally present in the cell because it is naturally encoded within the cell's genome, such that the cell inherently expresses the SNAP-25 without the need of an external source of SNAP-25 or an external source of genetic material encoding a SNAP-25. The expression of an endogenous SNAP-25 may be with or without environmental stimulation such as, e.g., cell differentiation. By definition, an endogenous SNAP-25 can only be a naturally-occurring SNAP-25 or variants thereof. For example, the following established cell lines express an endogenous SNAP-25: BE(2)-M17, Kelly, LA1-55n, N1E-115, N4TG3, N18, Neuro-2a, NG108-15, PC12, SH-SY5Y, SiMa, and SK-N-BE(2)-C.

As used herein, the term "exogenous SNAP-25" refers to a SNAP-25 expressed in a cell through the introduction of an external source of SNAP-25 or an external source of genetic material encoding a SNAP-25 by human manipulation. The expression of an exogenous SNAP-25 may be with or without environmental stimulation such as, e.g., cell differentiation. As a non-limiting example, cells from an established clonal cell line can express an exogenous SNAP-25 by transient or stably transfection of a SNAP-25 coding sequence. As another non-limiting example, cells from an established clonal cell line can express an exogenous SNAP-25 by protein transfection of a SNAP-25. An exogenous SNAP-25 can be a naturally-occurring SNAP-25 or variants thereof, or a non-naturally occurring SNAP-25 or variants thereof.

Thus in an embodiment, cells from an established clonal cell line express an endogenous SNAP-25. In aspects of this embodiment, the endogenous SNAP-25 expressed by cells from an established clonal cell line is a naturally-occurring SNAP-25. In other aspects of this embodiment, the endogenous SNAP-25 expressed by cells from an established clonal cell line is SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, the endogenous SNAP-25 expressed by cells from an established clonal cell line is a naturally occurring SNAP-25, such as, e.g., a SNAP-25 isoform or a SNAP-25 subtype. In other aspects of this embodiment, the endogenous SNAP-25 expressed by cells from an established clonal cell line is a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another embodiment, cells from an established clonal cell line are transiently or stably engineered to express an exogenous SNAP-25. In an aspect of this embodiment, cells from an established clonal cell line are transiently or stably engineered to express a naturally-occurring SNAP-25. In other aspects of this embodiment, cells from an established clonal cell line are transiently or stably engineered to express the naturally-occurring SNAP-25 of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established clonal cell line are transiently or stably engineered to express a naturally occurring SNAP-25, such as, e.g., a SNAP-25 isoform or a SNAP-25 subtype. In still other aspects of this embodiment, cells from an established clonal cell line are transiently or stably engineered to express a naturally occurring SNAP-25 having, e.g., at least 70% amino acid identity, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

In another aspect of the embodiment, cells from an established clonal cell line are transiently or stably engineered to express a non-naturally occurring SNAP-25. In other aspects of this embodiment, cells from an established clonal cell line are transiently or stably engineered to express a non-naturally occurring SNAP-25 having, e.g., at least 70%, at least 75%, at least 80%, at least 85%, at least 90%, or at least 95% amino acid identity with SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In other aspects of this embodiment, cells from an established clonal cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24. In yet other aspects of this embodiment, cells from an established clonal cell line are transiently or stably engineered to express a non-naturally occurring SNAP-25 having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, or SEQ ID NO: 24.

Assays that detect the cleavage of a BoNT/A substrate after exposure to a BoNT/A can be used to assess whether a cell is expressing an endogenous or an exogenous SNAP-25. In these assays, generation of a SNAP-25 cleavage-product would be detected in cells expressing a SNAP-25 after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for SNAP-25 cleavage can be useful in identifying cells expressing an endogenous or an exogenous SNAP-25.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, α-SNAP-25 mouse monoclonal antibody SMI-81 (Sternberger Monoclonals Inc., Lutherville, Md.), mouse α-SNAP-25 monoclonal antibody Cl 71.1 (Synaptic Systems, Goettingen, Germany), α-SNAP-25 mouse monoclonal antibody Cl 71.2 (Synaptic Systems, Goettingen, Germany), α-SNAP-25 mouse monoclonal antibody SP12 (Abcam, Cambridge, Mass.), α-SNAP-25 rabbit polyclonal antiserum (Synaptic Systems, Goettingen, Germany), α-SNAP-25 rabbit polyclonal antiserum (Abcam, Cambridge, Mass.), and α-SNAP-25 rabbit polyclonal antiserum S9684 (Sigma, St Louis, Mo.). Aspects of the present disclosure comprise, in part, a BoNT/A receptor. As used herein, the term "BoNT/A receptor" refers to either a naturally-occurring BoNT/A receptor or a non-naturally occurring BoNT/A receptor which preferentially interacts with BoNT/A in a manner that elicits a BoNT/A intoxication response. As used herein, the term "preferentially interacts" refers to that the equilibrium dissociation constant (KD) of BoNT/A for a BoNT/A receptor is at least one order of magnitude less than that of BoNT/A for any other receptor. The equilibrium dissociation constant, a specific type of equilibrium constant that measures the propensity of an BoNT/A-BoNT/A receptor complex to separate (dissociate) reversibly into its component molecules, namely the BoNT/A and the BoNT/A receptor complex. The disassociation constant is defined as KD=[L][R]/[C], where [L] equals the molar concentration of BoNT/A, [R] is the molar concentration of a BoNT/A receptor, and [C] is the molar concentration of the BoNT/A-BoNT/A receptor complex, and where all concentrations are of such components when the system is at equilibrium. The smaller the dissociation constant, the more tightly bound the BoNT/A is to its receptor, or the higher the binding affinity between BoNT/A and BoNT/A receptor. In aspects of this embodiment, the disassociation constant of BoNT/A for a BoNT/A receptor is at least two orders of magnitude less, at least three orders of magnitude less, at least four orders of magnitude less, or at least five orders of magnitude less than that of BoNT/A for any other receptor. In other aspects of this embodiment, the binding affinity of a BoNT/A that preferentially interacts with a BoNT/A receptor can have an equilibrium disassociation constant of, e.g., of 500 nM or less, 400 nM or less, 300 nM or less, 200 nM, or less 100 nM or less. In other aspects of this embodiment, the binding affinity of a BoNT/A that preferentially interacts with a BoNT/A receptor can have an equilibrium disassociation constant of, e.g., of 90 nM or less, 80 nM or less, 70 nM or less, 60 nM or less, 50 nM or less, 40 nM or less, 30 nM or less, 20 nM, or less 10 nM or less. As used herein, the term "elicits a BoNT/A intoxication response" refers to the ability of a BoNT/A receptor to interact with a BoNT/A to form a neurotoxin/receptor complex and the subsequent internalization of that complex into the cell cytoplasm.

As used herein, the term "naturally occurring BoNT/A receptor" refers to any BoNT/A receptor produced by a naturally-occurring process, including, without limitation, BoNT/A receptor isoforms produced from a post-translational modification, an alternatively-spliced transcript, or a spontaneous mutation, and BoNT/A receptor subtypes. A naturally occurring BoNT/A receptor includes, without limitation, a fibroblast growth factor receptor 2 (FGFR2), a fibroblast growth factor receptor 3 (FGFR3), a synaptic vesicle glycoprotein 2 (SV2), and a complex ganglioside like GT1b, such as those described in Ester Fernandez-Salas, et al., *Botulinum Toxin Screening Assays*, U.S. Patent Publication 2008/0003240; Ester Fernandez-Salas, et al., *Botulinum Toxin Screening Assays*, U.S. Patent Publication 2008/0182799; Min Dong et al., *SV2 is the Protein Receptor for Botulinum Neurotoxin A*, Science (2006); S. Mahrhold et al, The Synaptic Vesicle Protein 2C Mediates the Uptake of Botulinum Neurotoxin A into Phrenic Nerves, 580(8) FEBS Lett. 2011-2014 (2006), each of which is hereby incorporated by reference in its entirety. A naturally occurring FGFR2 includes, without limitation, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, and SEQ ID NO: 70. A naturally occurring FGFR3 includes, without limitation, SEQ ID NO: 25, SEQ ID NO: 26, and SEQ ID NO: 27, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, and SEQ ID NO: 27. A naturally occurring SV2 includes, without limitation, SEQ ID NO: 28, SEQ ID NO: 29, SEQ ID NO: 30, and SEQ ID NO: 31, or one that substitutes, deletes or adds, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 28, SEQ ID NO: 29, SEQ ID NO: 30, and SEQ ID NO: 31.

As used herein, the term "non-naturally occurring BoNT/A receptor variant" refers to any BoNT/A receptor produced with the aid of human manipulation or design, including, without limitation, a BoNT/A receptor produced by genetic engineering using random mutagenesis or rational design and a BoNT/A receptor produced by chemical synthesis. Non-limiting examples of non-naturally occurring BoNT/A variants include, e.g., conservative BoNT/A receptor variants, non-conservative BoNT/A receptor variants, BoNT/A receptor chimeric variants and active BoNT/A receptor fragments. As used herein, the term "non-naturally occurring BoNT/A receptor" refers to any BoNT/A receptor whose structure was modified with the aid of human manipulation, including, without limitation, a BoNT/A receptor produced by genetic engineering using random mutagenesis or rational design and a BoNT/A receptor produced by in vitro chemical synthesis. Non-limiting examples of non-naturally occurring BoNT/A receptors are described in, e.g., Ester Fernandez-Salas, et al., *Botulinum Toxin Screening Assays*, U.S. Patent Publication 2008/0003240; Ester Fernandez-Salas, et al., *Botulinum Toxin Screening Assays*, U.S. Patent Publication 2008/0182799, each of which is hereby incorporated by reference in its entirety. A non-naturally occurring BoNT/A receptor may substitute, delete or add, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more amino acids from SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

Thus in an embodiment, a BoNT/A receptor is a naturally occurring BoNT/A receptor such as, e.g., FGFR2, FGFR3 or SV2. In aspects of this embodiment, the BoNT/A receptor is a BoNT/A receptor isoform or a BoNT/A receptor subtype. In aspects of this embodiment, the naturally occurring BoNT/A receptor is the naturally occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, a BoNT/A receptor is a non-naturally occurring BoNT/A receptor, such as, e.g., a genetically-engineered FGFR2, a genetically-engineered FGFR3, or a genetically-engineered SV2. In other aspects of this embodiment, the BoNT/A receptor is a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, the BoNT/A receptor is a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

A BoNT/A receptor can be an endogenous BoNT/A receptor or an exogenous BoNT/A receptor. As used herein, the term "endogenous BoNT/A receptor" refers to a BoNT/A receptor naturally present in the cell because it is naturally encoded within the cell's genome, such that the cell inherently expresses the BoNT/A receptor without the need an external source of BoNT/A receptor or an external source of genetic material encoding a BoNT/A receptor. Expression of an endogenous BoNT/A receptor may be with or without environmental stimulation such as e.g., cell differentiation or promoter activation. For example, the following established clonal cell lines express at least one endogenous BoNT/A receptor: BE(2)-M17, Kelly, LA1-55n, N1E-115, N4TG3, N18, Neuro-2a, NG108-15, PC12, SH-SY5Y, SiMa, and SK-N-BE(2)-C. An endogenous BoNT/A receptor can only be a naturally-occurring BoNT/A receptor or naturally-occurring variants thereof.

As used herein, the term "exogenous BoNT/A receptor" refers to a BoNT/A receptor expressed in a cell through the introduction of an external source of BoNT/A receptor or an external source of genetic material encoding a BoNT/A receptor by human manipulation. The expression of an exogenous BoNT/A receptor may be with or without environmental stimulation such as, e.g., cell differentiation or promoter activation. As a non-limiting example, cells from an established clonal cell line can express one or more exogenous BoNT/A receptors by transient or stably transfection of a polynucleotide molecule encoding a BoNT/A receptor, such as, e.g., a FGFR2, a FGFR3, or a SV2. As another non-limiting example, cells from an established clonal cell line can express one or more exogenous BoNT/A receptors by protein transfection of the BoNT/A receptors, such as, e.g., a FGFR2, a FGFR3, or a SV2. An exogenous BoNT/A receptor can be a naturally-occurring BoNT/A receptor or naturally occurring variants thereof, or non-naturally occurring BoNT/A receptor or non-naturally occurring variants thereof. Thus in an embodiment, cells from an established clonal cell line express an endogenous BoNT/A receptor. In aspects of this embodiment, the endogenous BoNT/A receptor expressed by cells from an established clonal cell line is a naturally-occurring BoNT/A receptor. In other aspects of this embodiment, the endogenous BoNT/A receptor expressed by cells from an established clonal cell line is SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet aspects of this embodiment, the endogenous BoNT/A receptor expressed by cells from an established clonal cell line is a naturally occurring BoNT/A receptor, such as, e.g., a BoNT/A receptor isoform or a BoNT/A receptor subtype. In other aspects of this embodiment, the endogenous BoNT/A receptor expressed by cells from an established clonal cell line is a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another embodiment, cells from an established clonal cell line are transiently or stably engineered to express an exogenous BoNT/A receptor. In an aspect of this embodiment, cells from an established clonal cell line are transiently or stably engineered to express a naturally-occurring BoNT/A receptor. In other aspects of this embodiment, cells from an established clonal cell line are transiently or stably engineered to express the naturally-occurring BoNT/A receptor of SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established clonal cell line are transiently or stably engineered to express a naturally occurring BoNT/A receptor, such as, e.g., a BoNT/A receptor isoform or a BoNT/A receptor subtype. In still other aspects of this embodiment, cells from an established clonal cell line are transiently or stably engineered to express a naturally occurring BoNT/A receptor having, e.g., at least 70% amino acid identity, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70.

In another aspect of the embodiment, cells from an established clonal cell line are transiently or stably engineered to express a non-naturally occurring BoNT/A receptor. In other aspects of this embodiment, cells from an established clonal cell line are transiently or stably engineered to express a non-naturally occurring BoNT/A receptor having, e.g., at least 70%, at least 75%, at least 80%, at least 85%, at least 90%, or at least 95% amino acid identity with SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In other aspects of this embodiment, cells from an established clonal cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more non-contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70. In yet other aspects of this embodiment, cells from an established clonal cell line are transiently or stably engineered to express a non-naturally occurring BoNT/A receptor having, e.g., 1 or more, 2 or more, 3 or more, 4 or more, 5 or more, 6 or more, 7 or more, 8 or more, 9 or more, 10 or more, 20 or more, 30 or more, 40 or more, 50 or more, or 100 or more contiguous amino acid substitutions, deletions, or additions relative to SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, or SEQ ID NO: 70

In another embodiment, cells from an established clonal cell line are transiently or stably engineered to express an exogenous FGFR2, an exogenous FGFR3, an exogenous SV2, or any combination thereof. In aspects of this embodiment, cells from an established clonal cell line are transiently or stably engineered to express a naturally-occurring FGFR2, a naturally-occurring FGFR3, a naturally-occurring SV2, or any combination thereof. In yet other aspects of this embodiment, cells from an established clonal cell line are transiently or stably engineered to express a non-naturally-occurring FGFR2, a non-naturally-occurring FGFR3, a non-naturally-occurring SV2, or any combination thereof. In still other aspects of this embodiment, cells from an established clonal cell line are transiently or stably engineered to express either a naturally-occurring FGFR2 or a non-naturally-occurring FGFR2, a naturally-occurring FGFR3 or a non-naturally-occurring FGFR3, a naturally-occurring SV2 or a non-naturally-occurring SV2, or any combination thereof.

Cells that express one or more endogenous or exogenous BoNT/A receptors can be identified by routine methods including direct and indirect assays for toxin uptake. Assays that determine BoNT/A binding or uptake properties can be used to assess whether a cell is expressing a BoNT/A receptor. Such assays include, without limitation, cross-linking assays using labeled BoNT/A, such as, e.g., [$^{125}$I] BoNT/A, see, e.g., Noriko Yokosawa et al., *Binding of Clostridium botulinum type C neurotoxin to different neuroblastoma cell lines*, 57(1) Infect. Immun. 272-277 (1989); Noriko Yokosawa et al., *Binding of botulinum type Cl, D and E neurotoxins to neuronal cell lines and synaptosomes*, 29(2) Toxicon 261-264 (1991); and Tei-ichi Nishiki et al., *Identification of protein receptor for Clostridium botulinum type B neurotoxin in rat brain synaptosomes*, 269(14) J. Biol. Chem. 10498-10503 (1994). Other non-limiting assays include immunocytochemical assays that detect BoNT/A binding using labeled or unlabeled antibodies, see, e.g., Atsushi Nishikawa et al., *The receptor and transporter for internalization of Clostridium botulinum type C progenitor toxin into HT-29 cells*, 319(2) Biochem. Biophys. Res. Commun. 327-333 (2004) and immunoprecipitation assays, see, e.g., Yukako Fujinaga et al., *Molecular characterization of binding subcomponents of Clostridium botulinum type C progenitor toxin for intestinal epithelial cells and erythrocytes*, 150(Pt 5) Microbiology 1529-1538 (2004), that detect bound toxin using labeled or unlabeled antibodies. Antibodies useful for these assays include, without limitation, antibodies selected against BoNT/A, antibodies selected against a BoNT/A receptor, such as, e.g., FGFR2, FGFR3, or SV2, and/or antibodies selected against a ganglioside, such as, e.g., GD1a, GD1b, GD3, GQ1b, or GT1b. If the antibody is labeled, the binding of the molecule can be detected by various means, including Western blot analysis, direct microscopic observation of the cellular location of the antibody, measurement of cell or substrate-bound antibody following a wash step, flow cytometry, electrophoresis or capillary electrophoresis, employing techniques well-known to those of skill in the art. If the antibody is unlabeled, one may employ a labeled secondary antibody for indirect detection of the bound molecule, and detection can proceed as for a labeled antibody. It is understood that these and similar assays that determine BoNT/A uptake properties or characteristics can be useful in identifying cells expressing endogenous or exogenous BoNT/A receptors.

Assays that monitor the release of a molecule after exposure to BoNT/A can also be used to assess whether a cell is expressing one or more endogenous or exogenous BoNT/A receptors. In these assays, inhibition of the molecule's release would occur in cells expressing a BoNT/A receptor after BoNT/A treatment. Well known assays include methods that measure inhibition of radio-labeled catecholamine release from neurons, such as, e.g., [3H] noradrenaline or [3H] dopamine release, see e.g., A Fassio et al., *Evidence for calcium-dependent vesicular transmitter release insensitive to tetanus toxin and botulinum toxin type F,* 90(3) Neuroscience 893-902 (1999); and Sara Stigliani et al., *The sensitivity of catecholamine release to botulinum toxin C1 and E suggests selective targeting of vesicles set into the readily releasable pool,* 85(2) J. Neurochem. 409-421 (2003), or measures catecholamine release using a fluorometric procedure, see, e.g., Anton de Paiva et al., *A role for the interchain disulfide or its participating thiols in the internalization of botulinum neurotoxin A revealed by a toxin derivative that binds to ecto-acceptors and inhibits transmitter release intracellularly,* 268(28) J. Biol. Chem. 20838-20844 (1993); Gary W. Lawrence et al., *Distinct exocytotic responses of intact and permeabilised chromaffin cells after cleavage of the 25-kDa synaptosomal-associated protein (SNAP-25) or synaptobrevin by botulinum toxin A or B,* 236(3) Eur. J. Biochem. 877-886 (1996); and Patrick Foran et al., *Botulinum neurotoxin C1 cleaves both syntaxin and SNAP-25 in intact and permeabilized chromaffin cells: correlation with its blockade of catecholamine release,* 35(8) Biochemistry 2630-2636 (1996). Other non-limiting examples include assays that measure inhibition of hormone release from endocrine cells, such as, e.g., anterior pituitary cells or ovarian cells. It is understood that these and similar assays for molecule release can be useful in identifying cells expressing endogenous or exogenous or BoNT/A receptors.

Assays that detect the cleavage of a BoNT/A substrate after exposure to a BoNT/A can also be used to assess whether a cell is expressing one or more endogenous or exogenous BoNT/A receptors. In these assays, generation of a BoNT/A substrate cleavage-product, or disappearance of the intact BoNT/A substrate, would be detected in cells expressing a BoNT/A receptor after BoNT/A treatment. Non-limiting examples of specific Western blot analysis, as well as well-characterized reagents, conditions and protocols are readily available from commercial vendors that include, without limitation, Amersham Biosciences, Piscataway, N.J.; Bio-Rad Laboratories, Hercules, Calif.; Pierce Biotechnology, Inc., Rockford, Ill.; Promega Corporation, Madison, Wis., and Stratagene, Inc., La Jolla, Calif. It is understood that these and similar assays for BoNT/A substrate cleavage can be useful in identifying cells expressing endogenous or exogenous BoNT/A receptors.

As non-limiting examples, Western blot analysis using an antibody that recognizes BoNT/A SNAP-25-cleaved product or both the cleaved and uncleaved forms of SNAP-25 can be used to assay for uptake of BoNT/A. Examples of α-SNAP-25 antibodies useful for these assays include, without limitation, SMI-81α-SNAP-25 mouse monoclonal antibody (Sternberger Monoclonals Inc., Lutherville, Md.), Cl 71.1 mouse α-SNAP-25 monoclonal antibody (Synaptic Systems, Goettingen, Germany), Cl 71.2 α-SNAP-25 mouse monoclonal antibody (Synaptic Systems, Goettingen, Germany), SP12 α-SNAP-25 mouse monoclonal antibody (Abcam, Cambridge, Mass.), α-SNAP-25 rabbit polyclonal antiserum (Synaptic Systems, Goettingen, Germany), α-SNAP-25 rabbit polyclonal antiserum S9684 (Sigma, St. Louis, Mo.), and α-SNAP-25 rabbit polyclonal antiserum (Abcam, Cambridge, Mass.).

Aspects of the present disclosure provide cells that through genetic manipulation or recombinant engineering are made to express an exogenous SNAP-25 and/or one or more exogenous BoNT/A receptors. Cells useful to express an exogenous SNAP-25 and/or one or more exogenous BoNT/A receptors through genetic manipulation or recombinant engineering include neuronal cells and non-neuronal cells that may or may not express an endogenous SNAP-25 and/or one or more endogenous BoNT/A receptors. It is further understood that such genetically manipulated or recombinantly engineered cells may express an exogenous SNAP-25 and one or more exogenous BoNT/A receptors under control of a constitutive, tissue-specific, cell-specific or inducible promoter element, enhancer element or both. It is understood that any cell is useful as long as the cell can be genetically manipulated or recombinantly engineered to expresses an exogenous SNAP-25 and/or one or more exogenous BoNT/A receptors and is capable of undergoing BoNT/A intoxication.

Methods useful for introducing into a cell an exogenous polynucleotide molecule encoding a component necessary for the cells to undergo the overall cellular mechanism whereby a BoNT/A proteolytically cleaves a SNAP-25 substrate, such as, e.g., a SNAP-25, a FGFR2, a FGFR3, or a SV2, include, without limitation, chemical-mediated delivery methods, such as, e.g., calcium phosphate-mediated, diethyl-aminoethyl (DEAE) dextran-mediated, lipid-mediated, polyethyleneimine (PEI)-mediated, polylysine-mediated and polybrene-mediated; physical-mediated delivery methods, such as, e.g., biolistic particle delivery, microinjection, protoplast fusion and electroporation; and viral-mediated delivery methods, such as, e.g., retroviral-mediated transfection, see e.g., Introducing Cloned Genes into Cultured Mammalian Cells, pp. 16.1-16.62 (Sambrook & Russell, eds., Molecular Cloning A Laboratory Manual, Vol. 3, 3$^{rd}$ ed. 2001); Alessia Colosimo et al., *Transfer and Expression of Foreign Genes in Mammalian Cells,* 29(2) Biotechniques 314-318, 320-322, 324 (2000); Philip Washbourne & A. Kimberley McAllister, Techniques for Gene Transfer into Neurons, 12(5) Curr. Opin. Neurobiol. 566-573 (2002); and Current Protocols in Molecular Biology, John Wiley and Sons, pp 9.16.4-9.16.11 (2000), each of which is incorporated by reference in its entirety. One skilled in the art understands that selection of a specific method to introduce a polynucleotide molecule into a cell will depend, in part, on whether the cell will transiently or stably contain a component necessary for the cells to undergo the overall cellular mechanism whereby a BoNT/A proteolytically cleaves a SNAP-25 substrate. Non-limiting examples of polynucleotide molecule encoding a component necessary for the cells to undergo the overall cellular mechanism whereby a BoNT/A proteolytically cleaves a SNAP-25 substrate as follows: FGFR2 polynucleotide molecule of SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, or SEQ ID NO: 138; FGFR3 polynucleotide molecule of SEQ ID NO: 139, SEQ ID NO: 140, or SEQ ID NO: 141; SV2 polynucleotide molecule of SEQ ID NO: 142, SEQ ID NO: 143, or SEQ ID NO: 144; and SNAP-25 polynucleotide molecule of SEQ ID NO: 145, or SEQ ID NO: 146.

Chemical-mediated delivery methods are well-known to a person of ordinary skill in the art and are described in, e.g., Martin Jordan & Florian Worm, *Transfection of Adherent and Suspended Cells by Calcium Phosphate,* 33(2) Methods 136-

143 (2004); Chun Zhang et al., *Polyethylenimine Strategies for Plasmid Delivery to Brain-Derived Cells,* 33(2) Methods 144-150 (2004), each of which is hereby incorporated by reference in its entirety. Such chemical-mediated delivery methods can be prepared by standard procedures and are commercially available, see, e.g., CellPhect Transfection Kit (Amersham Biosciences, Piscataway, N.J.); Mammalian Transfection Kit, Calcium phosphate and DEAE Dextran, (Stratagene, Inc., La Jolla, Calif.); Lipofectamine™ Transfection Reagent (Invitrogen, Inc., Carlsbad, Calif.); ExGen 500 Transfection kit (Fermentas, Inc., Hanover, Md.), and SuperFect and Effectene Transfection Kits (Qiagen, Inc., Valencia, Calif.).

Physical-mediated delivery methods are well-known to a person of ordinary skill in the art and are described in, e.g., Jeike E. Biewenga et al., *Plasmid-Mediated Gene Transfer in Neurons using the Biolistics Technique,* 71(1) J. Neurosci. Methods. 67-75 (1997); John O'Brien & Sarah C. R. Lummis, *Biolistic and Diolistic Transfection: Using the Gene Gun to Deliver DNA and Lipophilic Dyes into Mammalian Cells,* 33(2) Methods 121-125 (2004); M. Golzio et al., *In Vitro and In Vivo Electric Field-Mediated Permeabilization, Gene Transfer, and Expression,* 33(2) Methods 126-135 (2004); and Oliver Greschet al., *New Non-Viral Method for Gene Transfer into Primary Cells,* 33(2) Methods 151-163 (2004), each of which is hereby incorporated by reference in its entirety.

Viral-mediated delivery methods are well-known to a person of ordinary skill in the art and are described in, e.g., Chooi M. Lai et al., *Adenovirus and Adeno-Associated Virus Vectors,* 21(12) DNA Cell Biol. 895-913 (2002); Ilya Frolov et al., *Alphavirus-Based Expression Vectors: Strategies and Applications,* 93(21) Proc. Natl. Acad. Sci. U.S.A. 11371-11377 (1996); Roland Wolkowicz et al., Lentiviral Vectors for the Delivery of DNA into Mammalian Cells, 246 Methods Mol. Biol. 391-411 (2004); A. Huser & C. Hofmann, Baculovirus Vectors: *Novel Mammalian Cell Gene-Delivery Vehicles and Their Applications,* 3(1) Am. J. Pharmacogenomics 53-63 (2003); Tiziana Tonini et al., *Transient Production of Retroviral-and Lentiviral-Based Vectors for the Transduction of Mammalian Cells,* 285 Methods Mol. Biol. 141-148 (2004); Manfred Gossen & Hermann Bujard, *Tight Control of Gene Expression in Eukaryotic Cells by Tetracycline-Responsive Promoters,* U.S. Pat. No. 5,464,758; Hermann Bujard & Manfred Gossen, *Methods for Regulating Gene Expression,* U.S. Pat. No. 5,814,618; David S. Hogness, *Polynucleotides Encoding Insect Steroid Hormone Receptor Polypeptides and Cells Transformed With Same,* U.S. Pat. No. 5,514,578; David S. Hogness, *Polynucleotide Encoding Insect Ecdysone Receptor,* U.S. Pat. No. 6,245,531; Elisabetta Vegeto et al., *Progesterone Receptor Having C. Terminal Hormone Binding Domain Truncations,* U.S. Pat. No. 5,364,791; Elisabetta Vegeto et al., *Mutated Steroid Hormone Receptors, Methods for Their Use and Molecular Switch for Gene Therapy,* U.S. Pat. No. 5,874,534, each of which is hereby incorporated by reference in its entirety. Such viral-mediated delivery methods can be prepared by standard procedures and are commercially available, see, e.g., VIRAPOWER™ Adenoviral Expression System (Invitrogen, Inc., Carlsbad, Calif.) and VIRAPOWER™ Adenoviral Expression System Instruction Manual 25-0543 version A, Invitrogen, Inc., (Jul. 15, 2002); and ADEASY™ Adenoviral Vector System (Stratagene, Inc., La Jolla, Calif.) and ADEASY™ Adenoviral Vector System Instruction Manual 064004f, Stratagene, Inc. Furthermore, such viral delivery systems can be prepared by standard methods and are commercially available, see, e.g., BD™ Tet-Off and Tet-On Gene Expression Systems (BD Biosciences-Clonetech, Palo Alto, Calif.) and BD™ Tet-Off and Tet-On Gene Expression Systems User Manual, PT3001-1, BD Biosciences Clonetech, (Mar. 14, 2003), GeneSwitch™ System (Invitrogen, Inc., Carlsbad, Calif.) and GENESWITCH™ System A Mifepristone-Regulated Expression System for Mammalian Cells version D, 25-0313, Invitrogen, Inc., (Nov. 4, 2002); VIRAPOWER™ Lentiviral Expression System (Invitrogen, Inc., Carlsbad, Calif.) and VIRAPOWER™ Lentiviral Expression System Instruction Manual 25-0501 version E, Invitrogen, Inc., (Dec. 8, 2003); and COMPLETE CONTROL® Retroviral Inducible Mammalian Expression System (Stratagene, La Jolla, Calif.) and COMPLETE CONTROL® Retroviral Inducible Mammalian Expression System Instruction Manual, 064005e.

As mentioned above, an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification can be introduced into a cell. Any and all methods useful for introducing such an exogenous component with a delivery agent into a cell population can be useful with the proviso that this method introduce the exogenous component disclosed in the present specification in at least 50% of the cells within a given cell population. Thus, aspects of this embodiment can include a cell population in which, e.g., at least 50%, at least 60%, at least 70%, at least 80%, or at least 90% of the given cell population contains an exogenous component necessary for the cells to undergo the overall cellular mechanism whereby a BoNT/A proteolytically cleaves a SNAP-25 substrate, such as, e.g., a SNAP-25, a FGFR2, a FGFR3, or a SV2 disclosed in the present specification. As used herein, the term "delivery agent" refers to any molecule that enables or enhances internalization of a covalently-linked, non-covalently-linked or in any other manner associated with a polypeptide into a cell. Thus, the term "delivery agent" encompasses, without limitation, proteins, peptides, peptidomimetics, small molecules, polynucleotide molecules, liposomes, lipids, viruses, retroviruses and cells that, without limitation, transport a covalently or non-covalently linked molecule to the cell membrane, cell cytoplasm or nucleus. It further is understood that the term "delivery agent" encompasses molecules that are internalized by any mechanism, including delivery agents which function via receptor mediated endocytosis and those which are independent of receptor mediated endocytosis.

A delivery agent can also be an agent that enables or enhances cellular uptake of a covalently linked component, like FGFR2, FGFR3, SV2, or SNAP-25, such as, e.g., by chemical conjugation or by genetically produced fusion proteins. Methods that covalently link delivery agents and methods of using such agents are described in, e.g., Steven F. Dowdy, *Protein Transduction System and Methods of Use Thereof*, International Publication No WO 00/34308; Gérard Chassaing & Alain Prochiantz, Peptides which can be *Used as Vectors for the Intracellular Addressing of Active Molecules*, U.S. Pat. No. 6,080,724; Alan Frankel et al., *Fusion Protein Comprising TAT-derived Transport Moiert*, U.S. Pat. No. 5,674,980; Alan Frankel et al., *TAT-derived Transport Polypeptide Conjugates*, U.S. Pat. No. 5,747,641; Alan Frankel et al., *TAT-derived Transport Polypeptides and Fusion Proteins*, U.S. Pat. No. 5,804,604; Peter F. J. O'Hare et al., *Use of Transport Proteins*, U.S. Pat. No. 6,734,167; Yao-Zhong Lin & Jack J. Hawiger, *Method for Importing Biologically Active Molecules into Cells*, U.S. Pat. No. 5,807,746; Yao-Zhong Lin & Jack J. Hawiger, *Method for Importing Biologically Active Molecules into Cells*, U.S. Pat. No. 6,043, 339; Yao-Zhong Lin et al., *Sequence and Method for Genetic Engineering of Proteins with Cell Membrane Translocating Activity*, U.S. Pat. No. 6,248,558; Yao-Zhong Lin et al., *Sequence and Method for Genetic Engineering of Proteins with Cell Membrane Translocating Activity*, U.S. Pat. No. 6,432,680; Jack J. Hawiger et al., *Method for Importing Biologically Active Molecules into Cells*, U.S. Pat. No. 6,495,518; Yao-Zhong Lin et al., *Sequence and Method for Genetic Engineering of Proteins with Cell Membrane Translocating Activity*, U.S. Pat. No. 6,780,843; Jonathan B. Rothbard & Paul A Wender, *Method and Composition for Enhancing Transport Across Biological Membranes*, U.S. Pat. No. 6,306,993; Jonathan B. Rothbard & Paul A Wender, *Method and Composition for Enhancing Transport Across Biological Membranes*, U.S. Pat. No. 6,495,663; and Pamela B. Davis et al., *Fusion Proteins for Protein Delivery*, U.S. Pat. No. 6,287,817, each of which is incorporated by reference in its entirety.

A delivery agent can also be an agent that enables or enhances cellular uptake of a non-covalently associated component, like FGFR2, FGFR3, SV2c, or SNAP-25. Methods that function in the absence of covalent linkage and methods of using such agents are described in, e.g., Gilles Divita et al, *Peptide-Mediated Transfection Agents and Methods of Use*, U.S. Pat. No. 6,841,535; Philip L Feigner and Olivier Zelphati, *Intracellular Protein Delivery Compositions and Methods of Use*, U.S. Patent Publication No. 2003/0008813; and Michael Karas, *Intracellular Delivery of Small Molecules, Proteins and Nucleic Acids*, U.S. Patent Publication 2004/0209797, each of which is incorporated by reference in its entirety. Such peptide delivery agents can be prepared and used by standard methods and are commercially available, see, e.g. the CHARIOT™ Reagent (Active Motif, Carlsbad, Calif.); BIO-PORTER® Reagent (Gene Therapy Systems, Inc., San Diego, Calif.), BIO TREK™ Protein Delivery Reagent (Stratagene, La Jolla, Calif.), and PRO-JECT™ Protein Transfection Reagent (Pierce Biotechnology Inc., Rockford, Ill.).

Aspects of the present disclosure can also be described as follows:

1. An established clonal cell line comprising a cell susceptible to intoxication by BoNT/A.
2. The established clonal cell line of 1, wherein the clonal cell line is selected from a parental SiMa cell line.
3. The established clonal cell line of 1 or 2, wherein the cell is susceptible to BoNT/A intoxication by about 100 pM or less, by about 50 pM or less, by about 10 pM or less, by about 5 pM or less, by about 1 pM or less, by about 0.5 pM or less, or by about 0.1 pM or less of a BoNT/A.
4. The established clonal cell line of 1 or 2, wherein susceptibility to BoNT/A intoxication is measured before differentiation of the cell.
5. The established clonal cell line of 2, wherein in the undifferentiated state, the cell exhibits at least a 1.5-fold increase in gene expression of one or more genes relative to the expression of the one or more genes in a cell from a 2D6 cell line, the genes being taken from Table 5, or wherein the cell exhibits at least a 1.5-fold decrease in gene expression of one or more genes relative to the expression of the one or more genes in a cell from a 2D6 cell line, the genes being taken from Table 6.
6. The established clonal cell line of 2, wherein in the differentiated state, the cell exhibits at least a 1.5-fold increase in gene expression of one or more genes relative to the expression of the one or more genes in a cell from a 2D6 cell line, the genes being taken from Table 9, or wherein the cell exhibits at least a 1.5-fold decrease in gene expression of one or more genes relative to the expression of the one or more genes in a cell from a 2D6 cell line, the genes being taken from Table 10.
7. The established clonal cell line of 2, wherein in the undifferentiated state, the cell exhibits at least a 1.5-fold increase in gene expression of one or more genes relative to the expression of the one or more genes in a cell from a parental SiMa cell line, the genes being taken from Table 7, or wherein the cell exhibits at least a 1.5-fold decrease in gene expression of one or more genes relative to the expression of the one or more genes in a cell from a parental SiMa cell line, the genes being taken from Table 8.
8. The established clonal cell line of 2, wherein in the differentiated state, the cell exhibits at least a 1.5-fold increase in gene expression of one or more genes relative to the expression of the one or more genes in a cell from a parental SiMa cell line, the genes being taken from Table 11, or wherein the cell exhibits at least a 1.5-fold decrease in gene expression of one or more genes relative to the expression of the one or more genes in a cell from a parental SiMa cell line, the genes being taken from Table 12.
9. The established clonal cell line of 1 or 2, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.
10. The established clonal cell line of 1 or 2, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.
11. An established clonal cell line comprising a cell susceptible to intoxication by BoNT/A produced from a parental SiMa cell line, wherein the cell is susceptible to BoNT/A intoxication by about 100 pM or less, by about 50 pM or less, by about 10 pM or less, by about 5 pM or less, by about 1 pM or less, by about 0.5 pM or less, or by about 0.1 pM or less of a BoNT/A.
12. An established clonal cell line comprising cells susceptible to intoxication by BoNT/A, wherein the clonal cell line is selected from a parental SiMa cell line; and wherein the clonal cell line comprises cells susceptible to BoNT/A intoxication by about 100 pM or less of a BoNT/A.
13. The established clonal cell line of 12, wherein the parental SiMa cell line is the parental SiMa cell line DSMZ ACC 164.
14. The established clonal cell line of 12, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.
15. The established clonal cell line of 12, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

16. The established clonal cell line of 12, wherein susceptibility to BoNT/A intoxication is measured before differentiation of the cell or after differentiation of the cell.

17. An established clonal cell line comprising cells susceptible to intoxication by BoNT/A, wherein the cells exhibits at least a 1.5-fold difference in gene expression levels of three or more genes as compared to the expression levels of these genes in cells from the 2D6 cell line; wherein the gene expression levels are selected from the group ADAMTS9, ASCL1, BASP1, DOK5, DPYD, GNB4, GNG11, GTSF1, MAOA, MINA, MSN, PEG3, PLK2, PRSS12, RNF182, SLC44A5, SPARC, TFPI2, and TPTE; and wherein the clonal cell line comprises cells susceptible to BoNT/A intoxication by about 100 pM or less of a BoNT/A.

18. The established clonal cell line of 17, wherein the cells exhibits at least a 2.0-fold difference in gene expression levels of one or more genes as compared to the expression levels of these genes in cells from the 2D6 cell line, at least a 3.0-fold difference in gene expression levels of one or more genes as compared to the expression levels of these genes in cells from the 2D6 cell line, or at least a 4.0-fold difference in gene expression levels of one or more genes as compared to the expression levels of these genes in cells from the 2D6 cell line.

19. The established clonal cell line of 17, wherein the gene expression levels are measured before differentiation of the cell or after differentiation of the cell.

20. The established clonal cell line of 17, wherein the cell exhibits a sensitivity for BoNT/A activity that is 100 pM or less or about 25 pM for about 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passages, or 60 or more cell passage.

21. The established clonal cell line of 17, wherein the cell from an established clonal cell line exhibits a well defined signal to noise ratio for the upper asymptote for BoNT/A activity of at least 3:1, at least 4:1, at least 5:1, at least 6:1, at least 7:1, at least 8:1, at least 9:1, at least 10:1, over, e.g., 5 or more cell passages, 10 or more cell passages, 15 or more cell passages, 20 or more cell passages, 25 or more cell passages, 30 or more cell passages, 35 or more cell passages, 40 or more cell passages, 45 or more cell passages, 50 or more cell passage, 55 or more cell passage, or 60 or more cell passage.

EXAMPLES

Example I

Screening for Cell Lines Comprising Cells Susceptible to BoNT/A Intoxication

The following example illustrates how to identify clonal cells from a parental established cell line that are susceptible to BoNT/A intoxication or have neurotoxin uptake capacity.

1. Isolation of Clonal Cell Lines.

Companion patent application Ester Fernandez-Salas, et al., *Immuno-Based Botulinum Toxin Serotype A Activity Assays*, U.S. patent application Ser. No. 12/403,531 identified several established cell lines useful for conducting the disclosed immuno-based methods of detecting BoNT/A activity, including, e.g., LA1-55n (ECACC 06041203), N18 (ECACC 88112301), Neuro-2a (ATCC CCL-131), PC12 (ATCC CRL-1721), SH-SY5Y (ATCC CRL-2266), and SiMa (DSMZ ACC 164). During characterization of the SiMa cell line, it was discovered that the cells comprising this established cell line comprised at least five different cellular phenotypes. To determine whether any one of these phenotypically-distinct cell types was responsible for the susceptibility of this cell line to BoNT/A intoxication, two different limited-dilution screens were conducted to obtain single colony isolates for each phenotypically-distinct cell type.

In both screens, a suitable density of cells from a SiMa stock were grown in RPMI 1640 medium, having 10% fetal bovine serum, 1% Penicillin-Streptomycin, 2 mM L-Glutamine, contained in a T175 Collagen IV coated flask. After the second passage, the cells were trypsin-treated to produce a cell suspension and the cell concentration was determined. About $4.0 \times 10^6$ cells from this cell suspension was transferred into a 50 mL tube and the cells were dissociated into single cells by repeated vigorous expulsion through an 18.5 gauge needle using a 10 mL syringe. Cells from this disassociated single-cell suspension were then diluted to a concentration of $0.2 \times 10^6$ cells/mL by adding 15 mL of fresh growth medium, and 2.5 µL of this dilution was added to 50 mL of fresh growth medium to obtain a concentration of 10 cells/mL. From this final dilution stock, 100 µL of growth medium was added to each well of a 96-well Collagen IV coated plates (final average density of one cell/well), and the cells were grown undisturbed in a 37° C. incubator under 5% carbon dioxide for four weeks. A total of nineteen 96-well plates were setup for analysis. Plates were microscopically examined periodically to assess colony growth. After four weeks, each well was microscopically examined to identify growing colonies, and for each growing colony identified, 100 µL of fresh growth medium was added to each well and the cells were grown undisturbed in a 37° C. incubator under 5% carbon dioxide for two weeks. After two additional weeks of growth, the growing single colonies were trypsin-treated and transferred to a new 96-well plate for continued growth. Once colonies grew to about 1,000 cells, based on visual inspection, the cells were trypsin-treated and each cell-suspension was transferred into a new well from a 24-well Collagen IV-coated plate. The cells were grown in a 37° C. incubator under 5% carbon dioxide with fresh growth medium being replenished every 2-3 days, if needed. The cells were grown until the culture reached approximately 60% confluence or greater, at which point the cells were trypsin-treated and each cell-suspension was transferred into a 25 cm² Collagen IV-coated flask. The cells were grown in a 37° C. incubator under 5% carbon dioxide with fresh growth medium being replenished every 2-3 days, if needed. Once the cells in the flask reached 70-80% confluence, they were frozen and stored in liquid nitrogen until the clonal cell lines were tested to determine their susceptibility to BoNT/A intoxication. Of the 1,824 colony isolates initially setup from both screens, 130 clonal cell lines were selected based on viability and growth criteria and expanded for subsequent screening procedures.

2. Primary Screen for BoNT/a Intoxication Susceptibility of Cells from a Clonal Cell Line Using a BoNT/A Complex.

One way to determine whether cells from a clonal cell line were susceptible to BoNT/A intoxication was to conduct a primary screen using a CELLTITER-GLO® luminescent cell viability assay (Promega, Madison, Wis.) for normalizing the cell number in each well and an immuno-based method for determining BoNT/A activity as described in Ester Fernandez-Salas, et al., *Immuno-Based Botulinum Toxin Serotype A Activity Assays*, U.S. patent application Ser. No. 12/403,531, which is hereby incorporated by reference in its entirety. Two separate 96-well plates were set up, one for the BoNT/A activity assay and the other for the cell viability assay. To conduct the BoNT/A activity assay, a lysate was prepared from cells treated with BoNT/A by plating cells from each isolated clonal cell line into a well from a poly-D-lysine 96-well plate (BD Biosciences, Bedford, Mass.). The wells contained 0.1 mL of a serum-free medium comprising Minimum Essential Medium, 2 mM GlutaMAXT™ I with Earle's salts, 1×B27 supplement, 1×N2 supplement, 0.1 mM Non-Essential Amino Acids, 10 mM HEPES and 25 μg/mL GT1b (302-011-M005, Alexis Biochemicals, San Diego, Calif.). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing 1 nM of a BoNT/A complex. After a 24 hrs incubation, the cells were washed by aspirating the growth media and rinsing each well with 200 μL of 1×PBS. To harvest the cells, 1×PBS was aspirated, the cells lysed by adding 30 μl of Lysis Buffer comprising 20 mM Tris-HCl (pH 7,5), 150 mM NaCl, 1 mM EDTA, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

To prepare an α-SNAP-25 capture antibody solution, the α-SNAP-25 mouse monoclonal antibody contained in the ascites from hybridoma cell line 2E2A6 (Example VII) was purified using a standard Protein A purification protocol.

To prepare an α-SNAP-25 detection antibody solution, α-SNAP-25 rabbit polyclonal antibody S9684 (Sigma, St. Louis, Mo.) was conjugated to Ruthenium(II)-tris-bipyridine-(4-methysulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare an α-SNAP-25 solid phase support comprising an α-SNAP-25 capture antibody, approximately 5 μL of the appropriate α-SNAP-25 monoclonal antibody solution (20 μg/mL in 1×PBS) is added to each well of a 96-well MSD High Bind plate and the solution is allowed to air dry in a biological safety cabinet for 2-3 hours in order to liquid evaporate the solution. The capture antibody-bound wells were sealed and stored at 4° C. until needed.

To detect the presence of a cleaved SNAP-25 product by ECL sandwich ELISA, the wells from an α-SNAP-25 solid phase support were then blocked by adding 150 μL of Blocking Buffer comprising 2% Amersham Blocking Reagent (GE Life Sciences, Piscataway, N.J.) and 10% goat serum (VWR, West Chester, Pa.) at room temperature for 2 hours. The Blocking Buffer was aspirated, 25 μL of a lysate from cells treated with BoNT/A was added to each well and the plates were incubated at 4° C. for overnight. Plate wells were washed three times by aspirating the cell lysate and rinsing each well three times with 200 μL1×PBS, 0.1% TWEEN-20® (polyoxyethylene (20) sorbitan monolaureate). After washing, 25 μl of 5 μg/mL α-SNAP-25 detection antibody solution comprising 2% Amersham Blocking Reagent in 1×PBS, 0.1% TWEEN-20® (polyoxyethylene (20) sorbitan monolaureate) was added to each well, sealed, and incubated at room temperature for 1 hour with shaking. After α-SNAP-25 detection antibody incubation, the wells were washed three times with 200 μL×PBS, 0.1% TWEEN-20® (polyoxyethylene (20) sorbitan monolaureate). After washing 150 μL of 1×Read Buffer (Meso Scale Discovery, Gaithersburg, Md.) was added to each well and the plates were read using a SECTOR™ Imager 6000 Image Reader (Meso Scale Discovery, Gaithersburg, Md.). The raw data was collected using the ECL imager. To conduct the luminescent cell viability assay, cells from each isolated clonal cell line were plated and differentiated as described above. The media from the differentiated cells was aspirated from each well and replaced with 100 μl of the reagent mixture comprising the CELLTITER-GLO® substrate and CELLTITER-GLO® buffer according to the manufacturer's instructions. The plate was then protected from light and mixed for two minutes on an orbital shaker. The solution from the 96-well cell plate with clear bottom was transferred to a white luminometer plate and after 10 minutes incubation was read on the luminometer.

These results indicated that the cell viability readings ranged from 9,838 to 10,423,188 and BoNT/A activity signals ranged from 84 to 27,242 (Table 1). In addition, a ratio of BoNT/A activity over cell viability was calculated to normalize the data, although there was not always a 1:1 ratio of viability and activity. Seven clonal cell lines exhibited activity/viability ratios of about $0.2\times10^{-2}$ or greater: H1, A7, A11, F10, A9, A10, and C11 (Table 1). Nine clonal cell lines exhibited activity/viability ratios of about $0.125\times10^{-2}$ to about $0.150\times10^{-2}$: H3, H8, E11, H10, A6, C5, C12, D11, and B5 (Table 1). Two cell lines exhibited activity/viability ratios of about $0.100\times10^{-2}$: D7 and B10 (Table 1). Based on these activity/viability ratios in conjunction with the cell viability and BoNT/A activity signal measurements, these 18 clonal cell lines were selected for further testing by conducting a secondary screen using a BoNT/A activity assay in order to generate a dose-response curve to BoNT/A.

TABLE 1

Primary Screen for Clonal Cell Lines Susceptible to BoNT/A Intoxication Using Viability and Activity Signals

| Well | Cell Viability Reading (RLU) | BoNT/A Activity Signal (RLU) | Activity/ Viability Ratio |
|---|---|---|---|
| A1 | 2634417 | 2425 | $0.092\times10^{-2}$ |
| B1 | 731808 | 198 | $0.027\times10^{-2}$ |
| C1 | 4258160 | 1641 | $0.039\times10^{-2}$ |
| D1 | 6554606 | 4885 | $0.075\times10^{-2}$ |
| E1 | 2374483 | 897 | $0.038\times10^{-2}$ |
| F1 | 2801444 | 1842 | $0.066\times10^{-2}$ |
| G1 | 5094510 | 4579 | $0.090\times10^{-2}$ |

TABLE 1-continued Primary Screen for Clonal Cell Lines Susceptible to BoNT/A
Intoxication Using Viability and Activity Signals

| Well | Cell Viability Reading (RLU) | BoNT/A Activity Signal (RLU) | Activity/Viability Ratio |
|---|---|---|---|
| H1 | 3808699 | 10861 | $0.285 \times 10^{-2}$ |
| A2 | 9593106 | 7090 | $0.074 \times 10^{-2}$ |
| B2 | 5374966 | 5673 | $0.106 \times 10^{-2}$ |
| C2 | 4170158 | 2972 | $0.071 \times 10^{-2}$ |
| D2 | 31283 | 88 | $0.281 \times 10^{-2}$ |
| E2 | 5706902 | 3743 | $0.066 \times 10^{-2}$ |
| F2 | 4884798 | 4568 | $0.094 \times 10^{-2}$ |
| G2 | 3552045 | 2190 | $0.062 \times 10^{-2}$ |
| H2 | 3743690 | 3421 | $0.091 \times 10^{-2}$ |
| A3 | 15372 | 89 | $0.579 \times 10^{-2}$ |
| B3 | 5381672 | 1551 | $0.029 \times 10^{-2}$ |
| C3 | 4270534 | 3959 | $0.093 \times 10^{-2}$ |
| D3 | 48702 | 97 | $0.199 \times 10^{-2}$ |
| E3 | 4707349 | 2671 | $0.057 \times 10^{-2}$ |
| F3 | 3053132 | 1539 | $0.050 \times 10^{-2}$ |
| G3 | 5518292 | 4195 | $0.076 \times 10^{-2}$ |
| H3 | 4156632 | 6339 | $0.153 \times 10^{-2}$ |
| A4 | 19793 | 89 | $0.450 \times 10^{-2}$ |
| B4 | 6224766 | 4299 | $0.069 \times 10^{-2}$ |
| C4 | 3212859 | 3202 | $0.100 \times 10^{-2}$ |
| D4 | 4376180 | 2367 | $0.054 \times 10^{-2}$ |
| E4 | 3931793 | 3975 | $0.101 \times 10^{-2}$ |
| F4 | 1150134 | 526 | $0.046 \times 10^{-2}$ |
| G4 | 19023 | 94 | $0.494 \times 10^{-2}$ |
| H4 | 3368425 | 2645 | $0.079 \times 10^{-2}$ |
| A5 | 8231689 | 7809 | $0.095 \times 10^{-2}$ |
| B5 | 5332004 | 6545 | $0.123 \times 10^{-2}$ |
| C5 | 3869441 | 5042 | $0.130 \times 10^{-2}$ |
| D5 | 2554300 | 1161 | $0.045 \times 10^{-2}$ |
| E5 | 3781403 | 764 | $0.020 \times 10^{-2}$ |
| F5 | 4608801 | 3720 | $0.081 \times 10^{-2}$ |
| G5 | 7105403 | 7330 | $0.103 \times 10^{-2}$ |
| H5 | 5585607 | 7544 | $0.135 \times 10^{-2}$ |
| A6 | 7698708 | 10152 | $0.132 \times 10^{-2}$ |
| B6 | 4706560 | 3196 | $0.068 \times 10^{-2}$ |
| C6 | 5866251 | 6145 | $0.105 \times 10^{-2}$ |
| D6 | 2285787 | 768 | $0.034 \times 10^{-2}$ |
| E6 | 2471979 | 1038 | $0.042 \times 10^{-2}$ |
| F6 | 10958 | 91 | $0.830 \times 10^{-2}$ |
| G6 | 19590 | 91 | $0.465 \times 10^{-2}$ |
| H6 | 2057687 | 2564 | $0.125 \times 10^{-2}$ |
| A7 | 10132753 | 27242 | $0.269 \times 10^{-2}$ |
| B7 | 2977371 | 1642 | $0.055 \times 10^{-2}$ |
| C7 | 5746577 | 4878 | $0.085 \times 10^{-2}$ |
| D7 | 5861338 | 6044 | $0.103 \times 10^{-2}$ |
| E7 | 2819910 | 1399 | $0.050 \times 10^{-2}$ |
| F7 | 23523 | 84 | $0.357 \times 10^{-2}$ |
| G7 | 6232344 | 4031 | $0.065 \times 10^{-2}$ |
| H7 | 4916756 | 2759 | $0.056 \times 10^{-2}$ |
| A8 | 5945833 | 5611 | $0.094 \times 10^{-2}$ |
| B8 | 4591002 | 2128 | $0.046 \times 10^{-2}$ |
| C8 | 5648241 | 8758 | $0.155 \times 10^{-2}$ |
| D8 | 4207887 | 3360 | $0.080 \times 10^{-2}$ |
| E8 | 5894699 | 3844 | $0.065 \times 10^{-2}$ |
| F8 | 5585487 | 4651 | $0.083 \times 10^{-2}$ |
| G8 | 4758800 | 4545 | $0.096 \times 10^{-2}$ |
| H8 | 5439137 | 8017 | $0.147 \times 10^{-2}$ |
| A9 | 10423188 | 20706 | $0.199 \times 10^{-2}$ |
| B9 | 6493893 | 4444 | $0.068 \times 10^{-2}$ |
| C9 | 5742047 | 5788 | $0.101 \times 10^{-2}$ |
| D9 | 3424405 | 1848 | $0.054 \times 10^{-2}$ |
| E9 | 5771943 | 8064 | $0.140 \times 10^{-2}$ |
| F9 | 24524 | 88 | $0.359 \times 10^{-2}$ |
| G9 | 7291510 | 6674 | $0.092 \times 10^{-2}$ |
| H9 | 4169883 | 6048 | $0.145 \times 10^{-2}$ |
| A10 | 9050811 | 17617 | $0.195 \times 10^{-2}$ |
| B10 | 5590113 | 5175 | $0.093 \times 10^{-2}$ |
| C10 | 2325807 | 1713 | $0.074 \times 10^{-2}$ |
| D10 | 2644116 | 2589 | $0.098 \times 10^{-2}$ |
| E10 | 4210945 | 2666 | $0.063 \times 10^{-2}$ |
| F10 | 2932749 | 6390 | $0.218 \times 10^{-2}$ |
| G10 | 3980127 | 3114 | $0.078 \times 10^{-2}$ |
| H10 | 4519035 | 6187 | $0.137 \times 10^{-2}$ |
| A11 | 9870025 | 24690 | $0.250 \times 10^{-2}$ |
| B11 | 4973892 | 2235 | $0.045 \times 10^{-2}$ |
| C11 | 3326448 | 6405 | $0.193 \times 10^{-2}$ |
| D11 | 5747961 | 7169 | $0.125 \times 10^{-2}$ |
| E11 | 5831546 | 8432 | $0.145 \times 10^{-2}$ |
| F11 | 5291803 | 4317 | $0.082 \times 10^{-2}$ |
| G11 | 3499587 | 2790 | $0.080 \times 10^{-2}$ |
| H11 | 3225750 | 4518 | $0.140 \times 10^{-2}$ |
| A12 | 9838 | 89 | $0.905 \times 10^{-2}$ |
| B12 | 3728293 | 2016 | $0.054 \times 10^{-2}$ |
| C12 | 4086862 | 5308 | $0.130 \times 10^{-2}$ |
| D12 | 5044526 | 3860 | $0.077 \times 10^{-2}$ |
| E12 | 4787913 | 2719 | $0.057 \times 10^{-2}$ |
| F12 | 5101695 | 2585 | $0.051 \times 10^{-2}$ |
| G12 | 2887390 | 1622 | $0.056 \times 10^{-2}$ |
| H12 | 2829307 | 5105 | $0.180 \times 10^{-2}$ |

To conduct BoNT/A activity assay in order to generate a dose-response curve to BoNT/A, cells from each isolated clonal cell line were seeded in a poly-D-lysine 96-well plate and differentiated as described above. Of the top 18 clonal cell lines selected for further testing, only 8 remained viable, the remaining 10 clonal cell lines failed to regrow and were lost. The media from the differentiated cells was aspirated from each well and replaced with fresh media containing either 0 (untreated sample), 0.03 pM, 0.1 pM, 0.3 pM, 0.9 pM, 2.8 pM, 8.3 pM, and 25 pM of a BoNT/A complex. After a 24 hrs treatment, the cells were washed, incubated for an additional two days in serum-free medium without toxin to allow for the cleavage of the SNAP-25 substrate, and harvested as described above. The supernatant was transferred to a capture antibody coated 96-well plate to perform the detection step.

The α-SNAP-25 capture antibody solution, the α-SNAP-25 detection antibody solution, and the α-SNAP-25 solid phase support were prepared as described above. Detection of the presence of cleaved SNAP-25 product by ECL sandwich ELISA analysis was performed as described above. The raw data obtained from the ECL imager was then transferred to SigmaPlot v. 9.0 and a 4-parameter logistics fit was used to define the dose-response curves. There were no constraints used for the 4-parameter logistic function when plotting the data. Graphical reports were generated using the following analysis: R2 (correlation coefficient), a (Max for data set), b (hillslope), and X0±SE ($EC_{50}$ value±standard error).

These results indicate that of the 8 clonal cell lines tested, only two were more susceptible to BoNT/A intoxication when compared to cells comprising the parental SiMa cell line (Table 2). For example, cells comprising the parental SiMa cell line exhibited an $EC_{50}$ activity for BoNT/A of 2.20 pM, whereas cells comprising the H1 and A10 cell lines exhibited an $EC_{50}$ activity for BoNT/A of 1.76 pM or less. Conversely, cells comprising the H10 and D11 cell line exhibited an $EC_{50}$ activity for BoNT/A that was higher than that observed for cells comprising the parental SiMa cell line, but less than 5.0 pM. It should be noted that any clonal cell line exhibiting an $EC_{50}$ activity for BoNT/A that is 5.0 pM or less (100 U/mL or less) is useful for an immuno-based method for determining BoNT/A activity described in Ester Fernandez-Salas, et al., *Immuno-Based Botulinum Toxin Serotype A Activity Assays*, U.S. patent application Ser. No. 12/403,531.

TABLE 2

Secondary Screen for Clonal Cell Lines Susceptible to BoNT/A Intoxication

| Clone | BoNT/A Activity | | |
|---|---|---|---|
| | $EC_{50}$ (pM) | $Signal_{MIN}$ (RLU) | $Signal_{MAX}$ (RLU) |
| SiMa | 2.20 | 123 | 47,611 |
| H1 | 0.77 | 193 | 125,252 |
| H3 | ND | ND | ND |
| B5 | >25.0 | 115 | 22,277 |
| C5 | ND | ND | ND |
| A6 | ND | ND | ND |
| A7 | 5.59 | 153 | 100,412 |
| D7 | ND | ND | ND |
| H8 | ND | ND | ND |
| A9 | ND | ND | ND |
| A10 | 1.76 | 207 | 113,029 |
| B10 | 6.35 | 147 | 101,935 |
| F10 | >25.0 | 111 | 32,663 |
| H10 | 2.80 | 171 | 120,975 |
| A11 | ND | ND | ND |
| C11 | ND | ND | ND |
| D11 | 4.4 | 1.84 | 105,527 |
| E11 | ND | ND | ND |
| C12 | ND | ND | ND |

ND = Not determined.

3. Primary Screen for BoNT/a Intoxication Susceptibility of Cells from a Clonal Cell Line Using a Formulated BoNT/A Pharmaceutical Product.

Another way to determine whether cells from a clonal cell line were susceptibility to BoNT/A intoxication was to conduct a primary screen by generating a dose-response curve to BoNT/A and calculate the $EC_{50}$ value using an immuno-based method for determining BoNT/A activity as described in Ester Fernandez-Salas, et al., *Immuno-Based Botulinum Toxin Serotype A Activity Assays*, U.S. patent application Ser. No. 12/403,531, which is hereby incorporated by reference in its entirety.

Initially six of 35 clonal cell line isolates were examined using a full dose response to BoNT/A. To prepare a lysate from cells treated with BoNT/A, cells from six clonal cell line were seeded in a poly-D-lysine 96-well plate and differentiated as described above in Section 2 except that the serum-free medium comprised 60 μg/mL GT1b. The clonal cell lines used were 3D8, YB8, 1D4, 2D6, 1E11, 2F5. The H1 and H10 clonal cell lines identified above, along with the parental SiMa cell line, were used as references to identify cell lines highly susceptible to BoNT/A intoxication. The media from the differentiated cells was aspirated from each well and replaced with fresh media containing either 0 (untreated sample), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a formulated BoNT/A pharmaceutical product. After a 24 hrs treatment, the cells were washed, incubated for an additional two days in serum-free medium without toxin to allow for the cleavage of the SNAP-25 substrate. To harvest the cells, 1×PBS was aspirated, the cells lysed by adding 30 μl of Lysis Buffer comprising 20 mM Tris-HCl (pH 7,5), 150 mM NaCl, 1 mM EDTA, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris. The protein concentration was determined using standard methods. The supernatant was transferred to a capture antibody coated 96-well plate to perform the detection step of the immuno-based method.

The α-SNAP-25 capture antibody solution, the α-SNAP-25 detection antibody solution, and the α-SNAP-25 solid phase support were prepared as described above in Section 2. Detection of the presence of SNAP-25 cleavage product by ECL sandwich ELISA analysis was performed, collected data was analyzed and the $EC_{50}$ calculated as described above in Section 2, except that SigmaPlot v. 10 was used.

These results show that clonal cell line H1 comprises cells that are more susceptible to BoNT/A than the parental SiMa cell line (Table 3). In addition, results indicate that although clonal cell lines H10, 1D4, 1E11, 2D6, 2F5, 3D8, and YB8 all comprise cells that are less susceptible to BoNT/A than the parental SiMa cell line, all have an $EC_{50}$ of BoNT/A activity that is below 30 U/mL (Table 3). It should be noted that any clonal cell line exhibiting an $EC_{50}$ activity for BoNT/A that is 100 U/mL or less (5.0 pM or less) is useful for an immuno-based method for determining BoNT/A activity described in Ester Fernandez-Salas, et al., *Immuno-Based Botulinum Toxin Serotype A Activity Assays*, U.S. patent application Ser. No. 12/403,531.

TABLE 3

Primary Screen for Clonal Cell Lines Susceptible to BoNT/A Intoxication

| Clone | BoNT/A Activity | | |
|---|---|---|---|
| | $EC_{50}$ (U/mL) | $Signal_{MIN}$ (RLU) | $Signal_{MAX}$ (RLU) |
| SiMa | 10.8 ± 1.0 | 10,519 | 253,484 |
| H1 | 10.2 ± 0.6 | 13,996 | 276,982 |
| H10 | 22.2 ± 2.0 | 5,379 | 296,168 |
| 1D4 | 22.4 ± 0.8 | 6,064 | 239,096 |
| 1E11 | 14.2 ± 1.7 | 8,698 | 276,323 |
| 2D6 | 27.3 ± 1.8 | 3,347 | 179,454 |
| 2F5 | 15.8 ± 0.9 | 7,007 | 265,461 |
| 3D8 | 13.4 ± 0.6 | 11,658 | 266,279 |
| YB8 | 19.7 ± 1.3 | 8,477 | 293,559 |

This initial primary screen using a dose-response curve with the 10 different BoNT/A concentrations identified three concentrations that were useful for a shortened assay using 3 different BoNT/A concentrations, with one concentration being slightly higher than the lower asymptote (8 U/mL), one concentration near the $EC_{50}$ (25 U/mL), and one concentration representing about 80% of the upper asymptote (80 U/mL). In these subsequent primary screens the remaining 29 clonal cell line isolates were tested as described above except that the cells were treated with either 0 (untreated sample), 8 U/mL, 25 U/mL, or 80 U/mL of a formulated BoNT/A pharmaceutical product. The clonal cell lines tested were 1E3, 2B9, 2D2, 2E4, 3B8, 3D5, 3G10, 4B5, 4C8, 4D3, 5C10, 5F3, AC9, AF4, BB3, BB10, BE3, BFB, CC11, CD6, CE6, CG8, CG10, DC4, DD10, DE7, DFS, YB7, and YF5. In addition, the parental SiMa was used as positive control.

These results show that clonal cell lines 2E4, 3B8, 3D5, 5F3, AF4, BB3, BB10, and DC4 all comprise cells that are more susceptible to BoNT/A than the parental SiMa cell line (Table 4). In addition, these results indicate that clonal cell lines 1E3, 2B9, 3G10, 4B5, 4C8, AC9, BE3, BFB, CC11, CD6, CE6, CG8, CG10, DD10, DE7, and YF5 all comprise cells that are of similar susceptibility to BoNT/A to that of the parental SiMa cell line (Table 4). Lastly, these results reveal that clonal cell lines 2D2, 4D3, 5C10, DFS, and YB7 all comprise cells that are less susceptible to BoNT/A than the parental SiMa cell line (Table 4).

TABLE 4

Primary Screen for Clonal Cell Lines Susceptible to BoNT/A Intoxication

| Clone | 8 U/mL BoNT/A Activity Signal (RLU) | Fold Difference | 25 U/mL BoNT/A Activity Signal (RLU) | Fold Difference | 80 U/mL BoNT/A Activity Signal (RLU) | Fold Difference |
|---|---|---|---|---|---|---|
| SiMa | 75811/80562* | — | 138952/175685* | — | 173979/225768* | — |
| 1E3 | 71040 | 0.9 | 128771 | 0.9 | 155107 | 0.9 |
| 2B9 | 66962 | 0.9 | 135006 | 1.0 | 166871 | 1.0 |
| 2D2 | 60224* | 0.8 | 136947* | 0.8 | 199786* | 0.9 |
| 2E4 | 103680 | 1.4 | 217980 | 1.6 | 270463 | 1.6 |
| 3B8 | 123521 | 1.6 | 227367 | 1.6 | 249218 | 1.4 |
| 3D5 | 113532 | 1.5 | 201683 | 1.5 | 270578 | 1.6 |
| 3G10 | 83049 | 1.1 | 130930 | 0.9 | 175540 | 1.0 |
| 4B5 | 74344 | 1.0 | 137604 | 1.0 | 177363 | 1.0 |
| 4C8 | 87047 | 1.1 | 144395 | 1.0 | 185115 | 1.1 |
| 4D3 | 38063 | 0.5 | 80180 | 0.6 | 101724 | 0.6 |
| 5C10 | 16024* | 0.2 | 49030 | 0.3 | 116396* | 0.6 |
| 5F3 | 98263* | 1.7 | 182902* | 1.4 | 212275* | 1.5 |
| AC9 | 60016* | 1.0 | 127030* | 1.0 | 180384* | 1.4 |
| AF4 | 115460 | 1.5 | 179901 | 1.3 | 190867 | 1.1 |
| BB3 | 74668 | 1.3 | 120966 | 1.4 | 170177 | 1.4 |
| BB10 | 152748 | 2.0 | 232406 | 1.7 | 266555 | 1.5 |
| BE3 | 100849 | 1.0 | 199487 | 0.9 | 236415 | 1.0 |
| BF8 | 55763* | 1.0 | 111746* | 1.0 | 153074* | 1.3 |
| CC11 | 54421* | 1.0 | 123576* | 1.0 | 155337* | 1.2 |
| CD6 | 74970 | 1.0 | 151862 | 1.1 | 183377 | 1.1 |
| CE6 | 70019 | 0.9 | 146292 | 1.1 | 208184 | 1.2 |
| CG8 | 81790* | 1.0 | 159098* | 1.0 | 189209* | 1.3 |
| CG10 | 69503 | 0.9 | 141079 | 1.0 | 185801 | 1.1 |
| DC4 | 112085 | 1.5 | 163319 | 1.2 | 169352 | 1.0 |
| DD10 | 116325 | 1.5 | 205445 | 1.5 | 223473 | 1.3 |
| DE7 | 60994* | 0.9 | 131237* | 0.9 | 174487* | 0.9 |
| DF5 | 34,165* | 0.5 | 104,696* | 0.7 | 179,314* | 0.9 |
| YB7 | 50433 | 0.7 | 103707 | 0.7 | 143423 | 0.8 |
| YF5 | 65848 | 0.9 | 122487 | 0.9 | 146263 | 0.4 |

*Two separate screens were done. In the first, the signal detected for the SiMa cell line was 75811 RLU and this value was used to determine the fold difference for clonal cell lines tested in this screen (numbers with no asterisk). For the second screen, the signal detected for the SiMa cell line was 80562 RLU and this value was used to determine the fold difference for clonal cell lines tested in this screen (numbers with asterisk).

Example II

Stability Analysis of Clonal Cell Lines

The following example illustrates how to characterize the stability of cells from an established clonal cell line that are susceptible to BoNT/A intoxication or have neurotoxin uptake capacity.

During characterization of the SiMa cell line, it was determined that the parental SiMa cell line became unstable in terms of a significant loss of sensitivity to BoNT/A. For example, prior to passage 13, cells comprising the parental SiMa cell line routinely exhibited an $EC_{50}$ for BoNT/A activity that was under 5.0 pM. However, after passages about 14 to about 20 passages, cells comprising the parental SiMa cell exhibited an $EC_{50}$ for BoNT/A activity that was routinely over 25.0 pM. One reason for this dramatic reduction in the $EC_{50}$ value may be because the SiMa cell line is heterogeneous in nature since it comprises at least five different cell types. Over time, one of these cell types could overtake the culture to the exclusion of the other four. If the overtaking cell type was less susceptible to BoNT/A intoxication, or not susceptible at all, then as this cell type became the dominant one in the cell line the $EC_{50}$ for BoNT/A activity in this overtaken SiMa cell line would decrease. Thus, because the established clonal cell lines were derived from only one of these cell types, then it follows that the clonal cell line would exhibit greater stability in terms of maintaining an $EC_{50}$ for BoNT/A activity that was routinely under 5.0 pM.

To determine whether the cells from the established clonal cell lines showed increased stability relative to the cells comprising the parental SiMa cell line, the $EC_{50}$ for BoNT/A activity was determined for clonal cell lines BB10, H1, H10, and the parental SiMa cell line at different passage numbers using an immuno-based method for determining BoNT/A activity. The media from the differentiated cells was aspirated from each well and replaced with fresh media containing either 0 (untreated sample), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a formulated BoNT/A pharmaceutical product. After a 24 hrs treatment, the cells were washed, incubated for an additional two days in serum-free medium without toxin to allow for the cleavage of the SNAP-25 substrate, and harvested as described above. The supernatant was transferred to a capture antibody coated 96-well plate to perform the detection step.

Similarly, the preparation of the α-SNAP-25 capture antibody solution, α-SNAP-25 detection antibody solution, and the solid phase support comprising an α-SNAP-25 capture antibody were as described in Section 3. Lastly, detection of the presence of SNAP-25 cleavage product by ECL sandwich ELISA was performed, collected data was analyzed, and the $EC_{50}$ calculated as described above in Section 2, except that PLA v. 2 was used for the 4-parameter logistics fit.

The results from this stability experiments indicated that BB10, H1 and H10 cell lines all exhibited increase stability as compared to the parental SiMa cell line. For example, where cells from the parental SiMa cell line exhibited an $EC_{50}$ for BoNT/A activity that was over 500 U/mL (or 25 pM) after passages about 14 to about 20 passages, cells comprising the BB10, H1 and H10 cell lines all exhibited an $EC_{50}$ for BoNT/A activity that was below 10 U/mL (or 0.5 pM) after passage about 30.

Example III

Gene Expression Profile of Cell Lines Comprising Cells Susceptible to BoNT/A Intoxication The following example illustrates how to characterize cells from an established clonal cell line that are susceptible to BoNT/A intoxication or have neurotoxin uptake capacity by gene expression profiling. To determine the changes in genome-wide gene transcription levels in cells susceptible to BoNT/A intoxication, gene expression analysis was performed on cells from H1, BB10, 2D6 and the parental SiMa cell line, in both differentiated and undifferentiated states using GENECHIP® U133 Plus 2 microarray technology (Affymetrix, Inc., Santa Clara, Calif.) according to the manufacturer's instructions, see, e.g., GENECHIP® Expression Analysis Technical Manual, 702232, Rev. 2 (2006) which is hereby incorporated by reference in its entirety.

To prepare differentiated cells for these cell lines, a suitable density of cells from the H1, BB10, 2D6, and SiMa cell lines were seeded in separate T175 tissue culture flasks containing 50 mL of a serum-free medium comprising Enhanced Minimum Essential Medium, 10 mM HEPES, 1 mM sodium pyruvate, 0.1 mM Non-Essential Amino Acids, 1×B27 supplement, 1×N2 supplement, and 60 μg/mL GT1b (302-011-M005, Alexis Biochemicals, San Diego, Calif.). These cells were incubated in a 37° C. incubator under 5% carbon dioxide until the cells differentiated, as assessed by standard and routine morphological criteria, such as growth arrest and neurite extension, and attained 80% confluence (approximately 3 days). The cells were then washed with 50 mL of 1×PBS, trypsin-treated for 5 min at room temperature, and then 15 mL of growth medium was added to the flask to inactivate the trypsin. The cell suspension was transferred to a 50 mL tube and centrifuge at 200 RCF for 5 min at room temperature to pellet the cells. The cell pellet was washed once in 50 mL of 1×PBS, centrifuge at 200 RCF for 5 min at room temperature to pellet the cells, and the supernatant was removed. The cell pellet was quick frozen on dry ice and stored at −80° C. until needed.

To prepare undifferentiated cells for these cell lines, a suitable density of cells from the H1, BB10, 2D6, and SiMa cell lines were seeded in separate T175 tissue culture flasks containing 50 mL of growth medium comprising RPMI 1640, 10% fetal bovine serum, 10 mM HEPES, 1 mM sodium pyruvate, 0.1 mM Non-Essential Amino Acids, and 60 μg/mL GT1b. These cells were incubated in a 37° C. incubator under 5% carbon dioxide until the cells attained 80% confluence (approximately 3 days). The cells were then processed as described above and the cell pellet was quick frozen on dry ice and stored at −80° C. until needed.

To prepare total RNA, cells for each cell line were lysed and total RNA isolated and purified using a RNA isolation kit (QIAGEN, Valencia, Calif.) according to the manufacturer's protocols. DNA was digested using an on-column DNase I procedure (QIAGEN, Valencia, Calif.). RNA was quantified photospectrometrically at 260 nm and purity assessed by the A260A280 ratio using a spectrophotometer. RNA integrity was assessed using a Bioanalyser 2100 (Agilent Technologies, Inc., Santa Clara, Calif.). Extracted total RNA aliquots were snap-frozen in liquid nitrogen and stored at −80° C.

To prepare cDNA probes for the gene microarray chips, about 1-15 pg was reversed transcribed using a T7-Oligo(dT) promoter primer in the first strand cDNA synthesis reaction. Following RNase H-mediated second strand cDNA synthesis, the double-stranded cDNA was purified and served as a template for subsequent in vitro transcription reaction. The in vitro transcription reaction was carried out in the presence of T7 RNA polymerase and a biotinylated nucleotide analog/ribonucleotide mix for complementary RNA (cRNA) amplification and biotin labeling. The biotinylated cRNA targets were then cleaned up, fragmented, and hybridized to microchip expression arrays for 17 hours at 65° C. according to the manufacturer's instructions, see, e.g., GENECHIP® Expression Analysis Technical Manual, 702232, Rev. 2 (2006) which is hereby incorporated by reference in its entirety. To identify substantial treatment-related up- or down-regulated gene expression differences compared to control cell lines, greater than 1.5-fold differences ($\log_2$ 0.58) were considered significant, and only those genes that displayed consistent changes in expression in the triplicate analysis were considered (Tables 5-12).

Expression profiling for cell lines H1, BB10 and 2D6 analyzed in the undifferentiated state revealed that 1,323 genes were identified as having their expression levels increase by 1.5-fold ($\log_2$ 0.58) or more in the H1 and BB10 cell lines as compared to the gene expression levels obtained from the 2D6 cell line (Table 5). Of these, 686 genes exhibited an increase in expression levels in the H1 and BB10 cell lines by 2-fold ($\log_2$ 1.0) or more as compared to the expression level for these genes determined from the 2D6 cell line; and 231 genes exhibited an increase in expression levels in the H1 and BB10 cell lines by 4-fold ($\log_2$ 2.0) or more as compared to the expression level for these genes determined from the 2D6 cell line. With respect to decreased expression, 1,438 genes were identified as having their expression levels decreased by 1.5-fold ($\log_2$ 0.58) or more in the H1 and BB10 cell lines as compared to the gene expression levels obtained from the 2D6 cell line (Table 6). Of these, 668 genes exhibited a decrease in expression levels in the H1 and BB10 cell lines by 2-fold ($\log_2$ 1.0) or more as compared to the expression level for these genes determined from the 2D6 cell line; and 107 genes exhibited a decrease in expression levels in the H1 and BB10 cell lines by 4-fold ($\log_2$ 2.0) or more as compared to the expression level for these genes determined from the 2D6 cell line.

Expression profiling for cell lines H1, BB10 and 2D6 analyzed in the differentiated state revealed that 2,556 genes were identified as having their expression levels increased by 1.5-fold ($\log_2$ 0.58) or more in the H1 and BB10 cell lines as compared to the gene expression levels obtained from the 2D6 cell line (Table 7). Of these, 1,634 genes exhibited an increase in expression levels in the H1 and BB10 cell lines by 2-fold ($\log_2$ 1.0) or more as compared to the expression level for these genes determined from the 2D6 cell line; and 696 genes exhibited an increase in expression levels in the H1 and BB10 cell lines by 4-fold ($\log_2$ 2.0) or more as compared to the expression level for these genes determined from the 2D6 cell line. With respect to decreased expression, 2,087 genes were identified as having their expression levels decreased by 1.5-fold ($\log_2$ 0.58) or more in the H1 and BB10 cell lines as compared to the gene expression levels obtained from the 2D6 cell line (Table 8). Of these, 1,215 genes exhibited a decrease in expression levels in the H1 and BB10 cell lines by 2-fold ($\log_2$ 1.0) or more as compared to the expression level for these genes determined from the 2D6 cell line; and 280 genes exhibited a decrease in expression levels in the H1 and BB10 cell lines by 4-fold ($\log_2$ 2.0) or more as compared to the expression level for these genes determined from the 2D6 cell line.

Expression profiling for cell lines H1, BB10 and SiMa analyzed in the undifferentiated state revealed that 1,232 genes were identified as having their expression levels increase by 1.5-fold ($\log_2$ 0.58) or more in the H1 and BB10 cell lines as compared to the gene expression levels obtained from the SiMa parental cell line (Table 9). Of these, 764 genes exhibited an increase in expression levels in the H1 and BB10 cell lines by 2-fold ($\log_2$ 1.0) or more as compared to the expression level for these genes determined from the SiMa parental cell line; and 228 genes exhibited an increase in expression levels in H1 and BB10 cell lines by 4-fold ($\log_2$ 2.0) or more as compared to the expression level for these genes determined from the SiMa parental cell line. With respect to decreased expression, 1,265 genes were identified as having their expression levels decreased by 1.5-fold ($\log_2$ 0.58) or more in the H1 and BB10 cell lines as compared to the gene expression levels obtained from the SiMa parental cell line (Table 10). Of these, 648 genes exhibited a decrease in expression levels in the H1 and BB10 cell lines by 2-fold ($\log_2$ 1.0) or more as compared to the expression level for these genes determined from the SiMa parental cell line; and 189 genes exhibited a decrease in expression levels in H1 and BB10 cell lines by 4-fold ($\log_2$ 2.0) or more as compared to the expression level for these genes determined from the SiMa parental cell line.

Expression profiling for cell lines H1, BB10 and SiMa analyzed in the differentiated state revealed that 756 genes were identified as having their expression levels increase by 1.5-fold ($\log_2$ 0.58) or more in the H1 and BB10 cell lines as compared to the gene expression levels obtained from the SiMa parental cell line (Table 11). Of these, 472 genes exhibited an increase in expression levels in the H1 and BB10 cell lines by 2-fold ($\log_2$ 1.0) or more as compared to the expression level for these genes determined from the SiMa parental cell line; and 150 genes exhibited an increase in expression levels in H1 and BB10 cell lines by 4-fold ($\log_2$ 2.0) or more as compared to the expression level for these genes determined from the SiMa parental cell line. With respect to decreased expression, 912 genes were identified as having their expression levels decreased by 1.5-fold ($\log_2$ 0.58) or more in the H1 and BB10 cell lines as compared to the gene expression levels obtained from the SiMa parental cell line (Table 12). Of these, 411 genes exhibited a decrease in expression levels in the H1 and BB10 cell lines by 2-fold ($\log_2$ 1.0) or more as compared to the expression level for these genes determined from the SiMa parental cell line; and 108 genes exhibited a decrease in expression levels in H1 and BB10 cell lines by 4-fold ($\log_2$ 2.0) or more as compared to the expression level for these genes determined from the SiMa parental cell line.

Example IV

Pathway Analysis of Gene Expression Profiles from Clonal Cell Lines

The following example illustrates how to characterize gene expression profiles from clonal cells from an established clonal cell line that are susceptible to BoNT/A intoxication or have neurotoxin uptake capacity in order to identify biological networks or pathways associated with BoNT/A intoxication.

An Ingenuity Pathway Analysis (IPA) Core Analysis (Ingenuity Systems Inc., Redwood City, Calif.) was performed to characterize the RNA expression phenotype of two independently derived BoNT/A very sensitive single clone cell lines, BB10 and H1, compared to a related but much less BoNT/A sensitive single clone cell line, 2D6. The analysis was done to identify the specific gene expression phenotype of a BoNT/A sensitive cell line. The result can also be used to predict and potentially identify proteins that function to enhance BoNT/A uptake.

An Ingenuity Pathway Analysis (IPA) Core Analysis was performed that identified biologically relevant networks to BoNT/A intoxication based on connectivity among the genes from an IPA library and the genes exhibiting significant changes as determined from the expression profiling discussed above. For this analysis, all genes that exhibited an increased or decrease in expression levels in the H1 and BB10 cell lines by 4-fold ($\log_2$ 2.0) or more as compared to the expression level for these genes determined from the 2D6 cell line were used, in conjunction with, selected genes with known or suspected relevance to BoNT/A intoxication, hereafter referred to as the Profile genes. The significance of the association to a given network was measured and ranked by the ratio of the number of Profile genes that mapped to the specific network divided by the total number of genes that map to that network. Fisher's exact test was used to calculate p-scores, which represent the association between the Profile genes and the network, and based on the p-scores the genes from the Profile genes were used to rank the networks. The p-scores were derived from p-values. If there are n genes in the network and f of them are Profile genes, then the p-value is the probability of finding f or more Profile genes in a set of n genes randomly selected from the Global Molecular Network. Since significant p-values are quite low (e.g., $1\times10^{-8}$), a p-score was defined as the component of the p-value; p-score=–log 10 (p-value). The identified networks were overlaid with differentially expressed genes which had more than 1.5-fold differential expression and a p-value 0.001 either before or after differentiation.

Using IPA Core Analysis the differentially expressed Profile genes were connected to 26 Networks. Nineteen of these included 10 or more Profile genes (Table 13). Among these nineteen networks three overall networks groups, named A, B and C were identified (Table 13). Within the networks in these three groups there were overlapping genes and the expression for more than three genes was increased after differentiation. Group A genes include the FGFR2 receptor which has been shown to function in the BoNT/A intoxication process as a receptor for BoNT/A and are as follows: genes exhibiting a 1.5-fold or more decrease in expression levels in the H1 and BB10 cell lines as compared to their expression in cells from the 2D6 cell line, ANXA2, AQP1, ARHGAP9, CDH10, CDKN2A, CHPT1, CNTN2, ERAP1, and RGS11; genes exhibiting a 1.5-fold or more increase in expression levels in the H1 and BB10 cell lines as compared to their expression in cells from the 2D6 cell line, ADAMTS9, ATAD2, C11ORF82, CDC45L, CNTN1, CNTN4, Cyclin A, Cyclin E, E2F1, E2F2, E2F7, ELOVL7, EME1, FGFR, FGFR2, KIAA1524, MELK, MYBL1, MYBL2, NDC80, NDN, ORC1L, PLS3, PRIMA1, RAD54L, RBL1, RBPMS, RRM2, S1PR3, SCLY, SLC1A3, SPC24, SPC25, ST8SIA4, TFDP1, TFP12, TK1, TMEM35, TTK, TWIST1, TYMS, TYK, and ZWINT.

Group B genes include the EGFR, a receptor which is regulated by NGF, which has been shown to increase BoNT/A uptake in cell culture experiments and are as follows: genes exhibiting a 1.5-fold or more decrease in expression levels in the H1 and BB10 cell lines as compared to their expression in cells from the 2D6 cell line, ABCC8, AELIM3, CAP2, IL17B, MEF2A, NEEBL, PHC, S100A6, SLC1A6, SMAD1, SMAD5, SMAD8, SYT13, and SYTL1; genes exhibiting a 1.5-fold or more increase in expression levels in the H1 and BB10 cell lines as compared to their expression in cells from the 2D6 cell line, AURKB, BIRCS, BRCA1, BRCA2, BRIP1, BUB1B, CD9, DLGAP3, DYNLT3, ENC1, FBLN1, FOXM1, Gβγ, GNAI1, GNG11, GNG12, GPSM2, GUCY1B3, HGF, ITGA6, JNK, KCNJS, KIF18A, KITLG, MMD, MSN, MYRIP, NEK2, NR3C1, NXPH1, OSBPL3, PKMYT1, PTPRM, RAD51, RAD51AP1, SLC7A2, SLC43A3, SMC6, SNAI2, SNCAIP, SSH2, STK17A, SYNPO2, TOP2A, TPTE, TRAF4, TSPAN, TSPAN4, UBE3, UBE3B, and VAV3.

Group C genes include a number of microtubule motor proteins of the kinesin family that may function in the intracellular trafficking of BoNT/A and are as follows: genes exhibiting a 1.5-fold or more decrease in expression levels in the H1 and BB10 cell lines as compared to their expression in cells from the 2D6 cell line, CSTB, GPCR, GRIM5, KISSR, SCN2A, SLC1A2, and THBS2; genes exhibiting a 1.5-fold or more increase in expression levels in the H1 and BB10 cell lines as compared to their expression in cells from the 2D6 cell line, ALCAM, AURKA, CHEK, CIT, CSRP2, E2F, ECT2, EFNB2, ERK, ESPL1, GNAI, GPR161, HMMR, KIF4A, KIF14, KIF15, KIF22, KIF23, KIFC1, LPAR1, MK167, OIP5, PHLPP, PP1/PP2A, PPP1R3c, PRC1, PTTG1, RACGAP, RB, RGS5, SDC2, and TPX2.

The remaining networks identified did not share common genes between any other network. For Network 3, genes exhibiting a 1.5-fold or more decrease in expression levels in the H1 and BB10 cell lines as compared to their expression in cells from the 2D6 cell line, ADARB1, ADM, PTPPH, and SLCO1A2; genes exhibiting a 1.5-fold or more increase in expression levels in the H1 and BB10 cell lines as compared to their expression in cells from the 2D6 cell line, ASCL1, HES6, MAPK, NMU, PEG3, PTPRK, PRLHR, PTPRK, SGOL2, SPARC, and ZNF217. For Network 6, genes exhibiting a 1.5-fold or more decrease in expression levels in the H1 and BB10 cell lines as compared to their expression in cells from the 2D6 cell line, CNGA3, HIST1H3E and PTGS1; genes exhibiting a 1.5-fold or more increase in expression levels in the H1 and BB10 cell lines as compared to their expression in cells from the 2D6 cell line, ASF1B, BASP1, CHAF1A, NCAPH, PBK, PRAME, SMC2, UHRF1, and VRK1. For Network 9, genes exhibiting a 1.5-fold or more decrease in expression levels in the H1 and BB10 cell lines as compared to their expression in cells from the 2D6 cell line, HIST1H2BD and OSCAR; genes exhibiting a 1.5-fold or more increase in expression levels in the H1 and BB10 cell lines as compared to their expression in cells from the 2D6 cell line, C14ORF106, CEP72, KIF20A, PCNA, PEX13, PFCS, POLQ, SPAGS, SYTL4, TROAP, and WDR51A. For Network 12, genes exhibiting a 1.5-fold or more increase in expression levels in the H1 and BB10 cell lines as compared to their expression in cells from the 2D6 cell line, ANLN, ARHGAP24, ASPM, BUB1, CCDC99, CEP55, CKAP2, DRAM, E2F8, PLXNA2, SLC16A10, UBE2C, UBE2S, and WDHD1. For Network 13, genes exhibiting a 1.5-fold or more decrease in expression levels in the H1 and BB10 cell lines as compared to their expression in cells from the 2D6 cell line, CALY; genes exhibiting a 1.5-fold or more increase in expression levels in the H1 and BB10 cell lines as compared to their expression in cells from the 2D6 cell line, ARHGEF3, CTSL2, DIAPH3, FBP1, KIF2C, KIF11, PFKFB3, and PLK4. For Network 14, genes exhibiting a 1.5-fold or more decrease in expression levels in the H1 and BB10 cell lines as compared to their expression in cells from the 2D6 cell line, COL5A1 and MICAL2; genes exhibiting a 1.5-fold or more increase in expression levels in the H1 and BB10 cell lines as compared to their expression in cells from the 2D6 cell line, FNDCS, HSPC159, MAB21L2, SLITRKS, SYN2, and ZNF367. For Network 15, genes exhibiting a 1.5-fold or more decrease in expression levels in the H1 and BB10 cell lines as compared to their expression in cells from the 2D6 cell line, OLFML2A and SIGIRR; genes exhibiting a 1.5-fold or more increase in expression levels in the H1 and BB10 cell lines as compared to their expression in cells from the 2D6 cell line, EXO1, KCTD12, MYO6, PHEBL1, SHCBP1, TPBG, and TUBB6. For Network 17, genes exhibiting a 1.5-fold or more decrease in expression levels in the H1 and BB10 cell lines as compared to their expression in cells from the 2D6 cell line, HPCAL1 and LPAR5; genes exhibiting a 1.5-fold or more increase in expression levels in the H1 and BB10 cell lines as compared to their expression in cells from the 2D6 cell line, BTG3, GABRA5, TR1P10, and ZNF521. For Network 19, genes exhibiting a 1.5-fold or more decrease in expression levels in the H1 and BB10 cell lines as compared to their expression in cells from the 2D6 cell line, HTR1E and SORCS1; genes exhibiting a 1.5-fold or more increase in expression levels in the H1 and BB10 cell lines as compared to their expression in cells from the 2D6 cell line, BNC2, DPYD, EMILIN2, PPILS, and TACC3.

TABLE 13

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| A | 1 | ADAMTS9, ATAD2, CDC45L, CDKN2A, CNTN1, CNTN2, Cyclin A, Cyclin E, DIRAS3, E2F1, E2F2, E2F7, FGFR2, HDAC, MYBL1, MYBL2, NDC80, NDN, NFkB, ORC1L, PLS3, RAD54L, RBL1, RRM2, S1PR3, SPC24, SPC25, TFDP1, TFPI2, TK1, TNFRSF10D, TTK, TYMS, TYK, ZWINT | 51 | 30 | CDKN2A | ADAMTS9, CNTN1, HDAC, NDN, PLS3, S1PR3, TFPI2 | CDKN2A, CNTN2, | ADAMTS9, ATAD2, CDC45L, CNTN1, Cyclin A, Cyclin E, E2F1, E2F2, E2F7, FGFR2, MYBL1, MYBL2, NDC80, NDN, ORC1L, PLS3, RAD54L, RBL1, RRM2, S1PR3, SPC24, SPC25, TFDP1, TFPI2, TK1, TTK, TYMS, TYK, ZWINT |
| C | 2 | ALCAM, ANK2, ANK3, AURKA, DOK5, E2F, ERK, ESPL1, GDF15, GFRA2, HMMR, ITGA9, KIF15, KIF22, KISS1R, KPNA, KPNB, LGI1, MAFB, MAP2K1, MAP2K2, | 46 | 28 | ANK2, ANK3, PHKA2, PPP2R2C, SCN2A | ALCAM, DOK5, ERK, GFRA2, PP1/PP2A, PP2A, PPP1R3C, | KISSR, SCN2A | ALCAM, AURKA, E2F, ERK, ESPL1, HMMR, KIF15, KIF22, MKI67, OIP5, PHLPP, PP1/PP2A, PPP1R3C, PTTG1, RB, TPX2 |

TABLE 13-continued IPA Core Analysis of Profile Genes

| Group | Net-work | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| | | MKI67, NRG3, OIP5, PHKA2, PHLPP, POSTN, PP1/PP2A, PP2A, PPP1R3C, PPP2R2B, PPP2R2C, PTTG1, RAF1, RB, SCN2A, TPX2 | | | | PPP2R2B | | |
| — | 3 | ADARB1, ADM, AKAP12, ALP, ASCL1, BHLHB2, CRH, DLL1, FRZB, FSH, GRIA2, GRIP2, hCG, HES6, HTATIP2, IL13RA2, MAPK, NMU, PDGF BB, PDLIM3, PEG3, PLAT, PPFIA4, PRLHR, PTPRH, PTPRK, SGOL2, SLCO1A2, SMAD6, SPARC, STC1, TEAD4, TGFB, VEGF, ZNF217 | 46 | 28 | ADARB1, GRIP2, SLCO1A2 | ASCL1, DLL1, FRZB, MAPK, PEG3, PLAT, PRLHR, SMAD6, SPARC, ZNF217 | ADARB1, ADM, PTPPH, SLCO1A2 | ASCL1, HES6, MAPK, NMU, PEG3, PRLHR, PTPRK, SGOL2, SPARC, ZNF217 |
| C | 4 | AKT, ACTN1, ACTN2, ACTN3, ATF5, ATM/ATR, BDKRB2, CHEK1, CHEK2, CIT, CSRP2, CSTB, CTSH, ECT2, EFNB2, ELMO1, GNAI, GABBR2, GPCR, GPR161, GRM5, ICAM2, KIF4A, KIF14, KIF23, KIFC1, LPAR1, MMP, PDGFA PDGFB, PRC1, RAC, RAC2, RACGAP1, RGS5, SDC2, SLC1A2, THBS2 | 43 | 27 | CSTB, GPCR, GRIM5, SLC1A2 | GNAI, GPR161, LPAR1, RGS5 | CSTB, GPCR, GRIM5, SLC1A2, THBS2 | CIT, CSRP2, ECT2, EFNB2, CHEK, GNAI, GPR161, KIF4A, KIF14, KIF23, KIFC1, LPAR1, PRC1, RACGAP, RGS5, SDC2, |
| B | 5 | ABLIM3, F-ACTF, G-ACT, CD9, CXCR4, DTNA, ENC1, FNBP1, Gβγ, GNAI1, GNG11, GNG12, GPSM2, ITG, ITA5, ITGA6, JNK, KCNJ4, MLC, MSN, MYRIP, NOX, NET1, NRXN1, NXPH1, PI3K, RHO, S100A6, STK17A SYT13, SYTL1, TRAF4, TSPAN, TSPAN3, TSPAN4, VAV3 | 38 | 25 | SYT13, S100A6 | CD9, CXCR4, ENC1, Gβγ, GNAI1, GNG11, GNG12, ITGA6, JNK, MSN, MYRIP, STK17A | AELIM3, S100A6, SYT13, SYTL1 | CD9, ENC1, Gβγ, GNAI1, GNG11, GNG12, GPSM2, ITGA6, JNK, KCNJ4, MSN, MYRIP, NXPH1, STK17A, TRAF4, TSPAN, TSPAN4, VAV3 |
| — | 6 | ADCY, ADCY1, AP1, ASF1B, ATP2B4, BASP1, BCL11B, CAM, CAMK2B, CHAF1A, CNGA3, CYP2E1, DACH1, HIST1H3E, HISH3, HRH3, HSP90, IL1, IL12, INS, INFA, ISG20, KCNN2, LDL, MMP14, NCAPH, PBK, PDGF, PIAS1, PRAME, PTGS1, SEC31A, SMC2, UHRF1, VRK1 | 36 | 24 | CAMK2B | BASP1, HRH3 | CNGA3, HIST1H3E, PTGS1 | ASF1B, BASP1, CHAF1A, NCAPH, PBK, PRAME, SMC2, UHRF1, VRK1 |
| B | 7 | BARD1, BRCA1, BRCA2, BRIP1, BUB1B, CNA, CAP2, CK2, DLGAP5, FAT, GUCY1B3, HSP70, KITLG, MEF2A, NEK2, NFAT, NR3C1, NF1, PHLDA2, PKC(s), RAD51, RAD51AP1, TOP2, SAMD4A, SLC1A6, SMC6, SNAI2, SNCAIP, STAT5a, STAT5b, TCF7L2, UBE3, UBE3B, UBN, XPO1 | 32 | 24 | CAP2, CNA, PHLDA2, PKC(s) | NR3C1, SMC6, SNCAIP, TCF7L2 | CAP2, MEF2A, PKC(s), SLC1A6 | BRCA1, BRCA2, BRIP1, BUB1B, DLGAP3, GUCY1B3, NEK2, KITLG, NR3C1, RAD51, RAD51AP1, SMC6, SNAI2, SNCAIP, UBE3, UBE3B |
| B | 8 | CBP, AURKB, BIRC5, CACNA1D, CBP/p300, CD3, CREB, CREB5, DBH, EGR1, ERK1, ERK2, FBLN1, FBN1, FOXM1, HGF, INCENP, KCNMA1, LGALS1, MAOA, MEK, NDRG1, NID1, P38 MAPK, PKA, PKMYT1, PRKAC, PRKACB, RAF, RAP1, RAS, RGMA, RSK, SMAD1, SMAD5, SMAD8, SYNPO2, TOP2A | 30 | 21 | KCNMA1, NDRG1, RAS | ERK1, ERK2, MAOA, P38 MAPK, RGMA | NDRG1, SMAD1, SMAD5, SMAD8 | AURKB, BIRC5, ERK1, ERK2, FBLN1, FOXM1, HGF, MAOA, P38 MAPK, PKMYT1, SYNPO2, TOP2A |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| — | 9 | C14ORF106, CDKN1A, CEP72, DHX8, FKBPL, HIST1H2BD, HNF4A, KIF20A, KRT18, MTHFS, OSCAR, PCGF5, PCNA, PELO, PEX13, PFC5, POLD4, POLK, POLL, POLM, POLQ, POLS, R3HDM1, RASL12, RFC5, SLC33A1, SPAG5, STAT4, SULT1A1, SULT1C2, SYTL4, TCEAL3, TROAP, VEZT, WDR51A, ZBTB16 | 19 | 15 | — | PCGF5 | HIST1H2BD, OSCAR | C14ORF106, CEP72, KIF20A, PCNA, PEX13, PFC5, POLQ, SPAG5, SYTL4, TROAP, WDR51A |
| A | 10 | ARHGAP9, CDH10, CDS1, CDS2, CHPT1, CNTN4, ELOVL7, EME1, FGFR, GAS6, HAND1, IFI202B, ISL1, KIAA1524, KRT74, MIRN31, MUS81, MYF6, MYOD1, NFYB, OTX1, PRIMA1, QKI, RBM9, RBPMS, RORA, SHOX2, SLC39A8, SOX2, SOX15, ST8SIA4, STAT3, TWIST1, VPS39, ZFHX3 | 18 | 15 | CHPT1 | CNTN4, ELOVL7, HAND1, ODS2, SOX2, TWIST1 | ARHGAP9, CDH10 | CNTN4, ELOVL7, EME1, FGFR, KIAA1524, PRIMA1, RBPMS, ST8SIA4, TWIST1 |
| B | 11 | ALDH3A2, B3GALT2, BAMBI, CNN2, CTNNAL1, CTNNB1, CTSC, CUGBP2, DYNLT3, IL13, KIF18A, LIN7C, MFI2, MPP5, MRC2, NDST1, PDGF-CC, PHLDA2, LAU, PPM1J, PPP1CA, PTPN14, PTPRM, SLC16A3, SLC26A2, SLC43A3, SLC7A2, SSH2, STK17A, TAX1BP3, TCF7L1, TGFB1, TPTE, TSPAN8 | 18 | 15 | PHLDA2 | BAMBI, CUGBP2, DYNLT3, SLC7A2, SLC43A3, STK17A, TPTE | — | DYNLT3, KIF18A, PTPRM, SLC7A2, SLC43A3, SSH2, STK17A, TPTE |
| — | 12 | AHR, AHRR, ANLN, APH1B, ARHGAP24, ASPM, BUB1, CCDC99, CEP55, CKAP2, DRAM, E2F8, HS3ST1, JPH1, MIRN124-1, NMT2, PDZRN3, PLXNA2, PMM1, PPP1R13L, PVRL3, RFFL, S100A2, SLC16A10, TP53, UBE2A, UBE2C, UBE2D2, UBE2S, UBE2V1, UBE2V2, UBL3, VPS37C, WDHD1 | 17 | 15 | HS3ST1 | PDZRN3, PVRL3 | — | ANLN, ARHGAP24, ASPM, BUB1, CCDC99, CEP55, CKAP2, DRAM, E2F8, PLXNA2, SLC16A10, UBE2C, UBE2S, WDHD1 |
| — | 13 | ARHGEF3, CALY, CSH2, CTSL2, DIAPH3, ECEL1, FBP1, FFAR2, FRAT2, GSK3B, HSD17B4, IL6, IL19, KIF11, KIF2C, KNG1, LARGE, LEFTY2, LGR5, LIF, LPAR3, MPZ, MSLN, ORM2, PFKFB3, PLK4, PMP22, PRPH, PRSS8, PTGER3, SCN7A, SCNN1B, SLC4A11, TAL1 | 17 | 14 | CALY | ARHGEF3, GSK3B, RMP22 | CALY | ARHGEF3, CTSL2, DIAPH3, FBP1, KIF2C, KIF11, PFKFB3, PLK4 |
| — | 14 | AGT, AGTRAP, Beta ARK, CADPS, CD160, COL5A1, CPNE8, FNDC5, HSPC159, INA, ITGA7, LIMA1, LPP, MAB21L2, MAPK1, MERTK, MICAL2, MIRN294, MIRN185, MIRN352, NTN1, PLCG1, PLCG2, PTGFR, RASGEF1B, RBM4B, RSU1, SKAP1, SLITRK5, SPRED1, ST8SIA2, SYN2, TGFB3, TNS1, ZNF367 | 15 | 13 | CPNE3 | CADPS, FNDC5, MAB21L2, SLITRK5, ST8SIA2 | COL5A1, MICAL2 | FNDC5, HSPC159, MAB21L2, SLITRK5, SYN2, ZNF367 |
| — | 15 | ACT1, BAG5, CPVL, EXO1, GIPC1, GJC1, GPR37, HSPA5, HSPA1A, HSPBP1, IkBKB, KCTD12, MAP3K3, | 15 | 13 | — | KCTD12, TPBG | OLFML2A, SIGIRR | EXO1, KCTD12, MYO6, PHEBL1, SHCBP1, TPBG, TUBB6 |

TABLE 13-continued

IPA Core Analysis of Profile Genes

| Group | Network | Proteins in Network | pvalue | Profile Gene Number | Expression Undifferentiated State Decreased | Expression Undifferentiated State Increased | Expression Differentiated State Decreased | Expression Differentiated State Increased |
|---|---|---|---|---|---|---|---|---|
| B | 16 | MAP3K14, MEKK3/NIK, MIRN30B, MYO6, OLFML2A, PELI3, RHEBL1, RNF126, RPL10A, RPN1, SEC16A, SHC1, SHCBP1, SIGIRR, TJP3, TPBG, TRAF6, TRAF2-TRAF5, TRAF2-TRAF5, TRAF6, TUBB6, TUBB2B ABCC8, BACE2, CLASP1, COLEC12, CXCR7, DACT1, ENTPD5, FGD6, FMO1, GSTT1, IL17B, KRT34, KYNU, LAMP3, LMCD1, MIRN101B, MMD, NEBL, NFRKB, OSBPL3, PCDH8, PEMT, RASAL2, SAMD4A, ST3GAL3, SYNGR3, SYNPO2, TNF, TNNC1, TXN2, YWHAG, ZNF267, ZYX | 15 | 13 | IL17B | DACT1, PCDH8 | ABCC8, IL17B, NEEBL | MMD, OSBPL3, SYNPO2 |
| — | 17 | ARPP-19, BTG3, CBFA2T2, CBLN1, CNGA2, EBF1, EGF, EGFR, GABA, GABRA5, GABRB3, GABRD, GABRR1, HDAC9, HPCAL1, HTT, IDS, INSL3, LPAR5, OPRL1, PCDH9, PDE10A, PDE11A, PDE1A, PDE1B, PDE2A, PDE4C, PDE6H, PPAP2B, PPP1R1B, ROBO2, SH3D2C1, TRIP10, ZNF521 | 14 | 13 | HPCAL1 | PPAP2B | HPCAL1, LPAR5 | BTG3, GABRA5, TRIP10, ZNF521 |
| A | 18 | ANXA2, AQP1, C11ORF82, CCNI, CDKN2A, DEFB104A, DEFB4, EGLN3, ERAP1, FAM129A, GNAO1, IFNG, IL1B, IL1F7, INCA, LOC729687, MELK, MINA, MIRN210, MPA2L, MYC, NNAT, PDE5A, RGS11, RNASE7, RT1-B, SCLY, SCUBE1, SLC11A1, SLC14A1, SLC1A3, ST18, TSH, TMEM35, TREM3 | 14 | 12 | AQP1, CDKN2A | MINA, PDE5A | ANXA2, CDKN2A, ERAP1, RGS11 | C11ORF82, MELK, MINA, PDE5A, SCLY, SLC1A3, TMEM35 |
| — | 19 | BIRC8, BNC2, CASP5, CASP10, CASP14, CASP, CBLN2, DEDD2, DNASE1L1, DPYD, DSG3, EIF4E, EMILIN2, HTR1D, HTR1E, HTR1F, HTR3A, IFT57, KHDC1, MIRN20A, MTCH1, NGFR, PLXNA4, PPIL5, RB1, RP11-257K9.7, SEMA6D, SERPINA3K, SORCS1, STK25, SYT5, TACC3, TERT | 10 | 10 | — | EMILIN2, PLXNA4 | HTR1E, SORCS1 | BNC2, DPYD, EMILIN2, PPIL5, TACC3 |
| — | 20 | EGFL7, GFI1B | 2 | 1 | — | — | — | — |
| — | 21 | AGRN, PRSS12 | 2 | 1 | — | — | — | — |
| — | 22 | KCNB1, KCNG3 | 2 | 1 | — | — | — | — |
| — | 23 | NUP37, NUP43 | 2 | 1 | — | — | — | — |
| — | 24 | HS6ST1, HS6ST2 | 2 | 1 | — | — | — | — |
| — | 25 | FUCA1, FUCA2 | 2 | 1 | — | — | — | — |
| — | 26 | IQGAP, IQGAP3, MIRN339 | 2 | 1 | — | — | — | — |

Example V

Pathway Analysis of Gene Expression Profiles from Clonal Cell Lines

The following example illustrates how to characterize gene expression profiles from clonal cells from an established clonal cell line that are susceptible to BoNT/A intoxication or have neurotoxin uptake capacity in order to identify biological networks or pathways associated with BoNT/A intoxication. Computer analysis was performed to characterize the RNA expression phenotype of two independently derived single clone cell lines, BB10 and H1, very sensitive to BoNT/A activity and a single clone cell line, 2D6, that was less sensitive BoNT/A activity. The results are useful in identifying clonal cell lines selected from the SiMa parental cell line that are useful to practice the methods disclosed in the present specification.

To identify the specific gene expression phenotype associated with a BoNT/A sensitive cell line, the data was analyzed using JMP Genomic (SAS Institute Inc., Cary, N.C.). To perform a JMP Genomics analysis, the RNA expression data was imported to JMP Genomics by creating two SAS files, designated "data" and "Experiment design." A basic expression workflow was performed, including a variance analysis and one-way analysis of variance (one-way ANOVA) to identify differences in mean expression values. The variance analysis was used to identify differences between the cell lines and the differentiation state of each cell line (differentiated or non-differentiated). The expression values of all four cell lines were compared pair wise, independent of differentiation and genes that were 4-fold over-expressed in the H1 cell line as compared to the 2D6 cell line, in the BB10 cell line as compared to the 2D6 cell line, and in SiMa parental cell line (PA) compared to the 2D6 cell line. The variance analysis treats all factors in the study as random effects, to find out what their contribution is to the proportion of variance explained (total variance=100%). About half of the variance, 46.9% was assigned to differences among the different cell types, while 26% was assigned to differences before and after differentiation. Only 4.6% of the variance was assigned to differences among differentiated or non-differentiated cells types, meaning that the genes that were differentially expressed after differentiation were similar for all cell types examined, suggesting that the difference in BoNT/A sensitivity among the cell lines is independent of differentiation state. As such, the focus was placed on genes that are different among the different cells types irrespective of differentiation.

Based on the results from the variance analysis, the expression values of all cell lines were compared pair wise, independent of differentiation (FIG. 2). Only gene probes that were ≧4-fold over-expressed in the H1 cell line as compared to the 2D6 cell line, and in the BB10 cell line as compared to the 2D6 cell line are shown. The gene probes were plotted as expression value ($Log_2$) on the x-axis and p-value ($-log_{10}$(p-value)) on the y-axis. The red dashed line marks the 95% confidence interval. The genes probes that were 4-fold over-expressed in the H1 cell line as compared to the 2D6 cell line (FIG. 2A), and the BB10 cell line as compared to the 2D6 cell line (FIG. 2B), were also to a large extend among the genes that were over-expressed in the BB10 cell line as compared to the SiMa parental cell line (PA, FIG. 2C), in the H1 cell line as compared to the SiMa parental cell line (FIG. 2D), and in the SiMa parental cell line as compared to the 2D6 cell line (FIG. 2E). These data suggest that BoNT/A sensitivity was related to a gradual increase in expression of these genes. Based on this finding, the number of gene probes was further narrowed down to 119 by including only gene probes that were also over-expressed in the SiMa parental cell line compared to the 2D6 cell line, rationalizing that gene probes that were differential expressed across one more cell line would be even more likely to be important for BoNT/A sensitivity. As such, the JMP Genomic analysis resulted in the identification of 119 gene probes, designated the JMP probe set.

The JMP probe set was exported to Ingenuity Pathway Analysis (IPA) Core Analysis (Ingenuity Systems Inc., Redwood City, Calif.) to further characterize the JMP probe set. Using this analysis, biologically relevant networks to BoNT/A intoxication were identified based on connectivity among the genes from an IPA library and the gene probes contained in the JMP probe set. The significance of the association to a given network was measured and ranked by the ratio of the number of gene probes from the JMP probe set that mapped to the specific network divided by the total number of genes that map to that network. Fisher's exact test was used to calculate p-scores, and based on the p-scores the genes from the JMP probe set were used to rank the networks. The p-scores were derived from p-values. If there are n genes in the network and f of them are gene probes from the JMP probe set, then the p-value is the probability of finding f or more gene probes from the JMP probe set in a set of n genes randomly selected from the Global Molecular Network. Since significant p-values are quite low (e.g., $1\times10^{-8}$), a p-score was defined as the component of the p-value; p-score=−log 10 (p-value). The identified networks were overlaid with differentially expressed genes which had more than 1.5-fold differential expression and a p-value≦0.001 either before or after differentiation. Using IPA Core Analysis, 111 of the 119 gene probes from the JMP probe set were mapped to networks. The eight unmapped probes most likely represent either a probe with an outdated nomenclature or one representing a gene without a known gene product. The 111 gene probes corresponded to 79 genes that were greater than 4.0-fold differentially expressed in the H1 and BB10 cell lines when compared to the 2D6 cell line and that were also greater than 4.0-fold differentially expressed in the SiMa parental cell lines when compared to the 2D6 cell line, when the p-value cut off was set to 0.05 (Table 14).

TABLE 14

Genes Identified using IPA Core Analysis

| Gene Name | Gene Symbol | Probe ID. No. | Location | Type | Log Ratio |
|---|---|---|---|---|---|
| Achaete-scute complex homolog 1 | ASCL1 | 209985_s_at | Nucleus | Transcription regulator | 4.469 |
| Achaete-scute complex homolog 1 | ASCL1 | 209988_s_at | Nucleus | Transcription regulator | 2.774 |
| Achaete-scute complex homolog 1 | ASCL1 | 213768_s_at | Nucleus | Transcription regulator | 2.955 |
| Acyl-CoA thioesterase 9 | ACOT9 | 221641_s_at | Cytoplasm | Enzyme | 2.251 |
| ADAM metallopeptidase with thrombospondin type 1 motif, 9 | ADAMTS9 | 226814_at | Extracellular Space | Peptidase | 4.034 |
| Ankyrin 2, neuronal | ANK2 | 216195_at | Plasma Membrane | Other | −2.673 |
| Ankyrin 2, neuronal | ANK2 | 232606_at | Plasma Membrane | Other | −2.621 |
| Blood vessel epicardial substance | BVES | 228783_at | Plasma Membrane | Other | 3.174 |
| Brain abundant, membrane attached signal protein 1 | BASP1 | 202391_at | Plasma Membrane | Other | 4.549 |

TABLE 14-continued Genes Identified using IPA Core Analysis

| Gene Name | Gene Symbol | Probe ID. No. | Location | Type | Log Ratio |
|---|---|---|---|---|---|
| BRCA1 associated RING domain 1 | BARD1 | 205345_at | Nucleus | Transcription regulator | 3.44 |
| Calsyntenin 2 | CLSTN2 | 219414_at | Plasma Membrane | Transporter | 2.024 |
| cAMP responsive element binding protein 5 | CREB5 | 232555_at | Nucleus | Transcription | −2.67 |
| Cathepsin L2 | CTSL2 | 210074_at | Cytoplasm | Peptidase | 2.119 |
| CD9 molecule | CD9 | 201005_at | Plasma Membrane | Other | 2.887 |
| Cell division cycle associated 7-like | CDCA7L | 225081_s_at | Nucleus | Other | 3.737 |
| Centromere protein L | CENPL | 1554271_a_at | Unknown | Other | 2.582 |
| Chromosome 11 open reading frame 75 | C11ORF75 | 219806_s_at | Unknown | Other | 3.914 |
| Chromosome 3 open reading frame 70 | C3ORF70 | 242447_at | Unknown | Other | 2.705 |
| Coiled-coil domain containing 109B | CCDC109B | 218802_at | Unknown | Other | 2.881 |
| Contactin 1 | CNTN1 | 211203_s_at | Plasma Membrane | Enzyme | 3.684 |
| Contactin 1 | CNTN1 | 227202_at | Plasma Membrane | Enzyme | 3.184 |
| Contactin 1 | CNTN1 | 227209_at | Plasma Membrane | Enzyme | 3.188 |
| Copine VIII | CPNE8 | 228365_at | Unknown | Other | −3.355 |
| Copine VIII | CPNE8 | 241706_at | Unknown | Other | −2.736 |
| CUG triplet repeat, RNA binding protein 2 | CUGBP2 | 202157_s_at | Nucleus | Other | 3.588 |
| Cyclin-dependent kinase 2 | CDK2 | 204252_at | Nucleus | Kinase | 2.744 |
| Cysteine and glycine-rich protein 2 | CSRP2 | 207030_s_at | Nucleus | Other | 2.487 |
| Cysteine and glycine-rich protein 2 | CSRP2 | 211126_s_at | Nucleus | Other | 2.109 |
| DEP domain containing 1 | DEPDC1 | 220295_x_at | Unknown | Other | 2.795 |
| Diaphanous homolog 3 | DIAPH3 | 232596_at | Cytoplasm | Enzyme | 2.434 |
| Dihydropyrimidine dehydrogenase | DPYD | 204646_at | Cytoplasm | Enzyme | 4.248 |
| Docking protein 5 | DOK5 | 214844_s_at | Plasma Membrane | Other | 4.56 |
| Dynein, light chain, Tctex-type 3 | DYNLT3 | 203303_at | Cytoplasm | Other | 3.449 |
| Elastin microfibril interfacer 2 | EMILIN2 | 224374_s_at | Extracellular Space | Other | 2.603 |
| Ets variant 1 | ETV1 | 206501_x_at | Nucleus | Transcription regulator | 2.578 |
| Ets variant 1 | ETV1 | 217053_x_at | Nucleus | Transcription regulator | 2.499 |
| Ets variant 1 | ETV1 | 217061_s_at | Nucleus | Transcription regulator | 2.557 |
| Family with sequence similarity 101, member B | FAM101B | 226876_at | Unknown | Other | 2.399 |
| Fibroblast growth factor receptor 2 | FGFR2 | 203638_s_at | Plasma Membrane | Kinase | 2.306 |
| Fibroblast growth factor receptor 2 | FGFR2 | 203639_s_at | Plasma Membrane | Kinase | 3.239 |
| Fibroblast growth factor receptor 2 | FGFR2 | 208228_s_at | Plasma Membrane | Kinase | 2.151 |
| Fibronectin type III domain containing 5 | FNDC5 | 226096_at | Unknown | Other | 2.054 |
| Fibulin 1 | FBLN1 | 201787_at | Extracellular Space | Other | 2.801 |
| Fibulin 1 | FBLN1 | 202994_s_at | Extracellular Space | Other | 2.378 |
| Fibulin 1 | FBLN1 | 202995_s_at | Extracellular Space | Other | 3.733 |
| G protein-coupled receptor 177 | GPR177 | 221958_s_at | Unknown | Other | 2.389 |
| G protein-coupled receptor 177 | GPR177 | 228950_s_at | Unknown | Other | 2.622 |
| G-2 and S-phase expressed 1 | GTSE1 | 204317_at | Cytoplasm | Other | 3.334 |
| Gametocyte specific factor 1 | GTSF1 | 227711_at | Unknown | Other | 6.407 |
| Guanine nucleotide binding protein (G protein), alpha inhibiting activity polypeptide 1 | GNAI1 | 227692_at | Plasma Membrane | Enzyme | 3.123 |
| Guanine nucleotide binding protein (G protein), beta polypeptide 4 | GNB4 | 225710_at | Plasma Membrane | Enzyme | 6.066 |
| Guanine nucleotide binding protein (G protein), gamma 11 | GNG11 | 204115_at | Plasma Membrane | Enzyme | 4.251 |
| Guanine nucleotide binding protein (G protein), gamma 12 | GNG12 | 212294_at | Plasma Membrane | Enzyme | 2.315 |

TABLE 14-continued

Genes Identified using IPA Core Analysis

| Gene Name | Gene Symbol | Probe ID. No. | Location | Type | Log Ratio |
|---|---|---|---|---|---|
| Guanine nucleotide binding protein (G protein), gamma 12 | GNG12 | 222834_s_at | Plasma Membrane | Enzyme | 3.403 |
| Hepatocyte growth factor (hepapoietin A) | HGF | 209960_at | Extracellular Space | Growth factor | 2.939 |
| Hypothetical protein LOC100289109 | LOC100289109 | 216189_at | Unknown | Other | −3.256 |
| Hypothetical protein LOC144571 | LOC144571 | 1564139_at | Unknown | Other | −2.394 |
| Inositol 1,4,5-triphosphate receptor interacting protein | ITPRIP | 225582_at | Unknown | Other | 3.522 |
| Interleukin 17B | IL17B | 220273_at | Extracellular Space | Cytokine | −4.735 |
| KDEL (Lys-Asp-Glu-Leu) containing 2 | KDELC2 | 225128_at | Unknown | Other | 3.003 |
| KIAA0125 | KIAA0125 | 206478_at | Unknown | Other | −8.436 |
| KIT ligand | KITLG | 226534_at | Extracellular Space | Growth factor | 2.59 |
| LY6/PLAUR domain containing 6 | LYPD6 | 227764_at | Extracellular Space | Other | 2.64 |
| Lysophosphatidic acid receptor 1 | LPAR1 | 204036_at | Plasma Membrane | Receptor | 3.151 |
| MAB-21-like 2 | MAB21L2 | 210303_at | Unknown | Other | 3.817 |
| Minichromosome maintenance complex component 10 | MCM10 | 223570_at | Nucleus | Other | 2.249 |
| Moesin | MSN | 200600_at | Plasma Membrane | Other | 5.842 |
| Monoamine oxidase A | MAOA | 204388_s_at | Cytoplasm | Enzyme | 4.029 |
| Monoamine oxidase A | MAOA | 204389_at | Cytoplasm | Enzyme | 3.355 |
| Monoamine oxidase A | MAOA | 212741_at | Cytoplasm | Enzyme | 4.157 |
| MYC induced nuclear antigen | MINA | 213188_s_at | Nucleus | Other | 4.019 |
| MYC induced nuclear antigen | MINA | 213189_at | Nucleus | Other | 4.636 |
| Myosin VI | MYO6 | 203216_s_at | Cytoplasm | Other | 2.406 |
| Myosin VIIA and Rab interacting protein | MYRIP | 214156_at | Cytoplasm | Other | 2.805 |
| Neuronal PAS domain protein 4 | NPAS4 | 1554299_at | Nucleus | Transcription regulator | −2.515 |
| Paternally expressed 3 | PEG3 | 209242_at | Nucleus | Kinase | 5.896 |
| Paternally expressed 3 | PEG3 | 209243_s_at | Nucleus | Kinase | 4.556 |
| Phosphoprotein associated with glycosphingolipid microdomains 1 | PAG1 | 225626_at | Plasma Membrane | Other | 2.193 |
| Poliovirus receptor-related 3 | PVRL3 | 213325_at | Plasma Membrane | Other | 2.325 |
| Polo-like kinase 2 | PLK2 | 201939_at | Nucleus | Kinase | 4.93 |
| Polymerase (DNA directed), alpha 2 (70kD subunit) | POLA2 | 204441_s_at | Nucleus | Enzyme | 2.198 |
| Prolactin releasing hormone receptor | PRLHR | 231805_at | Plasma Membrane | Receptor | 3.19 |
| Prostaglandin reductase 1 | PTGR1 | 228824_s_at | Cytoplasm | Enzyme | 2.398 |
| Prostaglandin reductase 1 | PTGR1 | 231897_at | Cytoplasm | Enzyme | 2.33 |
| Protease, serine, 12 (neurotrypsin, motopsin) | PRSS12 | 205515_at | Extracellular Space | Peptidase | 5.146 |
| Protein phosphatase 1, regulatory (inhibitor) subunit 3C | PPP1R3C | 204284_at | Cytoplasm | Phosphatase | 2.827 |
| Protein tyrosine phosphatase, receptor type, K | PTPRK | 203038_at | Plasma Membrane | Phosphatase | 3.451 |
| RAB32, member RAS oncogene family | RAB32 | 204214_s_at | Cytoplasm | Other | 2.192 |
| RELT-like 1 | RELL1 | 226430_at | Unknown | Other | 2.88 |
| Rho GTPase activating protein 24 | ARHGAP24 | 223422_s_at | Cytoplasm | Other | 3.043 |
| Rho guanine nucleotide exchange factor (GEF) 3 | ARHGEF3 | 218501_at | Cytoplasm | Other | 2.473 |
| Ring finger protein 182 | RNF182 | 230720_at | Unknown | Other | 4.746 |
| RNA binding protein with multiple splicing | RBPMS | 209487_at | Unknown | Other | 2.329 |
| RNA binding protein with multiple splicing | RBPMS | 209488_s_at | Unknown | Other | 3.292 |
| Secreted protein, acidic, cysteine-rich (osteonectin) | SPARC | 200665_s_at | Extracellular Space | Other | 4.919 |
| Secreted protein, acidic, cysteine-rich (osteonectin) | SPARC | 212667_at | Extracellular Space | Other | 4.58 |
| Shugoshin-like 2 | SGOL2 | 230165_at | Nucleus | Other | 3.108 |
| Similar to hCG2031213 | LOC728052 | 1558795_at | Unknown | Other | 3.402 |
| Solute carrier family 1 (glial high affinity glutamate transporter), member 2 | SLC1A2 | 225491_at | Plasma Membrane | Transporter | −4.354 |
| Solute carrier family 43, member 3 | SLC43A3 | 210692_s_at | Extracellular Space | Other | 3.126 |

TABLE 14-continued

Genes Identified using IPA Core Analysis

| Gene Name | Gene Symbol | Probe ID. No. | Location | Type | Log Ratio |
|---|---|---|---|---|---|
| Solute carrier family 43, member 3 | SLC43A3 | 213113_s_at | Extracellular Space | Other | 2.804 |
| Solute carrier family 44, member 5 | SLC44A5 | 1569112_at | Unknown | Other | 3.923 |
| Solute carrier family 44, member 5 | SLC44A5 | 235763_at | Unknown | Other | 4.439 |
| Solute carrier family 7 (cationic amino acid transporter, y+ system), member 2 | SLC7A2 | 225516_at | Plasma Membrane | Transporter | 3.23 |
| Sortilin-related VPS10 domain containing receptor 1 | SORCS1 | 1556891_at | Plasma Membrane | Transporter | −2.424 |
| SPC25, NDC80 kinetochore complex component, homolog | SPC25 | 209891_at | Unknown | Other | 2.634 |
| ST8 alpha-N-acetyl-neuraminide alpha-2,8-sialyltransferase 4 | ST8SIA4 | 230836_at | Cytoplasm | Enzyme | 2.705 |
| Structural maintenance of chromosomes 2 | SMC2 | 204240_s_at | Nucleus | Transporter | 2.442 |
| Structural maintenance of chromosomes 6 | SMC6 | 218781_at | Nucleus | Other | 3.327 |
| Structural maintenance of chromosomes 6 | SMC6 | 236535_at | Nucleus | Other | 3.44 |
| Syndecan 2 | SDC2 | 212154_at | Plasma Membrane | Other | 2.367 |
| Syndecan 2 | SDC2 | 212158_at | Plasma Membrane | Other | 2.098 |
| Thrombospondin 2 | THBS2 | 203083_at | Extracellular Space | Other | −2.81 |
| Thyroid hormone receptor interactor 10 | TRIP10 | 202734_at | Cytoplasm | Other | 2.663 |
| Tissue factor pathway inhibitor 2 | TFPI2 | 209278_s_at | Extracellular Space | Other | 4.666 |
| Transcription factor 7-like 1 (T-cell specific, HMG-box) | TCF7L1 | 221016_s_at | Nucleus | Transcription regulator | 2.835 |
| Transmembrane phosphatase with tensin homology | TPTE | 220205_at | Plasma Membrane | Phosphatase | 6.04 |
| Transmembrane protein 178 | TMEM178 | 229302_at | Unknown | Other | 3.194 |
| Transmembrane protein 35 | TMEM35 | 219685_at | Unknown | Other | 2.879 |
| Tumor necrosis factor, alpha-induced protein 8 | TNFAIP8 | 210260_s_at | Cytoplasm | Other | 2.389 |
| Twist homolog 1 | TWIST1 | 213943_at | Nucleus | Transcription regulator | 2.573 |
| Zinc finger protein 521 | ZNF521 | 226676_at | Nucleus | Other | 2.382 |
| Zinc finger protein 521 | ZNF521 | 226677_at | Nucleus | Other | 2.943 |
| Zinc finger protein 814 | ZNF814 | 1556204_a_at | Unknown | Other | −2.505 |

The log ratio represent $\log_2$ values where 0.585 is $\log_2(1.5)$ which is a 1.5-fold difference, 1 is $\log_2(2)$ which is a 2-fold difference, 1.584 is $\log_2(3)$ which is a 3-fold difference, 2 is $\log_2(4)$ which is a 4-fold difference, 2.321 is $\log_2(5)$ which is a 5-fold difference, 2.584 is $\log_2(6)$ which is a 6-fold difference, 2.807 is $\log_2(7)$ which is a 7-fold difference, 3 is $\log_2(8)$ which is a 8-fold difference, 3.169 is $\log_2(9)$ which is a 9-fold difference, and 3.321 is $\log_2(10)$ which is a 10-fold difference.

Using IPA Core Analysis, 73 of the 79 genes were mapped to 5 different protein networks (Table 15). Based on overlapping gene mapping, 73 of the 79 genes that were up-regulated could be associated with two major protein network groups, named A and B (Table 15). Networks 1, 2 and 5 belong to Group A, and Networks 3 and 4 belong to Group B. Similarly, all down-regulated genes were all associated with one network, named C (Table 15).

Group A genes include the FGFR2 receptor which has been shown to function in the BoNT/A intoxication process as a receptor for BoNT/A and are as follows: genes exhibiting a 1.5-fold or more increase in expression levels in the H1 and BB10 cell lines as compared to their expression in cells from the 2D6 cell line, ADAMTS9, ARHGAP24, ARHGEF3, ASCL1, BARD1, CD9, CDK2, CSRP2, CTSL2, DIAPH3, DOK5, DYNLT3, EMILIN2, ETV1, FBLN1, FGFR2, GNAI1, GNB4, GNG11, GNG12, HGF, KITLG, LPAR1, MCM10, MSN, PAG1, PEG3, PLK2, POLA2, PPP1R3c, PTPRK, RAB32, SDC2, SLC43A3, SLC7A2, SMC6, SPARC, SPC25, ST8SIA4, TCF7L1, TFPI2, TMEM35, TNFAIP8, TPTE, TRIP10, and TWIST1.

Group B genes are as follows: genes exhibiting a 1.5-fold or more increase in expression levels in the H1 and BB10 cell lines as compared to their expression in cells from the 2D6 cell line, ACOT9, BASP1, C11ORF75, CCDC109B, CDCA7L, CLSTN2, CNTN1, CUGBP2, DEPDC1, DPYD, FAM101B, FNDC5, GTSE1, MAOA, MINA, MYO6, MYRIP, PLK2, PRLHR, PVRL3, RBPMS, SGOL2, SMC2, TFP12, TMEM178, and ZNF521.

Group C genes are as follows: genes exhibiting a 1.5-fold or more decrease in expression levels in the H1 and BB10 cell lines as compared to their expression in cells from the 2D6 cell line, ANK2, CPNE8, CREBS, IL17B, KIAA0125, LOC100289109, LOC144571, NPAS4, SLC1A2, SORCS1, THBS2, and/or ZNF814.

The remaining networks identified did not share common genes between any other network. Individually, however, genes exhibiting a 1.5-fold or more increase in expression levels in the H1 and BB10 cell lines as compared to their expression in cells from the 2D6 cell line were as follows: C3ORF70 (Network 6), MAB21L2 (Network 7), PRSS12 (Network 8), CENPL (Network 9), GPR177 (Network 10), and PTGR1 (Network 11).

TABLE 15

IPA Core Analysis of Genes

| Network | Group | Proteins in Network | JMP pvalue | Gene Number | Expression Profile Increased | Decreased |
|---|---|---|---|---|---|---|
| 1 | A | ADAMTS9, AKT, ASCL1, CDK2, CSRP2, CTSL2, DOK5, E2F, FBLN1, FSH, GNAI1, GNG11, hCG, HGF, KITLG, LPAR1, MAPK, MCM10, MEK, MSN, NFκB, P38, MAPK, PAG1, PDGF BB, PEG3, PLK2, RAC, RAS, SDC2, SPARC, TFPI2, TGFβ, TNFAIP8, TRIP10, VEGF | 48 | 22 | ADAMTS9, ASCL1, CDK2, CSRP2, CTSL2, DOK5, FBLN1, GNAI1, GNG11, HGF, KITLG, LPAR1, MCM10, MSN, PAG1, PEG3, PLK2, SDC2, SPARC, TFPI2, TNFAIP8, TRIP10 | — |
| 2 | A | CASP3, Caspase 3/7, CCL6, DIAPH3, DYNLT3, EMILIN2, EPM2A, ETV1, EYA2, FAM3B, FASTK, GNAI1, GNB4, GNG10, GNG11, GNG12, GSTM2, HK1, IGFBP3, IL13, PLCE1, POLA2, PPP1R3C, PTPRK, PTPRZ1, RAB32, SLC43A3, SLC7A2, SRC, ST8SIA4, TNF, TPTE, TWIST1 | 35 | 17 | DIAPH3, DYNLT3, EMILIN2, ETV1, GNAI1, GNB4, GNG11, GNG12, POLA2, PPP1R3C, PTPRK, RAB32, SLC43A3, SLC7A2, ST8SIA4, TPTE, TWIST1 | — |
| 3 | B | ACOT9, AR, ATXN7, BASP1, CCNE2, CCNK, CLSTN2, CNTN1, CUGBP2, DGKA, FNDC5, GTSE1, IL4, MAOA, MSH2, NOVA1, NF1, PICK1, PLK2, PNRC1, POM121, PRLHR, PTP4A1, PTP4A2, PVRL1, PVRL3, PVRL4, RBPMS, SERPINB5, SMARCA4, SPN, TFPI2, TP53, ZNF521 | 26 | 14 | ACOT9, BASP1, CLSTN2, CNTN1, CUGBP2, FNDC5, GTSE1, MAOA, PLK2, PRLHR, PVRL3, RBPMS, TFPI2, ZNF521 | — |
| 4 | B | ARHGAP17, AXL, C11ORF75, CAPN6, CCDC109B, CDCA7L, DEPDC1, DPYD, EIF4E, FAM101B, GRB2, HNRNPF, HTATIP2, MAOA, MINA, MIR124, MIRLET7A1, MYC, MYO6, MYRIP, NCAPD3, NF2, PPP2R5A, PPP2R5D, PPP2R5E, RPS16, RPS23, SGOL2, SLC25A12, SMC2, SMC4, TMEM178, TUSC2, TXNIP, ZBTB16 | 24 | 13 | C11ORF75, CCDC109B, CDCA7L, DEPDC1, DPYD, FAM101B, MAOA, MINA, MYO6, MYRIP, SGOL2, SMC2, TMEM178 | — |
| 5 | A | ARHGAP24, ARHGEF, ARHGEF3, BARD1, CD9, CD53, CTNNB1, DUSP3, ERK, ERM, FGF9, FGF18, FGF21, FGF23, FGFR2, IL1, IL6, IL17RD, Integrin6β1, KLB, LEF/TCF, LPAR1, MIRN297-2, PI3K, RAS homolog, RNAPOLII, SLC26A2, SMC6, SPC25, SREBF1, TACC1, TCF7L1, TMEM35, TPT1, WISP1 | 17 | 10 | ARHGAP24, ARHGEF3, BARD1, CD9, FGFR2, LPAR1, SMC6, SPC25, TCF7L1, TMEM35 | — |
| 6 | — | C3ORF70, MIR31 | 2 | 1 | C3ORF70 | — |
| 7 | — | MAB21L2, MIRN294 | 2 | 1 | MAB21L2 | — |
| 8 | — | AGPN, PRSS12 | 2 | 1 | PRSS12 | — |
| 9 | — | CENPL, MIRN340 | 2 | 1 | CENPL | — |
| 10 | — | GPR177, MIRN324 | 2 | 1 | GPR177 | — |
| 11 | — | ADH, PTGR1 | 2 | 1 | PTGR1 | — |
| 12 | C | ANK2, ATP2A2, BDNF, CEBPG, CPNE8, CREB5, GRM3, GRM5, IGFBP2, IL17B, ITPR, ITPR1, K+, L1CAM, MIRN330, Neurotrophin, NFE2L1, NGFR, NME1, NPAS4, Pro-inflammatory Cytokine, PSEN1, SCN2A, SCN3A, SCNN1B, SLC1A2, SLC8A1, SORCS1, SORT1, TGFA, THBS2, TNF, TNFAIP6 | 22 | 8 | — | ANK2, CPNE8, CREB5, IL17B, KIAA0125, LOC100289109, LOC144571, NPAS4, SLC1A2, SORCS1, THBS2, ZNF814 |

Computer analysis was performed as in Example V, except that the list of probes reflects genes that were greater than 1.5-fold differential expressed in the H1 and the BB10 cell lines when compared to both the 2D6 and SiMa parental cell lines. When the p-value cut off was set to 0.05, this analysis identified 439 gene probes that could be classified to 369 genes (Table 16).

TABLE 16

Genes Identified using IPA Core Analysis

| Gene Name | Gene Symbol | Probe ID. No. | Location | Type | Log Ratio |
|---|---|---|---|---|---|
| 6-phosphofructo-2-kinase/fructose-2,6-biphosphatase 3 | PFKFB3 | 202464_s_at | Cytoplasm | kinase | 1.811 |
| achaete-scute complex homolog 1 | ASCL1 | 209985_s_at | Nucleus | transcription regulator | 2.429 |
| achaete-scute complex homolog 1 | ASCL1 | 209987_s_at | Nucleus | transcription regulator | 2.097 |
| achaete-scute complex homolog 1 | ASCL1 | 209988_s_at | Nucleus | transcription regulator | 1.446 |
| achaete-scute complex homolog 1 | ASCL1 | 213768_s_at | Nucleus | transcription regulator | 1.578 |
| activated leukocyte cell adhesion molecule | ALCAM | 1569362_at | Plasma Membrane | other | 2.612 |
| activated leukocyte cell adhesion molecule | ALCAM | 201951_at | Plasma Membrane | other | 1.774 |
| activated leukocyte cell adhesion molecule | ALCAM | 201952_at | Plasma Membrane | other | 1.521 |
| acyl-CoA thioesterase 1 | ACOT1 | 202982_s_at | Cytoplasm | enzyme | −2.875 |
| acylphosphatase 2, muscle type | ACYP2 | 206833_s_at | unknown | enzyme | −1.15 |
| additional sex combs like 3 | ASXL3 | 233536_at | unknown | other | 1.572 |
| adenosine deaminase, RNA-specific, B1 | ADARB1 | 203865_s_at | Nucleus | enzyme | −2.474 |
| adenylate cyclase 1 | ADCY1 | 213245_at | Plasma Membrane | enzyme | −1.935 |
| adipocyte-specific adhesion molecule | ASAM | 228082_at | Plasma Membrane | other | −2.802 |
| ADP-ribosylation factor 1 | ARF1 | 1565651_at | Cytoplasm | enzyme | 1.063 |
| ADP-ribosylation factor-like 17A | ARL17A | 243899_at | unknown | other | 0.741 |
| anaphase promoting complex subunit 7 | ANAPC7 | 225554_s_at | unknown | other | 0.679 |
| ankyrin repeat and BTB (POZ) domain containing 1 | ABTB1 | 229164_s_at | Cytoplasm | translation regulator | −0.656 |
| ankyrin repeat domain 50 | ANKRD50 | 225731_at | unknown | other | −0.654 |
| ankyrin repeat domain 50 | ANKRD50 | 225735_at | unknown | other | −1.114 |
| aspartate beta-hydroxylase domain containing 1 | ASPHD1 | 214993_at | unknown | other | −0.763 |
| ataxin 2-binding protein 1 | A2BP1 | 1553422_s_at | Cytoplasm | other | 1.453 |
| ataxin 2-binding protein 1 | A2BP1 | 221217_s_at | Cytoplasm | other | 1.497 |
| ATPase, Ca++ transporting, plasma membrane 3 | ATP2B3 | 207026_s_at | Plasma Membrane | transporter | −1.248 |
| ATPase, Ca++ transporting, plasma membrane 3 | ATP2B3 | 242036_x_at | Plasma Membrane | transporter | −1.777 |
| basonuclin 2 | BNC2 | 220272_at | Nucleus | other | 2.466 |
| basonuclin 2 | BNC2 | 230722_at | Nucleus | other | 1.641 |
| βγcrystallin domain containing 3 | CRYBG3 | 214030_at | unknown | other | 4.74 |
| β-site APP-cleaving enzyme 1 | BACE1 | 217904_s_at | Cytoplasm | peptidase | −1.57 |
| brain abundant, membrane attached signal protein 1 | BASP1 | 202391_at | Plasma Membrane | other | 1.146 |
| bromodomain and WD repeat domain containing 1 | BRWD1 | 225446_at | Nucleus | transcription regulator | −1.018 |
| bruno-like 4, RNA binding protein | BRUNOL4 | 238966_at | Nucleus | translation regulator | −0.81 |
| butyrophilin, subfamily 3, member A3 | BTN3A3 | 38241_at | unknown | other | −1.108 |
| C2 calcium-dependent domain containing 2 | C2CD2 | 212875_s_at | unknown | other | −1.27 |
| C2 calcium-dependent domain containing 4A | C2CD4A | 241031_at | unknown | other | −2.615 |
| cadherin 12, type 2 (N-cadherin 2) | CDH12 | 207149_at | Plasma Membrane | other | −1.408 |
| calcium/calmodulin-dependent protein kinase II inhibitor 2 | CAMK2N2 | 230706_s_at | Nucleus | other | −0.692 |
| calmin (calponin-like, transmembrane) | CLMN | 213839_at | Cytoplasm | other | −1.911 |
| calpain 2, (m/II) large subunit | CAPN2 | 208683_at | Cytoplasm | peptidase | −1.429 |
| CAP, adenylate cyclase-associated protein, 2 | CAP2 | 212551_at | Plasma Membrane | other | −1.974 |
| CAP, adenylate cyclase-associated protein, 2 | CAP2 | 212554_at | Plasma Membrane | other | −3.68 |

TABLE 16-continued

Genes Identified using IPA Core Analysis

| Gene Name | Gene Symbol | Probe ID. No. | Location | Type | Log Ratio |
|---|---|---|---|---|---|
| carboxypeptidase, vitellogenic-like | CPVL | 208146_s_at | unknown | peptidase | 1.708 |
| CART prepropeptide | CARTPT | 206339_at | Extracellular Space | other | −4.676 |
| Cas-Br-M (murine) ecotropic retroviral transforming sequence b | CBLB | 209682_at | Nucleus | other | 1.032 |
| CCR4-NOT transcription complex, subunit 6-like | CNOT6L | 227119_at | Cytoplasm | other | −0.785 |
| CD302 molecule | CD302 | 203799_at | Plasma Membrane | receptor | −1.518 |
| CD9 molecule | CD9 | 201005_at | Plasma Membrane | other | 1.415 |
| CDP-diacylglycerol synthase (phosphatidate cytidylyltransferase) 1 | CDS1 | 226185_at | Cytoplasm | enzyme | −1.74 |
| cell division cycle 25 homolog B (*S. pombe*) | CDC25B | 201853_s_at | Nucleus | phosphatase | 1.453 |
| chemokine (C—X—C motif) receptor 4 | CXCR4 | 209201_x_at | Plasma Membrane | receptor | 4.135 |
| chemokine (C—X—C motif) receptor 4 | CXCR4 | 211919_s_at | Plasma Membrane | receptor | 3.957 |
| chemokine (C—X—C motif) receptor 4 | CXCR4 | 217028_at | Plasma Membrane | receptor | 3.176 |
| chloride channel 3 | CLCN3 | 201733_at | Plasma Membrane | ion channel | −0.908 |
| chloride channel 3 | CLCN3 | 201734_at | Plasma Membrane | ion channel | −0.987 |
| cholinergic receptor, nicotinic, alpha 7 | CHRNA7 | 210123_s_at | Plasma Membrane | receptor | 3.098 |
| chromosome 1 open reading frame 21 | C1ORF21 | 221272_s_at | unknown | other | −0.74 |
| chromosome 1 open reading frame 21 | C1ORF21 | 223127_s_at | unknown | other | −0.748 |
| chromosome 1 open reading frame 43 | C1ORF43 | 1555225_at | unknown | other | 1.604 |
| chromosome 10 open reading frame 58 | C10ORF58 | 224435_at | Extracellular Space | other | 0.918 |
| chromosome 12 open reading frame 49 | C12ORF49 | 218867_s_at | unknown | other | 0.692 |
| chromosome 16 open reading frame 52 | C16ORF52 | 230721_at | unknown | other | −0.87 |
| chromosome 20 open reading frame 7 | C20ORF7 | 227160_s_at | unknown | other | 0.624 |
| chromosome 21 open reading frame 57 | C21ORF57 | 227421_at | unknown | other | −1.086 |
| chromosome 21 open reading frame 57 | C21ORF57 | 239208_s_at | unknown | other | −0.657 |
| chromosome 3 open reading frame 23 | C3ORF23 | 1555905_a_at | Cytoplasm | other | −2.797 |
| chromosome 3 open reading frame 23 | C3ORF23 | 1555906_s_at | Cytoplasm | other | −1.502 |
| chromosome 3 open reading frame 23 | C3ORF23 | 241666_at | Cytoplasm | other | −1.017 |
| chromosome 9 open reading frame 150 | C9ORF150 | 227443_at | unknown | other | −1.773 |
| claudin 12 | CLDN12 | 223249_at | Plasma Membrane | other | −0.766 |
| COBW domain containing 1 | CBWD1 | 226193_x_at | unknown | other | 0.849 |
| coiled-coil domain containing 3 | CCDC3 | 223316_at | Cytoplasm | other | 3.357 |
| collagen, type VI, alpha 1 | COL6A1 | 213428_s_at | Extracellular Space | other | −1.638 |
| cripto, FRL-1, cryptic family 1 | CFC1 | 223753_s_at | Extracellular Space | other | −2.834 |
| cripto, FRL-1, cryptic family 1 | CFC1 | 236724_at | Extracellular Space | other | −1.636 |
| CSE1 chromosome segregation 1-like | CSE1L | 210765_at | Nucleus | transporter | 1.581 |
| CUG triplet repeat, RNA binding protein 2 | CUGBP2 | 202156_s_at | Nucleus | other | 1.318 |
| CUG triplet repeat, RNA binding protein 2 | CUGBP2 | 202157_s_at | Nucleus | other | 2.156 |
| CUG triplet repeat, RNA binding protein 2 | CUGBP2 | 202158_s_at | Nucleus | other | 2.539 |
| cyclic nucleotide gated channel alpha 3 | CNGA3 | 207261_at | Plasma Membrane | ion channel | −3.182 |

TABLE 16-continued

Genes Identified using IPA Core Analysis

| Gene Name | Gene Symbol | Probe ID. No. | Location | Type | Log Ratio |
|---|---|---|---|---|---|
| cyclin M1 | CNNM1 | 220166_at | Plasma Membrane | other | −1.214 |
| cyclin-dependent kinase inhibitor 2A (melanoma, p16, inhibits CDK4) | CDKN2A | 209644_x_at | Nucleus | transcription regulator | −1.277 |
| cylindromatosis (turban tumor syndrome) | CYLD | 213295_at | Nucleus | transcription regulator | −0.815 |
| cytochrome P450, family 2, subfamily E, polypeptide 1 | CYP2E1 | 1431_at | Cytoplasm | enzyme | −4.466 |
| cytochrome P450, family 2, subfamily E, polypeptide 1 | CYP2E1 | 209975_at | Cytoplasm | enzyme | −3.946 |
| cytochrome P450, family 2, subfamily E, polypeptide 1 | CYP2E1 | 209976_s_at | Cytoplasm | enzyme | −3.429 |
| cytoglobin | CYGB | 1553572_a_at | Cytoplasm | transporter | −4.921 |
| cytokine-like 1 | CYTL1 | 219837_s_at | Extracellular Space | cytokine | −6.33 |
| dapper, antagonist of beta-catenin, homolog 1 | DACT1 | 219179_at | Cytoplasm | other | 1.682 |
| dCMP deaminase | DCTD | 201572_x_at | unknown | enzyme | −0.649 |
| DEAH (Asp-Glu-Ala-His) box polypeptide 35 | DHX35 | 218579_s_at | unknown | enzyme | 0.735 |
| deleted in azoospermia 1 | DAZ1 | 207909_x_at | Nucleus | translation regulator | 6.92 |
| deleted in azoospermia 1 | DAZ1 | 207912_s_at | Nucleus | translation regulator | 5.558 |
| deleted in azoospermia 1 | DAZ1 | 208281_x_at | Nucleus | translation regulator | 5.258 |
| deleted in azoospermia 1 | DAZ1 | 208282_x_at | Nucleus | translation regulator | 7.008 |
| deleted in azoospermia 1 | DAZ1 | 216351_x_at | Nucleus | translation regulator | 3.596 |
| deleted in azoospermia 1 | DAZ1 | 216922_x_at | Nucleus | translation regulator | 5.185 |
| deleted in lymphocytic leukemia 2 (non-protein coding) | DLEU2 | 216870_x_at | unknown | other | 1.233 |
| delta-like 3 (*Drosophila*) | DLL3 | 219537_x_at | Extracellular Space | other | 0.779 |
| DNA segment on chromosome 4 (unique) 234 expressed sequence | D4S234E | 209569_x_at | Cytoplasm | other | −1.247 |
| DNA segment on chromosome 4 (unique) 234 expressed sequence | D4S234E | 209570_s_at | Cytoplasm | other | −1.488 |
| DNA segment on chromosome 4 (unique) 234 expressed sequence | D4S234E | 213533_at | Cytoplasm | other | −1.507 |
| dopamine beta-hydroxylase (dopamine beta-monooxygenase) | DBH | 206450_at | Cytoplasm | enzyme | 1.311 |
| doublecortin-like kinase 1 | DCLK1 | 215303_at | Cytoplasm | kinase | −1.62 |
| dual specificity phosphatase 16 | DUSP16 | 224832_at | Nucleus | phosphatase | −0.918 |
| echinoderm microtubule associated protein like 1 | EML1 | 204797_s_at | Cytoplasm | other | 2.668 |
| ectodermal-neural cortex (with BTB-like domain) | ENC1 | 201340_s_at | Nucleus | peptidase | 2.445 |
| ectodermal-neural cortex (with BTB-like domain) | ENC1 | 201341_at | Nucleus | peptidase | 1.91 |
| electron-transferring-flavoprotein dehydrogenase | ETFDH | 33494_at | Cytoplasm | enzyme | −0.807 |
| ELL associated factor 2 | EAF2 | 219551_at | Nucleus | transcription regulator | 0.693 |
| ELOVL family member 7, elongation of long chain fatty acids | ELOVL7 | 227180_at | unknown | other | 2.644 |
| endoplasmic reticulum aminopeptidase 1 | ERAP1 | 214012_at | Extracellular Space | peptidase | −1.885 |
| enhancer of zeste homolog 2 | EZH2 | 203358_s_at | Nucleus | transcription regulator | 0.94 |
| ephrin-A5 | EFNA5 | 214036_at | Plasma Membrane | kinase | 2.041 |
| ephrin-A5 | EFNA5 | 227955_s_at | Plasma Membrane | kinase | 1.84 |
| ephrin-A5 | EFNA5 | 233814_at | Plasma Membrane | kinase | 1.805 |

TABLE 16-continued

Genes Identified using IPA Core Analysis

| Gene Name | Gene Symbol | Probe ID. No. | Location | Type | Log Ratio |
|---|---|---|---|---|---|
| ephrin-B3 | EFNB3 | 205031_at | Plasma Membrane | kinase | −0.816 |
| eukaryotic translation initiation factor 3, subunit C | EIF3C | 236700_at | Cytoplasm | translation regulator | 1.378 |
| exophilin 5 | EXPH5 | 214734_at | unknown | other | 3.973 |
| exosome component 6 | EXOSC6 | 231916_at | Nucleus | other | 1.057 |
| family with sequence similarity 162, member B | FAM162B | 228875_at | unknown | other | −0.743 |
| family with sequence similarity 165, member B | FAM165B | 228239_at | Plasma Membrane | other | −0.822 |
| family with sequence similarity 181, member B | FAM181B | 231430_at | unknown | other | 0.794 |
| family with sequence similarity 19 (chemokine (C-C motif)-like), member A4 | FAM19A4 | 242348_at | Extracellular Space | other | 1.282 |
| family with sequence similarity 46, member A | FAM46A | 224973_at | unknown | other | −1.509 |
| family with sequence similarity 7, member A3 | FAM7A3 | 243356_at | unknown | other | 3.495 |
| far upstream element (FUSE) binding protein 3 | FUBP3 | 239193_at | Nucleus | transcription regulator | 1.192 |
| F-box and WD repeat domain containing 7 | FBXW7 | 229419_at | Nucleus | transcription regulator | −0.921 |
| fibroblast growth factor 13 | FGF13 | 205110_s_at | Extracellular Space | growth factor | −3.522 |
| follistatin-like 1 | FSTL1 | 208782_at | Extracellular Space | other | −1.275 |
| forkhead box O6 | FOXO6 | 239657_x_at | Nucleus | other | −1.512 |
| frizzled homolog 5 | FZD5 | 221245_s_at | Plasma Membrane | receptor | 2.347 |
| FYVE, RhoGEF and PH domain containing 5 | FGD5 | 226985_at | Cytoplasm | other | −1.952 |
| G protein-coupled receptor 123 | GPR123 | 239221_at | Plasma Membrane | receptor | −1.302 |
| G protein-coupled receptor 125 | GPR125 | 210473_s_at | Plasma Membrane | receptor | 0.714 |
| galanin prepropeptide | GAL | 207466_at | Extracellular Space | other | −1.434 |
| galanin prepropeptide | GAL | 214240_at | Extracellular Space | other | −3.128 |
| gastrin-releasing peptide | GRP | 206326_at | Extracellular Space | growth factor | 4.698 |
| GDNF family receptor alpha 2 | GFRA2 | 205721_at | Plasma Membrane | receptor | 1.847 |
| GDNF family receptor alpha 2 | GFRA2 | 205722_s_at | Plasma Membrane | receptor | 2.265 |
| glutamate receptor, metabotropic 5 | GRM5 | 214217_at | Plasma Membrane | receptor | −2.231 |
| glutathione peroxidase 7 | GPX7 | 213170_at | Cytoplasm | enzyme | −2.692 |
| glutathione synthetase | GSS | 211630_s_at | Cytoplasm | enzyme | 0.599 |
| glycosyltransferase 25 domain containing 2 | GLT25D2 | 209883_at | unknown | other | −1.223 |
| GNAS complex locus | GNAS | 214157_at | Plasma Membrane | enzyme | −1.794 |
| growth associated protein 43 | GAP43 | 204471_at | Plasma Membrane | other | 0.869 |
| growth associated protein 43 | GAP43 | 216963_s_at | Plasma Membrane | other | 1.151 |
| guanine nucleotide binding protein (G protein), alpha inhibiting activity polypeptide 1 | GNAI1 | 209576_at | Plasma Membrane | enzyme | 2.225 |
| guanine nucleotide binding protein (G protein), alpha inhibiting activity polypeptide 1 | GNAI1 | 227692_at | Plasma Membrane | enzyme | 2.111 |
| guanine nucleotide binding protein (G protein), beta polypeptide 4 | GNB4 | 225710_at | Plasma Membrane | enzyme | 4.695 |
| guanine nucleotide binding protein (G protein), gamma 11 | GNG11 | 204115_at | Plasma Membrane | enzyme | 2.587 |
| guanylate cyclase 1, soluble, alpha 3 | GUCY1A3 | 221942_s_at | Cytoplasm | enzyme | −1.522 |
| guanylate cyclase 1, soluble, alpha 3 | GUCY1A3 | 229530_at | Cytoplasm | enzyme | −1.696 |
| helicase, POLQ-like | HELQ | 228736_at | Nucleus | enzyme | −1.28 |
| HERPUD family member 2 | HERPUD2 | 236170_x_at | unknown | other | −0.897 |

TABLE 16-continued

Genes Identified using IPA Core Analysis

| Gene Name | Gene Symbol | Probe ID. No. | Location | Type | Log Ratio |
|---|---|---|---|---|---|
| heterogeneous nuclear ribonucleoprotein R | HNRNPR | 208765_s_at | Nucleus | other | −0.64 |
| hippocalcin-like 1 | HPCAL1 | 205462_s_at | Cytoplasm | other | −1.551 |
| hippocalcin-like 1 | HPCAL1 | 212552_at | Cytoplasm | other | −1.387 |
| histone cluster 1, H2ac | HIST1H2AC | 215071_s_at | Nucleus | other | −2.462 |
| histone cluster 1, H2bd | HIST1H2BD | 209911_x_at | Nucleus | other | −2.036 |
| histone cluster 1, H2bk | HIST1H2BK | 209806_at | Nucleus | other | −1.575 |
| histone cluster 2, H2be | HIST2H2BE | 202708_s_at | Nucleus | other | −1.735 |
| hypothetical LOC100130522 | LOC100130522 | 230477_at | unknown | other | −0.928 |
| hypothetical LOC26082 | DKFZP434L187 | 230861_at | unknown | other | 0.968 |
| hypothetical protein LOC100128844 | LOC100128844 | 229110_at | unknown | other | 2.106 |
| hypothetical protein LOC643401 | LOC340109 | 1557765_at | unknown | other | 2.848 |
| integrin, alpha 6 | ITGA6 | 201656_at | Plasma Membrane | other | 2.822 |
| integrin, alpha 6 | ITGA6 | 215177_s_at | Plasma Membrane | other | 2.024 |
| integrin, beta 5 | ITGB5 | 201125_s_at | Plasma Membrane | other | 0.913 |
| interleukin 10 receptor, beta | IL10RB | 209575_at | Plasma Membrane | transmembrane receptor | −1.444 |
| junction mediating and regulatory protein, p53 cofactor | JMY | 226352_at | Nucleus | transcription regulator | −0.744 |
| K (lysine) acetyltransferase 2B | KAT2B | 203845_at | Nucleus | transcription regulator | −0.731 |
| KDEL (Lys-Asp-Glu-Leu) containing 2 | KDELC2 | 225128_at | unknown | other | 1.085 |
| kelch domain containing 1 | KLHDC1 | 1552733_at | unknown | other | −0.952 |
| kelch repeat and BTB (POZ) domain containing 11 | KBTBD11 | 204301_at | unknown | other | −0.733 |
| kelch-like 13 (Drosophila) | KLHL13 | 227875_at | unknown | other | 0.902 |
| KH domain containing, RNA binding, signal transduction associated 3 | KHDRBS3 | 209781_s_at | Nucleus | other | 1.082 |
| KH homology domain containing 1 | KHDC1 | 230055_at | unknown | other | −1.656 |
| KIAA1598 | KIAA1598 | 221802_s_at | unknown | other | −2.811 |
| kinesin family member 16B | KIF16B | 232083_at | Cytoplasm | other | 1.688 |
| lectin, galactoside-binding, soluble, 3 binding protein | LGALS3BP | 200923_at | Plasma Membrane | transmembrane receptor | −1.417 |
| leukemia inhibitory factor receptor alpha | LIFR | 225575_at | Plasma Membrane | transmembrane receptor | −0.941 |
| limb bud and heart development homolog (mouse) | LBH | 221011_s_at | Nucleus | transcription regulator | 0.788 |
| LRP2 binding protein | LRP2BP | 207797_s_at | unknown | other | −1.365 |
| lumican | LUM | 201744_s_at | Extracellular Space | other | 5.638 |
| LYR motif containing 5 | LYRM5 | 225469_at | unknown | other | −0.93 |
| mab-21-like 1 | MAB21L1 | 206163_at | unknown | other | 2.722 |
| mab-21-like 2 | MAB21L2 | 210302_s_at | unknown | other | 2.871 |
| mab-21-like 2 | MAB21L2 | 210303_at | unknown | other | 2.204 |
| macrophage stimulating 1 (hepatocyte growth factor-like) | MST1 | 216320_x_at | Extracellular Space | growth factor | −1.012 |
| major facilitator superfamily domain containing 4 | MFSD4 | 229254_at | unknown | other | −1.752 |
| mannosidase, alpha, class 2A, member 1 | MAN2A1 | 226538_at | Cytoplasm | enzyme | 0.864 |
| mannosyl (alpha-1,3-)-glycoprotein beta-1,4-N-acetylglucosaminyltransferase, isozyme A | MGAT4A | 226039_at | unknown | enzyme | −0.904 |
| mesenchyme homeobox 2 | MEOX2 | 206201_s_at | Nucleus | transcription regulator | −4.213 |
| microtubule-associated protein 9 | MAP9 | 220145_at | unknown | other | −0.7 |
| microtubule-associated protein 9 | MAP9 | 228423_at | unknown | other | −1.108 |
| microtubule-associated protein 9 | MAP9 | 235550_at | unknown | other | −0.863 |
| mitochondrial ribosomal protein S33 | MRPS33 | 218654_s_at | Cytoplasm | other | −0.609 |
| mitogen-activated protein kinase kinase kinase 5 | MAP3K5 | 203836_s_at | Cytoplasm | kinase | −1.159 |
| moesin | MSN | 200600_at | Plasma Membrane | other | 2.082 |
| monoamine oxidase A | MAOA | 204388_s_at | Cytoplasm | enzyme | 2.15 |
| monoamine oxidase A | MAOA | 204389_at | Cytoplasm | enzyme | 1.88 |
| monoamine oxidase A | MAOA | 212741_at | Cytoplasm | enzyme | 2.048 |

TABLE 16-continued

Genes Identified using IPA Core Analysis

| Gene Name | Gene Symbol | Probe ID. No. | Location | Type | Log Ratio |
|---|---|---|---|---|---|
| monocyte to macrophage differentiation-associated | MMD | 244523_at | Plasma Membrane | other | 1.045 |
| multiple C2 domains, transmembrane 1 | MCTP1 | 220122_at | unknown | other | −1.597 |
| MYC induced nuclear antigen | MINA | 213188_s_at | Nucleus | other | 1.391 |
| MYC induced nuclear antigen | MINA | 213189_at | Nucleus | other | 1.641 |
| myosin IB | MYO1B | 212365_at | Cytoplasm | other | 0.71 |
| myosin VI | MYO6 | 203216_s_at | Cytoplasm | other | 1.104 |
| myosin VI | MYO6 | 210480_s_at | Cytoplasm | other | 1.41 |
| Na+/H+ exchanger domain containing 2 | NHEDC2 | 1564746_at | Plasma Membrane | other | −1.462 |
| N-acylethanolamine acid amidase | NAAA | 214765_s_at | Cytoplasm | enzyme | 0.911 |
| NADH dehydrogenase (ubiquinone) 1 alpha subcomplex, 4-like 2 | NDUFA4L2 | 218484_at | unknown | enzyme | −3.507 |
| NADH dehydrogenase (ubiquinone) flavoprotein 3, 10 kDa | NDUFV3 | 226616_s_at | Cytoplasm | enzyme | −0.875 |
| nebulette | NEBL | 203961_at | Cytoplasm | other | −1.359 |
| neural precursor cell expressed, developmentally down-regulated 9 | NEDD9 | 202150_s_at | Nucleus | other | 2.41 |
| NIPA-like domain containing 3 | NIPAL3 | 225876_at | unknown | other | −1.203 |
| nitric oxide synthase 1 (neuronal) | NOS1 | 239132_at | Cytoplasm | enzyme | 1.138 |
| nitric oxide synthase 1 (neuronal) | NOS1 | 240911_at | Cytoplasm | enzyme | 1.187 |
| NLR family member X1 | NLRX1 | 219680_at | unknown | other | −1.541 |
| non-protein coding RNA 171 | NCRNA00171 | 215985_at | unknown | other | −0.692 |
| nuclear receptor coactivator 7 | NCOA7 | 225344_at | Nucleus | other | −0.842 |
| nucleosome assembly protein 1-like 3 | NAP1L3 | 204749_at | Nucleus | other | −1.53 |
| nudix (nucleoside diphosphate linked moiety X)-type motif 19 | NUDT19 | 235384_at | Cytoplasm | other | −1.685 |
| olfactomedin 3 | OLFM3 | 1554524_a_at | Cytoplasm | other | −0.927 |
| oxysterol binding protein-like 3 | OSBPL3 | 209626_s_at | Cytoplasm | other | 2.083 |
| pecanex-like 2 | PCNXL2 | 1554256_a_at | unknown | other | −0.728 |
| pellino homolog 2 | PELI2 | 219132_at | Cytoplasm | other | 0.732 |
| peptidase M20 domain containing 2 | PM20D2 | 225421_at | unknown | other | 1.6 |
| peptidylglycine alpha-amidating monooxygenase | PAM | 202336_s_at | Plasma Membrane | enzyme | −0.861 |
| peripherin | PRPH | 213847_at | Plasma Membrane | other | −1.417 |
| PHD finger protein 20 | PHF20 | 235389_at | Nucleus | other | 0.596 |
| phosphatidic acid phosphatase type 2 domain containing 1A | PPAPDC1A | 236044_at | unknown | phosphatase | −2.621 |
| phosphatidylinositol glycan anchor biosynthesis, class H | PIGH | 209625_at | Cytoplasm | enzyme | −0.597 |
| phosphoinositide-interacting regulator of transient receptor potential channels | HCG1776018 | 232887_at | unknown | other | −2.019 |
| phosphorylase kinase, alpha 1 (muscle) | PHKA1 | 229876_at | Cytoplasm | kinase | −1.2 |
| plastin 3 (T isoform) | PLS3 | 201215_at | Cytoplasm | other | 1.068 |
| platelet-derived growth factor receptor, beta polypeptide | PDGFRB | 202273_at | Plasma Membrane | kinase | −1.373 |
| pleiotrophin | PTN | 209466_x_at | Extracellular Space | growth factor | −1.426 |
| pleiotrophin | PTN | 211737_x_at | Extracellular Space | growth factor | −2.929 |
| pleiotropic regulator 1 | PLRG1 | 225194_at | Nucleus | transcription regulator | −0.701 |
| pleiotropic regulator 1 | PLRG1 | 227246_at | Nucleus | transcription regulator | −1.228 |
| plexin A2 | PLXNA2 | 213030_s_at | Plasma Membrane | other | 0.946 |
| plexin A4 | PLXNA4 | 232317_at | Plasma Membrane | receptor | 1.368 |
| polo-like kinase 2 | PLK2 | 201939_at | Nucleus | kinase | 3.606 |
| polycomb group ring finger 5 | PCGF5 | 227935_s_at | unknown | other | 0.791 |
| polymerase (DNA directed), epsilon | POLE | 216026_s_at | Nucleus | enzyme | 1.053 |

TABLE 16-continued

Genes Identified using IPA Core Analysis

| Gene Name | Gene Symbol | Probe ID. No. | Location | Type | Log Ratio |
|---|---|---|---|---|---|
| potassium channel tetramerisation domain containing 12 | KCTD12 | 212188_at | unknown | ion channel | 3.396 |
| potassium channel tetramerisation domain containing 12 | KCTD12 | 212192_at | unknown | ion channel | 4.806 |
| potassium large conductance calcium-activated channel, subfamily M, alpha member 1 | KCNMA1 | 221584_s_at | Plasma Membrane | ion channel | −2.389 |
| potassium voltage-gated channel, KQT-like subfamily, member 2 | KCNQ2 | 205737_at | Plasma Membrane | ion channel | −1.246 |
| pregnancy-associated plasma protein A, pappalysin 1 | PAPPA | 201982_s_at | Extracellular Space | peptidase | −1.672 |
| prostaglandin E receptor 2 (subtype EP2), 53 kDa | PTGER2 | 206631_at | Plasma Membrane | receptor | −2.328 |
| prostaglandin F2 receptor negative regulator | PTGFRN | 224937_at | Plasma Membrane | other | 2.301 |
| proteasome (prosome, macropain) subunit, alpha type, 7 | PSMA7 | 216088_s_at | Cytoplasm | peptidase | 0.658 |
| protein kinase, cAMP-dependent, catalytic, beta | PRKACB | 235780_at | Cytoplasm | kinase | −2.17 |
| protein tyrosine phosphatase, receptor type, D | PTPRD | 214043_at | Plasma Membrane | phosphatase | −1.16 |
| protein tyrosine phosphatase, receptor type, E | PTPRE | 221840_at | Plasma Membrane | phosphatase | 3.044 |
| protein tyrosine phosphatase, receptor type, G | PTPRG | 204944_at | Plasma Membrane | phosphatase | 1.237 |
| RAB35, member RAS oncogene family | RAB35 | 205461_at | Cytoplasm | enzyme | 0.737 |
| RAB6B, member RAS oncogene family | RAB6B | 225259_at | Cytoplasm | enzyme | −1.229 |
| Rac/Cdc42 guanine nucleotide exchange factor (GEF) 6 | ARHGEF6 | 209539_at | Cytoplasm | other | 2.719 |
| RAN, member RAS oncogene family | RAN | 200750_s_at | Nucleus | enzyme | 0.59 |
| RAS and EF-hand domain containing | RASEF | 1553986_at | unknown | other | 1.393 |
| ras homolog gene family, member U | RHOU | 223168_at | Cytoplasm | enzyme | −1.154 |
| regulator of G-protein signaling 5 | RGS5 | 1555725_a_at | Plasma Membrane | other | 4.038 |
| regulator of G-protein signaling 5 | RGS5 | 209070_s_at | Plasma Membrane | other | 3.729 |
| regulator of G-protein signaling 5 | RGS5 | 209071_s_at | Plasma Membrane | other | 3.468 |
| regulator of G-protein signaling 5 | RGS5 | 218353_at | Plasma Membrane | other | 3.65 |
| RELT-like 1 | RELL1 | 226430_at | unknown | other | 1.214 |
| retinoblastoma-like 1 (p107) | RBL1 | 1559307_s_at | Nucleus | other | 0.959 |
| retrotransposon gag domain containing 4 | RGAG4 | 227823_at | unknown | other | −1.775 |
| Rho GTPase activating protein 6 | ARHGAP6 | 206167_s_at | Cytoplasm | other | 2.809 |
| ribosomal L1 domain containing 1 | RSL1D1 | 213750_at | Cytoplasm | other | −0.816 |
| RIMS binding protein 2 | RIMBP2 | 238817_at | Plasma Membrane | other | 1.679 |
| ring finger protein 13 | RNF13 | 201780_s_at | Nucleus | other | −0.707 |
| ring finger protein 182 | RNF182 | 230720_at | unknown | other | 2.696 |
| ring finger protein 34 | RNF34 | 219035_s_at | Cytoplasm | enzyme | 0.85 |
| ring finger protein 41 | RNF41 | 201962_s_at | Cytoplasm | other | −0.591 |
| RNA polymerase I transcription factor homolog pseudogene 1 | LOC94431 | 216908_x_at | unknown | other | −0.674 |
| sal-like 4 | SALL4 | 229661_at | Nucleus | other | 1.586 |
| salt-inducible kinase 1 | SIK1 | 208078_s_at | Cytoplasm | kinase | −1.403 |
| seizure related 6 homolog (mouse)-like | SEZ6L | 207873_x_at | Plasma Membrane | other | 0.866 |
| seizure related 6 homolog (mouse)-like | SEZ6L | 211894_x_at | Plasma Membrane | other | 0.797 |
| sema domain, transmembrane domain (TM), and cytoplasmic domain, (semaphorin) 6A | SEMA6A | 220454_s_at | Plasma Membrane | other | 1.356 |
| serine peptidase inhibitor, Kunitz type, 2 | SPINT2 | 210715_s_at | Extracellular Space | other | −1.889 |
| SH3 domain containing, Ysc84-like 1 | SH3YL1 | 204019_s_at | unknown | other | −0.859 |

TABLE 16-continued

Genes Identified using IPA Core Analysis

| Gene Name | Gene Symbol | Probe ID. No. | Location | Type | Log Ratio |
|---|---|---|---|---|---|
| SH3-domain GRB2-like 2 | SH3GL2 | 205751_at | Plasma Membrane | enzyme | −1.605 |
| similar to hCG2031213 | LOC728052 | 1558795_at | unknown | other | 2.239 |
| similar to hCG2031213 | LOC728052 | 1558796_a_at | unknown | other | 1.887 |
| single immunoglobulin and toll-interleukin 1 receptor (TIR) domain | SIGIRR | 52940_at | Plasma Membrane | receptor | −1.42 |
| single-minded homolog 1 | SIM1 | 1556300_s_at | Nucleus | transcription regulator | 6.36 |
| single-minded homolog 1 | SIM1 | 206876_at | Nucleus | transcription regulator | 5.737 |
| SLIT and NTRK-like family, member 5 | SLITRK5 | 214930_at | unknown | other | 4.094 |
| SMG1 homolog, phosphatidylinositol 3-kinase-related kinase pseudogene | LOC641298 | 244766_at | unknown | other | 1.065 |
| solute carrier family 12 (potassium/chloride transporters), member 7 | SLC12A7 | 218066_at | Plasma Membrane | transporter | −1.258 |
| solute carrier family 22, member 17 | SLC22A17 | 218675_at | Plasma Membrane | transporter | −0.724 |
| solute carrier family 35, member F3 | SLC35F3 | 229065_at | unknown | other | −3.048 |
| solute carrier family 44, member 5 | SLC44A5 | 1569112_at | unknown | other | 2.738 |
| solute carrier family 44, member 5 | SLC44A5 | 235763_at | unknown | other | 1.845 |
| solute carrier family 7 (cationic amino acid transporter, y+ system), member 2 | SLC7A2 | 225516_at | Plasma Membrane | transporter | 1.892 |
| solute carrier organic anion transporter family, member 3A1 | SLCO3A1 | 219229_at | Plasma Membrane | transporter | 1.622 |
| solute carrier organic anion transporter family, member 3A1 | SLCO3A1 | 227367_at | Plasma Membrane | transporter | 1.045 |
| sparc/osteonectin, cwcv and kazal-like domains proteoglycan (testican) 2 | SPOCK2 | 202524_s_at | Extracellular Space | other | −0.83 |
| sperm associated antigen 6 | SPAG6 | 210032_s_at | Cytoplasm | other | 1.687 |
| sperm associated antigen 6 | SPAG6 | 210033_s_at | Cytoplasm | other | 2.774 |
| spermatogenesis associated, serine-rich 2-like | SPATS2L | 222154_s_at | unknown | other | 0.907 |
| sphingosine-1-phosphate receptor 3 | S1PR3 | 228176_at | Plasma Membrane | receptor | 1.9 |
| ST8 alpha-N-acetyl-neuraminide alpha-2,8-sialyltransferase 1 | ST8SIA1 | 210073_at | Cytoplasm | enzyme | 1.114 |
| ST8 alpha-N-acetyl-neuraminide alpha-2,8-sialyltransferase 3 | ST8SIA3 | 230262_at | Cytoplasm | enzyme | −1.039 |
| stathmin-like 3 | STMN3 | 222557_at | Nucleus | other | 0.788 |
| STEAP family member 3 | STEAP3 | 218424_s_at | Cytoplasm | transporter | −1.827 |
| steroidogenic acute regulatory protein | STAR | 204548_at | Cytoplasm | transporter | −1.093 |
| stimulated by retinoic acid gene 6 homolog | STRA6 | 1569334_at | Plasma Membrane | other | 1.359 |
| stimulated by retinoic acid gene 6 homolog | STRA6 | 1569335_a_at | Plasma Membrane | other | 1.167 |
| storkhead box 2 | STOX2 | 226822_at | unknown | other | −0.854 |
| synaptojanin 1 | SYNJ1 | 212990_at | Cytoplasm | phosphatase | −0.624 |
| synaptotagmin XIII | SYT13 | 226086_at | unknown | transporter | −4.754 |
| synuclein, alpha (non A4 component of amyloid precursor) | SNCA | 236081_at | Cytoplasm | other | −0.935 |
| taxilin beta | TXLNB | 227834_at | Cytoplasm | other | −2.226 |
| teashirt zinc finger homeobox 3 | TSHZ3 | 223392_s_at | Nucleus | transcription regulator | 1.472 |
| teashirt zinc finger homeobox 3 | TSHZ3 | 223393_s_at | Nucleus | transcription regulator | 0.962 |
| tetratricopeptide repeat domain 39C | TTC39C | 238480_at | unknown | other | −0.824 |
| TH1-like | TH1L | 220607_x_at | Nucleus | other | 1.027 |
| TH1-like | TH1L | 225006_x_at | Nucleus | other | 0.884 |
| TH1-like | TH1L | 225261_x_at | Nucleus | other | 0.883 |
| TH1-like | TH1L | 225865_x_at | Nucleus | other | 0.904 |
| thioredoxin reductase 1 | TXNRD1 | 201266_at | Cytoplasm | enzyme | 1.032 |
| THO complex 4 | THOC4 | 226319_s_at | Nucleus | transcription regulator | 0.996 |
| TIMP metallopeptidase inhibitor 3 | TIMP3 | 201147_s_at | Extracellular Space | other | 5.151 |

TABLE 16-continued

Genes Identified using IPA Core Analysis

| Gene Name | Gene Symbol | Probe ID. No. | Location | Type | Log Ratio |
|---|---|---|---|---|---|
| TIMP metallopeptidase inhibitor 3 | TIMP3 | 201148_s_at | Extracellular Space | other | 3.637 |
| TIMP metallopeptidase inhibitor 3 | TIMP3 | 201149_s_at | Extracellular Space | other | 5.037 |
| TIMP metallopeptidase inhibitor 3 | TIMP3 | 201150_s_at | Extracellular Space | other | 4.312 |
| tissue factor pathway inhibitor 2 | TFPI2 | 209277_at | Extracellular Space | other | 1.592 |
| tissue factor pathway inhibitor 2 | TFPI2 | 209278_s_at | Extracellular Space | other | 2.326 |
| TM2 domain containing 1 | TM2D1 | 213882_at | Plasma Membrane | receptor | −0.769 |
| transcription factor 7-like 2 (T-cell specific, HMG-box) | TCF7L2 | 212761_at | Nucleus | transcription regulator | 1.005 |
| transcription factor 7-like 2 (T-cell specific, HMG-box) | TCF7L2 | 212762_s_at | Nucleus | transcription regulator | 1.224 |
| transcription factor 7-like 2 (T-cell specific, HMG-box) | TCF7L2 | 216035_x_at | Nucleus | transcription regulator | 1.072 |
| transcription factor 7-like 2 (T-cell specific, HMG-box) | TCF7L2 | 216037_x_at | Nucleus | transcription regulator | 0.81 |
| transcription factor 7-like 2 (T-cell specific, HMG-box) | TCF7L2 | 216511_s_at | Nucleus | transcription regulator | 1.003 |
| transducin-like enhancer of split 3 | TLE3 | 212770_at | Nucleus | other | 0.976 |
| transformer 2 alpha homolog | TRA2A | 213593_s_at | Nucleus | other | 1.12 |
| transmembrane inner ear | TMIE | 1553601_a_at | unknown | other | −3.334 |
| transmembrane protein 132C | TMEM132C | 232313_at | unknown | other | 4.02 |
| transmembrane protein 178 | TMEM178 | 229302_at | unknown | other | 1.697 |
| transmembrane protein 184C | TMEM184C | 219074_at | unknown | other | −0.779 |
| transmembrane protein 5 | TMEM5 | 204808_s_at | Plasma Membrane | other | −1.074 |
| transmembrane protein 59-like | TMEM59L | 219005_at | Cytoplasm | other | −0.845 |
| tripartite motif-containing 29 | TRIM29 | 211002_s_at | Cytoplasm | transcription regulator | 2.005 |
| tripartite motif-containing 36 | TRIM36 | 219736_at | Cytoplasm | other | 2.221 |
| trophoblast glycoprotein | TPBG | 203476_at | Plasma Membrane | other | 2.158 |
| tumor suppressor candidate 3 | TUSC3 | 232770_at | Extracellular Space | enzyme | −1.407 |
| U2 small nuclear RNA auxiliary factor 1 | U2AF1 | 232141_at | Nucleus | other | 0.776 |
| ubiquitin-conjugating enzyme E2 variant 1 | UBE2V1 | 201003_x_at | Nucleus | transcription regulator | 0.663 |
| urocortin | UCN | 206072_at | Extracellular Space | other | −0.961 |
| vacuolar protein sorting 29 homolog | VPS29 | 223026_s_at | Cytoplasm | transporter | 0.805 |
| v-erb-a erythroblastic leukemia viral oncogene homolog 4 | ERBB4 | 206794_at | Plasma Membrane | kinase | −1.537 |
| v-erb-a erythroblastic leukemia viral oncogene homolog 4 | ERBB4 | 214053_at | Plasma Membrane | kinase | −1.708 |
| v-erb-b2 erythroblastic leukemia viral oncogene homolog 2, neuro/glioblastoma derived oncogene homolog | ERBB2 | 216836_s_at | Plasma Membrane | kinase | −0.698 |
| v-raf-1 murine leukemia viral oncogene homolog 1 | RAF1 | 1557675_at | Cytoplasm | kinase | 0.696 |
| WD repeat and FYVE domain containing 3 | WDFY3 | 212602_at | Cytoplasm | enzyme | −0.626 |
| WD repeat and FYVE domain containing 3 | WDFY3 | 212606_at | Cytoplasm | enzyme | −0.785 |
| zinc finger homeobox 4 | ZFHX4 | 219779_at | unknown | other | 1.36 |
| zinc finger homeobox 4 | ZFHX4 | 241700_at | unknown | other | 1.234 |
| zinc finger protein 217 | ZNF217 | 203739_at | Nucleus | transcription regulator | 1.096 |
| zinc finger protein 503 | ZNF503 | 227195_at | Nucleus | other | 1.373 |
| zinc finger protein 641 | ZNF641 | 226509_at | unknown | other | −1.427 |
| zinc finger protein 662 | ZNF662 | 228538_at | unknown | other | −3.352 |
| zinc finger, CCCH-type with G patch domain | ZGPAT | 221848_at | unknown | other | 0.991 |

Computer analysis was performed as in Example V, except that the list of probes reflects genes that were greater than 1.5-fold differential expressed in the H1 cell line and the BB10 cell line when compared to both the 2D6 and SiMa parental cell lines, and also a greater than 1.5-fold differential expressed in the SiMa parental cell line when compared to the 2D6 cell line. When the p-value cut off was set to 0.05, this analysis identified 94 gene probes that could be classified to 70 genes (Table 17).

TABLE 17

Genes Identified using IPA Core Analysis

| Gene Name | Gene Symbol | Probe ID. No. | Location | Type | Log Ratio |
|---|---|---|---|---|---|
| achaete-scute complex homolog 1 | ASCL1 | 209985_s_at | Nucleus | transcription regulator | 2.429 |
| achaete-scute complex homolog 1 | ASCL1 | 209988_s_at | Nucleus | transcription regulator | 1.446 |
| achaete-scute complex homolog 1 | ASCL1 | 213768_s_at | Nucleus | transcription regulator | 1.578 |
| activated leukocyte cell adhesion molecule | ALCAM | 201952_at | Plasma Membrane | other | 1.521 |
| ADP-ribosylation factor 1 | ARF1 | 1565651_at | Cytoplasm | enzyme | 1.063 |
| ADP-ribosylation factor-like 17A | ARL17A | 243899_at | unknown | other | 0.741 |
| ataxin 2-binding protein 1 | A2BP1 | 1553422_s_at | Cytoplasm | other | 1.453 |
| ataxin 2-binding protein 1 | A2BP1 | 221217_s_at | Cytoplasm | other | 1.497 |
| brain abundant, membrane attached signal protein 1 | BASP1 | 202391_at | Plasma Membrane | other | 1.146 |
| CAP, adenylate cyclase-associated protein, 2 | CAP2 | 212551_at | Plasma Membrane | other | −1.974 |
| CD9 molecule | CD9 | 201005_at | Plasma Membrane | other | 1.415 |
| CUG triplet repeat, RNA binding protein 2 | CUGBP2 | 202157_s_at | Nucleus | other | 2.156 |
| cyclic nucleotide gated channel alpha 3 | CNGA3 | 207261_at | Plasma Membrane | ion channel | −3.182 |
| cyclin-dependent kinase inhibitor 2A (melanoma, p16, inhibits CDK4) | CDKN2A | 209644_x_at | Nucleus | transcription regulator | −1.277 |
| ELL associated factor 2 | EAF2 | 219551_at | Nucleus | transcription regulator | 0.693 |
| eukaryotic translation initiation factor 3, subunit C | EIF3C | 236700_at | Cytoplasm | translation regulator | 1.378 |
| family with sequence similarity 162, member B | FAM162B | 228875_at | unknown | other | −0.743 |
| family with sequence similarity 181, member B | FAM181B | 231430_at | unknown | other | 0.794 |
| far upstream element (FUSE) binding protein 3 | FUBP3 | 239193_at | Nucleus | transcription regulator | 1.192 |
| fibroblast growth factor 13 | FGF13 | 205110_s_at | Extracellular Space | growth factor | −3.522 |
| follistatin-like 1 | FSTL1 | 208782_at | Extracellular Space | other | −1.275 |
| forkhead box O6 | FOXO6 | 239657_x_at | Nucleus | other | −1.512 |
| guanine nucleotide binding protein (G protein), alpha inhibiting activity polypeptide 1 | GNAI1 | 227692_at | Plasma Membrane | enzyme | 2.111 |
| guanine nucleotide binding protein (G protein), beta polypeptide 4 | GNB4 | 225710_at | Plasma Membrane | enzyme | 4.695 |
| guanine nucleotide binding protein (G protein), gamma 11 | GNG11 | 204115_at | Plasma Membrane | enzyme | 2.587 |
| KDEL (Lys-Asp-Glu-Leu) containing 2 | KDELC2 | 225128_at | unknown | other | 1.085 |
| kelch-like 13 | KLHL13 | 227875_at | unknown | other | 0.902 |
| KH domain containing, RNA binding, signal transduction associated 3 | KHDRBS3 | 209781_s_at | Nucleus | other | 1.082 |
| KH homology domain containing 1 | KHDC1 | 230055_at | unknown | other | −1.656 |
| leukemia inhibitory factor receptor alpha | LIFR | 225575_at | Plasma Membrane | transmembrane receptor | −0.941 |
| mab-21-like 2 | MAB21L2 | 210303_at | unknown | other | 2.204 |
| mesenchyme homeobox 2 | MEOX2 | 206201_s_at | Nucleus | transcription regulator | −4.213 |
| moesin | MSN | 200600_at | Plasma Membrane | other | 2.082 |
| monoamine oxidase A | MAOA | 204388_s_at | Cytoplasm | enzyme | 2.15 |
| monoamine oxidase A | MAOA | 204389_at | Cytoplasm | enzyme | 1.88 |
| monoamine oxidase A | MAOA | 212741_at | Cytoplasm | enzyme | 2.048 |

TABLE 17-continued

Genes Identified using IPA Core Analysis

| Gene Name | Gene Symbol | Probe ID. No. | Location | Type | Log Ratio |
|---|---|---|---|---|---|
| multiple C2 domains, transmembrane 1 | MCTP1 | 220122_at | unknown | other | −1.597 |
| MYC induced nuclear antigen | MINA | 213188_s_at | Nucleus | other | 1.391 |
| MYC induced nuclear antigen | MINA | 213189_at | Nucleus | other | 1.641 |
| myosin VI | MYO6 | 203216_s_at | Cytoplasm | other | 1.104 |
| phosphatidic acid phosphatase type 2 domain containing 1A | PPAPDC1A | 236044_at | unknown | phosphatase | −2.621 |
| plastin 3 (T isoform) | PLS3 | 201215_at | Cytoplasm | other | 1.068 |
| pleiotrophin | PTN | 209466_x_at | Extracellular Space | growth factor | −1.426 |
| pleiotrophin | PTN | 211737_x_at | Extracellular Space | growth factor | −2.929 |
| polo-like kinase 2 (*Drosophila*) | PLK2 | 201939_at | Nucleus | kinase | 3.606 |
| potassium large conductance calcium-activated channel, subfamily M, alpha member 1 | KCNMA1 | 221584_s_at | Plasma Membrane | ion channel | −2.389 |
| RELT-like 1 | RELL1 | 226430_at | unknown | other | 1.214 |
| ring finger protein 182 | RNF182 | 230720_at | unknown | other | 2.696 |
| seizure related 6 homolog-like | SEZ6L | 207873_x_at | Plasma Membrane | other | 0.866 |
| seizure related 6 homolog (mouse)-like | SEZ6L | 211894_x_at | Plasma Membrane | other | 0.797 |
| similar to hCG2031213 | LOC728052 | 1558795_at | unknown | other | 2.239 |
| single-minded homolog 1 (*Drosophila*) | SIM1 | 1556300_s_at | Nucleus | transcription regulator | 6.36 |
| single-minded homolog 1 (*Drosophila*) | SIM1 | 206876_at | Nucleus | transcription regulator | 5.737 |
| SLIT and NTRK-like family, member 5 | SLITRK5 | 214930_at | unknown | other | 4.094 |
| SMG1 homolog, phosphatidylinositol 3-kinase-related kinase pseudogene | LOC641298 | 244766_at | unknown | other | 1.065 |
| solute carrier family 44, member 5 | SLC44A5 | 1569112_at | unknown | other | 2.738 |
| solute carrier family 44, member 5 | SLC44A5 | 235763_at | unknown | other | 1.845 |
| solute carrier family 7 (cationic amino acid transporter, y+ system), member 2 | SLC7A2 | 225516_at | Plasma Membrane | transporter | 1.892 |
| solute carrier organic anion transporter family, member 3A1 | SLCO3A1 | 219229_at | Plasma Membrane | transporter | 1.622 |
| spermatogenesis associated, serine-rich 2-like | SPATS2L | 222154_s_at | unknown | other | 0.907 |
| synaptotagmin XIII | SYT13 | 226086_at | unknown | transporter | −4.754 |
| tissue factor pathway inhibitor 2 | TFPI2 | 209278_s_at | Extracellular Space | other | 2.326 |
| transcription factor 7-like 2 (T-cell specific, HMG-box) | TCF7L2 | 212761_at | Nucleus | transcription regulator | 1.005 |
| transformer 2 alpha homolog | TRA2A | 213593_s_at | Nucleus | other | 1.12 |
| transmembrane inner ear | TMIE | 1553601_a_at | unknown | other | −3.334 |
| transmembrane protein 178 | TMEM178 | 229302_at | unknown | other | 1.697 |
| U2 small nuclear RNA auxiliary factor 1 | U2AF1 | 232141_at | Nucleus | other | 0.776 |
| v-raf-1 murine leukemia viral oncogene homolog 1 | RAF1 | 1557675_at | Cytoplasm | kinase | 0.696 |
| zinc finger protein 217 | ZNF217 | 203739_at | Nucleus | transcription regulator | 1.096 |
| zinc finger protein 662 | ZNF662 | 228538_at | unknown | other | −3.352 |

The log ratio represent log$_2$ values where 0.585 is log$_2$(1.5) which is a 1.5-fold difference, 1 is log$_2$(2) which is a 2-fold difference, 1.584 is log$_2$(3) which is a 3-fold difference, 2 is log$_2$(4) which is a 4-fold difference, 2.321 is log$_2$(5) which is a 5-fold difference, 2.584 is log$_2$(6) which is a 6-fold difference, 2.807 is log$_2$(7) which is a 7-fold difference, 3 is log$_2$(8) which is a 8-fold difference, 3.169 is log$_2$(9) which is a 9-fold difference, and 3.321 is log$_2$(10) which is a 10-fold difference.

Example VI

Immuno-Based Method to Detect Picomolar Amounts of BoNT/A

The following example illustrates how to perform immuno-based methods of detecting BoNT/A activity that can detect picomolar amounts of the BoNT/A pharmaceutical product, such as, e.g., BOTOX® DYSPORT®/RELOXIN®, PURTOX®, XEOMIN®, NEURONOX®, or BTX-A.

1. Immuno-based Method of Detecting BoNT/A Using ECL Sandwich ELISA.

To prepare a lysate from cells treated with a BoNT/A, approximately 150,000 cells from an established clonal cell line was plated into the wells of 96-well tissue culture poly-D-lysine plates containing 100 μL of a serum-free medium containing Minimum Essential Medium, 2 mM GlutaMAXT™ I with Earle's salts, 1×B27 supplement, 1×N2 supplement, 0.1 mM Non-Essential Amino Acids, 10 mM HEPES and 60 μg/mL GT1b. The cell lines used were BB10, H1, and SiMa. These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing one of the following: 1) SiMa cell line, 0 (untreated), 0.98 U/mL, 1.9 U/mL, 3.91 U/mL, 7.81 U/mL, 15.6 U/mL, 31.3 U/mL, 62.5 U/mL, 125 U/mL, 250 U/mL, or 500 U/mL of a BoNT/A pharmaceutical product reconstituted in a sodium chloride free medium; 2) BB10, 0 (untreated), 0.49 U/mL, 0.98 U/mL, 1.9 U/mL, 3.91 U/mL, 7.81 U/mL, 15.6 U/mL, 31.3 U/mL, 62.5 U/mL, 125 U/mL, 250 U/mL; 3) H1, 0 (untreated), 0.3 U/mL, 1 U/mL, 3 U/mL, 9 U/mL, 28 U/mL, 83 U/mL, and 250 U/mL. Because the BoNT/A pharmaceutical product contains sodium chloride, its addition to the culture medium resulted in a hypertonic media that was detrimental to cell viability. To circumvent the hypertonicity issue, 200 μL of MEM media made without sodium chloride was used to reconstitute the BoNT/A pharmaceutical product giving a final concentration of 25 pM BoNT/A (500 U/mL). The matrix was kept constant for all concentrations along the dose-response curve by adding sodium chloride in the media used to make the dilutions match the amount of excipients present at the highest concentration used (25 pM or 500 U/mL). After a 24 hr treatment, the cells were washed, and incubated for an additional two days without toxin. To harvest the cells, 1×PBS was aspirated, the cells lysed by adding 75 μL of Lysis Buffer comprising 50 mM HEPES, 150 mM NaCl, 1.5 mM $MgCl_2$, 1 mM EGTA, 1% Triton X-100 to each well, and the plate incubated on a shaker rotating at 500 rpm for 30 minutes at 4° C. The plate was centrifuged at 4000 rpm for 20 minutes at 4° C. to pellet cellular debris and the supernatant was transferred to a capture antibody coated 96-well plate to perform the detection step.

To prepare the α-SNAP-25 capture antibody solution, the α-SNAP-25 monoclonal antibody contained in the ascites from hybridoma cell line 2E2A6 (Example VII) was purified using a standard Protein A purification protocol. To prepare the α-SNAP-25 detection antibody solution, α-SNAP-25 rabbit polyclonal antibody S9684 (Sigma, St. Louis, Mo.) was conjugated to Ruthenium(II)-tris-bipyridine-(4-methysulfonate) NHS ester labeling reagent (Meso Scale Discovery, Gaithersburg, Md.) according to the manufacturer's instructions (Meso Scale Discovery, Gaithersburg, Md.). The conjugation reaction was performed by adding 30 μL of distilled water reconstituted MSD SULFO-TAG™ stock solution to 200 μL of 2 mg/mL α-SNAP-25 polyclonal antibodies and incubating the reaction at room temperature for 2 hours in the dark. The labeled antibodies were purified using a standard spin column protocol and the protein concentration determined using a standard colorimetric protein assay. The absorbance of the α-SNAP-25 antibody/MSD SULFO-TAG™ conjugate was measured at 455 nm using a spectrophotometer to determine the concentration in moles per liter. The detection antibody solution was stored at 4° C. until needed.

To prepare the solid phase support comprising the capture antibody that is specific for a SNAP-25 cleaved product, approximately 1 μL of α-SNAP-25 monoclonal antibody 2E2A6 solution (45 μg/mL in 1×PBS, 750 μg/mL of BSA) was added to each well of a 96-well MSD High Bind plate (Meso Scale Discovery, Gaithersburg, Md.) and the solution is allowed to air dry in a biological safety cabinet for 2-3 hours in order to liquid evaporate the solution, and then the plates were sealed and stored at 4° C. until needed. The dried capture antibody-bound wells were then blocked by adding 150 μL of Blocking Buffer comprising 1×PBS, 0.05% Tween-20, 2% ECL Blocking reagent (GE Healthcare-Amersham), and 1% goat serum (Rockland Immunochemicals, Gilbertsville, Pa.) at room temperature for 2 hours with rotation at 600 rpm.

To detect the presence of a SNAP-25 cleavage product by ECL sandwich ELISA analysis, the Blocking Buffer from plates was aspirated, 25 μL of a lysate from cells treated with BoNT/A was added to each well and the plates were incubated at 4° C. for overnight. Plate wells were washed three times by aspirating the cell lysate and rinsing each well three times with 200 μL 1×PBS, 0.1% TWEEN-20® (polyoxyethylene (20) sorbitan monolaureate). After washing, 25 μl of 5 μg/mL α-SNAP-25 detection antibody solution comprising 2% Amersham Blocking Reagent in 1×PBS, 0.1% TWEEN-20® (polyoxyethylene (20) sorbitan monolaureate) was added to each well, the plate was sealed, and the sealed plate was incubated at room temperature for 1 hour with shaking. After α-SNAP-25 detection antibody incubation, the wells were washed three times with 250 μL 1×PBS, 0.1% TWEEN-20® (polyoxyethylene (20) sorbitan monolaureate). After washing 150 μL of 1× Read Buffer (Meso Scale Discovery, Gaithersburg, Md.) was added to each well and the plates were read using a SECTOR™ Imager 6000 Image Reader (Meso Scale Discovery, Gaithersburg, Md.). The raw data was then transferred to SigmaPlot v 10.0 and a 4-parameter logistics fit was used to define the dose-response curves. There were no constraints used for the 4-parameter logistic function when plotting the data. Graphical reports were generated using the following analysis: R2 (correlation coefficient), a (Max for data set), b (hillslope), and X0±SE ($EC_{50}$ value±standard error).

These results indicated that on average the cells comprising the BB10 and H1 clonal cell lines were more susceptible to BoNT/A intoxication as compared to cells comprising the parental SiMa cell line. Cells from a BB10 cell line exhibited an $EC_{50}$ for BoNT/A activity of 7 U/mL, cells from a H1 cell line exhibited an $EC_{50}$ for BoNT/A activity of 8 U/mL, and cells from the parental SiMa cell line exhibited an $EC_{50}$ for BoNT/A activity of 13 U/mL. This method can also be performed in a multiplex fashion as described in Ester Fernandez-Salas, et al., *Immuno-Based Botulinum Toxin Serotype A Activity Assays*, U.S. patent application Ser. No. 12/403,531, which is hereby incorporated by reference in its entirety.

Example VII

Transfection of BoNT/A Receptor DNA into Sensitive Clonal Cell Lines Further Improves Sensitivity of the Clonal Cell Line for BoNT/A The following example illustrates how to introduce a polynucleotide molecule encoding a BoNT/A receptor into cells from a clonal cell line to further improve susceptibility to BoNT/A intoxication or improve BoNT/A uptake capacity.

To introduce an exogenous BoNT/A receptor into cells comprising an established clonal cell line, a mammalian expression construct comprising a polynucleotide molecule of SEQ ID NO: 139 encoding the FGFR3 of SEQ ID NO: 25, was transfected into cells from a H1 clonal cell line by a cationic lipid method. A suitable density (about $5×10^6$ cells) of cells from an established clonal cell line are plated in a 100 mm tissue culture dish containing 5 mL of complete culture media and grown in a 37° C. incubator under 5% carbon dioxide until the cells reached a density appropriate for transfection. A 3 mL transfection solution is prepared by adding 1.5 mL of OPTI-MEM® Reduced Serum Medium containing 60 μL of LIPOFECTAMINE® 2000 (Invitrogen, Carlsbad, Calif.) incubated at room temperature for 5 minutes to 1.5 mL of OPTI-MEM® Reduced Serum Medium containing 24 pg of an expression construct encoding the FGFR3 of SEQ ID NO: 25. This transfection mixture is incubated at room temperature for approximately 30 minutes. The complete media on the cells is replaced with the 3 mL transfection solution and the cells are incubated in a 37° C. incubator under 5% carbon dioxide for approximately 8 hours. Transfection media is replaced with 3 mL of fresh complete culture media and the cells are incubated in a 37° C. incubator under 5% carbon dioxide for approximately 24 hours. Media is replaced with 3 mL of fresh complete culture media containing approximately 1 mM G418 (Invitrogen, Carlsbad, Calif.) for selection of transfected cells. Cells are incubated in a 37° C. incubator under 5% carbon dioxide for approximately 1 week, the old media is replaced with fresh complete culture media containing 0.5 mM G418 and the cells are plated onto one 96-well collagen IV coated plate at a plating density of 0.5 cells per well. Cell growth and viability was monitored by microscopic examination and after about 3 weeks single clones appeared in about 20% of the wells. These clones were grown for an additional 2 weeks and then transferred to duplicate 24-well collagen IV coated plates, one to maintain the clonal cell line and the other to test for BoNT/A susceptibility.

To determine the susceptibility of the cells comprising the clonal cell lines overexpressing a BoNT/A receptor, a Western blot analysis was done to determine sensitivity and an ECL sandwich ELISA was done to determine an $EC_{50}$ value. A total of eight clones were tested for the FGFR3 stably transfected H1 cells.

To prepare a cell lysate for the Western blot analysis, cells from the clonal cell line were plated into two wells in a poly-D-lysine coated 96-well plate in serum-free medium containing Minimum Essential Medium, 2 mM GLUTAMAX™ I with Earle's salts, 1×B27 supplement, 1×N2 supplement, 0.1 mM Non-Essential Amino Acids, 10 mM HEPES and 25 pg/mL GT1b (Alexis Biochemicals, Lausen, Switzerland). These cells were incubated in a 37° C. incubator under 5% carbon dioxide until the cells differentiated, as assessed by standard and routine morphological criteria, such as growth arrest and neurite extension (approximately 3 days). The media from the differentiated cells was aspirated from each well and replaced with fresh media containing either 0 (untreated), 0.5 nM or 0.25 nM of a BoNT/A complex. After a 6 hr treatment, the cells were washed, and incubated for an additional 18 hr without toxin. After the incubation, the cells were washed by aspirating the growth media and rinsing each well with 200 μl of 1×PBS. To harvest the cells, the 1×PBS was aspirated, the cells were lysed by adding 40 μL of 2×SDS Loading Buffer and the plate was swirled for an even coating of Loading Buffer. The lysate was transferred to a new 96-well PCR plate (Axygen, Union City, Calif.) and the plate was heated to 95° C. for 5 min to complete cell lysis and denature proteins.

To detect for the presence of both uncleaved SNAP-25 substrate and cleaved SNAP-25 products, an aliquot from each harvested sample was analyzed by Western blot. In this analysis, a 12 μL aliquot of the harvested sample was separated by MOPS polyacrylamide gel electrophoresis using NUPAGE® Novex 12% Bis-Tris precast polyacrylamide gels (Invitrogen Inc., Carlsbad, Calif.) under denaturing, reducing conditions. Separated proteins were transferred from the gel onto nitrocellulose membranes (Bio-Rad Laboratories, Hercules, Calif.) by Western blotting using a "Transfer +4 cassettes & Cooler" transfer chamber (GE Healthcare, Piscataway, N.J.). Membranes were blocked by incubating at room temperature for 1 hr with gentle agitation in a solution containing Tris-Buffered Saline (TBS) (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20® (polyoxyethylene (20) sorbitan monolaureate), 2% Bovine Serum Albumin (BSA), 5% nonfat dry milk. Blocked membranes were incubated at 4° C. for overnight in TBS, 0.1% TWEEN-20® (polyoxyethylene (20) sorbitan monolaureate), 2% BSA, and 5% nonfat dry milk containing a 1:5,000 dilution of α-SNAP-25 rabbit polyclonal antiserum S9684 (Sigma, St. Louis, Mo.) as the primary antibody. The α-SNAP-25 rabbit polyclonal antibodies can detect both the uncleaved SNAP-25 substrate and the SNAP-25 cleavage product, allowing for the assessment of overall SNAP-25 expression in each cell line and the percent of SNAP-25 cleaved after BoNT/A treatment as a parameter to assess the amount of BoNT/A uptake. Primary antibody probed blots were washed three times for 5 minutes each time in TBS, TWEEN-20® (polyoxyethylene (20) sorbitan monolaureate). Washed membranes were incubated at room temperature for 2 hours in TBS, 0.1% TWEEN-20® (polyoxyethylene (20) sorbitan monolaureate), 2% BSA, and 5% nonfat dry milk containing a 1:10,000 dilution of goat polyclonal anti-rabbit immunoglobulin G, heavy and light chains (IgG, H+L) antibody conjugated to horseradish peroxidase (Invitrogen, Inc., Carlsbad, Calif.) as a secondary antibody. Secondary antibody-probed blots were washed five times for 5 minutes each time in TBS, 0.1% TWEEN-20® (polyoxyethylene (20) sorbitan monolaureate). Signal detection of the labeled SNAP-25 products were visualized using the ECL PIus™ Western Blot Detection System (GE Healthcare, Amersham Biosciences, Piscataway, N.J.) and the membrane was imaged and the percent of cleaved SNAP-25 products quantified with a Typhoon 9410 Variable Mode Imager and Imager Analysis software (GE Healthcare, Amersham Biosciences, Piscataway, N.J.). The choice of pixel size (100 to 200 pixels) and PMT voltage settings (350 to 600, normally 400) depended on the individual blot. The volumes of the bands corresponding to either intact and cleaved SNAP-25 product were quantified using Image Quant TL and the total amount of SNAP-25 and the percentage of SNAP-25 cleaved were calculated based on the intensity of these two SNAP-25 bands.

Clone H1 1.4 had a high percentage of SNAP-25 cleavage and high levels of total SNAP25 and was selected for further testing. The selected clone was first grown on a 10 $cm^2$ dish and then in T175 flasks to ensure that enough cells were produced for both ECL sandwich ELISA assay and for freezing stocks. Frozen stocks were made with $1\times10^6$ cells and 1 mL of Recovery Cell Culture Freezing Media (GIBCO-Invitrogen, #12648-010 Freezing media).

To prepare a cell lysate for the ECL sandwich ELISA, approximately 50,000 cells from H1 clonal cell line and from H1 1.4 clonal cell line overexpressing FGFR3 were plated and differentiated as described above. The media from the differentiated cells was aspirated from each well and replaced with fresh media containing either (untreated), 0.27 pM, 0.82 pM, 2.47 pM, 7.4 pM, 22.2 pM, 66.6 pM, or 200 pM of a BoNT/A complex of a BoNT/A complex. After a 6 hr treatment, the cells were washed, and incubated overnight without toxin. After a 24 hr treatment, the cells were washed by aspirating the BoNT/A containing media and rinsing each well with 200 μL of 1×PBS. Washed cells were harvested by lysing in freshly prepared Triton X-100 Lysis Buffer (150 mM NaCl, 20 mM Tris-HCl (pH 7.5), 1 mM EDTA, 1 mM EGTA, 1% Triton X-100 plus protease inhibitors) at 4° C. for 30 minutes with constant agitation. Lysed cells were centrifuged at 4000 rpm for 20 min at 4° C. to pellet cellular debris.

The α-SNAP-25 capture antibody solution, the α-SNAP-25 detection antibody solution, and the solid phase support comprising the capture antibody that is specific for a SNAP-25 cleaved product were prepared as described in Example V. To detect the presence of a cleaved SNAP-25 product by ECL sandwich ELISA, the plates were processed, and the data collected and analyzed, and the $EC_{50}$ calculated as described in Example VI. The $EC_{50}$ for H1 1.4 cells was estimated to about 1.7 pM, compared to an $EC_{50}$ about 8.7 pM for H1 cells indicating that the newly generated H1 1.4 cell line is about 5 times more sensitive than the H1 cell line for BoNT/A uptake (average of two independent experiments with similar results). The maximum signal for both cell lines was identical indicating similar efficacy towards SNAP25 cleavage. The increase in sensitivity is especially prominent at lower concentrations of BoNT/A, where the H1 1.4 cells are many times more sensitive to BoNT/A compared to H1 cells producing a very robust signal over background at the 0.27 pM concentration. Over-expression of FGFR3 was verified in a Western blot using α-FGFR3 antibodies sc-123 (Santa Cruz Biotechnologies, Santa Cruz, Calif.).

Example VIII

Development of α-SNAP-25 Monoclonal Antibodies that Selectively Bind a SNAP-25 Epitope Having a Free Carboxyl-terminus at the $P_1$ Residue of the BoNT/A Cleavage Site Scissile Bond The following example illustrates how to make α-SNAP-25 monoclonal antibodies that can selectively bind to a SNAP-25 epitope having a carboxyl-terminus at the $P_1$ residue of the BoNT/A cleavage site scissile bond.

1. Generation of α-SNAP-25 Monoclonal Antibodies.

α-SNAP-25 monoclonal antibodies with higher binding affinity for a SNAP-25 cleavage product and/or α-SNAP-25 antibodies with a higher binding specificity for a SNAP-25 cleavage product were developed. In addition, because a permanent, stable and renewable source of α-SNAP-25 antibodies is preferable for an FDA-approved assay, screens to isolate monoclonal antibodies were undertaken. To develop monoclonal α-SNAP-25 antibodies the 13-residue peptide CDSNKTRIDEANQ$_{COOH}$ (SEQ ID NO: 38) was designed as a SNAP-25 antigen having a carboxyl-terminus at the $P_1$ residue of the BoNT/A cleavage site scissile bond. This peptide comprises a flexible linker region and a N-terminal Cysteine residue for conjugation to KLH and amino acids 186-197 of human SNAP-25 (SEQ ID NO: 5) with a carboxylated C-terminal glutamine (SEQ ID NO: 38). The generation of monoclonal antibodies to well-chosen, unique peptide sequences provides control over epitope specificity, allowing the identification of a particular subpopulation of protein among a pool of closely related isoforms. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Six Balb/c mice were immunized with this peptide, and after three immunizations in about eight weeks, the mice were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μL aliquots and stored at −20° C. until needed. A similar strategy based on other SNAP-25 antigens disclosed in the present specification is used to develop α-SNAP-25 monoclonal antibodies that can selectively bind to a SNAP-25 having a carboxyl-terminus at the $P_1$ residue of the BoNT/A cleavage site scissile bond. For example, the SNAP-25 antigen of SEQ ID NO: 45 can be conjugated to KLH instead of the SNAP-25 antigen of SEQ ID NO: 38. As another example, the amino acids 186-197 of human SNAP-25 from the SNAP-25 antigen of SEQ ID NO: 38 can be replaced with SEQ ID NO: 32, SEQ ID NO: 33, SEQ ID NO: 34, SEQ ID NO: 35, SEQ ID NO: 36, SEQ ID NO: 39, SEQ ID NO: 40, SEQ ID NO: 41, SEQ ID NO: 42, SEQ ID NO: 43, SEQ ID NO: 44, SEQ ID NO: 147, or SEQ ID NO: 148.

2. Screening for the Presence of α-SNAP-25 Monoclonal Antibodies.

To determine the presence of an α-SNAP-25 monoclonal antibody that can selectively bind to a SNAP-25 antigen having a carboxyl-terminus at the $P_1$ residue of the BoNT/A cleavage site scissile bond, comparative ELISA and cell-based cleavage assay were performed using the extracted mouse serum. For comparative ELISA, two fusion proteins were constructed: BIRA-HIS TAG®-SNAP-$25_{134-197}$ of SEQ ID NO: 48 and the BIRA-HIS TAG®-SNAP-$25_{134-206}$ of SEQ ID NO: 49. BIRA-HIS TAG®-SNAP-$25_{134-197}$ comprised a naturally-biotinylated 16 amino acid BirA peptide of SEQ ID NO: 50 amino-terminally linked to a SNAP-25 peptide comprising amino acids 134-197 of SEQ ID NO: 5. BIRA-HIS TAG®-SNAP-$25_{134-206}$ comprised a naturally-biotinylated 16 amino acid BirA peptide of SEQ ID NO: 50 amino-terminally linked to a SNAP-25 peptide comprising amino acids 134-206 of SEQ ID NO: 5. These two substrates were suspended in 1×PBS at a concentration of 10 μg/mL BIRA-HIS TAG®-SNAP-$25_{134-197}$ and the BIRA-HIS TAG®-SNAP-$25_{134-206}$. The BIRA-HIS TAG®-SNAP-$25_{134-197}$ and the BIRA-HIS TAG®-SNAP-$25_{134-206}$ were coated onto separate plates by adding approximately 100 μl of the appropriate Substrate Solution and incubating the plates at room temperature for one hour. Washed plates were incubated at 37° C. for one hour in 0.5% BSA in 1×TBS containing a 1:10 to 1:100 dilution of an antibody-containing serum derived from one of the six immunized mice (Mouse 1, Mouse 2, Mouse 3, Mouse 4, Mouse 5, and Mouse 6). Primary antibody probed plates were washed four times for 5 minutes each time in 200 μl TBS, 0.1% TWEEN-20® (polyoxyethylene (20) sorbitan monolaureate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaureate). Chromogenic detection of the labeled SNAP-25 products were visualized by chromogenic detection using ImmunoPure TMB substrate kit (Pierce Biotechnology, Rockford, Ill.). The development of a yellow color in the BIRA-HIS TAG®-SNAP-$25_{134-197}$ coated plates, but not the BIRA-HIS TAG®-SNAP-$25_{134-206}$ coated plates, indicated that the α-SNAP-25 antibody preferentially recognized the SNAP-$25_{197}$ cleavage product. The resulted indicated that of the six mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

These results were confirmed using an ELISA light chain activity assay. A 96-well Reacti-Bind Streptavidin coated plates (Pierce Biotechnology, Rockford, Ill.) were prepared by adding approximately 100 μl of the following Substrate Solution: Rows A-C were coated with 100 μL of BIRA-HIS TAG®-SNAP-$25_{134-197}$ at twelve different concentrations; Rows D-H were coated with 100 μL of BIRA-HIS TAG®-SNAP-$25_{134-206}$ at 10 μg/mL. The plates were washed by aspirating the Substrate Solution and rinsing each well three times with 200 μl TBS, 0.1% TWEEN-20® (polyoxyethylene (20) sorbitan monolaureate). Dilutions of BoNT/A were pre-reduced at 37° C. for 20 minutes in BoNT/A Incubation Buffer (50 mM HEPES, pH 7.4, 1% fetal bovine serum, 10 μM $ZnCl_2$, 10 mM dithiothrietol) and 100 μl of the pre-reduced BoNT/A was added to the substrate-coated plates and incubated at 37° C. for 90 minutes. BoNT/A treated plates were washed by aspirating the BoNT/A Incubation Buffer and rinsing each plate three times with 200 μl TBS, 0.1% TWEEN-20® (polyoxyethylene (20) sorbitan monolaureate). Washed plates were incubated at 37° C. for one hour in 0.5% BSA in 1×TBS containing a 1:10 to 1:100 dilution of the antibody-containing serum being tested. Primary antibody probed plates were washed four times for 5 minutes each time in 200 μl TBS, 0.1% TWEEN-20® (polyoxyethylene (20) sorbitan monolaureate). Washed plates were incubated at 37° C. for 1 hour in 1×TBS containing a 1:10,000 dilution of goat polyclonal anti-mouse IgG antibody conjugated to Horseradish peroxidase (Pierce Biotechnology, Rockford, Ill.) as a secondary antibody. Secondary antibody-probed plates were washed four times in 200 μl TBS, 0.1% TWEEN-20® (polyoxyethylene (20) sorbitan monolaureate). Chromogenic detection of the labeled SNAP-25 products were visualized by chromogenic detection using ImmunoPure TMB substrate kit (Pierce Biotechnology, Rockford, Ill.). The development of a yellow color, which correlated with the presence of the SNAP-$25_{197}$ cleavage product was detected in BoNT/A treated samples, but not untreated controls, using antibody-containing serum derived from all six immunized mice (Mouse 1, Mouse 2, Mouse 3, Mouse 4, Mouse 5, and Mouse 6). Thus, the comparative ELISA analysis indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

For cell-based cleavage assay, a suitable density of PC12 cells were plated into 60 $mm^2$ tissue culture plates containing 3 mL of an appropriate serum medium (Table 1). The cells were grown in a 37° C. incubator under 5% carbon dioxide until cells reached the appropriate density. A 500 μL transfection solution was prepared by adding 250 μL of OPTI-MEM® Reduced Serum Medium containing 15 μL of LIPOFECTAINE® 2000 (Invitrogen Inc., Carlsbad, Calif.) incubated at room temperature for 5 minutes to 250 μL of OPTI-MEM® Reduced Serum Medium containing 10 pg of a pQBI-25/GFP-BoNT/A-LC expression construct (SEQ ID NO: 51). The pQBI-25/GFP-BoNT/A-LC expression construct comprises a pQBI-25 expression vector (Qbiogene Inc., Carlsbad, Calif.) whose promoter elements are functionally linked to a polynucleotide encoding the GFP-BoNT/A light chain of SEQ ID NO: 52. This transfection mixture was incubated at room temperature for approximately 20 minutes. The media was replaced with fresh unsupplemented media and the 500 μL transfection solution was added to the cells. The cells were then incubated in a 37° C. incubator under 5% carbon dioxide for approximately 6 to 18 hours. The cells were washed and harvested as described in Example II. To detect for the presence of the cleaved SNAP-$25_{197}$ product, an aliquot from each harvested sample was analyzed by Western blot as described in Example II, except that the primary antibody used was a 1:1,000 dilution of the antibody-containing serum and the secondary antibody used was a 1:20,000 of mouse α-IgG Horseradish Peroxidase (Pierce Biotechnology, Rockford, Ill.). A single band corresponding to the SNAP-$25_{197}$ cleavage product was detected in BoNT/A treated samples, but not untreated controls, using antibody-containing serum derived from three mice (Mouse 2, Mouse 3, and Mouse 4). Thus, the cell-based cleavage assay indicated that of the mice used for immunization, three mice (Mouse 2, Mouse 3, and Mouse 4) had higher titers and more specificity towards a SNAP-25 antigen having a carboxyl-terminus at the $P_1$ residue of the BoNT/A cleavage site scissile bond.

3. Production of Hybridomas.

To make hybridomas producing α-SNAP-25 monoclonal antibodies that can selectively bind to a SNAP-25 antigen having a carboxyl-terminus at the $P_1$ residue of the BoNT/A cleavage site scissile bond, the spleen from Mouse 2 was harvested three days subsequent to a final "booster" immunization and the spleen cells were fused with myeloma cells P3-X63 Ag8.653 using standard hybridoma protocols. These cells were plated into five 96-well plates and hybrids were selected using HAT medium. Within 8-14 days after fusion, the first screening of the approximately 480 parent clones was carried out using comparative ELISA with the BIRA-HIS TAG®-SNAP-$25_{134-197}$ and the BIRA-HIS TAG®-SNAP-$25_{134-206}$ peptides coated in two separate plates. The comparative ELISA provided a quick screen method to identify hybridomas producing antibodies specific for the cleaved SNAP-$25_{197}$. The top 18 clones were subjected to further screening using the cell-based cleavage assay described above and immunostaining of LC/A transfected cells. (Table 18).

TABLE 18

Analysis of Supernatants Containing α-SNAP-25 Monoclonal Antibody

| | Comparative ELISA | | | | Cell-Based Assay | |
|---|---|---|---|---|---|---|
| Clone | OD SNAP-$25_{197}$ | OD SNAP-$25_{206}$ | $Ratio_{197/206}$ | $Ratio_{206/197}$ | SNAP-$25_{197}$ | SNAP-$25_{206}$ |
| 1D3 | 1.805 | 0.225 | 8.02 | 0.13 | +++ | − |
| 1F12 | 0.365 | 0.093 | 3.92 | 0.25 | − | − |
| 1G10 | 0.590 | 0.137 | 4.31 | 0.23 | ++ | − |
| 1H1 | 0.335 | 0.121 | 2.77 | 0.36 | − | − |
| 1H8 | 0.310 | 0.302 | 1.03 | 0.97 | + | − |
| 2C9 | 0.139 | 0.274 | 0.51 | 1.97 | − | − |
| 2E2 | 0.892 | 0.036 | 24.78 | 0.04 | ++ | − |

TABLE 18-continued Analysis of Supernatants Containing α-SNAP-25 Monoclonal Antibody

| | Comparative ELISA | | | | Cell-Based Assay | |
|---|---|---|---|---|---|---|
| Clone | OD SNAP-25$_{197}$ | OD SNAP-25$_{206}$ | Ratio$_{197/206}$ | Ratio$_{206/197}$ | SNAP-25$_{197}$ | SNAP-25$_{206}$ |
| 2E4 | 0.228 | 0.069 | 3.30 | 0.30 | + | − |
| 2F11 | 1.095 | 1.781 | 0.61 | 1.63 | − | − |
| 3C1 | 1.268 | 0.053 | 23.92 | 0.04 | ++ | − |
| 3C3 | 0.809 | 0.052 | 15.56 | 0.06 | ++ | − |
| 3E1 | 0.086 | 0.155 | 0.55 | 1.80 | 0 | − |
| 3E8 | 2.048 | 0.053 | 38.64 | 0.03 | +++ | − |
| 3G2 | 0.053 | 0.158 | 0.34 | 2.98 | − | − |
| 4D1 | 0.106 | 0.218 | 0.49 | 2.06 | − | − |
| 4G6 | 0.061 | 0.159 | 0.38 | 2.61 | − | − |
| 5A5 | 0.251 | 0.106 | 2.37 | 0.42 | + | − |
| 5F11 | 0.243 | 0.061 | 3.98 | 0.25 | − | − |

Clones 1D3, 1G10, 2E2, 3C1, 3C3, and 3E8 were further cloned by limiting dilution because the conditioned media produced by these clones comprised α-SNAP-25 antibodies with a preferential binding specificity having a ratio$_{197/206}$ of at least 4:1 for the SNAP-25$_{197}$ cleavage product relative to the SNAP-25$_{206}$ uncleaved substrate and detected the SNAP-25$_{197}$-cleavage product using the cell-based cleavage assay and the immunostaining of PC12 cells transfected with GFP-LC/A. Similarly clones 2C9, 2F11, 3G2, 4D1 and 4G6 were further cloned by limiting dilution because the conditioned media produced by these clones comprised α-SNAP-25 antibodies with a preferential binding specificity having a $ratio_{206,197}$ of at least 1.5:1 for the SNAP-$25_{206}$ uncleaved substrate relative to the SNAP-$25_{197}$ cleavage product and detected the SNAP-$25_{206}$-uncleaved substrate using the cell-based cleavage assay. These single-cell derived clones were screened again using comparative ELISA, cell-based cleavage, and immunostaining to confirm their affinity and specificity, and the antibodies were isotyped using standard procedures. Ascites were produced from clones 1D3B8 (IgM.k), 1G10Al2 (IgG3.k), 2C9B10 (IgG3.k), 2E2A6 (IgG3.k), 2F11B6 (IgM.k), 3C1A5 (IgG2a.k), and 3C3E2 (IgG2a.k). Clone 3E8 stopped producing antibodies during the cloning process and could not be further evaluated.

4. Evaluation of Binding Specificity of α-SNAP-25 Monoclonal Antibodies.

To evaluate binding specificity of an α-SNAP-25 monoclonal antibody that can selectively bind to a SNAP-25 antigen having a carboxyl-terminus at the $P_1$ residue of the BoNT/A cleavage site scissile bond, ascites from clones 1D3B8, 1G10Al2, 2C9B10, 2E2A6, 2F11B6, 3C1A5, and 3C3E2 were used to detect SNAP-25 cleavage product using the cell-based activity assay, immunocytochemistry and immunoprecipitation.

For the cell-based activity assay, binding specificity was determined by analyzing the ability of α-SNAP-25 antibody-containing ascites to detect the uncleaved SNAP-$25_{206}$ substrate and the cleaved SNAP-$25_{197}$ product by Western blot analysis. A suitable density of PC12 cells were plated into 60 mm2 tissue culture plates containing 3 mL of an appropriate serum medium, grown in a 37° C. incubator under 5% carbon dioxide until an appropriate cell density was reached, and transfected with the either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed and harvested as described in Example I. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:100 dilution of the α-SNAP-25 monoclonal antibody-containing ascites and the secondary antibody used was a 1:20,000 of α-mouse IgG conjugated to Horseradish Peroxidase (Pierce Biotechnology, Rockford, Ill.). In addition, three commercially available mouse α-SNAP-25 monoclonal antibodies were tested. SMI-81 (Sternberger Monoclonals Inc., Lutherville, Md.), an α-SNAP-25 antibody the manufacturer indicates detects both the uncleaved SNAP-$25_{206}$ substrate and the cleaved SNAP-$25_{197}$ product, was used at a 15,000 dilution according to the manufacturer's recommendations. MC-6050 (Research & Diagnostic Antibodies, Las Vegas, Nev.), an α-SNAP-25 antibody the manufacturer indicates detects both the uncleaved SNAP-$25_{206}$ substrate and the cleaved SNAP-$25_{197}$ product, was used at a 1:100 dilution according to the manufacturer's recommendations. MC-6053 (Research & Diagnostic Antibodies, Las Vegas, Nev.), an α-SNAP-25 antibody the manufacturer indicates detects only the cleaved SNAP-$25_{197}$ product, was used at a 1:100 dilution according to the manufacturer's recommendations.

Table 19 indicates the α-SNAP-25 antibody-containing ascites that detected only the SNAP-$25_{197}$ cleavage product. The cell-based cleavage assay indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the selective recognition of this cleavage product relative to the SNAP-$25_{206}$ uncleaved substrate. Commercial antibody SMI-81 detected the SNAP-$25_{206}$ uncleaved substrate, but only poorly recognized the SNAP-$25_{197}$ cleavage product (Table 19). Surprisingly, commercial antibody MC-6050 only detected the SNAP-$25_{206}$ uncleaved substrate, and failed to recognize the SNAP-$25_{197}$ cleavage product (Table 19). Even more surprisingly, commercial antibody MC-6050 only detected the SNAP-$25_{206}$ uncleaved substrate, and failed to recognize the SNAP-$25_{197}$ cleavage product, even though the manufacturer advertises that this antibody selectively detects the SNAP-$25_{197}$ cleavage product (Table 19). Thus, this analysis indicates that while 1D3B8, 2C9B10, 2E2A6, 3C1A5, and 3C3E2 exhibit suitable selectivity for the SNAP-$25_{197}$ cleavage product, 1G10Al2 and 2F11B6 do not. In addition, commercial antibodies SMI-81, MC-6050 and MC-6053 all are unsuitable for the immuno-based methods disclosed in the present application because all failed to selectivity detect the SNAP-$25_{197}$ cleavage product.

For immunocytochemistry analysis, binding specificity was determined by analyzing the ability of α-SNAP-25 antibody-containing ascites to detect the uncleaved SNAP-25$_{206}$ substrate and the cleaved SNAP-25$_{197}$ product by immunostaining. See e.g., Ester Fernandez-Salas et al., *Plasma Membrane Localization Signals in the Light Chain of Botulinum Neurotoxin*, Proc. Natl. Acad. Sci., U.S.A. 101(9): 3208-3213 (2004). A suitable density of PC12 cells were plated, grown, and transfected with either a transfection solution lacking the pQBI-25/GFP-BoNT/A-LC expression construct (untransfected cells) or a transfection solution containing the pQBI-25/GFP-BoNT/A-LC expression construct (transfected cells) as described above. The cells were washed in 1×PBS and fixed in 5 mL of PAF at room temperature for 30 minutes. Fixed cells were washed in phosphate buffered saline, incubated in 5 mL of 0.5% Triton® X-100 (polyethylene glycol octylphenol ether) in 1×PBS, washed in 1×PBS, and permeabilized in 5 mL of methanol at −20° C. for six minutes. Permeabilized cells were blocked in 5 mL of 100 mM glycine at room temperature for 30 minutes, washed in 1×PBS, and blocked in 5 mL of 0.5% BSA in 1×PBS at room temperature for 30 minutes. Blocked cells were washed in 1×PBS and incubated at room temperature for two hours in 0.5% BSA in 1×PBS containing a 1:10 dilution of an ascites from a clonal hybridoma cell line being tested. Primary antibody probed cells were washed three times for 5 minutes each time in 1×PBS. Washed cells were incubated at room temperature for 2 hours in 1×PBS containing a 1:200 dilution of goat polyclonal anti-mouse immunoglobulin G, heavy and light chains (IgG, H+L) antibody conjugated to ALEXA® FLUOR 568 (Invitrogen Inc., Carlsbad, Calif.) as a secondary antibody. Secondary antibody-probed cells were washed three times for 5 minutes each time in 1×PBS. Washed cells were prepared for microscopic examination by mounting in VECTASHIELD® Mounting Media (Vector Laboratories, Burlingame, Calif.) and coverslipped. Images of signal detection were obtained with a Leica confocal microscope using appropriate laser settings. Table 19 indicates that the α-SNAP-25 antibody-containing ascites that specifically detected the SNAP-$25_{197}$-cleavage product. The immunocytochemistry analysis indicated that ascites produced from clones 1D3B8, 2C9B10, 2E2A6, 3C1A5, and 3C3E2 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

For immunoprecipitation analysis, binding specificity was determined by analyzing the ability of Protein A (HiTrap™ Protein A HP Columns, GE Healthcare, Amersham, Piscataway, N.J.), purified α-SNAP-25 monoclonal antibodies to precipitate the uncleaved SNAP-$25_{206}$ substrate and the cleaved SNAP-$25_{197}$ product. See e.g., Chapter 8 Storing and Purifying Antibodies, pp. 309-311, Harlow & Lane, supra, 1998a. A suitable density of PC12 cells were plated, grown, and transfected with either a transfection solution containing a pQBI-25/GFP expression construct (control cells; SEQ ID NO: 53) or a transfection solution containing the pQBI-25/GFP-BoNT/A-LC expression construct (experimental cells) as described above. The pQBI-25/GFP expression construct comprises an expression vector whose promoter elements are functionally linked to a polynucleotide encoding GFP of SEQ ID NO: 54. After an overnight incubation, the cells were washed by aspirating the growth media and rinsing each well with 200 μL1×PBS. To harvest the cells, the PBS was aspirated, the cells were lysed by adding an Immunoprecipitation Lysis Buffer comprising 50 mM HEPES, 150 mM NaCl, 1.5 mM $MgCl_2$, 1 mM EGDT, 10% glycerol, 1% Triton® X-100 (polyethylene glycol octylphenol ether) and a 1×COMPLETE™ Protease inhibitor cocktail (Roche Applied Biosciences, Indianapolis, Ind.) and incubating at 4° C. for one hour. The lysed cells were centrifuged at 3,000×g at 4° C. for 10 minutes to remove cellular debris and the supernatant transferred to a clean tube and diluted to a protein concentration of approximately 1 mg/mL. Approximately 5 pg of purified monoclonal antibody was added to 0.5 mL of diluted supernatant and incubated at 4° C. for two hours. After primary antibody incubation, approximately 50 μl of immobilized Protein G (Pierce Biotechnology, Rockford, Ill.) was added to the diluted supernatant and incubated at 4° C. for one hour. The incubated supernatant was washed three times for 30 minutes each time by adding 0.5 mL of Immunoprecipitation Lysis Buffer, centrifuging at 300×g at 4° C. for one minute to pellet the immobilized Protein G, and decanting the supernatant. After washing, the pellet was resuspended in 30 pL of 1×SDS Loading Buffer and the sample was heated to 95° C. for 5 minutes. To detect for the presence of both the uncleaved SNAP-$25_{206}$ substrate and the cleaved SNAP-$25_{197}$ product, an aliquot from each harvested sample was analyzed by Western blot as described in Example I, except that the primary antibody used was a 1:1,000 dilution of the α-SNAP-25 polyclonal antibody serum (see Example IV) and the secondary antibody used was a 1:20,000 of rabbit α-IgG Horseradish Peroxidase (Pierce Biotechnology, Rockford, Ill.). Table 19 indicates the α-SNAP-25 antibody-containing ascites that specifically pulled down the SNAP-$25_{197}$-cleavage product by immunoprecipitation analysis. The immunoprecipitation analysis indicated that ascites produced from clones 2E2A6 and 3C1A5 synthesize an α-SNAP-25 monoclonal antibody having high binding specificity for the SNAP-$25_{197}$ cleavage product that allows for the preferential recognition of this cleavage product relative to the SNAP-$25_{206}$ uncleaved substrate.

TABLE 19

Analysis of Clone Ascites Containing α-SNAP-25 Monoclonal Antibody

| | Cell-Based Assay | | Immunocytochemistry | | Immunoprecipitation | |
|---|---|---|---|---|---|---|
| Clone | SNAP-$25_{197}$ | SNAP-$25_{206}$ | SNAP-$25_{197}$ | SNAP-$25_{206}$ | SNAP-$25_{197}$ | SNAP-$25_{206}$ |
| 1D3B8 | ++ | − | ++ | − | Not Tested | Not Tested |
| 1G10A12 | ++ | ++ | Not Tested | Not Tested | Not Tested | Not Tested |
| 2C9B10 | ++ | − | ++ | − | Not Tested | Not Tested |
| 2E2A6 | ++ | − | ++ | − | ++ | − |
| 2F11B6 | + | + | + | + | Not Tested | Not Tested |
| 3C1A5 | ++ | − | ++ | − | ++ | − |
| 3C3E2 | + | − | Not Tested | Not Tested | Not Tested | Not Tested |
| MC-6050 | − | + | Not Tested | Not Tested | Not Tested | Not Tested |
| MC-6053 | − | + | Not Tested | Not Tested | Not Tested | Not Tested |
| SMI-81 | −/+ | ++ | Not Tested | Not Tested | Not Tested | Not Tested |

5. Evaluation of Binding Affinity of α-SNAP-25 Monoclonal Antibodies.

To determine the binding affinity of an α-SNAP-25 monoclonal antibody showing high binding specificity for either the SNAP-25$_{197}$ cleavage product or the SNAP-25$_{206}$ uncleaved substrate, binding affinity assays were performed on a BIACORE 3000 instrument using carboxymethyl dextran (CM5) sensor chips (BIAcore, Inc., Piscataway, N.J.). Runs were conducted at 25° C. with HBS-EP buffer comprising 10 mM HEPES (pH 7.4), 150 mM sodium chloride, 3 mM EDTA, 0.005% (v/v) surfactant P20 at a flow rate of 10 μl/min. SNAP-25 peptides comprising amino acids 134-197 of SEQ ID NO: 5 (SNAP-25$_{134-197}$) or amino acids 134-206 of SEQ ID NO: 5 (SNAP-25$_{134-206}$) were covalently attached to the surface of the CM5 sensor chips using standard amine coupling. Briefly, the CM5 chips were activated by a 7 minute injection of a mixture of 0.2 M1-ethyl-3-(3-dimethylaminopropyl) carbodiimide and 0.05 M N-hydroxysuccimide; the SNAP-25 peptides were then injected in 10 mM sodium acetate (pH 4.0) for 20 min at a flow rate of 10 μL/min; and unreacted succimide esters were blocked by a 7-min injection of 1 M ethanolamine hydrochloride, pH 8.5. The immobilized amount of SNAP-25$_{134-197}$ or SNAP-25$_{134-206}$ on the chip was reflected by a 100-150 increase in response units (about 0.10-0.15 ng/mm$^2$). Antibody samples comprising either ascites or purified monoclonal antibodies produced from clones 1D3B8, 2C9B10, 2E2A6, 3C1A5, and 3C3E2, as well as, commercially available α-SNAP-25 antibodies were passed over the surface of the CM5 chips allowing an association time of 10 min and a dissociation time of 20 min. The surfaces were regenerated between runs by a 1 minute injection of 10 mM glycine-HCl (pH 2.5) at a flow rate of 15 μL/min. Sensorgram curves were fitted to a 1:1 kinetic binding model with the BIAevaluation 3.0 software.

The results indicate that both 2E2A6 and 3C1A5 were highly specific for cleaved SNAP-25$_{197}$ product over SNAP-25 uncleaved substrate (Table 20). When compared to the binding affinities of MC-6050 and MC-6053, 1D3B6 had an approximately 10-fold higher equilibrium disassociation constant for the SNAP-25 cleavage product relative to these commercial antibodies (Table 20). Interestingly, 2E2A6 had only a slightly lower equilibrium disassociation constant for the SNAP-25 cleavage product relative to these commercial antibodies (0.405 nM versus 0.497 and 0.508)(Table 20). As neither of these commercial α-SNAP-25 antibodies selectively recognized the SNAP-25 cleavage product (Table 19), an equilibrium disassociation constant lower than about 0.5 nM appears, in part, critical to achieve such selectivity. Similarly, when compared to the binding affinities of MC-6050 and MC-6053, 2E2A6 had an about at least one-fold slower off rate/dissociation constant (6.74×10$^{-5}$ versus 8.82×10$^{-4}$ s$^{-1}$ and 1.18×10$^{-3}$ s$^{-1}$) (Table 20). This further suggests that an off rate/dissociation constant lower than about 8.82×10$^{-4}$ appears, in part, critical to achieve selective binding for the SNAP-25 cleavage product. This result is consistent with 1 D3B8, which had an off rate/dissociation constant of 5.78×10$^{-5}$ s$^{-1}$ (Table 20).

TABLE 20

Analysis of Binding Affinity α-SNAP-25 Monoclonal Antibodies

| SPR | 1D3B8 | | 2E2A6 | |
|---|---|---|---|---|
| Parameter | SNAP-25$_{197}$ | SNAP-25$_{206}$[a] | SNAP-25$_{197}$ | SNAP-25$_{206}$[b] |
| Ka (M$^{-1}$ s$^{-1}$) | 1.06 × 10$^6$ | — | 1.70 × 10$^6$ (1.66 × 10$^5$) | — (—) |
| Kd (s$^{-1}$) | 5.78 × 10$^{-5}$ | — | 1.53 × 10$^{-4}$ (6.74 × 10$^{-5}$) | — (—) |
| KD (nM) | 0.050 | — | 0.090 (0.405) | — (—) |

TABLE 20-continued

Analysis of Binding Affinity α-SNAP-25 Monoclonal Antibodies

| SPR | 3C1A5 | | 2C9B10 | |
|---|---|---|---|---|
| Parameter | SNAP-25$_{197}$ | SNAP-25$_{206}$[c] | SNAP-25$_{197}$ | SNAP-25$_{206}$[d] |
| Ka (M$^{-1}$ s$^{-1}$) | 2.17 × 10$^5$ | — | 1.15 × 10$^4$ | — |
| Kd (s$^{-1}$) | 2.88 × 10$^{-4}$ | — | 3.11 × 10$^{-4}$ | — |
| KD (nM) | 1.33 | — | 27.1 | — |

| SPR | MC-6050 | | MC-6053 | |
|---|---|---|---|---|
| Parameter | SNAP-25$_{197}$ | SNAP-25$_{206}$ | SNAP-25$_{197}$ | SNAP-25$_{206}$ |
| Ka (M$^{-1}$ s$^{-1}$) | 1.78 × 10$^6$ | 3.06 × 10$^2$ | 2.32 × 10$^6$ | 1.06 × 10$^2$ |
| Kd (s$^{-1}$) | 8.82 × 10$^{-4}$ | 6.07 × 10$^{-3}$ | 1.18 × 10$^{-3}$ | 2.56 × 10$^{-5}$ |
| KD (nM) | 0.497 | 19,800 | 0.508 | 240 |

[a]No binding was observed when up to 125 nM of α-SNAP-25 monoclonal antibody 1D3B8 was passed over the surface of the CM5 sensor chip after a 10 minute association time.
[b]No binding was observed when up to 10 μM of α-SNAP-25 monoclonal antibody 2E2A6 was passed over the surface of the CM5 sensor chip after a 10 minute association time.
[c]No binding was observed when up to 100 nM of α-SNAP-25 monoclonal antibody 3C1A5 was passed over the surface of the CM5 sensor chip after a 10 minute association time.
[d]No binding was observed when up to 100 nM of α-SNAP-25 monoclonal antibody 2C9B10 was passed over the surface of the CM5 sensor chip after a 10 minute association time.

Figure 3A:
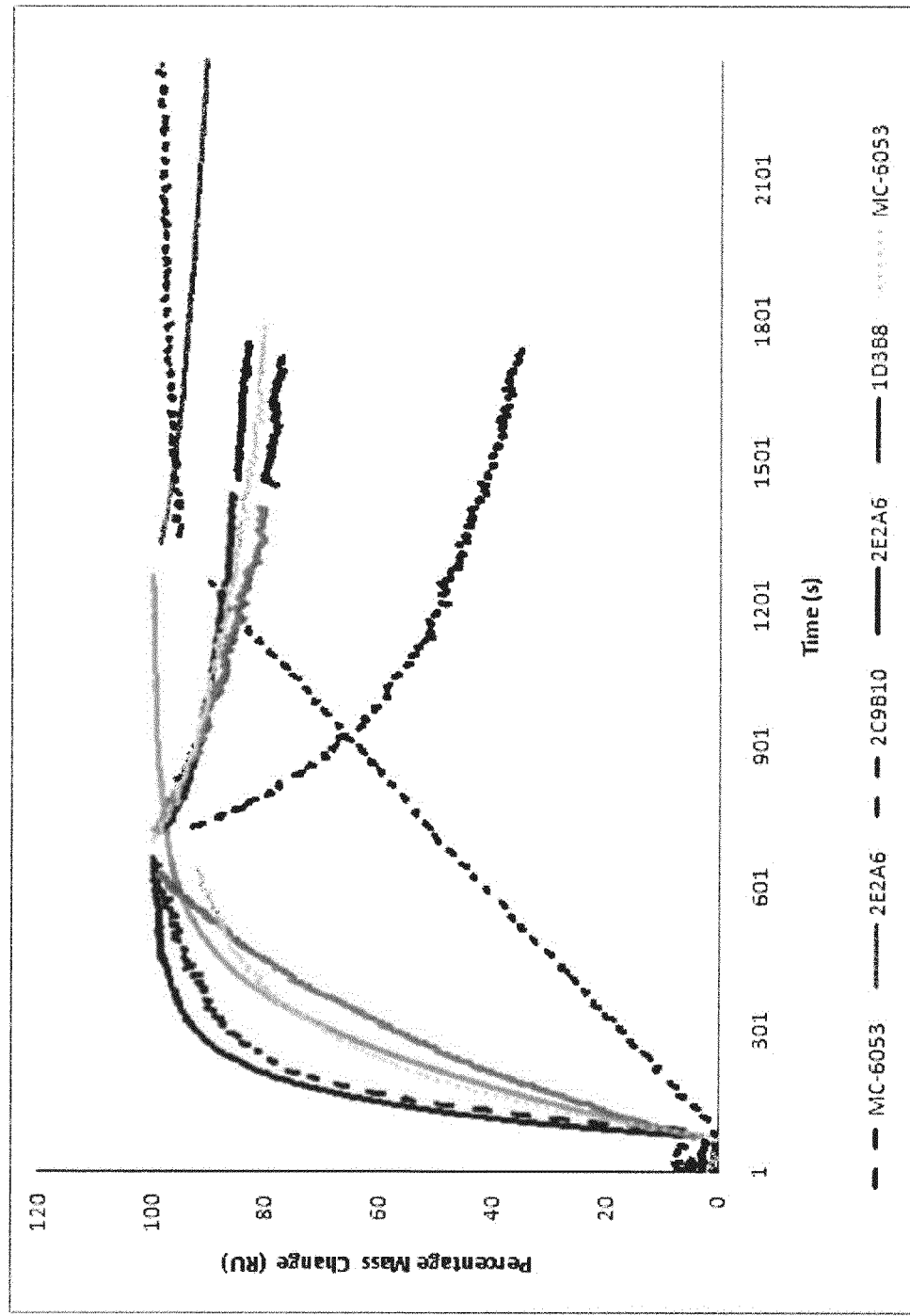
FIG. 3A shows the normalized data for the on-rate of each antibody.
Figure 3B:
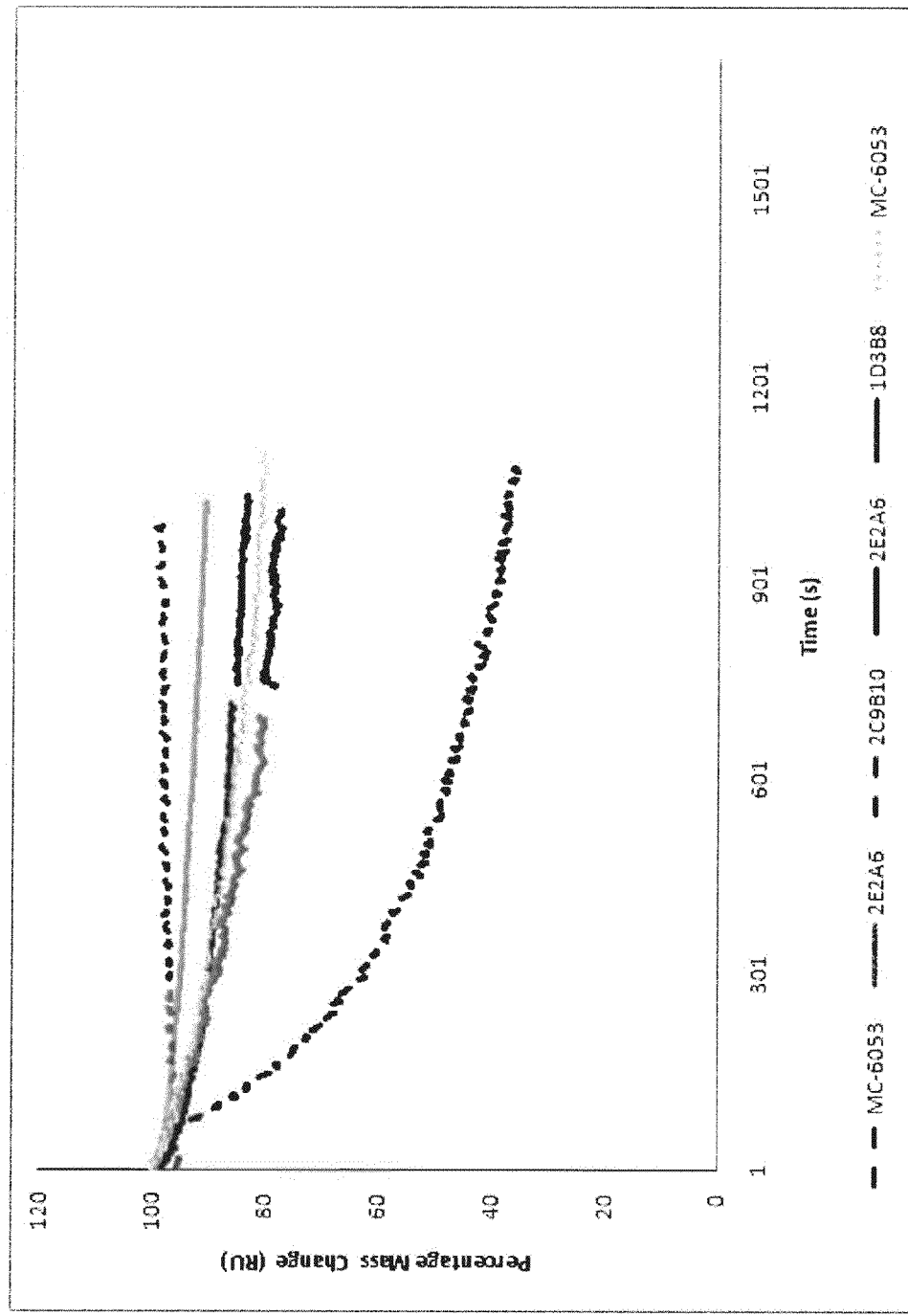
FIG. 3B shows the normalized data for the off-rate of each antibody.

To compare the six different antibodies, the on-rate (ka) and off-rate (kd) for each was normalized using a program from the BIA evaluation 4.1 software. For comparison of the on-rates, the data were first individually trimmed by deleting the re-generation portion and the injection spikes, and then normalized to a 0 to 100 scale. For comparison of the off-rate, the data were normalized to the injection stop/top point. This analysis showed that 2C9B10 had a much slower on-rate than the other antibodies (FIG. 3A), and that MC-6053 has a much faster off-rate (dissociation) that the other antibodies (FIG. 3B). The fast off-rate of MC-6053 indicates that this antibody will not perform well in the methods disclosed in the present specification because this antibody will have difficulty staying bound to the substrate antigen during the washing steps.

6. Sequencing of the Epitope from Isolated α-SNAP-25 Monoclonal Antibodies.

To determine the epitope of an isolated α-SNAP-25 monoclonal antibody that can selectively bind to a SNAP-25 antigen having a carboxyl-terminus at the P$_1$ residue of the BoNT/A cleavage site scissile bond, the polynucleotide molecule encoding the variable heavy (V$_H$) and variable light (V$_L$) chains of the α-SNAP-25 monoclonal antibody produced by hybridomas 1D3B8, 2C9B10, 2E2A6, 3C1A5 and 3C3E2 were sequenced. mRNA was extracted and purified from each hybridoma using standard protocols and reversed transcribed into cDNA using either an oligo dT anti-sense primer or a gene-specific (murine IgG1 CH and kappa CL) anti-sense primer. Specific murine and human const A. Sabbadini, et al., *Novel Bioactive Lipid Derivatives and Methods of Making and Using Same*, U.S. Patent Publication 2007/0281320; and Peter Amersdorfer, et al., *Molecular Characterization of Murine Humoral Immune Response to Botulinum Neurotoxin Type A Binding Domain as Assessed by Using Phage Antibody Libraries*, 65(9) Infect. Immun. 3743-3752, each of which is hereby incorporated by reference in its entirety. In addition, commercial services are available to sequence the variable heavy ($V_H$) and variable light ($V_L$) chains of an antibody and identify the CDR regions, see, e.g., Fusion Antibodies Ltd., Northern Ireland.

The polynucleotide sequence comprising the $V_H$ and $V_L$ chains of the α-SNAP-25 monoclonal antibody produced by the hybridomas disclosed in the present specification is as follows: 1 D3B8 $V_H$ (SEQ ID NO: 71), 2C9B10 $V_H$ (SEQ ID NO: 73), 2E2A6 $V_H$ (SEQ ID NO: 75), 3C1A5 $V_H$ (SEQ ID NO: 77), 3C3E2 $V_H$ variant 1 (SEQ ID NO: 79), 3C3E2 $V_H$ variant 2 (SEQ ID NO: 81), 3C3E2 $V_H$ variant 3 (SEQ ID NO: 149), 1D3B8 $V_L$ (SEQ ID NO: 83), 2C9B10 $V_L$ (SEQ ID NO: 85), 2E2A6 $V_L$ (SEQ ID NO: 87), 3C1A5 $V_L$ (SEQ ID NO: 89), and 3C3E2 $V_L$ (SEQ ID NO: 91). The amino acid sequence comprising the $V_H$ and $V_L$ chains of the α-SNAP-25 monoclonal antibody produced by the hybridomas disclosed in the present specification is as follows: 1D3B8 $V_H$ (SEQ ID NO: 72), 2C9B10 $V_H$ (SEQ ID NO: 74), 2E2A6 $V_H$ (SEQ ID NO: 76), 3C1A5 $V_H$ (SEQ ID NO: 78), 3C3E2 $V_H$ variant 1 (SEQ ID NO: 80), 3C3E2 $V_H$ variant 2 (SEQ ID NO: 82); 3C3E2 $V_H$ variant 2 (SEQ ID NO: 150), 1D3B8 $V_L$ (SEQ ID NO: 84), 2C9B10 $V_L$ (SEQ ID NO: 86), 2E2A6 $V_L$ (SEQ ID NO: 88), 3C1A5 $V_L$ (SEQ ID NO: 90), and 3C3E2 $V_L$ (SEQ ID NO: 92). The amino acid sequences comprising the $V_H$ and $V_L$ CDR domains of the α-SNAP-25 monoclonal antibody produced by the hybridomas 1 D3B8, 2C9B10, 2E2A6, 3C1A5, and 3C3E2 are given in Table 21.

TABLE 21

CDR Sequences of $V_H$ and $V_L$ domains from α-SNAP-25 Monoclonal Antibodies

| CDR | Sequence | Identified In | SEQ ID NO: |
|---|---|---|---|
| $V_H$ CDR 1 | TFTDHSIH | 2E2A6<br>2C9B10<br>3C1A5 | 93 |
| $V_H$ CDR 1 | TFTNYVIH | 3C3E2 | 94 |
| $V_H$ CDR 1 | IFTDHALH | 1D3B8 | 95 |
| $V_H$ CDR 2 | YIFPGNGNIEYNDKFKG | 2E2A6 | 96 |
| $V_H$ CDR 2 | YLFPGNGNFEYNEKFKG | 2C9B10<br>3C1A5 | 97 |
| $V_H$ CDR 2 | YINPYNDGSKYNEKFKG | 3C3E2 | 98 |
| $V_H$ CDR 2 | YIFPGNGNIEYNEKFKG | 1D3B8 | 99 |
| $V_H$ CDR 3 | KRMGY | 2E2A6<br>3C1A5 | 100 |
| $V_H$ CDR 3 | KKMDY | 2C9B10<br>1D3B8 | 101 |
| $V_H$ CDR 3 | ARMDY | 3C3E2var1 | 102 |
| $V_H$ CDR 3 | ARMGY | 3C3E2var2 | 151 |
| $V_H$ CDR 3 | ARHLANTYYYFDY | 3C3E2var3 | 152 |
| $V_L$ CDR 1 | RSSQSIVHSNGNTYLE | 1D3B8 | 103 |
| $V_L$ CDR 1 | RTTENIYSYFV | 2C9B10 | 104 |
| $V_L$ CDR 1 | KSSQSLLYTNGKTYLT | 2E2A6 | 105 |
| $V_L$ CDR 1 | KSSQSLLNTNGKTYLT | 3C1A5 | 106 |
| $V_L$ CDR 1 | RASQNIGNYLH | 3C3E2 | 107 |
| $V_L$ CDR 2 | KVSNRFS | 1D3B8 | 108 |
| $V_L$ CDR 2 | NAKSLAE | 2C9B10 | 109 |
| $V_L$ CDR 2 | LVSELDS | 2E2A6 | 110 |
| $V_L$ CDR 2 | LVSKLDS | 3C1A5 | 111 |
| $V_L$ CDR 2 | YASQSIS | 3C3E2 | 112 |
| $V_L$ CDR 3 | FQGSHVPPT | 1D3B8 | 113 |
| $V_L$ CDR 3 | QHHYGTPYT | 2C9B10 | 114 |
| $V_L$ CDR 3 | LQSAHFPFT | 2E2A6 | 115 |
| $V_L$ CDR 3 | LQSSHFPFT | 3C1A5 | 116 |
| $V_L$ CDR 3 | QQSDTWPLT | 3C3E2 | 117 |

Non-limiting examples of amino acid sequences comprising $V_H$ CDR domain variants of the α-SNAP-25 monoclonal antibody produced by the hybridomas disclosed in the present specification include $V_H$ CDR1 variant SEQ ID NO: 118 for 1D3B8; $V_H$ CDR1 variant SEQ ID NO: 119 for 2C9B10, 2E2A6 and 3C1A5 $V_H$; $V_H$ CDR1 variant SEQ ID NO: 120 for 3C1A5 $V_H$ and 3C3E2 variant 3; $V_H$ CDR2 variant SEQ ID NO: 121 for 1D3B8 and 2E2A6; $V_H$ CDR2 variant SEQ ID NO: 122 for 2C9B10 and 3C1A5 $V_H$; $V_H$ CDR2 variant SEQ ID NO: 123 for 3C1A5 $V_H$ and 3C3E2 variant 3; $V_H$ CDR3 variant MDY for 1D3B8 and 2C9B10; $V_H$ CDR3 variant MGY for 2E2A6 and 3C1A5 $V_H$; and $V_H$ CDR3 variant SEQ ID NO: 124 for 3C1A5 $V_H$ and 3C3E2 variant 3. Non-limiting examples of amino acid sequences comprising $V_L$ CDR domain variants of the α-SNAP-25 monoclonal antibody produced by the hybridomas disclosed in the present specification include $V_L$ CDR1 variant SEQ ID NO: 125 for 1 D3B8; $V_L$ CDR1 variant SEQ ID NO: 126 for 2C9B10; $V_L$ CDR1 variant SEQ ID NO: 127 for 2E2A6; $V_L$ CDR1 variant SEQ ID NO: 128 for 3C1A5; $V_L$ CDR1 variant SEQ ID NO: 129 for 3C3E2; $V_L$ CDR2 variant KVS for 1D3B8; $V_L$ CDR2 variant NAK for 2C9B10; $V_L$ CDR2 variant LVS for 2E2A6; $V_L$ CDR2 variant YAT for 3C1A5; and $V_L$ CDR2 variant YAS for 3C3E2.

Example IX

Development of α-SNAP-25 Polyclonal Antibodies that Selectively Bind a SNAP-25 Epitope Having a Free Carboxyl-Terminus at the $P_1$ Residue of the BoNT/A Cleavage Site Scissile Bond The following example illustrates how to make α-SNAP-25 polyclonal antibodies that can selectively bind to a SNAP-25 epitope having a carboxyl-terminus at the $P_1$ residue of the BoNT/A cleavage site scissile bond.

To develop α-SNAP-25 polyclonal antibodies that bind an epitope comprising a carboxyl-terminus at the P1 residue from the BoNT/A cleavage site scissile bond from a SNAP-25 cleavage product, the 10-residue peptide CGGGRIDEANQ (SEQ ID NO: 46) was designed as a SNAP-25 cleavage product antigen. This peptide comprising a N-terminal Cysteine residue for conjugation to KLH, a G-spacer flexible spacer (GGG) linked to amino acids 191-197 of human SNAP-25 (SEQ ID NO: 5) and has a carboxylated C-terminal glutamine. Blast searches revealed that this peptide has high homology only to SNAP-25 and almost no possible cross-reactivity with other proteins in neuronal cells. The sequence was also carefully scrutinized by utilizing computer algorithms to determine hydropathy index, protein surface probability, regions of flexibility, and favorable secondary structure, followed by proper orientation and presentation of the chosen peptide sequence. The peptide was synthesized and conjugated to Keyhole Limpet Hemocyanin (KLH) to increase immunogenicity. Before the animals were immunized, naïve rabbits were first screened against cell lysates from candidate cell lines in a Western blot in order to identify animals that had no immunoreactivity to the proteins present in the cell lysates. Two pre-screened rabbits were immunized with this peptide, and after three immunizations in about eight weeks, the rabbits were bled for testing. The blood was allowed to clot by incubating at 4° C. for 60 minutes. The clotted blood was centrifuged at 10,000×g at 4° C. for 10 minutes to pellet the cellular debris. The resulting serum sample was dispensed into 50 μL aliquots and stored at −20° C. until needed.

A similar strategy based on other SNAP-25 antigens disclosed in the present specification is used to develop α-SNAP-25 polyclonal antibodies that bind an epitope comprising a carboxyl-terminus at the P1 residue from the BoNT/A cleavage site scissile bond from a SNAP-25 cleavage product. For example, the SNAP-25 antigen of SEQ ID NO: 47 can be conjugated to KLH instead of the SNAP-25 antigen of SEQ ID NO: 46. As another example, the amino acids 191-197 of human SNAP-25 from the SNAP-25 antigen of SEQ ID NO: 38 can be replaced with SEQ ID NO: 33, SEQ ID NO: 34, SEQ ID NO: 35, SEQ ID NO: 36, SEQ ID NO: 37, SEQ ID NO: 39, SEQ ID NO: 40, SEQ ID NO: 41, SEQ ID NO: 42, SEQ ID NO: 43, or SEQ ID NO: 44.

2. Screening for the Presence of α-SNAP-25 Polyclonal Antibodies.

To determine the presence of α-SNAP-25 polyclonal antibodies that can selectively bind to a SNAP-25 antigen having a carboxyl-terminus at the $P_1$ residue of the BoNT/A cleavage site scissile bond, comparative ELISA and cell-based cleavage assays were performed using the extracted rabbit serum as described in Example VIII. The serum from both rabbits contained α-SNAP-25 polyclonal antibodies that can selectively bind to a SNAP-25 antigen having a carboxyl-terminus at the $P_1$ residue of the BoNT/A cleavage site scissile bond. The α-SNAP-25 rabbit polyclonal antibodies were designated as NTP 22 and NTP 23.

3. Purification of α-SNAP-25 Polyclonal Antibodies.

To purify α-SNAP-25 polyclonal antibodies that can selectively bind to a SNAP-25 antigen having a carboxyl-terminus at the $P_1$ residue of the BoNT/A cleavage site scissile bond, NTP 22 and NTP 23 antibodies from rabbit serum were purified using affinity columns containing the SNAP-25 antigen of SEQ ID NO: 46.

4. Evaluation of Binding Specificity of α-SNAP-25 Polyclonal Antibodies.

To evaluate binding specificity of an α-SNAP-25 polyclonal antibody that can selectively bind to a SNAP-25 antigen having a carboxyl-terminus at the $P_1$ residue of the BoNT/A cleavage site scissile bond, purified NTP 22 and NTP 23 α-SNAP-25 polyclonal antibodies were used to detect cleavage product using the cell-based activity assay, immunnocytochemistry and immunoprecipitation as described in Example VIII. The cell-based cleavage assay, immunocytochemistry analysis and immunoprecipitation analysis all indicated that NTP 22 and NTP 23 α-SNAP-25 polyclonal antibodies did not cross-react with uncleaved SNAP-25. Thus both NTP 22 and NTP 23 have high binding specificity for the SNAP-25$_{197}$ cleavage product that allows for the preferential recognition of this cleavage product relative to the SNAP-25$_{206}$ uncleaved substrate. Affinity for the antigens can be determined using SPR in the BiAcore as described in Example VIII.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

SEQUENCE LISTING

```
<160> NUMBER OF SEQ ID NOS: 152

<210> SEQ ID NO 1
<211> LENGTH: 1296
<212> TYPE: PRT
<213> ORGANISM: Clostridium botulinum

<400> SEQUENCE: 1

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
                100                 105                 110

Arg Gly Ile Pro Phe Trp Gly Gly Ser Thr Ile Asp Thr Glu Leu Lys
            115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
                180                 185                 190

Thr Phe Gly Phe Glu Glu Ser Leu Glu Val Asp Thr Asn Pro Leu Leu
            195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240
```

-continued

```
Arg Val Phe Lys Val Asn Thr Asn Ala Tyr Tyr Glu Met Ser Gly Leu
            245                 250                 255
Glu Val Ser Phe Glu Leu Arg Thr Phe Gly Gly His Asp Ala Lys
        260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
            325                 330                 335
Lys Phe Asp Lys Leu Tyr Lys Met Leu Thr Glu Ile Tyr Thr Glu Asp
        340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
        370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
            405                 410                 415
Lys Asn Phe Thr Gly Leu Phe Glu Phe Tyr Lys Leu Leu Cys Val Arg
        420                 425                 430
Gly Ile Ile Thr Ser Lys Thr Lys Ser Leu Asp Lys Gly Tyr Asn Lys
        435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
        530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
Leu Asn Pro Ser Arg Val Tyr Thr Phe Phe Ser Ser Asp Tyr Val Lys
        580                 585                 590
Lys Val Asn Lys Ala Thr Glu Ala Ala Met Phe Leu Gly Trp Val Glu
        595                 600                 605
Gln Leu Val Tyr Asp Phe Thr Asp Glu Thr Ser Glu Val Ser Thr Thr
        610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
            645                 650                 655
Ile Phe Ser Gly Ala Val Ile Leu Leu Glu Phe Ile Pro Glu Ile Ala
            660                 665                 670
```

```
Ile Pro Val Leu Gly Thr Phe Ala Leu Val Ser Tyr Ile Ala Asn Lys
        675                 680                 685

Val Leu Thr Val Gln Thr Ile Asp Asn Ala Leu Ser Lys Arg Asn Glu
    690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
            725                 730                 735

Glu Asn Gln Ala Glu Ala Thr Lys Ala Ile Asn Tyr Gln Tyr Asn
                740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
    770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
    850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
            885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
    930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
    995                 1000                1005

Asp Tyr Ile Asn Arg Trp Ile Phe Val Thr Ile Thr Asn Asn Arg Leu
    1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
            1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
    1075                1080                1085

Asp Asn Gln Ser Asn Ser Gly Ile Leu Lys Asp Phe Trp Gly Asp Tyr
```

-continued

```
            1090                1095                1100
Leu Gln Tyr Asp Lys Pro Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
            1125                1130                1135

Lys Gly Pro Arg Gly Ser Val Met Thr Thr Asn Ile Tyr Leu Asn Ser
                1140                1145                1150

Ser Leu Tyr Arg Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
            1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Met Lys Ser Lys Asn Asp Gln Gly Ile Thr
                1220                1225                1230

Asn Lys Cys Lys Met Asn Leu Gln Asp Asn Asn Gly Asn Asp Ile Gly
            1235                1240                1245

Phe Ile Gly Phe His Gln Phe Asn Asn Ile Ala Lys Leu Val Ala Ser
        1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
            1285                1290                1295

<210> SEQ ID NO 2
<211> LENGTH: 1296
<212> TYPE: PRT
<213> ORGANISM: Clostridium botulinum

<400> SEQUENCE: 2

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
                20                  25                  30

Val Lys Ala Phe Lys Ile His Asn Lys Ile Trp Val Ile Pro Glu Arg
            35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Asp Val Leu Asn Leu Thr
                165                 170                 175

Arg Asn Gly Tyr Gly Ser Thr Gln Tyr Ile Arg Phe Ser Pro Asp Phe
```

```
                180             185             190
Thr Phe Gly Phe Glu Glu Ser Leu Glu Val Asp Thr Asn Pro Leu Leu
            195                 200             205
Gly Ala Gly Lys Phe Ala Thr Asp Pro Ala Val Thr Leu Ala His Glu
            210                 215             220
Leu Ile His Ala Glu His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
                260                 265                 270
Phe Ile Asp Ser Leu Gln Glu Asn Glu Phe Arg Leu Tyr Tyr Tyr Asn
                275                 280                 285
Lys Phe Lys Asp Val Ala Ser Thr Leu Asn Lys Ala Lys Ser Ile Ile
            290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
                340                 345                 350
Asn Phe Val Asn Phe Phe Lys Val Ile Asn Arg Lys Thr Tyr Leu Asn
                355                 360                 365
Phe Asp Lys Ala Val Phe Arg Ile Asn Ile Val Pro Asp Glu Asn Tyr
            370                 375                 380
Thr Ile Lys Asp Gly Phe Asn Leu Lys Gly Ala Asn Leu Ser Thr Asn
385                 390                 395                 400
Phe Asn Gly Gln Asn Thr Glu Ile Asn Ser Arg Asn Phe Thr Arg Leu
                405                 410                 415
Lys Asn Phe Thr Gly Leu Phe Glu Phe Tyr Lys Leu Leu Cys Val Arg
            420                 425                 430
Gly Ile Ile Pro Phe Lys Thr Lys Ser Leu Asp Glu Gly Tyr Asn Lys
            435                 440                 445
Ala Leu Asn Asp Leu Cys Ile Lys Val Asn Asn Trp Asp Leu Phe Phe
            450                 455                 460
Ser Pro Ser Glu Asp Asn Phe Thr Asn Asp Leu Asp Lys Val Glu Glu
465                 470                 475                 480
Ile Thr Ala Asp Thr Asn Ile Glu Ala Ala Glu Asn Ile Ser Leu
                485                 490                 495
Asp Leu Ile Gln Gln Tyr Tyr Leu Thr Phe Asp Phe Asp Asn Glu Pro
                500                 505                 510
Glu Asn Ile Ser Ile Glu Asn Leu Ser Ser Asp Ile Ile Gly Gln Leu
            515                 520                 525
Glu Pro Met Pro Asn Ile Glu Arg Phe Pro Asn Gly Lys Lys Tyr Glu
            530                 535                 540
Leu Asp Lys Tyr Thr Met Phe His Tyr Leu Arg Ala Gln Glu Phe Glu
545                 550                 555                 560
His Gly Asp Ser Arg Ile Ile Leu Thr Asn Ser Ala Glu Glu Ala Leu
                565                 570                 575
Leu Lys Pro Asn Val Ala Tyr Thr Phe Phe Ser Ser Lys Tyr Val Lys
            580                 585                 590
Lys Ile Asn Lys Ala Val Glu Ala Phe Met Phe Leu Asn Trp Ala Glu
            595                 600                 605
```

-continued

```
Glu Leu Val Tyr Asp Phe Thr Asp Glu Thr Asn Glu Val Thr Thr Met
610                 615                 620
Asp Lys Ile Ala Asp Ile Thr Ile Ile Val Pro Tyr Ile Gly Pro Ala
625                 630                 635                 640
Leu Asn Ile Gly Asn Met Leu Ser Lys Gly Glu Phe Val Glu Ala Ile
                645                 650                 655
Ile Phe Thr Gly Val Val Ala Met Leu Glu Phe Ile Pro Glu Tyr Ala
                660                 665                 670
Leu Pro Val Phe Gly Thr Phe Ala Ile Val Ser Tyr Ile Ala Asn Lys
                675                 680                 685
Val Leu Thr Val Gln Thr Ile Asn Asn Ala Leu Ser Lys Arg Asn Glu
690                 695                 700
Lys Trp Asp Glu Val Tyr Lys Tyr Thr Val Thr Asn Trp Leu Ala Lys
705                 710                 715                 720
Val Asn Thr Gln Ile Asp Leu Ile Arg Glu Lys Met Lys Lys Ala Leu
                725                 730                 735
Glu Asn Gln Ala Glu Ala Thr Lys Ala Ile Ile Asn Tyr Gln Tyr Asn
                740                 745                 750
Gln Tyr Thr Glu Glu Lys Asn Asn Ile Asn Phe Asn Ile Asp Asp
                755                 760                 765
Leu Ser Ser Lys Leu Asn Glu Ser Ile Asn Ser Ala Met Ile Asn Ile
770                 775                 780
Asn Lys Phe Leu Asp Gln Cys Ser Val Ser Tyr Leu Met Asn Ser Met
785                 790                 795                 800
Ile Pro Tyr Ala Val Lys Arg Leu Lys Asp Phe Asp Ala Ser Val Arg
                805                 810                 815
Asp Val Leu Leu Lys Tyr Ile Tyr Asp Asn Arg Gly Thr Leu Val Leu
                820                 825                 830
Gln Val Asp Arg Leu Lys Asp Glu Val Asn Asn Thr Leu Ser Ala Asp
                835                 840                 845
Ile Pro Phe Gln Leu Ser Lys Tyr Val Asp Asn Lys Lys Leu Leu Ser
850                 855                 860
Thr Phe Thr Glu Tyr Ile Lys Asn Ile Val Asn Thr Ser Ile Leu Ser
865                 870                 875                 880
Ile Val Tyr Lys Lys Asp Asp Leu Ile Asp Leu Ser Arg Tyr Gly Ala
                885                 890                 895
Lys Ile Asn Ile Gly Asp Arg Val Tyr Tyr Asp Ser Ile Asp Lys Asn
                900                 905                 910
Gln Ile Lys Leu Ile Asn Leu Glu Ser Ser Thr Ile Glu Val Ile Leu
                915                 920                 925
Lys Asn Ala Ile Val Tyr Asn Ser Met Tyr Glu Asn Phe Ser Thr Ser
930                 935                 940
Phe Trp Ile Lys Ile Pro Lys Tyr Phe Ser Lys Ile Asn Leu Asn Asn
945                 950                 955                 960
Glu Tyr Thr Ile Ile Asn Cys Ile Glu Asn Asn Ser Gly Trp Lys Val
                965                 970                 975
Ser Leu Asn Tyr Gly Glu Ile Ile Trp Thr Leu Gln Asp Asn Lys Gln
                980                 985                 990
Asn Ile Gln Arg Val Val Phe Lys Tyr Ser Gln Met Val Asn Ile Ser
                995                 1000                1005
Asp Tyr Ile Asn Arg Trp Ile Phe Val Thr Ile Thr Asn Asn Arg Leu
     1010                1015                1020
Thr Lys Ser Lys Ile Tyr Ile Asn Gly Arg Leu Ile Asp Gln Lys Pro
1025                1030                1035                1040
```

```
Ile Ser Asn Leu Gly Asn Ile His Ala Ser Asn Lys Ile Met Phe Lys
            1045                1050                1055

Leu Asp Gly Cys Arg Asp Pro Arg Arg Tyr Ile Met Ile Lys Tyr Phe
            1060                1065                1070

Asn Leu Phe Asp Lys Glu Leu Asn Glu Lys Glu Ile Lys Asp Leu Tyr
            1075                1080                1085

Asp Ser Gln Ser Asn Ser Gly Ile Leu Lys Asp Phe Trp Gly Asn Tyr
            1090                1095                1100

Leu Gln Tyr Asp Lys Pro Tyr Tyr Met Leu Asn Leu Phe Asp Pro Asn
1105                1110                1115                1120

Lys Tyr Val Asp Val Asn Asn Ile Gly Ile Arg Gly Tyr Met Tyr Leu
            1125                1130                1135

Lys Gly Pro Arg Gly Ser Val Val Thr Thr Asn Ile Tyr Leu Asn Ser
            1140                1145                1150

Thr Leu Tyr Glu Gly Thr Lys Phe Ile Ile Lys Lys Tyr Ala Ser Gly
            1155                1160                1165

Asn Glu Asp Asn Ile Val Arg Asn Asn Asp Arg Val Tyr Ile Asn Val
            1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
            1205                1210                1215

Leu Ser Gln Val Val Val Met Lys Ser Lys Asp Asp Gln Gly Ile Arg
            1220                1225                1230

Asn Lys Cys Lys Met Asn Leu Gln Asp Asn Asn Gly Asn Asp Ile Gly
            1235                1240                1245

Phe Ile Gly Phe His Leu Tyr Asp Asn Ile Ala Lys Leu Val Ala Ser
            1250                1255                1260

Asn Trp Tyr Asn Arg Gln Val Gly Lys Ala Ser Arg Thr Phe Gly Cys
1265                1270                1275                1280

Ser Trp Glu Phe Ile Pro Val Asp Asp Gly Trp Gly Glu Ser Ser Leu
            1285                1290                1295

<210> SEQ ID NO 3
<211> LENGTH: 1292
<212> TYPE: PRT
<213> ORGANISM: Clostridium botulinum

<400> SEQUENCE: 3

Met Pro Phe Val Asn Lys Pro Phe Asn Tyr Arg Asp Pro Gly Asn Gly
  1               5                  10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110

Lys Gly Ile Pro Phe Trp Gly Gly Ser Thr Ile Asp Thr Glu Leu Lys
        115                 120                 125
```

```
Val Ile Asp Thr Asn Cys Ile Asn Val Ile Glu Pro Gly Gly Ser Tyr
    130                 135                 140

Arg Ser Glu Glu Leu Asn Leu Val Ile Thr Gly Pro Ser Ala Asp Ile
145                 150                 155                 160

Ile Gln Phe Glu Cys Lys Ser Phe Gly His Asp Val Phe Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Thr Phe Ala Thr Asp Pro Ala Val Thr Leu Ala His Glu
    210                 215                 220

Leu Ile His Ala Ala His Arg Leu Tyr Gly Ile Ala Ile Asn Pro Asn
225                 230                 235                 240

Arg Val Leu Lys Val Lys Thr Asn Ala Tyr Tyr Glu Met Ser Gly Leu
                245                 250                 255

Glu Val Ser Phe Glu Glu Leu Arg Thr Phe Gly Gly Asn Asp Thr Asn
            260                 265                 270

Phe Ile Asp Ser Leu Trp Gln Lys Phe Ser Arg Asp Ala Tyr Asp
        275                 280                 285

Asn Leu Gln Asn Ile Ala Arg Ile Leu Asn Glu Ala Lys Thr Ile Val
    290                 295                 300

Gly Thr Thr Thr Pro Leu Gln Tyr Met Lys Asn Ile Phe Ile Arg Lys
305                 310                 315                 320

Tyr Phe Leu Ser Glu Asp Ala Ser Gly Lys Ile Ser Val Asn Lys Ala
                325                 330                 335

Ala Phe Lys Glu Phe Tyr Arg Val Leu Thr Arg Gly Phe Thr Glu Leu
            340                 345                 350

Glu Phe Val Asn Pro Phe Lys Val Ile Asn Arg Lys Thr Tyr Leu Asn
        355                 360                 365

Phe Asp Lys Ala Val Phe Arg Ile Asn Ile Val Pro Asp Glu Asn Tyr
    370                 375                 380

Thr Ile Asn Glu Gly Phe Asn Leu Glu Gly Ala Asn Ser Asn Gly Gln
385                 390                 395                 400

Asn Thr Glu Ile Asn Ser Arg Asn Phe Thr Arg Leu Lys Asn Phe Thr
                405                 410                 415

Gly Leu Phe Glu Phe Tyr Lys Leu Leu Cys Val Arg Gly Ile Ile Pro
            420                 425                 430

Phe Lys Thr Lys Ser Leu Asp Glu Gly Tyr Asn Lys Ala Leu Asn Tyr
    435                 440                 445

Leu Cys Ile Lys Val Asn Asn Trp Asp Leu Phe Phe Ser Pro Ser Glu
450                 455                 460

Asp Asn Phe Thr Asn Asp Leu Asp Lys Val Glu Glu Ile Thr Ala Asp
465                 470                 475                 480

Thr Asn Ile Glu Ala Ala Glu Glu Asn Ile Ser Ser Asp Leu Ile Gln
                485                 490                 495

Gln Tyr Tyr Leu Thr Phe Asp Phe Asp Asn Glu Pro Glu Asn Ile Ser
            500                 505                 510

Ile Glu Asn Leu Ser Ser Asp Ile Ile Gly Leu Glu Pro Met Pro
        515                 520                 525

Asn Ile Glu Arg Phe Pro Asn Gly Lys Lys Tyr Glu Leu Asp Lys Tyr
    530                 535                 540

Thr Met Phe His Tyr Leu Arg Ala Gln Glu Phe Glu His Gly Asp Ser
```

-continued

```
              545                 550                 555                 560
        Arg Ile Ile Leu Thr Asn Ser Ala Glu Ala Leu Leu Lys Pro Asn
                            565                 570                 575
        Val Ala Tyr Thr Phe Ser Ser Lys Tyr Val Lys Lys Ile Asn Lys
                            580                 585                 590
        Ala Val Glu Ala Val Ile Phe Leu Ser Trp Ala Glu Glu Leu Val Tyr
                            595                 600                 605
        Asp Phe Thr Asp Glu Thr Asn Glu Val Thr Thr Met Asp Lys Ile Ala
                            610                 615                 620
        Asp Ile Thr Ile Ile Val Pro Tyr Ile Gly Pro Ala Leu Asn Ile Gly
        625                 630                 635                 640
        Asn Met Val Ser Lys Gly Glu Phe Val Glu Ala Ile Leu Phe Thr Gly
                            645                 650                 655
        Val Val Ala Leu Leu Glu Phe Ile Pro Glu Tyr Ser Leu Pro Val Phe
                            660                 665                 670
        Gly Thr Phe Ala Ile Val Ser Tyr Ile Ala Asn Lys Val Leu Thr Val
                            675                 680                 685
        Gln Thr Ile Asn Asn Ala Leu Ser Lys Arg Asn Glu Lys Trp Asp Glu
                            690                 695                 700
        Val Tyr Lys Tyr Thr Val Thr Asn Trp Leu Ala Lys Val Asn Thr Gln
        705                 710                 715                 720
        Ile Asp Leu Ile Arg Glu Lys Met Lys Lys Ala Leu Glu Asn Gln Ala
                            725                 730                 735
        Glu Ala Thr Arg Ala Ile Ile Asn Tyr Gln Tyr Asn Gln Tyr Thr Glu
                            740                 745                 750
        Glu Glu Lys Asn Asn Ile Asn Phe Asn Ile Asp Asp Leu Ser Ser Lys
                            755                 760                 765
        Leu Asn Arg Ser Ile Asn Arg Ala Met Ile Asn Ile Asn Lys Phe Leu
                            770                 775                 780
        Asp Gln Cys Ser Val Ser Tyr Leu Met Asn Ser Met Ile Pro Tyr Ala
        785                 790                 795                 800
        Val Lys Arg Leu Lys Asp Phe Asp Ala Ser Val Arg Asp Val Leu Leu
                            805                 810                 815
        Lys Tyr Ile Tyr Asp Asn Arg Gly Thr Leu Ile Leu Gln Val Asp Arg
                            820                 825                 830
        Leu Lys Asp Glu Val Asn Asn Thr Leu Ser Ala Asp Ile Pro Phe Gln
                            835                 840                 845
        Leu Ser Lys Tyr Val Asn Asp Lys Lys Leu Leu Ser Thr Phe Thr Glu
                            850                 855                 860
        Tyr Ile Lys Asn Ile Val Asn Thr Ser Ile Leu Ser Ile Val Tyr Lys
        865                 870                 875                 880
        Lys Asp Asp Leu Ile Asp Leu Ser Arg Tyr Gly Ala Lys Ile Asn Ile
                            885                 890                 895
        Gly Asp Arg Val Tyr Tyr Asp Ser Ile Asp Lys Asn Gln Ile Lys Leu
                            900                 905                 910
        Ile Asn Leu Glu Ser Ser Thr Ile Glu Val Ile Leu Lys Asn Ala Ile
                            915                 920                 925
        Val Tyr Asn Ser Met Tyr Glu Asn Phe Ser Thr Ser Phe Trp Ile Lys
                            930                 935                 940
        Ile Pro Lys Tyr Phe Ser Lys Ile Asn Leu Asn Asn Glu Tyr Thr Ile
        945                 950                 955                 960
        Ile Asn Cys Ile Glu Asn Asn Ser Gly Trp Lys Val Ser Leu Asn Tyr
                            965                 970                 975
```

```
Gly Glu Ile Ile Trp Thr Leu Gln Asp Asn Lys Gln Asn Ile Gln Arg
            980                 985                 990

Val Val Phe Lys Tyr Ser Gln Met Val Asn Ile Ser Asp Tyr Ile Asn
            995                 1000                1005

Arg Trp Met Phe Val Thr Ile Thr Asn Asn Arg Leu Thr Lys Ser Lys
        1010                1015                1020

Ile Tyr Ile Asn Gly Arg Leu Ile Asp Gln Lys Pro Ile Ser Asn Leu
1025                1030                1035                1040

Gly Asn Ile His Ala Ser Asn Lys Ile Met Phe Lys Leu Asp Gly Cys
            1045                1050                1055

Arg Asp Pro Arg Arg Tyr Ile Met Ile Lys Tyr Phe Asn Leu Phe Asp
            1060                1065                1070

Lys Glu Leu Asn Glu Lys Glu Ile Lys Asp Leu Tyr Asp Ser Gln Ser
            1075                1080                1085

Asn Pro Gly Ile Leu Lys Asp Phe Trp Gly Asn Tyr Leu Gln Tyr Asp
            1090                1095                1100

Lys Pro Tyr Tyr Met Leu Asn Leu Phe Asp Pro Asn Lys Tyr Val Asp
1105                1110                1115                1120

Val Asn Asn Ile Gly Ile Arg Gly Tyr Met Tyr Leu Lys Gly Pro Arg
            1125                1130                1135

Gly Ser Val Met Thr Thr Asn Ile Tyr Leu Asn Ser Thr Leu Tyr Met
            1140                1145                1150

Gly Thr Lys Phe Ile Ile Lys Lys Tyr Ala Ser Gly Asn Glu Asp Asn
            1155                1160                1165

Ile Val Arg Asn Asn Asp Arg Val Tyr Ile Asn Val Val Val Lys Asn
            1170                1175                1180

Lys Glu Tyr Arg Leu Ala Thr Asn Ala Ser Gln Ala Gly Val Glu Lys
1185                1190                1195                1200

Ile Leu Ser Ala Leu Glu Ile Pro Asp Val Gly Asn Leu Ser Gln Val
            1205                1210                1215

Val Val Met Lys Ser Lys Asp Asp Gln Gly Ile Arg Asn Lys Cys Lys
            1220                1225                1230

Met Asn Leu Gln Asp Asn Asn Gly Asn Asp Ile Gly Phe Val Gly Phe
            1235                1240                1245

His Leu Tyr Asp Asn Ile Ala Lys Leu Val Ala Ser Asn Trp Tyr Asn
            1250                1255                1260

Arg Gln Val Gly Lys Ala Ser Arg Thr Phe Gly Cys Ser Trp Glu Phe
1265                1270                1275                1280

Ile Pro Val Asp Asp Gly Trp Gly Glu Ser Ser Leu
            1285                1290

<210> SEQ ID NO 4
<211> LENGTH: 1296
<212> TYPE: PRT
<213> ORGANISM: Clostridium botulinum

<400> SEQUENCE: 4

Met Pro Leu Val Asn Gln Gln Ile Asn Tyr Tyr Asp Pro Val Asn Gly
1               5                   10                  15

Val Asp Ile Ala Tyr Ile Lys Ile Pro Asn Ala Gly Lys Met Gln Pro
            20                  25                  30

Val Lys Ala Phe Lys Ile His Asn Lys Val Trp Val Ile Pro Glu Arg
        35                  40                  45

Asp Ile Phe Thr Asn Pro Glu Glu Val Asp Leu Asn Pro Pro Glu
50                  55                  60
```

```
Ala Lys Gln Val Pro Ile Ser Tyr Tyr Asp Ser Ala Tyr Leu Ser Thr
 65                  70                  75                  80

Asp Asn Glu Lys Asp Asn Tyr Leu Lys Gly Val Ile Lys Leu Phe Glu
                 85                  90                  95

Arg Ile Tyr Ser Thr Asp Leu Gly Arg Met Leu Leu Ile Ser Ile Val
            100                 105                 110

Arg Gly Ile Pro Phe Trp Gly Gly Lys Ile Asp Thr Glu Leu Lys
        115                 120                 125

Val Ile Asp Thr Asn Cys Ile Asn Ile Ile Gln Leu Asp Asp Ser Tyr
130                 135                 140

Arg Ser Glu Glu Leu Asn Leu Ala Ile Ile Gly Pro Ser Ala Asn Ile
145                 150                 155                 160

Ile Glu Ser Gln Cys Ser Ser Phe Arg Asp Asp Val Leu Asn Leu Thr
                165                 170                 175

Arg Asn Gly Tyr Gly Ser Thr Gln Tyr Ile Arg Phe Ser Pro Asp Phe
            180                 185                 190

Thr Val Gly Phe Glu Glu Ser Leu Glu Val Asp Thr Asn Pro Leu Leu
        195                 200                 205

Gly Ala Gly Lys Phe Ala Gln Asp Pro Ala Val Ala Leu Ala His Glu
210                 215                 220

Leu Ile His Ala Glu His Arg Leu Tyr Gly Ile Ala Ile Asn Thr Asn
225                 230                 235                 240

Arg Val Phe Lys Val Asn Thr Asn Ala Tyr Tyr Glu Met Ala Gly Leu
                245                 250                 255

Glu Val Ser Leu Glu Glu Leu Ile Thr Phe Gly Gly Asn Asp Ala Lys
            260                 265                 270

Phe Ile Asp Ser Leu Gln Lys Lys Glu Phe Ser Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Ala Thr Gly Lys Phe Leu Val Asp Arg Leu
                325                 330                 335

Lys Phe Asp Glu Leu Tyr Lys Leu Leu Thr Glu Ile Tyr Thr Glu Asp
            340                 345                 350

Asn Phe Val Lys Phe Lys Val Leu Asn Arg Lys Thr Tyr Leu Asn
        355                 360                 365

Phe Asp Lys Ala Val Phe Lys Ile Asn Ile Val Pro Asp Val Asn Tyr
370                 375                 380

Thr Ile His Asp Gly Phe Asn Leu Arg Asn Thr Asn Leu Ala Ala Asn
385                 390                 395                 400

Phe Asn Gly Gln Asn Ile Glu Ile Asn Asn Lys Asn Phe Asp Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Glu Gly Tyr Asn Lys
        435                 440                 445

Ala Leu Asn Glu Leu Cys Ile Lys Val Asn Asn Trp Asp Leu Phe Phe
450                 455                 460

Ser Pro Ser Glu Asp Asn Phe Thr Asn Asp Leu Asp Lys Val Glu Glu
465                 470                 475                 480

Ile Thr Ser Asp Thr Asn Ile Glu Ala Ala Glu Glu Asn Ile Ser Leu
                485                 490                 495
```

```
Asp Leu Ile Gln Gln Tyr Tyr Leu Asn Phe Asn Phe Asp Asn Glu Pro
            500                 505                 510

Glu Asn Thr Ser Ile Glu Asn Leu Ser Ser Asp Ile Ile Gly Gln Leu
            515                 520                 525

Glu Pro Met Pro Asn Ile Glu Arg Phe Pro Asn Gly Lys Lys Tyr Glu
            530                 535                 540

Leu Asn Lys Tyr Thr Met Phe His Tyr Leu Arg Ala Gln Glu Phe Lys
545                 550                 555                 560

His Ser Asn Ser Arg Ile Ile Leu Thr Asn Ser Ala Lys Glu Ala Leu
                565                 570                 575

Leu Lys Pro Asn Ile Val Tyr Thr Phe Phe Ser Ser Lys Tyr Ile Lys
            580                 585                 590

Ala Ile Asn Lys Ala Val Glu Ala Val Thr Phe Val Asn Trp Ile Glu
            595                 600                 605

Asn Leu Val Tyr Asp Phe Thr Asp Glu Thr Asn Glu Val Ser Thr Met
            610                 615                 620

Asp Lys Ile Ala Asp Ile Thr Ile Val Ile Pro Tyr Ile Gly Pro Ala
625                 630                 635                 640

Leu Asn Ile Gly Asn Met Ile Tyr Lys Gly Glu Phe Val Glu Ala Ile
                645                 650                 655

Ile Phe Ser Gly Ala Val Ile Leu Leu Glu Ile Val Pro Glu Ile Ala
            660                 665                 670

Leu Pro Val Leu Gly Thr Phe Ala Leu Val Ser Tyr Val Ser Asn Lys
            675                 680                 685

Val Leu Thr Val Gln Thr Ile Asp Asn Ala Leu Ser Lys Arg Asn Glu
            690                 695                 700

Lys Trp Asp Glu Val Tyr Lys Tyr Ile Val Thr Asn Trp Leu Ala Ile
705                 710                 715                 720

Val Asn Thr Gln Ile Asn Leu Ile Arg Glu Lys Met Lys Lys Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Glu Lys Asn Asn Ile Asn Phe Asn Ile Asp Asp
            755                 760                 765

Leu Ser Ser Lys Leu Asn Glu Ser Ile Asn Ser Ala Met Ile Asn Ile
            770                 775                 780

Asn Lys Phe Leu Asp Gln Cys Ser Val Ser Tyr Leu Met Asn Ser Met
785                 790                 795                 800

Ile Pro Tyr Ala Val Lys Arg Leu Lys Asp Phe Asp Ala Ser Val Arg
                805                 810                 815

Asp Val Leu Leu Lys Tyr Ile Tyr Asp Asn Arg Gly Thr Leu Ile Gly
            820                 825                 830

Gln Val Asn Arg Leu Lys Asp Lys Val Asn Asn Thr Leu Ser Ala Asp
            835                 840                 845

Ile Pro Phe Gln Leu Ser Lys Tyr Val Asp Asn Lys Lys Leu Leu Ser
            850                 855                 860

Thr Phe Thr Glu Tyr Ile Lys Asn Ile Thr Asn Ala Ser Ile Leu Ser
865                 870                 875                 880

Ile Val Tyr Lys Asp Asp Leu Ile Asp Leu Ser Arg Tyr Gly Ala
                885                 890                 895

Glu Ile Tyr Asn Gly Asp Lys Val Tyr Tyr Asn Ser Ile Asp Lys Asn
            900                 905                 910

Gln Ile Arg Leu Ile Asn Leu Glu Ser Ser Thr Ile Glu Val Ile Leu
```

Lys Lys Ala Ile Val Tyr Asn Ser Met Tyr Glu Asn Phe Ser Thr Ser
            930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Phe Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg Ile
    1010                1015                1020

Thr Lys Ser Lys Ile Tyr Ile Asn Gly Arg Leu Ile Asp Gln Lys Pro
1025                1030                1035                1040

Ile Ser Asn Leu Gly Asn Ile His Ala Ser Asn Lys Ile Met Phe Lys
                1045                1050                1055

Leu Asp Gly Cys Arg Asp Pro His Arg Tyr Ile Val Ile Lys Tyr Phe
            1060                1065                1070

Asn Leu Phe Asp Lys Glu Leu Ser Glu Lys Glu Ile Lys Asp Leu Tyr
    1075                1080                1085

Asp Asn Gln Ser Asn Ser Gly Ile Leu Lys Asp Phe Trp Gly Asp Tyr
    1090                1095                1100

Leu Gln Tyr Asp Lys Ser Tyr Tyr Met Leu Asn Leu Tyr Asp Pro Asn
1105                1110                1115                1120

Lys Tyr Val Asp Val Asn Asn Val Gly Ile Arg Gly Tyr Met Tyr Leu
            1125                1130                1135

Lys Gly Pro Arg Asp Asn Val Met Thr Thr Asn Ile Tyr Leu Asn Ser
            1140                1145                1150

Ser Leu Tyr Met Gly Thr Lys Phe Ile Ile Lys Lys Tyr Ala Ser Gly
            1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
            1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Arg Glu Arg Pro Leu
            1285                1290                1295

<210> SEQ ID NO 5
<211> LENGTH: 206
<212> TYPE: PRT
<213> ORGANISM: Homo sapiens

<400> SEQUENCE: 5

Met Ala Glu Asp Ala Asp Met Arg Asn Glu Leu Glu Glu Met Gln Arg

```
                1               5                  10                 15
Arg Ala Asp Gln Leu Ala Asp Glu Ser Leu Glu Ser Thr Arg Arg Met
                20                 25                 30

Leu Gln Leu Val Glu Glu Ser Lys Asp Ala Gly Ile Arg Thr Leu Val
                35                 40                 45

Met Leu Asp Glu Gln Gly Glu Gln Leu Asp Arg Val Glu Glu Gly Met
    50                 55                 60

Asn His Ile Asn Gln Asp Met Lys Glu Ala Lys Asn Leu Lys Asp
65                  70                 75                 80

Leu Gly Lys Cys Cys Gly Leu Phe Ile Cys Pro Cys Asn Lys Leu Lys
                    85                 90                 95

Ser Ser Asp Ala Tyr Lys Lys Ala Trp Gly Asn Asn Gln Asp Gly Val
                100                105                110

Val Ala Ser Gln Pro Ala Arg Val Asp Glu Arg Glu Gln Met Ala
                115                120                125

Ile Ser Gly Gly Phe Ile Arg Arg Val Thr Asn Asp Ala Arg Glu Asn
                130                135                140

Glu Met Asp Glu Asn Leu Glu Gln Val Ser Gly Ile Ile Gly Asn Leu
145                150                155                160

Arg His Met Ala Leu Asp Met Gly Asn Glu Ile Asp Thr Gln Asn Arg
                    165                170                175

Gln Ile Asp Arg Ile Met Glu Lys Ala Asp Ser Asn Lys Thr Arg Ile
                180                185                190

Asp Glu Ala Asn Gln Arg Ala Thr Lys Met Leu Gly Ser Gly
                195                200                205

<210> SEQ ID NO 6
<211> LENGTH: 206
<212> TYPE: PRT
<213> ORGANISM: Homo sapiens

<400> SEQUENCE: 6

Met Ala Glu Asp Ala Asp Met Arg Asn Glu Leu Glu Glu Met Gln Arg
1               5                  10                 15

Arg Ala Asp Gln Leu Ala Asp Glu Ser Leu Glu Ser Thr Arg Arg Met
                20                 25                 30

Leu Gln Leu Val Glu Glu Ser Lys Asp Ala Gly Ile Arg Thr Leu Val
                35                 40                 45

Met Leu Asp Glu Gln Gly Glu Gln Leu Glu Arg Ile Glu Glu Gly Met
    50                 55                 60

Asp Gln Ile Asn Lys Asp Met Lys Glu Ala Glu Lys Asn Leu Thr Asp
65                  70                 75                 80

Leu Gly Lys Phe Cys Gly Leu Cys Val Cys Pro Cys Asn Lys Leu Lys
                    85                 90                 95

Ser Ser Asp Ala Tyr Lys Lys Ala Trp Gly Asn Asn Gln Asp Gly Val
                100                105                110

Val Ala Ser Gln Pro Ala Arg Val Val Asp Glu Arg Glu Gln Met Ala
                115                120                125

Ile Ser Gly Gly Phe Ile Arg Arg Val Thr Asn Asp Ala Arg Glu Asn
                130                135                140

Glu Met Asp Glu Asn Leu Glu Gln Val Ser Gly Ile Ile Gly Asn Leu
145                150                155                160

Arg His Met Ala Leu Asp Met Gly Asn Glu Ile Asp Thr Gln Asn Arg
                    165                170                175

Gln Ile Asp Arg Ile Met Glu Lys Ala Asp Ser Asn Lys Thr Arg Ile
                180                185                190
```

Asp Glu Ala Asn Gln Arg Ala Thr Lys Met Leu Gly Ser Gly
            195                 200                 205

<210> SEQ ID NO 7
<211> LENGTH: 206
<212> TYPE: PRT
<213> ORGANISM: Macaca mulatta

<400> SEQUENCE: 7

Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
             20                  25                  30

Leu Gln Leu Val Glu Glu Ser Lys Asp Ala Gly Ile Arg Thr Leu Val
         35                  40                  45

Met Leu Asp Glu Gln Gly Glu Gln Leu Glu Arg Ile Glu Glu Gly Met
     50                  55                  60

Asp Gln Ile Asn Lys Asp Met Lys Glu Ala Glu Lys Asn Leu Thr Asp
 65                  70                  75                  80

Leu Gly Lys Phe Cys Gly Leu Cys Val Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
            180                 185                 190

Asp Glu Ala Asn Gln Arg Ala Thr Lys Met Leu Gly Ser Gly
        195                 200                 205

<210> SEQ ID NO 8
<211> LENGTH: 206
<212> TYPE: PRT
<213> ORGANISM: Rattus norvegicus

<400> SEQUENCE: 8

Met Ala Glu Asp Ala Asp Met Arg Asn Glu Leu Glu Glu Met Gln Arg
  1               5                  10                  15

Arg Ala Asp Gln Leu Ala Asp Glu Ser Leu Glu Ser Thr Arg Arg Met
             20                  25                  30

Leu Gln Leu Val Glu Glu Ser Lys Asp Ala Gly Ile Arg Thr Leu Val
         35                  40                  45

Met Leu Asp Glu Gln Gly Glu Gln Leu Asp Arg Val Glu Glu Gly Met
     50                  55                  60

Asn His Ile Asn Gln Asp Met Lys Glu Ala Glu Lys Asn Leu Lys Asp
 65                  70                  75                  80

Leu Gly Lys Cys Cys Gly Leu Phe Ile Cys Pro Cys Asn Lys Leu Lys
                 85                  90                  95

Ser Ser Asp Ala Tyr Lys Lys Ala Trp Gly Asn Asn Gln Asp Gly Val
            100                 105                 110

Val Ala Ser Gln Pro Ala Arg Val Asp Glu Arg Glu Gln Met Ala
            115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
                195                 200                 205

<210> SEQ ID NO 9
<211> LENGTH: 206
<212> TYPE: PRT
<213> ORGANISM: Rattus norvegicus

<400> SEQUENCE: 9

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

Leu Gln Leu Val Glu Glu Ser Lys Asp Ala Gly Ile Arg Thr Leu Val
            35                  40                  45

Met Leu Asp Glu Gln Gly Glu Gln Leu Glu Arg Ile Glu Glu Gly Met
50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
                100                 105                 110

Val Ala Ser Gln Pro Ala Arg Val Val Asp Glu Arg Glu Gln Met Ala
            115                 120                 125

Ile Ser Gly Gly Phe Ile Arg Arg Val Thr Asn Asp Ala Arg Glu Asn
130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Thr Arg Ile
                180                 185                 190

Asp Glu Ala Asn Gln Arg Ala Thr Lys Met Leu Gly Ser Gly
                195                 200                 205

<210> SEQ ID NO 10
<211> LENGTH: 206
<212> TYPE: PRT
<213> ORGANISM: Mus musculus

<400> SEQUENCE: 10

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
                20                  25                  30

```
Leu Gln Leu Val Glu Glu Ser Lys Asp Ala Gly Ile Arg Thr Leu Val
        35                  40                  45
Met Leu Asp Glu Gln Gly Glu Gln Leu Glu Arg Ile Glu Glu Gly Met
 50                  55                  60
Asp Gln Ile Asn Lys Asp Met Lys Glu Ala Glu Lys Asn Leu Thr Asp
 65                  70                  75                  80
Leu Gly Lys Phe Cys Gly Leu Cys Val Cys Pro Cys Asn Lys Leu Lys
                 85                  90                  95
Ser Ser Asp Ala Tyr Lys Lys Ala Trp Gly Asn Asn Gln Asp Gly Val
                100                 105                 110
Val Ala Ser Gln Pro Ala Arg Val Val Asp Glu Arg Glu Gln Met Ala
            115                 120                 125
Ile Ser Gly Gly Phe Ile Arg Arg Val Thr Asn Asp Ala Arg Glu Asn
        130                 135                 140
Glu Met Asp Glu Asn Leu Glu Gln Val Ser Gly Ile Ile Gly Asn Leu
145                 150                 155                 160
Arg His Met Ala Leu Asp Met Gly Asn Glu Ile Asp Thr Gln Asn Arg
                165                 170                 175
Gln Ile Asp Arg Ile Met Glu Lys Ala Asp Ser Asn Lys Thr Arg Ile
            180                 185                 190
Asp Glu Ala Asn Gln Arg Ala Thr Lys Met Leu Gly Ser Gly
        195                 200                 205

<210> SEQ ID NO 11
<211> LENGTH: 206
<212> TYPE: PRT
<213> ORGANISM: Gallus gallus

<400> SEQUENCE: 11

Met Ala Glu Asp Ala Asp Met Arg Asn Glu Leu Glu Glu Met Gln Arg
 1               5                  10                  15
Arg Ala Asp Gln Leu Ala Asp Glu Ser Leu Glu Ser Thr Arg Arg Met
            20                  25                  30
Leu Gln Leu Val Glu Glu Ser Lys Asp Ala Gly Ile Arg Thr Leu Val
        35                  40                  45
Met Leu Asp Glu Gln Gly Glu Gln Leu Glu Arg Ile Glu Glu Gly Met
 50                  55                  60
Asp Gln Ile Asn Lys Asp Met Lys Glu Ala Glu Lys Asn Leu Thr Asp
 65                  70                  75                  80
Leu Gly Lys Phe Cys Gly Leu Cys Val Cys Pro Cys Asn Lys Leu Lys
                 85                  90                  95
Ser Ser Asp Ala Tyr Lys Lys Ala Trp Gly Asn Asn Gln Asp Gly Val
                100                 105                 110
Val Ala Ser Gln Pro Ala Arg Val Val Asp Glu Arg Glu Gln Met Ala
            115                 120                 125
Ile Ser Gly Gly Phe Ile Arg Arg Val Thr Asn Asp Ala Arg Glu Asn
        130                 135                 140
Glu Met Asp Glu Asn Leu Glu Gln Val Ser Gly Ile Ile Gly Asn Leu
145                 150                 155                 160
Arg His Met Ala Leu Asp Met Gly Asn Glu Ile Asp Thr Gln Asn Arg
                165                 170                 175
Gln Ile Asp Arg Ile Met Glu Lys Ala Asp Ser Asn Lys Thr Arg Ile
            180                 185                 190
Asp Glu Ala Asn Gln Arg Ala Thr Lys Met Leu Gly Ser Gly
        195                 200                 205
```

-continued

```
<210> SEQ ID NO 12
<211> LENGTH: 204
<212> TYPE: PRT
<213> ORGANISM: Carassius auratus

<400> SEQUENCE: 12
```

Met Ala Glu Asp Ala Asp Met Arg Asn Glu Leu Ser Asp Met Gln Gln
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Asp Ala Glu Lys Asn Leu Asn Asp
65                  70                  75                  80

Leu Gly Lys Phe Cys Gly Leu Cys Ser Cys Pro Cys Asn Lys Met Lys
                85                  90                  95

Ser Gly Gly Ser Lys Ala Trp Gly Asn Asn Gln Asp Gly Val Val Ala
            100                 105                 110

Ser Gln Pro Ala Arg Val Val Asp Glu Arg Glu Gln Met Ala Ile Ser
        115                 120                 125

Gly Gly Phe Ile Arg Arg Val Thr Asp Asp Ala Arg Glu Asn Glu Met
    130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
            180                 185                 190

Ala Asn Gln Arg Ala Thr Lys Met Leu Gly Ser Gly
        195                 200

```
<210> SEQ ID NO 13
<211> LENGTH: 203
<212> TYPE: PRT
<213> ORGANISM: Carassius auratus

<400> SEQUENCE: 13
```

Met Ala Asp Glu Ala Asp Met Arg Asn Glu Leu Thr Asp Met Gln Ala
1               5                   10                  15

Arg Ala Asp Gln Leu Gly Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Asn Leu Cys Gly Leu Cys Pro Cys Pro Cys Asn Lys Leu Lys
                85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp

```
                130                 135                 140
Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
                180                 185                 190

Asn Gln Arg Ala Thr Lys Met Leu Gly Ser Gly
                195                 200

<210> SEQ ID NO 14
<211> LENGTH: 204
<212> TYPE: PRT
<213> ORGANISM: Danio rerio

<400> SEQUENCE: 14

Met Ala Glu Asp Ser Asp Met Arg Asn Glu Leu Ala Asp Met Gln Gln
  1               5                  10                  15

Arg Ala Asp Gln Leu Ala Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Glu Arg Ile Glu Glu Gly Met
         50                  55                  60

Asp Gln Ile Asn Lys Asp Met Lys Asp Ala Glu Lys Asn Leu Asn Asp
 65                  70                  75                  80

Leu Gly Lys Phe Cys Gly Leu Cys Ser Cys Pro Cys Asn Lys Met Lys
                 85                  90                  95

Ser Gly Ala Ser Lys Ala Trp Gly Asn Asn Gln Asp Gly Val Val Ala
                100                 105                 110

Ser Gln Pro Ala Arg Val Val Asp Glu Arg Glu Gln Met Ala Ile Ser
            115                 120                 125

Gly Gly Phe Ile Arg Arg Val Thr Asp Asp Ala Arg Glu Asn Glu Met
        130                 135                 140

Asp Glu Asn Leu Glu Gln Val Gly Gly Ile Ile Gly Asn Leu Arg His
145                 150                 155                 160

Met Ala Leu Asp Met Gly Asn Glu Ile Asp Thr Gln Asn Arg Gln Ile
                165                 170                 175

Asp Arg Ile Met Glu Lys Ala Asp Ser Asn Lys Thr Arg Ile Asp Glu
                180                 185                 190

Ala Asn Gln Arg Ala Thr Lys Met Leu Gly Ser Gly
                195                 200

<210> SEQ ID NO 15
<211> LENGTH: 203
<212> TYPE: PRT
<213> ORGANISM: Danio rerio

<400> SEQUENCE: 15

Met Ala Asp Glu Ser Asp Met Arg Asn Glu Leu Asn Asp Met Gln Ala
  1               5                  10                  15

Arg Ala Asp Gln Leu Gly Asp Glu Ser Leu Glu Ser Thr Arg Arg Met
                 20                  25                  30

Leu Gln Leu Val Glu Glu Ser Lys Asp Ala Gly Ile Arg Thr Leu Val
             35                  40                  45

Met Leu Asp Glu Gln Gly Glu Gln Leu Glu Arg Ile Glu Glu Gly Met
         50                  55                  60
```

```
Asp Gln Ile Asn Lys Asp Met Lys Glu Ala Glu Lys Asn Leu Thr Asp
 65                  70                  75                  80

Leu Gly Asn Leu Cys Gly Leu Cys Pro Cys Pro Cys Asn Lys Leu Lys
                 85                  90                  95

Gly Gly Gly Gln Ser Trp Gly Asn Asn Gln Asp Gly Val Val Ser Ser
            100                 105                 110

Gln Pro Ala Arg Val Val Asp Glu Arg Glu Gln Met Ala Ile Ser Gly
        115                 120                 125

Gly Phe Ile Arg Arg Val Thr Asn Asp Ala Arg Glu Asn Glu Met Asp
    130                 135                 140

Glu Asn Leu Glu Gln Val Gly Ser Ile Ile Gly Asn Leu Arg His Met
145                 150                 155                 160

Ala Leu Asp Met Gly Asn Glu Ile Asp Thr Gln Asn Arg Gln Ile Asp
                165                 170                 175

Arg Ile Met Asp Met Ala Asp Ser Asn Lys Thr Arg Ile Asp Glu Ala
            180                 185                 190

Asn Gln Arg Ala Thr Lys Met Leu Gly Ser Gly
        195                 200

<210> SEQ ID NO 16
<211> LENGTH: 210
<212> TYPE: PRT
<213> ORGANISM: Torpedo marmorata

<400> SEQUENCE: 16

Met Glu Asn Ser Val Glu Asn Ser Met Asp Pro Arg Ser Glu Gln Glu
  1               5                  10                  15

Glu Met Gln Arg Cys Ala Asp Gln Ile Thr Asp Glu Ser Leu Glu Ser
             20                  25                  30

Thr Arg Arg Met Leu Gln Leu Val Glu Glu Ser Lys Asp Ala Gly Ile
         35                  40                  45

Arg Thr Leu Val Met Leu Asp Glu Gln Gly Glu Gln Leu Glu Arg Ile
 50                  55                  60

Glu Glu Gly Met Asp Gln Ile Asn Lys Asp Met Lys Glu Ala Glu Lys
 65                  70                  75                  80

Asn Leu Ser Asp Leu Gly Lys Cys Cys Gly Leu Cys Ser Cys Pro Cys
                 85                  90                  95

Asn Lys Leu Lys Asn Phe Glu Ala Gly Gly Ala Tyr Lys Lys Val Trp
            100                 105                 110

Gly Asn Asn Gln Asp Gly Val Val Ala Ser Gln Pro Ala Arg Val Met
        115                 120                 125

Asp Asp Arg Glu Gln Met Ala Met Ser Gly Gly Tyr Ile Arg Arg Ile
    130                 135                 140

Thr Asp Asp Ala Arg Glu Asn Glu Met Glu Glu Asn Leu Asp Gln Val
145                 150                 155                 160

Gly Ser Ile Ile Gly Asn Leu Arg His Met Ala Leu Asp Met Ser Asn
                165                 170                 175

Glu Ile Gly Ser Gln Asn Ala Gln Ile Asp Arg Ile Val Val Lys Gly
            180                 185                 190

Asp Met Asn Lys Ala Arg Ile Asp Glu Ala Asn Lys His Ala Thr Lys
        195                 200                 205

Met Leu
210

<210> SEQ ID NO 17
```

```
<211> LENGTH: 206
<212> TYPE: PRT
<213> ORGANISM: Xenopus laevis

<400> SEQUENCE: 17

Met Ala Asp Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Asp Arg Val Glu Glu Gly Met
50                  55                  60

Asn His Ile Asn Gln Asp Met Lys Glu Ala Glu Lys Asn Leu Lys Asp
65                  70                  75                  80

Leu Gly Lys Cys Cys Gly Leu Phe Ile Cys Pro Cys Asn Lys Leu Lys
                85                  90                  95

Ser Ser Gly Ala Tyr Asn Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
130                 135                 140

Glu Met Asp Glu Asn Leu Glu Gln Val Gly Gly Ile Ile Gly Asn Leu
145                 150                 155                 160

Arg His Met Ala Leu Asp Met Gly Asn Glu Ile Asp Thr Gln Asn Arg
                165                 170                 175

Gln Ile Asp Arg Ile Met Glu Lys Ala Asp Ser Asn Lys Ala Arg Ile
            180                 185                 190

Asp Glu Ala Asn Lys His Ala Thr Lys Met Leu Gly Ser Gly
        195                 200                 205

<210> SEQ ID NO 18
<211> LENGTH: 206
<212> TYPE: PRT
<213> ORGANISM: Xenopus laevis

<400> SEQUENCE: 18

Met Ala Asp Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Tyr Val Glu Gly Ser Lys Asp Ala Gly Ile Arg Thr Leu Val
        35                  40                  45

Met Leu Asp Glu Gln Gly Glu Gln Leu Glu Arg Ile Glu Glu Gly Met
50                  55                  60

Glu Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Val Arg Arg Val Thr Asn Asp Ala Arg Glu Thr
130                 135                 140
```

```
Glu Met Asp Glu Asn Leu Glu Gln Val Gly Ile Ile Gly Asn Leu
145                 150                 155                 160

Arg His Met Ala Leu Asp Met Gly Asn Glu Ile Asp Thr Gln Asn Arg
            165                 170                 175

Gln Ile Asp Arg Ile Met Glu Lys Ala Asp Ser Asn Lys Ala Arg Ile
        180                 185                 190

Asp Glu Ala Asn Lys His Ala Thr Lys Met Leu Gly Ser Gly
    195                 200                 205
```

<210> SEQ ID NO 19
<211> LENGTH: 212
<212> TYPE: PRT
<213> ORGANISM: Strongylocentrotus purpuratus

<400> SEQUENCE: 19

```
Met Glu Asp Gln Asn Asp Met Asn Met Arg Ser Glu Leu Glu Glu Ile
1               5                   10                  15

Gln Met Gln Ser Asn Met Gln Thr Asp Glu Ser Leu Glu Ser Thr Arg
            20                  25                  30

Arg Met Leu Gln Met Ala Glu Glu Ser Gln Asp Met Gly Ile Lys Thr
        35                  40                  45

Leu Val Met Leu Asp Glu Gln Gly Glu Gln Leu Asp Arg Ile Glu Glu
    50                  55                  60

Gly Met Asp Gln Ile Asn Thr Asp Met Arg Glu Ala Glu Lys Asn Leu
65                  70                  75                  80

Thr Gly Leu Glu Lys Cys Cys Gly Ile Cys Val Cys Pro Trp Lys Lys
                85                  90                  95

Leu Gly Asn Phe Glu Lys Gly Asp Asp Tyr Lys Lys Thr Trp Lys Gly
            100                 105                 110

Asn Asp Asp Gly Lys Val Asn Ser His Gln Pro Met Arg Met Glu Asp
        115                 120                 125

Asp Arg Asp Gly Cys Gly Gly Asn Ala Ser Met Ile Thr Arg Ile Thr
    130                 135                 140

Asn Asp Ala Arg Glu Asp Glu Met Asp Glu Asn Leu Thr Gln Val Ser
145                 150                 155                 160

Ser Ile Val Gly Asn Leu Arg His Met Ala Ile Asp Met Gln Ser Glu
                165                 170                 175

Ile Gly Ala Gln Asn Ser Val Gly Arg Ile Thr Ser Lys Ala Glu
            180                 185                 190

Ser Asn Glu Gly Arg Ile Asn Ser Ala Asp Lys Arg Ala Lys Asn Ile
        195                 200                 205

Leu Arg Asn Lys
    210
```

<210> SEQ ID NO 20
<211> LENGTH: 212
<212> TYPE: PRT
<213> ORGANISM: Drosophila melanogaster

<400> SEQUENCE: 20

```
Met Pro Ala Asp Pro Ser Glu Glu Val Ala Pro Gln Val Pro Lys Thr
1               5                   10                  15

Glu Leu Glu Glu Leu Gln Ile Asn Ala Gln Gly Val Ala Asp Glu Ser
            20                  25                  30

Leu Glu Ser Thr Arg Arg Met Leu Ala Leu Cys Glu Glu Ser Lys Glu
        35                  40                  45

Ala Gly Ile Arg Thr Leu Val Ala Leu Asp Asp Gln Gly Glu Gln Leu
```

```
                50                  55                  60
Asp Arg Ile Glu Glu Gly Met Asp Gln Ile Asn Ala Asp Met Arg Glu
 65                  70                  75                  80

Ala Glu Lys Asn Leu Ser Gly Met Glu Lys Cys Cys Gly Ile Cys Val
                 85                  90                  95

Leu Pro Cys Asn Lys Ser Gln Ser Phe Lys Glu Asp Asp Gly Thr Trp
                100                 105                 110

Lys Gly Asn Asp Asp Gly Lys Val Val Asn Asn Gln Pro Gln Arg Val
                115                 120                 125

Met Asp Asp Arg Asn Gly Met Met Ala Gln Ala Gly Tyr Ile Gly Arg
                130                 135                 140

Ile Thr Asn Asp Ala Arg Glu Asp Glu Met Glu Glu Asn Met Gly Gln
145                 150                 155                 160

Val Asn Thr Met Ile Gly Asn Leu Arg Asn Met Ala Leu Asp Met Gly
                165                 170                 175

Ser Glu Leu Glu Asn Gln Asn Arg Gln Ile Asp Arg Ile Asn Arg Lys
                180                 185                 190

Gly Glu Ser Asn Glu Ala Arg Ile Ala Val Ala Asn Gln Arg Ala His
                195                 200                 205

Gln Leu Leu Lys
    210

<210> SEQ ID NO 21
<211> LENGTH: 212
<212> TYPE: PRT
<213> ORGANISM: Hirudo medicinalis

<400> SEQUENCE: 21

Met Ala Lys Asp Ile Lys Pro Lys Pro Ala Asn Gly Arg Asp Ser Pro
 1               5                  10                  15

Thr Asp Leu Gln Glu Ile Gln Leu Gln Met Asn Ala Ile Thr Asp Asp
                 20                  25                  30

Ser Leu Glu Ser Thr Arg Arg Met Leu Ala Met Cys Glu Glu Ser Lys
                 35                  40                  45

Asp Ala Gly Ile Arg Thr Leu Val Met Leu Asp Glu Gln Gly Glu Gln
 50                  55                  60

Leu Asp Arg Ile Glu Glu Gly Met Asp Gln Ile Asn Gln Asp Met Arg
 65                  70                  75                  80

Asp Ala Glu Lys Asn Leu Glu Gly Met Glu Lys Cys Cys Gly Leu Cys
                 85                  90                  95

Ile Leu Pro Trp Lys Arg Thr Lys Asn Phe Asp Lys Gly Ala Glu Trp
                100                 105                 110

Asn Lys Gly Asp Glu Gly Lys Val Asn Thr Asp Gly Pro Arg Leu Val
                115                 120                 125

Val Gly Asp Gly Asn Met Gly Pro Ser Gly Gly Phe Ile Thr Lys Ile
                130                 135                 140

Thr Asn Asp Ala Arg Glu Glu Met Glu Gln Asn Met Gly Glu Val
145                 150                 155                 160

Ser Asn Met Ile Ser Asn Leu Arg Asn Met Ala Val Asp Met Gly Ser
                165                 170                 175

Glu Ile Asp Ser Gln Asn Arg Gln Val Asp Arg Ile Asn Asn Lys Met
                180                 185                 190

Thr Ser Asn Gln Leu Arg Ile Ser Asp Ala Asn Lys Arg Ala Ser Lys
                195                 200                 205

Leu Leu Lys Glu
```

-continued

```
<210> SEQ ID NO 22
<211> LENGTH: 212
<212> TYPE: PRT
<213> ORGANISM: Loligo pealei

<400> SEQUENCE: 22

Met Ser Ala Asn Gly Glu Val Glu Val Pro Lys Thr Glu Leu Glu Glu
 1               5                  10                  15

Ile Gln Gln Gln Cys Asn Gln Val Thr Asp Asp Ser Leu Glu Ser Thr
            20                  25                  30

Arg Arg Met Leu Asn Met Cys Glu Glu Ser Lys Glu Ala Gly Ile Arg
        35                  40                  45

Thr Leu Val Met Leu Asp Glu Gln Gly Glu Gln Leu Asp Arg Ile Glu
    50                  55                  60

Glu Gly Leu Asp Gln Ile Asn Gln Asp Met Lys Asp Ala Glu Lys Asn
65                  70                  75                  80

Leu Glu Gly Met Glu Lys Cys Cys Gly Leu Cys Val Leu Pro Trp Lys
                85                  90                  95

Arg Gly Lys Ser Phe Glu Lys Ser Gly Asp Tyr Ala Asn Thr Trp Lys
            100                 105                 110

Lys Asp Asp Gly Pro Thr Asn Thr Asn Gly Pro Arg Val Thr Val
            115                 120                 125

Gly Asp Gln Asn Gly Met Gly Pro Ser Ser Gly Tyr Val Thr Arg Ile
    130                 135                 140

Thr Asn Asp Ala Arg Glu Asp Asp Met Glu Asn Asn Met Lys Glu Val
145                 150                 155                 160

Ser Ser Met Ile Gly Asn Leu Arg Asn Met Ala Ile Asp Met Gly Asn
                165                 170                 175

Glu Ile Gly Ser Gln Asn Arg Gln Val Asp Arg Ile Gln Gln Lys Ala
            180                 185                 190

Glu Ser Asn Glu Ser Arg Ile Asp Glu Ala Asn Lys Lys Ala Thr Lys
        195                 200                 205

Leu Leu Lys Asn
    210

<210> SEQ ID NO 23
<211> LENGTH: 220
<212> TYPE: PRT
<213> ORGANISM: Lymnaea stagnalis

<400> SEQUENCE: 23

Met Thr Thr Asn Gly Glu Ile Leu Pro Val Gly Glu Glu Glu Glu Glu
 1               5                  10                  15

Glu Leu Gly Glu Asp Ala Leu Leu Arg Lys Gln Ile Asp Cys Asn Thr
            20                  25                  30

Asn Glu Ser Leu Glu Ser Thr Arg Arg Met Leu Ser Leu Cys Glu Glu
        35                  40                  45

Ser Lys Glu Ala Gly Ile Lys Thr Leu Val Met Leu Asp Glu Gln Gly
    50                  55                  60

Glu Gln Leu Asp Arg Ile Glu Glu Gly Met Gly Gln Ile Asn Gln Asp
65                  70                  75                  80

Met Arg Asp Ala Glu Lys Asn Leu Glu Gly Leu Glu Lys Cys Cys Gly
                85                  90                  95

Leu Cys Val Leu Pro Trp Lys Arg Ser Lys Asn Phe Glu Lys Gly Ser
            100                 105                 110
```

Asp Tyr Asn Lys Thr Trp Lys Ala Ser Glu Asp Gly Lys Ile Asn Thr
            115                 120                 125

Asn Gly Pro Arg Leu Val Val Asp Gln Gly Asn Gly Ser Gly Pro Thr
        130                 135                 140

Gly Gly Tyr Ile Thr Arg Ile Thr Asn Asp Ala Arg Glu Asp Glu Met
145                 150                 155                 160

Glu Gln Asn Ile Gly Glu Val Ala Gly Met Val Ser Asn Leu Arg Asn
                165                 170                 175

Met Ala Val Asp Met Gly Asn Glu Ile Glu Ser Gln Asn Lys Gln Leu
            180                 185                 190

Asp Arg Ile Asn Gln Lys Gly Gly Ser Leu Asn Val Arg Val Asp Glu
        195                 200                 205

Ala Asn Lys Arg Ala Asn Arg Ile Leu Arg Lys Gln
    210                 215                 220

<210> SEQ ID NO 24
<211> LENGTH: 207
<212> TYPE: PRT
<213> ORGANISM: Caenorhabditis elegans

<400> SEQUENCE: 24

Met Ser Gly Asp Asp Ile Pro Glu Gly Leu Glu Ala Ile Asn Leu
1               5                   10                  15

Lys Met Asn Ala Thr Thr Asp Asp Ser Leu Glu Ser Thr Arg Arg Met
            20                  25                  30

Leu Ala Leu Cys Glu Glu Ser Lys Glu Ala Gly Ile Lys Thr Leu Val
        35                  40                  45

Met Leu Asp Asp Gln Gly Glu Gln Leu Glu Arg Cys Glu Gly Ala Leu
    50                  55                  60

Asp Thr Ile Asn Gln Asp Met Lys Glu Ala Glu Asp His Leu Lys Gly
65                  70                  75                  80

Met Glu Lys Cys Cys Gly Leu Cys Val Leu Pro Trp Asn Lys Thr Asp
                85                  90                  95

Asp Phe Glu Lys Thr Glu Phe Ala Lys Ala Trp Lys Lys Asp Asp Asp
            100                 105                 110

Gly Gly Val Ile Ser Asp Gln Pro Arg Ile Thr Val Gly Asp Ser Ser
        115                 120                 125

Met Gly Pro Gln Gly Gly Tyr Ile Thr Lys Ile Thr Asn Asp Ala Arg
    130                 135                 140

Glu Asp Glu Met Asp Glu Asn Val Gln Gln Val Ser Thr Met Val Gly
145                 150                 155                 160

Asn Leu Arg Asn Met Ala Ile Asp Met Ser Thr Glu Val Ser Asn Gln
                165                 170                 175

Asn Arg Gln Leu Asp Arg Ile His Asp Lys Ala Gln Ser Asn Glu Val
            180                 185                 190

Arg Val Glu Ser Ala Asn Lys Arg Ala Lys Asn Leu Ile Thr Lys
        195                 200                 205

<210> SEQ ID NO 25
<211> LENGTH: 808
<212> TYPE: PRT
<213> ORGANISM: Homo sapiens

<400> SEQUENCE: 25

Met Gly Ala Pro Ala Cys Ala Leu Ala Leu Cys Val Ala Val Ala Ile
1               5                   10                  15

```
Val Ala Gly Ala Ser Ser Glu Ser Leu Gly Thr Glu Gln Arg Val Val
            20                  25                  30

Gly Arg Ala Ala Glu Val Pro Gly Pro Glu Pro Gly Gln Gln Glu Gln
        35                  40                  45

Leu Val Phe Gly Ser Gly Asp Ala Val Glu Leu Ser Cys Pro Pro Pro
 50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
                115                 120                 125

Pro Ser Ser Gly Asp Asp Glu Asp Gly Glu Asp Glu Ala Glu Asp Thr
    130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
            195                 200                 205

Gln Gln Trp Ser Leu Val Met Glu Ser Val Val Pro Ser Asp Arg Gly
    210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
            290                 295                 300

Tyr Val Thr Val Leu Lys Ser Trp Ile Ser Glu Ser Val Glu Ala Asp
305                 310                 315                 320

Val Arg Leu Arg Leu Ala Asn Val Ser Glu Arg Asp Gly Gly Glu Tyr
                325                 330                 335

Leu Cys Arg Ala Thr Asn Phe Ile Gly Val Ala Glu Lys Ala Phe Trp
                340                 345                 350

Leu Ser Val His Gly Pro Arg Ala Ala Glu Glu Glu Leu Val Glu Ala
            355                 360                 365

Asp Glu Ala Gly Ser Val Tyr Ala Gly Ile Leu Ser Tyr Gly Val Gly
    370                 375                 380

Phe Phe Leu Phe Ile Leu Val Val Ala Ala Val Thr Leu Cys Arg Leu
385                 390                 395                 400

Arg Ser Pro Pro Lys Lys Gly Leu Gly Ser Pro Thr Val His Lys Ile
                405                 410                 415

Ser Arg Phe Pro Leu Lys Arg Gln Val Ser Leu Glu Ser Asn Ala Ser
                420                 425                 430

Met Ser Ser Asn Thr Pro Leu Val Arg Ile Ala Arg Leu Ser Ser Gly
            435                 440                 445
```

Glu Gly Pro Thr Leu Ala Asn Val Ser Glu Leu Glu Leu Pro Ala Asp
    450                 455                 460

Pro Lys Trp Glu Leu Ser Arg Ala Arg Leu Thr Leu Gly Lys Pro Leu
465                 470                 475                 480

Gly Glu Gly Cys Phe Gly Gln Val Val Met Ala Glu Ala Ile Gly Ile
                485                 490                 495

Asp Lys Asp Arg Ala Ala Lys Pro Val Thr Val Ala Val Lys Met Leu
                500                 505                 510

Lys Asp Asp Ala Thr Asp Lys Asp Leu Ser Asp Leu Val Ser Glu Met
                515                 520                 525

Glu Met Met Lys Met Ile Gly Lys His Lys Asn Ile Ile Asn Leu Leu
530                 535                 540

Gly Ala Cys Thr Gln Gly Gly Pro Leu Tyr Val Leu Val Glu Tyr Ala
545                 550                 555                 560

Ala Lys Gly Asn Leu Arg Glu Phe Leu Arg Ala Arg Arg Pro Pro Gly
                565                 570                 575

Leu Asp Tyr Ser Phe Asp Thr Cys Lys Pro Pro Glu Glu Gln Leu Thr
                580                 585                 590

Phe Lys Asp Leu Val Ser Cys Ala Tyr Gln Val Ala Arg Gly Met Glu
                595                 600                 605

Tyr Leu Ala Ser Gln Lys Cys Ile His Arg Asp Leu Ala Ala Arg Asn
610                 615                 620

Val Leu Val Thr Glu Asp Asn Val Met Lys Ile Ala Asp Phe Gly Leu
625                 630                 635                 640

Ala Arg Asp Val His Asn Leu Asp Tyr Tyr Lys Lys Thr Thr Asn Gly
                645                 650                 655

Arg Leu Pro Val Lys Trp Met Ala Pro Glu Ala Leu Phe Asp Arg Val
                660                 665                 670

Tyr Thr His Gln Ser Asp Val Trp Ser Phe Gly Val Leu Leu Trp Glu
                675                 680                 685

Ile Phe Thr Leu Gly Gly Ser Pro Tyr Pro Gly Ile Pro Val Glu Glu
                690                 695                 700

Leu Phe Lys Leu Leu Lys Glu Gly His Arg Met Asp Lys Pro Ala Asn
705                 710                 715                 720

Cys Thr His Asp Leu Tyr Met Ile Met Arg Glu Cys Trp His Ala Ala
                725                 730                 735

Pro Ser Gln Arg Pro Thr Phe Lys Gln Leu Val Glu Asp Leu Asp Arg
                740                 745                 750

Val Leu Thr Val Thr Ser Thr Asp Glu Tyr Leu Asp Leu Ser Ala Pro
                755                 760                 765

Phe Glu Gln Tyr Ser Pro Gly Gly Gln Asp Thr Pro Ser Ser Ser Ser
                770                 775                 780

Ser Gly Asp Asp Ser Val Phe Ala His Asp Leu Leu Pro Pro Ala Pro
785                 790                 795                 800

Pro Ser Ser Gly Gly Ser Arg Thr
                805

<210> SEQ ID NO 26
<211> LENGTH: 806
<212> TYPE: PRT
<213> ORGANISM: Homo sapiens

<400> SEQUENCE: 26

Met Gly Ala Pro Ala Cys Ala Leu Ala Leu Cys Val Ala Val Ala Ile
1               5                   10                  15

```
Val Ala Gly Ala Ser Ser Glu Ser Leu Gly Thr Glu Gln Arg Val Val
            20                  25                  30
Gly Arg Ala Ala Glu Val Pro Gly Pro Glu Pro Gly Gln Gln Glu Gln
            35                  40                  45
Leu Val Phe Gly Ser Gly Asp Ala Val Glu Leu Ser Cys Pro Pro Pro
 50                  55                  60
Gly Gly Gly Pro Met Gly Pro Thr Val Trp Val Lys Asp Gly Thr Gly
 65                  70                  75                  80
Leu Val Pro Ser Glu Arg Val Leu Val Gly Pro Gln Arg Leu Gln Val
                85                  90                  95
Leu Asn Ala Ser His Glu Asp Ser Gly Ala Tyr Ser Cys Arg Gln Arg
            100                 105                 110
Leu Thr Gln Arg Val Leu Cys His Phe Ser Val Arg Val Thr Asp Ala
            115                 120                 125
Pro Ser Ser Gly Asp Asp Glu Asp Gly Glu Asp Glu Ala Glu Asp Thr
 130                 135                 140
Gly Val Asp Thr Gly Ala Pro Tyr Trp Thr Arg Pro Glu Arg Met Asp
145                 150                 155                 160
Lys Lys Leu Leu Ala Val Pro Ala Ala Asn Thr Val Arg Phe Arg Cys
                165                 170                 175
Pro Ala Ala Gly Asn Pro Thr Pro Ser Ile Ser Trp Leu Lys Asn Gly
            180                 185                 190
Arg Glu Phe Arg Gly Glu His Arg Ile Gly Gly Ile Lys Leu Arg His
            195                 200                 205
Gln Gln Trp Ser Leu Val Met Glu Ser Val Val Pro Ser Asp Arg Gly
 210                 215                 220
Asn Tyr Thr Cys Val Val Glu Asn Lys Phe Gly Ser Ile Arg Gln Thr
225                 230                 235                 240
Tyr Thr Leu Asp Val Leu Glu Arg Ser Pro His Arg Pro Ile Leu Gln
                245                 250                 255
Ala Gly Leu Pro Ala Asn Gln Thr Ala Val Leu Gly Ser Asp Val Glu
            260                 265                 270
Phe His Cys Lys Val Tyr Ser Asp Ala Gln Pro His Ile Gln Trp Leu
            275                 280                 285
Lys His Val Glu Val Asn Gly Ser Lys Val Gly Pro Asp Gly Thr Pro
 290                 295                 300
Tyr Val Thr Val Leu Lys Thr Ala Gly Ala Asn Thr Thr Asp Lys Glu
305                 310                 315                 320
Leu Glu Val Leu Ser Leu His Asn Val Thr Phe Glu Asp Ala Gly Glu
                325                 330                 335
Tyr Thr Cys Leu Ala Gly Asn Ser Ile Gly Phe Ser His His Ser Ala
            340                 345                 350
Trp Leu Val Val Leu Pro Ala Glu Glu Glu Leu Val Glu Ala Asp Glu
            355                 360                 365
Ala Gly Ser Val Tyr Ala Gly Ile Leu Ser Tyr Gly Val Gly Phe Phe
 370                 375                 380
Leu Phe Ile Leu Val Val Ala Ala Val Thr Leu Cys Arg Leu Arg Ser
385                 390                 395                 400
Pro Pro Lys Lys Gly Leu Gly Ser Pro Thr Val His Lys Ile Ser Arg
                405                 410                 415
Phe Pro Leu Lys Arg Gln Val Ser Leu Glu Ser Asn Ala Ser Met Ser
            420                 425                 430
Ser Asn Thr Pro Leu Val Arg Ile Ala Arg Leu Ser Ser Gly Glu Gly
```

```
                    435                 440                 445
Pro Thr Leu Ala Asn Val Ser Glu Leu Glu Leu Pro Ala Asp Pro Lys
450                 455                 460

Trp Glu Leu Ser Arg Ala Arg Leu Thr Leu Gly Lys Pro Leu Gly Glu
465                 470                 475                 480

Gly Cys Phe Gly Gln Val Val Met Ala Glu Ile Gly Ile Asp Lys
                    485                 490                 495

Asp Arg Ala Ala Lys Pro Val Thr Val Ala Val Lys Met Leu Lys Asp
                500                 505                 510

Asp Ala Thr Asp Lys Asp Leu Ser Asp Leu Val Ser Glu Met Glu Met
                515                 520                 525

Met Lys Met Ile Gly Lys His Lys Asn Ile Ile Asn Leu Leu Gly Ala
530                 535                 540

Cys Thr Gln Gly Gly Pro Leu Tyr Val Leu Val Glu Tyr Ala Ala Lys
545                 550                 555                 560

Gly Asn Leu Arg Glu Phe Leu Arg Ala Arg Arg Pro Pro Gly Leu Asp
                    565                 570                 575

Tyr Ser Phe Asp Thr Cys Lys Pro Pro Glu Glu Gln Leu Thr Phe Lys
                580                 585                 590

Asp Leu Val Ser Cys Ala Tyr Gln Val Ala Arg Gly Met Glu Tyr Leu
                595                 600                 605

Ala Ser Gln Lys Cys Ile His Arg Asp Leu Ala Ala Arg Asn Val Leu
610                 615                 620

Val Thr Glu Asp Asn Val Met Lys Ile Ala Asp Phe Gly Leu Ala Arg
625                 630                 635                 640

Asp Val His Asn Leu Asp Tyr Tyr Lys Lys Thr Thr Asn Gly Arg Leu
                    645                 650                 655

Pro Val Lys Trp Met Ala Pro Glu Ala Leu Phe Asp Arg Val Tyr Thr
                660                 665                 670

His Gln Ser Asp Val Trp Ser Phe Gly Val Leu Leu Trp Glu Ile Phe
                675                 680                 685

Thr Leu Gly Gly Ser Pro Tyr Pro Gly Ile Pro Val Glu Glu Leu Phe
690                 695                 700

Lys Leu Leu Lys Glu Gly His Arg Met Asp Lys Pro Ala Asn Cys Thr
705                 710                 715                 720

His Asp Leu Tyr Met Ile Met Arg Glu Cys Trp His Ala Ala Pro Ser
                    725                 730                 735

Gln Arg Pro Thr Phe Lys Gln Leu Val Glu Asp Leu Asp Arg Val Leu
                740                 745                 750

Thr Val Thr Ser Thr Asp Glu Tyr Leu Asp Leu Ser Ala Pro Phe Glu
                755                 760                 765

Gln Tyr Ser Pro Gly Gly Gln Asp Thr Pro Ser Ser Ser Ser Ser Gly
                770                 775                 780

Asp Asp Ser Val Phe Ala His Asp Leu Leu Pro Pro Ala Pro Pro Ser
785                 790                 795                 800

Ser Gly Gly Ser Arg Thr
                805

<210> SEQ ID NO 27
<211> LENGTH: 694
<212> TYPE: PRT
<213> ORGANISM: Homo sapiens

<400> SEQUENCE: 27

Met Gly Ala Pro Ala Cys Ala Leu Ala Leu Cys Val Ala Val Ala Ile
```

-continued

```
         1               5                  10                 15
Val Ala Gly Ala Ser Ser Glu Ser Leu Gly Thr Glu Gln Arg Val Val
                20                  25                  30

Gly Arg Ala Ala Glu Val Pro Gly Pro Glu Pro Gly Gln Gln Glu Gln
                35                  40                  45

Leu Val Phe Gly Ser Gly Asp Ala Val Glu Leu Ser Cys Pro Pro Pro
         50                  55                  60

Gly Gly Gly Pro Met Gly Pro Thr Val Trp Val Lys Asp Gly Thr Gly
 65                  70                  75                  80

Leu Val Pro Ser Glu Arg Val Leu Val Gly Pro Gln Arg Leu Gln Val
                85                  90                  95

Leu Asn Ala Ser His Glu Asp Ser Gly Ala Tyr Ser Cys Arg Gln Arg
                100                 105                 110

Leu Thr Gln Arg Val Leu Cys His Phe Ser Val Arg Val Thr Asp Ala
                115                 120                 125

Pro Ser Ser Gly Asp Asp Glu Asp Gly Glu Asp Glu Ala Glu Asp Thr
                130                 135                 140

Gly Val Asp Thr Gly Ala Pro Tyr Trp Thr Arg Pro Glu Arg Met Asp
145                 150                 155                 160

Lys Lys Leu Leu Ala Val Pro Ala Ala Asn Thr Val Arg Phe Arg Cys
                165                 170                 175

Pro Ala Ala Gly Asn Pro Thr Pro Ser Ile Ser Trp Leu Lys Asn Gly
                180                 185                 190

Arg Glu Phe Arg Gly Glu His Arg Ile Gly Gly Ile Lys Leu Arg His
                195                 200                 205

Gln Gln Trp Ser Leu Val Met Glu Ser Val Val Pro Ser Asp Arg Gly
                210                 215                 220

Asn Tyr Thr Cys Val Val Glu Asn Lys Phe Gly Ser Ile Arg Gln Thr
225                 230                 235                 240

Tyr Thr Leu Asp Val Leu Glu Arg Ser Pro His Arg Pro Ile Leu Gln
                245                 250                 255

Ala Gly Leu Pro Ala Asn Gln Thr Ala Val Leu Gly Ser Asp Val Glu
                260                 265                 270

Phe His Cys Lys Val Tyr Ser Asp Ala Gln Pro His Ile Gln Trp Leu
                275                 280                 285

Lys His Val Glu Val Asn Gly Ser Lys Val Gly Pro Asp Gly Thr Pro
                290                 295                 300

Tyr Val Thr Val Leu Lys Val Ser Leu Glu Ser Asn Ala Ser Met Ser
305                 310                 315                 320

Ser Asn Thr Pro Leu Val Arg Ile Ala Arg Leu Ser Ser Gly Glu Gly
                325                 330                 335

Pro Thr Leu Ala Asn Val Ser Glu Leu Glu Leu Pro Ala Asp Pro Lys
                340                 345                 350

Trp Glu Leu Ser Arg Ala Arg Leu Thr Leu Gly Lys Pro Leu Gly Glu
                355                 360                 365

Gly Cys Phe Gly Gln Val Val Met Ala Glu Ala Ile Gly Ile Asp Lys
                370                 375                 380

Asp Arg Ala Ala Lys Pro Val Thr Val Ala Val Lys Met Leu Lys Asp
385                 390                 395                 400

Asp Ala Thr Asp Lys Asp Leu Ser Asp Leu Val Ser Glu Met Glu Met
                405                 410                 415

Met Lys Met Ile Gly Lys His Lys Asn Ile Ile Asn Leu Leu Gly Ala
                420                 425                 430
```

```
Cys Thr Gln Gly Gly Pro Leu Tyr Val Leu Glu Tyr Ala Ala Lys
            435                 440                 445

Gly Asn Leu Arg Glu Phe Leu Arg Ala Arg Arg Pro Gly Leu Asp
        450                 455                 460

Tyr Ser Phe Asp Thr Cys Lys Pro Pro Glu Glu Gln Leu Thr Phe Lys
465                 470                 475                 480

Asp Leu Val Ser Cys Ala Tyr Gln Val Ala Arg Gly Met Glu Tyr Leu
                485                 490                 495

Ala Ser Gln Lys Cys Ile His Arg Asp Leu Ala Ala Arg Asn Val Leu
            500                 505                 510

Val Thr Glu Asp Asn Val Met Lys Ile Ala Asp Phe Gly Leu Ala Arg
        515                 520                 525

Asp Val His Asn Leu Asp Tyr Tyr Lys Lys Thr Thr Asn Gly Arg Leu
    530                 535                 540

Pro Val Lys Trp Met Ala Pro Glu Ala Leu Phe Asp Arg Val Tyr Thr
545                 550                 555                 560

His Gln Ser Asp Val Trp Ser Phe Gly Val Leu Leu Trp Glu Ile Phe
                565                 570                 575

Thr Leu Gly Gly Ser Pro Tyr Pro Gly Ile Pro Val Glu Glu Leu Phe
            580                 585                 590

Lys Leu Leu Lys Glu Gly His Arg Met Asp Lys Pro Ala Asn Cys Thr
        595                 600                 605

His Asp Leu Tyr Met Ile Met Arg Glu Cys Trp His Ala Ala Pro Ser
    610                 615                 620

Gln Arg Pro Thr Phe Lys Gln Leu Val Glu Asp Leu Asp Arg Val Leu
625                 630                 635                 640

Thr Val Thr Ser Thr Asp Glu Tyr Leu Asp Leu Ser Ala Pro Phe Glu
                645                 650                 655

Gln Tyr Ser Pro Gly Gly Gln Asp Thr Pro Ser Ser Ser Ser Ser Gly
            660                 665                 670

Asp Asp Ser Val Phe Ala His Asp Leu Leu Pro Pro Ala Pro Pro Ser
        675                 680                 685

Ser Gly Gly Ser Arg Thr
    690

<210> SEQ ID NO 28
<211> LENGTH: 604
<212> TYPE: PRT
<213> ORGANISM: Homo sapiens

<400> SEQUENCE: 28

Ala Gln Arg Arg Lys Glu Arg Glu Glu Leu Ala Gln Gln Tyr Glu Ala
 1               5                  10                  15

Ile Leu Arg Glu Cys Gly His Gly Arg Phe Gln Trp Thr Leu Tyr Phe
                20                  25                  30

Val Leu Gly Leu Ala Leu Met Ala Asp Gly Val Glu Val Phe Val Val
            35                  40                  45

Gly Phe Val Leu Pro Ser Ala Glu Lys Asp Met Cys Leu Ser Asp Ser
        50                  55                  60

Asn Lys Gly Met Leu Gly Leu Ile Val Tyr Leu Gly Met Met Val Gly
65                  70                  75                  80

Ala Phe Leu Trp Gly Gly Leu Ala Asp Arg Leu Gly Arg Arg Gln Cys
                85                  90                  95

Leu Leu Ile Ser Leu Ser Val Asn Ser Val Phe Ala Phe Phe Ser Ser
            100                 105                 110
```

-continued

```
Phe Val Gln Gly Tyr Gly Thr Phe Leu Phe Cys Arg Leu Leu Ser Gly
            115                 120                 125
Val Gly Ile Gly Gly Ser Ile Pro Ile Val Phe Ser Tyr Phe Ser Glu
            130                 135                 140
Phe Leu Ala Gln Glu Lys Arg Gly Glu His Leu Ser Trp Leu Cys Met
145                 150                 155                 160
Phe Trp Met Ile Gly Gly Val Tyr Ala Ala Met Ala Trp Ala Ile
                    165                 170                 175
Ile Pro His Tyr Gly Trp Ser Phe Gln Met Gly Ser Ala Tyr Gln Phe
                    180                 185                 190
His Ser Trp Arg Val Phe Val Leu Val Cys Ala Phe Pro Ser Val Phe
            195                 200                 205
Ala Ile Gly Ala Leu Thr Thr Gln Pro Glu Ser Pro Arg Phe Phe Leu
            210                 215                 220
Glu Asn Gly Lys His Asp Glu Ala Trp Met Val Leu Lys Gln Val His
225                 230                 235                 240
Asp Thr Asn Met Arg Ala Lys Gly His Pro Glu Arg Val Phe Ser Val
                    245                 250                 255
Thr His Ile Lys Thr Ile His Gln Glu Asp Glu Leu Ile Glu Ile Gln
                    260                 265                 270
Ser Asp Thr Gly Thr Trp Tyr Gln Arg Trp Gly Val Arg Ala Leu Ser
            275                 280                 285
Leu Gly Gly Gln Val Trp Gly Asn Phe Leu Ser Cys Phe Gly Pro Glu
            290                 295                 300
Tyr Arg Arg Ile Thr Leu Met Met Met Gly Val Trp Phe Thr Met Ser
305                 310                 315                 320
Phe Ser Tyr Tyr Gly Leu Thr Val Trp Phe Pro Asp Met Ile Arg His
                    325                 330                 335
Leu Gln Ala Val Asp Tyr Ala Ser Arg Thr Lys Val Phe Pro Gly Glu
                    340                 345                 350
Arg Val Glu His Val Thr Phe Asn Phe Thr Leu Glu Asn Gln Ile His
            355                 360                 365
Arg Gly Gly Gln Tyr Phe Asn Asp Lys Phe Ile Gly Leu Arg Leu Lys
            370                 375                 380
Ser Val Ser Phe Glu Asp Ser Leu Phe Glu Glu Cys Tyr Phe Glu Asp
385                 390                 395                 400
Val Thr Ser Ser Asn Thr Phe Arg Asn Cys Thr Phe Ile Asn Thr
                    405                 410                 415
Val Phe Tyr Asn Thr Asp Leu Phe Glu Tyr Lys Phe Val Asn Ser Arg
                    420                 425                 430
Leu Ile Asn Ser Thr Phe Leu His Asn Lys Glu Gly Cys Pro Leu Asp
            435                 440                 445
Val Thr Gly Thr Gly Glu Gly Ala Tyr Met Val Tyr Phe Val Ser Phe
            450                 455                 460
Leu Gly Thr Leu Ala Val Leu Pro Gly Asn Ile Val Ser Ala Leu Leu
465                 470                 475                 480
Met Asp Lys Ile Gly Arg Leu Arg Met Leu Ala Gly Ser Ser Val Met
                    485                 490                 495
Ser Cys Val Ser Cys Phe Phe Leu Ser Phe Gly Asn Ser Glu Ser Ala
                    500                 505                 510
Met Ile Ala Leu Leu Cys Leu Phe Gly Gly Val Ser Ile Ala Ser Trp
            515                 520                 525
Asn Ala Leu Asp Val Leu Thr Val Glu Leu Tyr Pro Ser Asp Lys Arg
            530                 535                 540
```

Thr Thr Ala Phe Gly Phe Leu Asn Ala Leu Cys Lys Leu Ala Val
545                 550                 555                 560

Leu Gly Ile Ser Ile Phe Thr Ser Phe Val Gly Ile Thr Lys Ala Ala
            565                 570                 575

Pro Ile Leu Phe Ala Ser Ala Ala Leu Ala Leu Gly Ser Ser Leu Ala
                580                 585                 590

Leu Lys Leu Pro Glu Thr Arg Gly Gln Val Leu Gln
        595                 600

<210> SEQ ID NO 29
<211> LENGTH: 683
<212> TYPE: PRT
<213> ORGANISM: Homo sapiens

<400> SEQUENCE: 29

Met Asp Asp Tyr Lys Tyr Gln Asp Asn Tyr Gly Gly Tyr Ala Pro Ser
1               5                   10                  15

Asp Gly Tyr Tyr Arg Gly Asn Glu Ser Asn Pro Glu Glu Asp Ala Gln
            20                  25                  30

Ser Asp Val Thr Glu Gly His Asp Glu Glu Asp Glu Ile Tyr Glu Gly
        35                  40                  45

Glu Tyr Gln Gly Ile Pro His Pro Asp Asp Val Lys Ala Lys Gln Ala
    50                  55                  60

Lys Met Ala Pro Ser Arg Met Asp Ser Leu Arg Gly Gln Thr Asp Leu
65              70                  75                  80

Met Ala Glu Arg Leu Glu Asp Glu Gln Leu Ala His Gln Tyr Glu
                85                  90                  95

Thr Ile Met Asp Glu Cys Gly His Gly Arg Phe Gln Trp Ile Leu Phe
            100                 105                 110

Phe Val Leu Gly Leu Ala Leu Met Ala Asp Gly Val Glu Val Phe Val
        115                 120                 125

Val Ser Phe Ala Leu Pro Ser Ala Glu Lys Asp Met Cys Leu Ser Ser
    130                 135                 140

Ser Lys Lys Gly Met Leu Gly Met Ile Val Tyr Leu Gly Met Met Ala
145                 150                 155                 160

Gly Ala Phe Ile Leu Gly Gly Leu Ala Asp Lys Leu Gly Arg Lys Arg
                165                 170                 175

Val Leu Ser Met Ser Leu Ala Val Asn Ala Ser Phe Ala Ser Leu Ser
            180                 185                 190

Ser Phe Val Gln Gly Tyr Gly Ala Phe Leu Phe Cys Arg Leu Ile Ser
        195                 200                 205

Gly Ile Gly Ile Gly Gly Ala Leu Pro Ile Val Phe Ala Tyr Phe Ser
    210                 215                 220

Glu Phe Leu Ser Arg Glu Lys Arg Gly Glu His Leu Ser Trp Leu Gly
225                 230                 235                 240

Ile Phe Trp Met Thr Gly Gly Leu Tyr Ala Ser Ala Met Ala Trp Ser
                245                 250                 255

Ile Ile Pro His Tyr Gly Trp Gly Phe Ser Met Gly Thr Asn Tyr His
            260                 265                 270

Phe His Ser Trp Arg Val Phe Val Ile Val Cys Ala Leu Pro Cys Thr
        275                 280                 285

Val Ser Met Val Ala Leu Lys Phe Met Pro Glu Ser Pro Arg Phe Leu
    290                 295                 300

Leu Glu Met Gly Lys His Asp Glu Ala Trp Met Ile Leu Lys Gln Val
305                 310                 315                 320

His Asp Thr Asn Met Arg Ala Lys Gly Thr Pro Glu Lys Val Phe Thr
                325                 330                 335

Val Ser Asn Ile Lys Thr Pro Lys Gln Met Asp Glu Phe Ile Glu Ile
            340                 345                 350

Gln Ser Ser Thr Gly Thr Trp Tyr Gln Arg Trp Leu Val Arg Phe Lys
        355                 360                 365

Thr Ile Phe Lys Gln Val Trp Asp Asn Ala Leu Tyr Cys Val Met Gly
    370                 375                 380

Pro Tyr Arg Met Asn Thr Leu Ile Leu Ala Val Val Trp Phe Ala Met
385                 390                 395                 400

Ala Phe Ser Tyr Tyr Gly Leu Thr Val Trp Phe Pro Asp Met Ile Arg
                405                 410                 415

Tyr Phe Gln Asp Glu Glu Tyr Lys Ser Lys Met Lys Val Phe Phe Gly
            420                 425                 430

Glu His Val Tyr Gly Ala Thr Ile Asn Phe Thr Met Glu Asn Gln Ile
        435                 440                 445

His Gln His Gly Lys Leu Val Asn Asp Lys Phe Thr Arg Met Tyr Phe
    450                 455                 460

Lys His Val Leu Phe Glu Asp Thr Phe Phe Asp Glu Cys Tyr Phe Glu
465                 470                 475                 480

Asp Val Thr Ser Thr Asp Thr Tyr Phe Lys Asn Cys Thr Ile Glu Ser
                485                 490                 495

Thr Ile Phe Tyr Asn Thr Asp Leu Tyr Glu His Lys Phe Ile Asn Cys
            500                 505                 510

Arg Phe Ile Asn Ser Thr Phe Leu Glu Gln Lys Glu Gly Cys His Met
        515                 520                 525

Asp Leu Glu Gln Asp Asn Asp Phe Leu Ile Tyr Leu Val Ser Phe Leu
    530                 535                 540

Gly Ser Leu Ser Val Leu Pro Gly Asn Ile Ile Ser Ala Leu Leu Met
545                 550                 555                 560

Asp Arg Ile Gly Arg Leu Lys Met Ile Gly Gly Ser Met Leu Ile Ser
                565                 570                 575

Ala Val Cys Cys Phe Phe Leu Phe Phe Gly Asn Ser Glu Ser Ala Met
            580                 585                 590

Ile Gly Trp Gln Cys Leu Phe Cys Gly Thr Ser Ile Ala Ala Trp Asn
        595                 600                 605

Ala Leu Asp Val Ile Thr Val Glu Leu Tyr Pro Thr Asn Gln Arg Ala
    610                 615                 620

Thr Ala Phe Gly Ile Leu Asn Gly Leu Cys Lys Phe Gly Ala Ile Leu
625                 630                 635                 640

Gly Asn Thr Ile Phe Ala Ser Phe Val Gly Ile Thr Lys Val Val Pro
                645                 650                 655

Ile Leu Leu Ala Ala Ala Ser Leu Val Gly Gly Leu Ile Ala Leu
            660                 665                 670

Arg Leu Pro Glu Thr Arg Glu Gln Val Leu Ile
        675                 680

<210> SEQ ID NO 30
<211> LENGTH: 727
<212> TYPE: PRT
<213> ORGANISM: Homo sapiens

<400> SEQUENCE: 30

Met Glu Asp Ser Tyr Lys Asp Arg Thr Ser Leu Met Lys Gly Ala Lys
1               5                   10                  15

Asp Ile Ala Arg Glu Val Lys Lys Gln Thr Val Lys Val Asn Gln
        20                  25                  30

Ala Val Asp Arg Ala Gln Asp Glu Tyr Thr Gln Arg Ser Tyr Ser Arg
            35                  40                  45

Phe Gln Asp Glu Glu Asp Asp Asp Tyr Tyr Pro Ala Gly Glu Thr
 50                  55                  60

Tyr Asn Gly Glu Ala Asn Asp Asp Glu Gly Ser Ser Glu Ala Thr Glu
 65                  70                  75                  80

Gly His Asp Glu Asp Asp Glu Ile Tyr Glu Gly Glu Tyr Gln Gly Ile
                85                  90                  95

Pro Ser Met Asn Gln Ala Lys Asp Ser Ile Val Ser Val Gly Gln Pro
                100                 105                 110

Lys Gly Asp Glu Tyr Lys Asp Arg Arg Glu Leu Glu Ser Glu Arg Arg
            115                 120                 125

Ala Asp Glu Glu Glu Leu Ala Gln Gln Tyr Glu Leu Ile Ile Gln Glu
130                 135                 140

Cys Gly His Gly Arg Phe Gln Trp Ala Leu Phe Val Leu Gly Met
145                 150                 155                 160

Ala Leu Met Ala Asp Gly Val Glu Val Phe Val Val Gly Phe Val Leu
                165                 170                 175

Pro Ser Ala Glu Thr Asp Leu Cys Ile Pro Asn Ser Gly Ser Gly Trp
            180                 185                 190

Leu Gly Ser Ile Val Tyr Leu Gly Met Met Val Gly Ala Phe Phe Trp
        195                 200                 205

Gly Gly Leu Ala Asp Lys Val Gly Arg Lys Gln Ser Leu Leu Ile Cys
        210                 215                 220

Met Ser Val Asn Gly Phe Ala Phe Leu Ser Ser Phe Val Gln Gly
225                 230                 235                 240

Tyr Gly Phe Phe Leu Phe Cys Arg Leu Leu Ser Gly Phe Gly Ile Gly
                245                 250                 255

Gly Ala Ile Pro Thr Val Phe Ser Tyr Phe Ala Glu Val Leu Ala Arg
            260                 265                 270

Glu Lys Arg Gly Glu His Leu Ser Trp Leu Cys Met Phe Trp Met Ile
        275                 280                 285

Gly Gly Ile Tyr Ala Ser Ala Met Ala Trp Ala Ile Ile Pro His Tyr
        290                 295                 300

Gly Trp Ser Phe Ser Met Gly Ser Ala Tyr Gln Phe His Ser Trp Arg
305                 310                 315                 320

Val Phe Val Ile Val Cys Ala Leu Pro Cys Val Ser Ser Val Val Ala
                325                 330                 335

Leu Thr Phe Met Pro Glu Ser Pro Arg Phe Leu Leu Glu Val Gly Lys
            340                 345                 350

His Asp Glu Ala Trp Met Ile Leu Lys Leu Ile His Asp Thr Asn Met
        355                 360                 365

Arg Ala Arg Gly Gln Pro Glu Lys Val Phe Thr Val Asn Lys Ile Lys
        370                 375                 380

Thr Pro Lys Gln Ile Asp Glu Leu Ile Glu Ile Glu Ser Asp Thr Gly
385                 390                 395                 400

Thr Trp Tyr Arg Arg Cys Phe Val Arg Ile Arg Thr Glu Leu Tyr Gly
                405                 410                 415

Ile Trp Leu Thr Phe Met Arg Cys Phe Asn Tyr Pro Val Arg Asp Asn
            420                 425                 430

Thr Ile Lys Leu Thr Ile Val Trp Phe Thr Leu Ser Phe Gly Tyr Tyr

```
                435                 440                 445
Gly Leu Ser Val Trp Phe Pro Asp Val Ile Lys Pro Leu Gln Ser Asp
    450                 455                 460
Glu Tyr Ala Leu Leu Thr Arg Asn Val Glu Arg Asp Lys Tyr Ala Asn
465                 470                 475                 480
Phe Thr Ile Asn Phe Thr Met Glu Asn Gln Ile His Thr Gly Met Glu
                485                 490                 495
Tyr Asp Asn Gly Arg Phe Ile Gly Val Lys Phe Lys Ser Val Thr Phe
                500                 505                 510
Lys Asp Ser Val Phe Lys Ser Cys Thr Phe Glu Asp Val Thr Ser Val
                515                 520                 525
Asn Thr Tyr Phe Lys Asn Cys Thr Phe Ile Asp Thr Val Phe Asp Asn
530                 535                 540
Thr Asp Phe Glu Pro Tyr Lys Phe Ile Asp Ser Glu Phe Lys Asn Cys
545                 550                 555                 560
Ser Phe Phe His Asn Lys Thr Gly Cys Gln Ile Thr Phe Asp Asp Asp
                565                 570                 575
Tyr Ser Ala Tyr Trp Ile Tyr Phe Val Asn Phe Leu Gly Thr Leu Ala
                580                 585                 590
Val Leu Pro Gly Asn Ile Val Ser Ala Leu Leu Met Asp Arg Ile Gly
                595                 600                 605
Arg Leu Thr Met Leu Gly Gly Ser Met Val Leu Ser Gly Ile Ser Cys
                610                 615                 620
Phe Phe Leu Trp Phe Gly Thr Ser Glu Ser Met Met Ile Gly Met Leu
625                 630                 635                 640
Cys Leu Tyr Asn Gly Leu Thr Ile Ser Ala Trp Asn Ser Leu Asp Val
                645                 650                 655
Val Thr Val Glu Leu Tyr Pro Thr Asp Arg Arg Ala Thr Gly Phe Gly
                660                 665                 670
Phe Leu Asn Ala Leu Cys Lys Ala Ala Val Leu Gly Asn Leu Ile
                675                 680                 685
Phe Gly Ser Leu Val Ser Ile Thr Lys Ser Ile Pro Ile Leu Leu Ala
    690                 695                 700
Ser Thr Val Leu Val Cys Gly Gly Leu Val Gly Leu Cys Leu Pro Asp
705                 710                 715                 720
Thr Arg Thr Gln Val Leu Met
                725

<210> SEQ ID NO 31
<211> LENGTH: 742
<212> TYPE: PRT
<213> ORGANISM: Homo sapiens

<400> SEQUENCE: 31

Met Glu Glu Gly Phe Arg Asp Arg Ala Ala Phe Ile Arg Gly Ala Lys
1               5                   10                  15
Asp Ile Ala Lys Glu Val Lys Lys His Ala Ala Lys Lys Val Val Lys
                20                  25                  30
Gly Leu Asp Arg Val Gln Asp Glu Tyr Ser Arg Arg Ser Tyr Ser Arg
            35                  40                  45
Phe Glu Glu Glu Asp Asp Asp Asp Phe Pro Ala Pro Ser Asp Gly
        50                  55                  60
Tyr Tyr Arg Gly Glu Gly Thr Gln Asp Glu Glu Gly Gly Ala Ser
65              70                  75                  80
Ser Asp Ala Thr Glu Gly His Asp Glu Asp Asp Glu Ile Tyr Glu Gly
```

-continued

```
                85                  90                  95
Glu Tyr Gln Asp Ile Pro Arg Ala Ser Gly Gly Lys Gly Glu Arg
            100                 105                 110
Met Ala Asp Gly Ala Pro Leu Ala Gly Val Arg Gly Gly Leu Ser Asp
            115                 120                 125
Gly Glu Gly Pro Pro Gly Gly Arg Gly Glu Ala Gln Arg Arg Lys Glu
            130                 135                 140
Arg Glu Glu Leu Ala Gln Gln Tyr Glu Ala Ile Leu Arg Glu Cys Gly
145                 150                 155                 160
His Gly Arg Phe Gln Trp Thr Leu Tyr Phe Val Leu Gly Leu Ala Leu
                165                 170                 175
Met Ala Asp Gly Val Glu Val Phe Val Val Gly Phe Val Leu Pro Ser
            180                 185                 190
Ala Glu Lys Asp Met Cys Leu Ser Asp Ser Asn Lys Gly Met Leu Gly
            195                 200                 205
Leu Ile Val Tyr Leu Gly Met Met Val Gly Ala Phe Leu Trp Gly Gly
            210                 215                 220
Leu Ala Asp Arg Leu Gly Arg Arg Gln Cys Leu Leu Ile Ser Leu Ser
225                 230                 235                 240
Val Asn Ser Val Phe Ala Phe Phe Ser Ser Phe Val Gln Gly Tyr Gly
                245                 250                 255
Thr Phe Leu Phe Cys Arg Leu Leu Ser Gly Val Gly Ile Gly Gly Ser
                260                 265                 270
Ile Pro Ile Val Phe Ser Tyr Phe Ser Glu Phe Leu Ala Gln Glu Lys
            275                 280                 285
Arg Gly Glu His Leu Ser Trp Leu Cys Met Phe Trp Met Ile Gly Gly
            290                 295                 300
Val Tyr Ala Ala Ala Met Ala Trp Ala Ile Ile Pro His Tyr Gly Trp
305                 310                 315                 320
Ser Phe Gln Met Gly Ser Ala Tyr Gln Phe His Ser Trp Arg Val Phe
                325                 330                 335
Val Leu Val Cys Ala Phe Pro Ser Val Phe Ala Ile Gly Ala Leu Thr
                340                 345                 350
Thr Gln Pro Glu Ser Pro Arg Phe Phe Leu Glu Asn Gly Lys His Asp
            355                 360                 365
Glu Ala Trp Met Val Leu Lys Gln Val His Asp Thr Asn Met Arg Ala
            370                 375                 380
Lys Gly His Pro Glu Arg Val Phe Ser Val Thr His Ile Lys Thr Ile
385                 390                 395                 400
His Gln Glu Asp Glu Leu Ile Glu Ile Gln Ser Asp Thr Gly Thr Trp
                405                 410                 415
Tyr Gln Arg Trp Gly Val Arg Ala Leu Ser Leu Gly Gly Gln Val Trp
                420                 425                 430
Gly Asn Phe Leu Ser Cys Phe Gly Pro Glu Tyr Arg Arg Ile Thr Leu
                435                 440                 445
Met Met Met Gly Val Trp Phe Thr Met Ser Phe Ser Tyr Tyr Gly Leu
            450                 455                 460
Thr Val Trp Phe Pro Asp Met Ile Arg His Leu Gln Ala Val Asp Tyr
465                 470                 475                 480
Ala Ser Arg Thr Lys Val Phe Pro Gly Glu Arg Val Gly His Val Thr
                485                 490                 495
Phe Asn Phe Thr Leu Glu Asn Gln Ile His Arg Gly Gly Gln Tyr Phe
                500                 505                 510
```

```
Asn Asp Lys Phe Ile Gly Leu Arg Leu Lys Ser Val Ser Phe Glu Asp
        515                 520                 525
Ser Leu Phe Glu Glu Cys Tyr Phe Glu Asp Val Thr Ser Ser Asn Thr
    530                 535                 540
Phe Phe Arg Asn Cys Thr Phe Ile Asn Thr Val Phe Tyr Asn Thr Asp
545                 550                 555                 560
Leu Phe Glu Tyr Lys Phe Val Asn Ser Arg Leu Ile Asn Ser Thr Phe
                565                 570                 575
Leu His Asn Lys Glu Gly Cys Pro Leu Asp Val Thr Gly Thr Gly Glu
            580                 585                 590
Gly Ala Tyr Met Val Tyr Phe Val Ser Phe Leu Gly Thr Leu Ala Val
        595                 600                 605
Leu Pro Gly Asn Ile Val Ser Ala Leu Leu Met Asp Lys Ile Gly Arg
    610                 615                 620
Leu Arg Met Leu Ala Gly Ser Ser Val Met Ser Cys Val Ser Cys Phe
625                 630                 635                 640
Phe Leu Ser Phe Gly Asn Ser Glu Ser Ala Met Ile Ala Leu Leu Cys
                645                 650                 655
Leu Phe Gly Gly Val Ser Ile Ala Ser Trp Asn Ala Leu Asp Val Leu
            660                 665                 670
Thr Val Glu Leu Tyr Pro Ser Asp Lys Arg Thr Thr Ala Phe Gly Phe
        675                 680                 685
Leu Asn Ala Leu Cys Lys Leu Ala Ala Val Leu Gly Ile Ser Ile Phe
    690                 695                 700
Thr Ser Phe Val Gly Ile Thr Lys Ala Ala Pro Ile Leu Phe Ala Ser
705                 710                 715                 720
Ala Ala Leu Ala Leu Gly Ser Ser Leu Ala Leu Lys Leu Pro Glu Thr
                725                 730                 735
Arg Gly Gln Val Leu Gln
            740

<210> SEQ ID NO 32
<211> LENGTH: 7
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 32

Arg Ile Asp Glu Ala Asn Gln
1               5

<210> SEQ ID NO 33
<211> LENGTH: 8
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 33

Thr Arg Ile Asp Glu Ala Asn Gln
1               5

<210> SEQ ID NO 34
<211> LENGTH: 9
<212> TYPE: PRT
<213> ORGANISM: Artificial Sequence
```

```
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 34

Lys Thr Arg Ile Asp Glu Ala Asn Gln
 1               5

<210> SEQ ID NO 35
<211> LENGTH: 10
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 35

Asn Lys Thr Arg Ile Asp Glu Ala Asn Gln
 1               5                  10

<210> SEQ ID NO 36
<211> LENGTH: 11
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 36

Ser Asn Lys Thr Arg Ile Asp Glu Ala Asn Gln
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 37

Asp Ser Asn Lys Thr Arg Ile Asp Glu Ala Asn Gln
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)
<223> OTHER INFORMATION: carboxylated glutamine

<400> SEQUENCE: 38

Cys Asp Ser Asn Lys Thr Arg Ile Asp Glu Ala Asn Gln
 1               5                  10

<210> SEQ ID NO 39
<211> LENGTH: 7
<212> TYPE: PRT
<213> ORGANISM: Artificial Sequence
<220> FEATURE:
<223> OTHER INFORMATION: SNAP-25 antigen having a free carboxyl-
``` terminus at the P1 residue of the scissile bond of the BoNT/A
cleavage site

<400> SEQUENCE: 39

Arg Ile Asp Glu Ala Asn Lys
1               5

<210> SEQ ID NO 40
<211> LENGTH: 8
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 40

Ala Arg Ile Asp Glu Ala Asn Lys
1               5

<210> SEQ ID NO 41
<211> LENGTH: 9
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 41

Lys Ala Arg Ile Asp Glu Ala Asn Lys
1               5

<210> SEQ ID NO 42
<211> LENGTH: 10
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 42

Asn Lys Ala Arg Ile Asp Glu Ala Asn Lys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 43

Met Asn Lys Ala Arg Ile Asp Glu Ala Asn Lys
1               5                   10

<210> SEQ ID NO 44
<211> LENGTH: 12
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 44

-continued

Asp Met Asn Lys Ala Arg Ile Asp Glu Ala Asn Lys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: SNAP-25 antigen having a free carboxylated
      carboxyl-terminus at the P1 residue of the
      scissile bond of the BoNT/A cleavage site
<221> NAME/KEY: SITE
<222> LOCATION: (13)...(13)
<223> OTHER INFORMATION: Carboxylated lysine

<400> SEQUENCE: 45

Cys Asp Met Asn Lys Ala Arg Ile Asp Glu Ala Asn Lys
1               5                   10

<210> SEQ ID NO 46
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 46

Cys Gly Gly Gly Arg Ile Asp Glu Ala Asn Gln
1               5                   10

<210> SEQ ID NO 47
<211> LENGTH: 11
<212> TYPE: PRT
<213> ORGANISM: Artificial Sequence
<220> FEATURE:
<223> OTHER INFORMATION: SNAP-25 antigen

<400> SEQUENCE: 47

Cys Gly Gly Gly Arg Ile Asp Glu Ala Asn Lys
1               5                   10

<210> SEQ ID NO 48
<211> LENGTH: 88
<212> TYPE: PRT
<213> ORGANISM: Artificial Sequence
<220> FEATURE:
<223> OTHER INFORMATION: BirA-HisTag?-SNAP-25-134-197

<400> SEQUENCE: 48

Met Gly Gly Gly Leu Asn Asp Ile Phe Glu Ala Gln Lys Ile Glu Trp
1               5                   10                  15

His His His His His His His His Ile Arg Arg Val Thr Asn Asp Ala
                20                  25                  30

Arg Glu Asn Glu Met Asp Glu Asn Leu Glu Gln Val Ser Gly Ile Ile
            35                  40                  45

Gly Asn Leu Arg His Met Ala Leu Asp Met Gly Asn Glu Ile Asp Thr
        50                  55                  60

Gln Asn Arg Gln Ile Asp Arg Ile Met Glu Lys Ala Asp Ser Asn Lys
65                  70                  75                  80

Thr Arg Ile Asp Glu Ala Asn Gln
                85

<210> SEQ ID NO 49
<211> LENGTH: 97
<212> TYPE: PRT
<213> ORGANISM: Artificial Sequence
<220> FEATURE:
<223> OTHER INFORMATION: BirA-HisTag?-SNAP-25-134-206

<400> SEQUENCE: 49

```
Met Gly Gly Gly Leu Asn Asp Ile Phe Glu Ala Gln Lys Ile Glu Trp
 1               5                  10                  15

His His His His His His His Ile Arg Arg Val Thr Asn Asp Ala
                20                  25                  30

Arg Glu Asn Glu Met Asp Glu Asn Leu Glu Gln Val Ser Gly Ile Ile
                35                  40                  45

Gly Asn Leu Arg His Met Ala Leu Asp Met Gly Asn Glu Ile Asp Thr
        50                  55                  60

Gln Asn Arg Gln Ile Asp Arg Ile Met Glu Lys Ala Asp Ser Asn Lys
65              70                  75                  80

Thr Arg Ile Asp Glu Ala Asn Gln Arg Ala Thr Lys Met Leu Gly Ser
                85                  90                  95

Gly
```

<210> SEQ ID NO 50
<211> LENGTH: 16
<212> TYPE: PRT
<213> ORGANISM: Artificial Sequence
<220> FEATURE:
<223> OTHER INFORMATION: BirA peptide

<400> SEQUENCE: 50

```
Gly Gly Gly Leu Asn Asp Ile Phe Glu Ala Gln Lys Ile Glu Trp His
 1               5                  10                  15
```

<210> SEQ ID NO 51
<211> LENGTH: 7570
<212> TYPE: DNA
<213> ORGANISM: Artificial Sequence
<220> FEATURE:
<223> OTHER INFORMATION: pQBI-25/GFP-BoNT/A-LC expression construct.

<400> SEQUENCE: 51

| | | | | | |
|---|---|

```
tccgcgggcc accatggagg gcccggttac cggtaccgga tccagatatc tgggcggccg    1020
ctcagcaagc ttcgcgaatt cgggaggcgg aggtggagct agcaaaggag aagaactctt    1080
cactggagtt gtcccaattc ttgttgaatt agatggtgat gttaacggcc acaagttctc    1140
tgtcagtgga gagggtgaag gtgatgcaac atacggaaaa cttaccctga agttcatctg    1200
cactactggc aaactgcctg ttccatggcc aacactagtc actactctgt gctatggtgt    1260
tcaatgcttt tcaagatacc cggatcatat gaaacggcat gacttttca agagtgccat    1320 gcccgaaggt tatgtacagg aaaggaccat cttcttcaaa gatgacggca actacaagac    1380
acgtgctgaa gtcaagtttg aaggtgatac ccttgttaat agaatcgagt taaaaggtat    1440
tgacttcaag gaagatggca acattctggg acacaaattg gaatacaact ataactcaca    1500
caatgtatac atcatggcag acaaacaaaa gaatggaatc aaagtgaact tcaagacccg    1560
ccacaacatt gaagatggaa gcgttcaact agcagaccat tatcaacaaa atactccaat    1620
tggcgatggc cctgtccttt taccagacaa ccattacctg tccacacaat ctgcccttc     1680 gaaagatccc aacgaaaaga gagaccacat ggtccttctt gagtttgtaa cagctgctgg    1740
gattacacat ggcatggatg aactgtacaa catcgatgga gcggaggtg  acctttgt     1800 taataaacaa tttaattata agatcctgt  aaatggtgtt gatattgctt atataaaat     1860 tccaaatgca ggacaaatgc aaccagtaaa agctttaaa  attcataata aaatatgggt    1920
tattccagaa agagatacat ttacaaatcc tgaagaagga gatttaaatc caccaccaga    1980
agcaaaacaa gttccagttt catattatga ttcaacatat ttaagtacag ataatgaaaa    2040
agataattat ttaaagggag ttacaaaatt atttgagaga atttattcaa ctgatcttgg    2100
aagaatgttg ttaacatcaa tagtaagggg aataccattt tggggtggaa gtacaataga    2160
tacagaatta aaagttattg atactaattg tattaatgtg atacaaccag atggtagtta    2220
tagatcagaa gaacttaatc tagtaataat aggaccctca gctgatatta tacagtttga    2280
atgtaaaagc tttggacatg aagttttgaa tcttacgcga aatggttatg gctctactca    2340
atacattaga tttagcccag attttacatt tggttttgag gagtcacttg aagttgatac    2400
aaatcctctt ttaggtgcag gcaaatttgc tacagatcca gcagtaacat tagcacatga    2460
acttatacat gctggacata gattatatgg aatagcaatt aatccaaata gggttttaa     2520 agtaaatact aatgcctatt atgaaatgag tgggttagaa gtaagctttg aggaacttag    2580
aacatttggg ggacatgatg caaagtttat agatagttta caggaaaacg aatttcgtct    2640
atattattat aataagttta agatatagc  aagtacactt aataaagcta atcaatagt     2700 aggtactact gcttcattac agtatatgaa aaatgttttt aaagagaaat atctcctatc    2760
tgaagataca tctggaaaat tttcggtaga taaattaaaa tttgataagt tatacaaat     2820 gttaacagag atttacacag aggataattt tgttaagttt tttaaagtac ttaacagaaa    2880 aacatattg  aattttgata agccgtatt  taagataaat atagtaccta aggtaaatta    2940
cacaatatat gatggattta atttaagaaa tacaaattta gcagcaaact ttaatggtca    3000
aaatacagaa attaataata tgaatttac  taaactaaaa aatttactg  gattgtttga    3060 attttataag ttgctatgtg taagagggat aatcacttcg aaatgaacgc gttggccta     3120 ttctatagtc tcacctaaat gctagagctc gctgatcagc ctcgactgtg ccttctagtt    3180
gccagccatc tgttgtttgc ccctcccccg tgccttcctt gaccctggaa ggtgccactc    3240
ccactgtcct ttcctaataa aatgaggaaa ttgcatcgca ttgtctgagt aggtgtcatt    3300
ctattctggg gggtggggtg gggcaggaca gcaagggga ggattgggaa gacaatagca     3360
```

```
ggcatgctgg ggatgcggtg ggctctatgg cttctgaggc ggaaagaacc agctggggct    3420 ctaggggta tccccacgcg ccctgtagcg gcgcattaag cgcggcgggt gtggtggtta     3480
cgcgcagcgt gaccgctaca cttgccagcg ccctagcgcc cgctcctttc gctttcttcc    3540
cttcctttct cgccacgttc gccggctttc cccgtcaagc tctaaatcgg ggcatccctt    3600
tagggttccg atttagtgct ttacggcacc tcgaccccaa aaacttgat tagggtgatg     3660 gttcacgtag tgggccatcg ccctgataga cggttttttcg ccctttgacg ttggagtcca   3720
cgttctttaa tagtggactc ttgttccaaa ctggaacaac actcaaccct atctcggtct    3780
attcttttga tttataaggg attttgggga tttcggccta ttggttaaaa aatgagctga    3840
tttaacaaaa atttaacgcg aattaattct gtggaatgtg tgtcagttag ggtgtggaaa    3900
gtccccaggc tccccaggca ggcagaagta tgcaaagcat gcatctcaat tagtcagcaa    3960
ccaggtgtgg aaagtcccca ggctcccag caggcagaag tatgcaaagc atgcatctca     4020
attagtcagc aaccatagtc ccgcccctaa ctccgcccat cccgcccta  actccgccca    4080 gttccgccca ttctccgccc catggctgac taatttttttt tatttatgca gaggccgagg   4140
ccgcctctgc ctctgagcta ttccagaagt agtgaggagg ctttttttgga ggcctaggct   4200 tttgcaaaaa gctcccggga gcttgtatat ccattttcgg atctgatcaa gagacaggat    4260
gaggatcgtt tcgcatgatt gaacaagatg gattgcacgc aggttctccg gccgcttggg    4320
tggagaggct attcggctat gactgggcac aacagacaat cggctgctct gatgccgccg    4380
tgttccggct gtcagcgcag gggcgcccgg ttcttttttgt caagaccgac ctgtccggtg    4440
ccctgaatga actgcaggac gaggcagcgc ggctatcgtg gctggccacg acgggcgttc    4500
cttgcgcagc tgtgctcgac gttgtcactg aagcgggaag ggactggctg ctattgggcg    4560
aagtgccggg gcaggatctc ctgtcatctc accttgctcc tgccgagaaa gtatccatca    4620
tggctgatgc aatgcggcgg ctgcatacgc ttgatccggc tacctgccca ttcgaccacc    4680
aagcgaaaca tcgcatcgag cgagcacgta ctcggatgga agccggtctt gtcgatcagg    4740
atgatctgga cgaagagcat caggggctcg cgccagccga actgttcgcc aggctcaagg    4800
cgcgcatgcc cgacggcgag gatctcgtcg tgacccatgg cgatgcctgc ttgccgaata    4860
tcatggtgga aaatggccgc ttttctggat tcatcgactg tggccggctg ggtgtggcgg    4920
accgctatca ggacatagcg ttggctaccc gtgatattgc tgaagagctt ggcggcgaat    4980
gggctgaccg cttcctcgtg ctttacggta tcgccgctcc cgattcgcag cgcatcgcct    5040
tctatcgcct tcttgacgag ttcttctgag cgggactctg gggttcgaaa tgaccgacca    5100
agcgacgccc aacctgccat cacgagattt cgattccacc gccgccttct atgaaaggtt    5160
gggcttcgga atcgttttcc gggacgccgg ctggatgatc ctccagcgcg ggatctcat     5220 gctggagttc ttcgcccacc ccaacttgtt tattgcagct tataatggtt acaaataaag    5280
caatagcatc acaaatttca caaataaagc atttttttca ctgcattcta gttgtggttt    5340
gtccaaactc atcaatgtat cttatcatgt ctgtataccg tcgacctcta gctagagctt    5400
ggcgtaatca tggtcatagc tgtttcctgt gtgaaattgt tatccgctca caattccaca    5460
caacatacga gccggaagca taaagtgtaa agcctggggt gcctaatgag tgagctaact    5520
cacattaatt gcgttgcgct cactgcccgc tttccagtcg ggaaacctgt cgtgccagct    5580
gcattaatga atcggccaac gcgcggggag aggcggtttg cgtattgggc gctcttccgc    5640
ttcctcgctc actgactcgc tgcgctcggt cgttcggctg cggcgagcgg tatcagctca    5700
ctcaaaggcg gtaatacggt tatccacaga atcagggga  taacgcaggaa agaacatgtg   5760
```

```
agcaaaaggc cagcaaaagg ccaggaaccg taaaaaggcc gcgttgctgg cgttttttcca   5820 taggctccgc ccccctgacg agcatcacaa aaatcgacgc tcaagtcaga ggtggcgaaa   5880
cccgacagga ctataaagat accaggcgtt tccccctgga agctccctcg tgcgctctcc   5940
tgttccgacc ctgccgctta ccggatacct gtccgccttt ctcccttcgg aagcgtggc    6000 gctttctcaa tgctcacgct gtaggtatct cagttcggtg taggtcgttc gctccaagct   6060
gggctgtgtg cacgaacccc ccgttcagcc cgaccgctgc gccttatccg gtaactatcg   6120
tcttgagtcc aacccggtaa gacacgactt atcgccactg gcagcagcca ctggtaacag   6180
gattagcaga gcgaggtatg taggcggtgc tacagagttc ttgaagtggt ggcctaacta   6240
cggctacact agaaggacag tatttggtat ctgcgctctg ctgaagccag ttaccttcgg   6300
aaaaagagtt ggtagctctt gatccggcaa acaaaccacc gctggtagcg gtggttttt    6360 tgtttgcaag cagcagatta cgcgcagaaa aaaaggatct caagaagatc ctttgatctt   6420
ttctacgggg tctgacgctc agtggaacga aaactcacgt taagggattt tggtcatgag   6480
attatcaaaa aggatcttca cctagatcct tttaaattaa aaatgaagtt ttaaatcaat   6540
ctaaagtata tatgagtaaa cttggtctga cagttaccaa tgcttaatca gtgaggcacc   6600
tatctcagcg atctgtctat ttcgttcatc catagttgcc tgactccccg tcgtgtagat   6660
aactacgata cgggagggct taccatctgg ccccagtgct gcaatgatac cgcgagaccc   6720
acgctcaccg gctccagatt tatcagcaat aaaccagcca gccggaaggg ccgagcgcag   6780
aagtggtcct gcaactttat ccgcctccat ccagtctatt aattgttgcc gggaagctag   6840
agtaagtagt tcgccagtta atagtttgcg caacgttgtt gccattgcta caggcatcgt   6900
ggtgtcacgc tcgtcgtttg gtatggcttc attcagctcc ggttcccaac gatcaaggcg   6960
agttacatga tcccccatgt tgtgcaaaaa agcggttagc tccttcggtc ctccgatcgt   7020
tgtcagaagt aagttggccg cagtgttatc actcatggtt atggcagcac tgcataattc   7080
tcttactgtc atgccatccg taagatgctt ttctgtgact ggtgagtact caaccaagtc   7140
attctgagaa tagtgtatgc ggcgaccgag ttgctcttgc ccggcgtcaa tacgggataa   7200
taccgcgcca catagcagaa ctttaaaagt gctcatcatt ggaaaacgtt cttcggggcg   7260
aaaactctca aggatcttac cgctgttgag atccagttcg atgtaaccca ctcgtgcacc   7320
caactgatct tcagcatctt ttactttcac cagcgtttct gggtgagcaa aaacaggaag   7380
gcaaaatgcc gcaaaaaagg gaataagggc gacacggaaa tgttgaatac tcatactctt   7440
cctttttcaa tattattgaa gcatttatca gggttattgt ctcatgagcg gatacatatt   7500
tgaatgtatt tagaaaaata acaaataggg gttccgcgc acatttcccc gaaaagtgcc   7560
acctgacgtc                                                          7570
```

<210> SEQ ID NO 52
<211> LENGTH: 682
<212> TYPE: PRT
<213> ORGANISM: Artificial Sequence
<220> FEATURE:
<223> OTHER INFORMATION: GFP-BoNT/A light chain amino acid sequence.

<400> SEQUENCE: 52

Ala Ser Lys Gly Glu Glu Leu Phe Thr Gly Val Val Pro Ile Leu Val
1 5 10 15

Glu Leu Asp Gly Asp Val Asn Gly His Lys Phe Ser Val Ser Gly Glu
20 25 30

Gly Glu Gly Asp Ala Thr Tyr Gly Lys Leu Thr Leu Lys Phe Ile Cys
35 40 45

```
Thr Thr Gly Lys Leu Pro Val Pro Trp Pro Thr Leu Val Thr Thr Leu
        50                  55                  60

Cys Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
                100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly Pro Phe Val Asn Lys Gln Phe Asn Tyr Lys Asp
                245                 250                 255

Pro Val Asn Gly Val Asp Ile Ala Tyr Ile Lys Ile Pro Asn Ala Gly
            260                 265                 270

Gln Met Gln Pro Val Lys Ala Phe Lys Ile His Asn Lys Ile Trp Val
        275                 280                 285

Ile Pro Glu Arg Asp Thr Phe Thr Asn Pro Glu Glu Gly Asp Leu Asn
    290                 295                 300

Pro Pro Pro Glu Ala Lys Gln Val Pro Val Ser Tyr Tyr Asp Ser Thr
305                 310                 315                 320

Tyr Leu Ser Thr Asp Asn Glu Lys Asp Asn Tyr Leu Lys Gly Val Thr
                325                 330                 335

Lys Leu Phe Glu Arg Ile Tyr Ser Thr Asp Leu Gly Arg Met Leu Leu
            340                 345                 350

Thr Ser Ile Val Arg Gly Ile Pro Phe Trp Gly Gly Ser Thr Ile Asp
        355                 360                 365

Thr Glu Leu Lys Val Ile Asp Thr Asn Cys Ile Asn Val Ile Gln Pro
    370                 375                 380

Asp Gly Ser Tyr Arg Ser Glu Glu Leu Asn Leu Val Ile Ile Gly Pro
385                 390                 395                 400

Ser Ala Asp Ile Ile Gln Phe Glu Cys Lys Ser Phe Gly His Glu Val
                405                 410                 415

Leu Asn Leu Thr Arg Asn Gly Tyr Gly Ser Thr Gln Tyr Ile Arg Phe
            420                 425                 430

Ser Pro Asp Phe Thr Phe Gly Phe Glu Glu Ser Leu Glu Val Asp Thr
        435                 440                 445

Asn Pro Leu Leu Gly Ala Gly Lys Phe Ala Thr Asp Pro Ala Val Thr
    450                 455                 460

Leu Ala His Glu Leu Ile His Ala Gly His Arg Leu Tyr Gly Ile Ala
```

```
                    465                 470                 475                 480
Ile Asn Pro Asn Arg Val Phe Lys Val Asn Thr Asn Ala Tyr Tyr Glu
                        485                 490                 495

Met Ser Gly Leu Glu Val Ser Phe Glu Glu Leu Arg Thr Phe Gly Gly
                500                 505                 510

His Asp Ala Lys Phe Ile Asp Ser Leu Gln Glu Asn Glu Phe Arg Leu
                515                 520                 525

Tyr Tyr Tyr Asn Lys Phe Lys Asp Ile Ala Ser Thr Leu Asn Lys Ala
                530                 535                 540

Lys Ser Ile Val Gly Thr Thr Ala Ser Leu Gln Tyr Met Lys Asn Val
545                 550                 555                 560

Phe Lys Glu Lys Tyr Leu Leu Ser Glu Asp Thr Ser Gly Lys Phe Ser
                565                 570                 575

Val Asp Lys Leu Lys Phe Asp Lys Leu Tyr Lys Met Leu Thr Glu Ile
                580                 585                 590

Tyr Thr Glu Asp Asn Phe Val Lys Phe Phe Lys Val Leu Asn Arg Lys
                595                 600                 605

Thr Tyr Leu Asn Phe Asp Lys Ala Val Phe Lys Ile Asn Ile Val Pro
                610                 615                 620

Lys Val Asn Tyr Thr Ile Tyr Asp Gly Phe Asn Leu Arg Asn Thr Asn
625                 630                 635                 640

Leu Ala Ala Asn Phe Asn Gly Gln Asn Thr Glu Ile Asn Asn Met Asn
                645                 650                 655

Phe Thr Lys Leu Lys Asn Phe Thr Gly Leu Phe Glu Phe Tyr Lys Leu
                660                 665                 670

Leu Cys Val Arg Gly Ile Ile Thr Ser Lys
                675                 680

<210> SEQ ID NO 53
<211> LENGTH: 6259
<212> TYPE: DNA
<213> ORGANISM: Artificial Sequence
<220> FEATURE:
<223> OTHER INFORMATION: pQBI-25/GFP expression construct.

<400> SEQUENCE: 53
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcc tcgaggcctg gccattgcat acgttgtatc     240
catatcataa tatgtacatt tatattggct catgtccaac attaccgcca tgttgacatt     300
gattattgac tagttattaa tagtaatcaa ttacggggtc attagttcat agcccatata     360
tggagttccg cgttacataa cttacggtaa atggcccgcc tggctgaccg cccaacgacc     420
cccgcccatt gacgtcaata atgacgtatg ttcccatagt aacgccaata gggactttcc     480
attgacgtca atgggtggag tatttacggt aaactgccca cttggcagta catcaagtgt     540
atcatatgcc aagtacgccc cctattgacg tcaatgacgg taaatggccc gcctggcatt     600
atgcccagta catgacctta tgggactttc ctacttggca gtacatctac gtattagtca     660
tcgctattac catggtgatg cggttttggc agtacatcaa tgggcgtgga tagcggtttg     720
actcacgggg atttccaagt ctccacccca ttgacgtcaa tgggagtttg ttttggcacc     780
aaaatcaacg ggactttcca aaatgtcgta acaactccgc cccattgacg caaatgggcg     840
gtaggcgtgt acggtgggag gtctatataa gcagagctcg tttagtgaac cgtcagatcg     900
```

```
cctggagacg ccatccacgc tgttttgacc tccatagaag acaccgggac cgatccagcc    960
tccgcgggcc accatggagg gcccggttac cggtaccgga tccagatatc tgggcggccg   1020
ctcagcaagc ttcgcgaatt cgggaggcgg aggtggagct agcaaaggag aagaactctt   1080
cactggagtt gtcccaattc ttgttgaatt agatggtgat gttaacggcc acaagttctc   1140
tgtcagtgga gagggtgaag gtgatgcaac atacggaaaa cttaccctga agttcatctg   1200
cactactggc aaactgcctg ttccatggcc aacactagtc actactctgt gctatggtgt   1260
tcaatgcttt tcaagatacc cggatcatat gaaacggcat gactttttca agagtgccat   1320
gcccgaaggt tatgtacagg aaaggaccat cttcttcaaa gatgacggca actacaagac   1380
acgtgctgaa gtcaagtttg aaggtgatac ccttgttaat agaatcgagt taaaaggtat   1440
tgacttcaag gaagatggca acattctggg acacaaattg gaatacaact ataactcaca   1500
caatgtatac atcatggcag acaaacaaaa gaatggaatc aaagtgaact tcaagacccg   1560
ccacaacatt gaagatggaa gcgttcaact agcagaccat tatcaacaaa atactccaat   1620
tggcgatggc cctgtccttt taccagacaa ccattacctg tccacacaat ctgccctttc   1680
gaaagatccc aacgaaaaga gagaccacat ggtccttctt gagtttgtaa cagctgctgg   1740
gattacacat ggcatggatg aactgtacaa catcgatgga ggcggaggtg atgaacgcg    1800 ttggccctat tctatagtgt cacctaaatg ctagagctcg ctgatcagcc tcgactgtgc   1860
cttctagttg ccagccatct gttgtttgcc cctccccgt gccttccttg accctggaag    1920
gtgccactcc cactgtcctt tcctaataaa atgaggaaat tgcatcgcat tgtctgagta   1980
ggtgtcattc tattctgggg ggtggggtgg ggcaggacag caaggggggag gattgggaag   2040 acaatagcag gcatgctggg gatgcggtgg gctctatggc ttctgaggcg aaagaaccca   2100
gctggggctc taggggggtat ccccacgcgc cctgtagcgg cgcattaagc gcggcgggtg   2160
tggtggttac gcgcagcgtg accgctacac ttgccagcgc cctagcgccc gctccttcg    2220 cttctcttccc ttcctttctc gccacgttcg ccggcttttc ccgtcaagct ctaaatcggg   2280
gcatcccttt agggttccga tttagtgctt tacggcacct cgaccccaaa aaacttgatt   2340
agggtgatgg ttcacgtagt gggccatcgc cctgatagac ggttttcgc cctttgacgt    2400 tggagtccac gttctttaat agtggactct tgttccaaac tggaacaaca ctcaacccta   2460
tctcggtcta ttcttttgat ttataaggga ttttggggat ttcggcctat tggttaaaaa   2520
atgagctgat ttaacaaaaa tttaacgcga attaattctg tggaatgtgt gtcagttagg   2580
gtgtggaaag tccccaggct ccccaggcag gcagaagtat gcaaagcatg catctcaatt   2640
agtcagcaac caggtgtgga aagtccccag gctccccagc aggcagaagt atgcaaagca   2700
tgcatctcaa ttagtcagca accatagtcc cgcccctaac tccgcccatc ccgcccctaa   2760
ctccgcccag ttccgcccat tctccgcccc atggctgact aatttttttt atttatgcag   2820
aggccgaggc cgcctctgcc tctgagctat tccagaagta gtgaggaggc ttttttggag   2880
gcctaggctt ttgcaaaaag ctcccgggag cttgtatatc cattttcgga tctgatcaag   2940
agacaggatg aggatcgttt cgcatgattg aacaagatgg attgcacgca ggttctccgg   3000
ccgcttgggt ggagaggcta ttcggctatg actgggcaca acagacaatc ggctgctctg   3060
atgccgccgt gttccggctg tcagcgcagg ggcgcccggt tctttttgtc aagaccgacc   3120
tgtccggtgc cctgaatgaa ctgcaggacg aggcagcgcg gctatcgtgg ctggccacga   3180
cgggcgttcc ttgcgcagct gtgctcgacg ttgtcactga agcgggaagg gactggctgc   3240
tattgggcga agtgccgggg caggatctcc tgtcatctca ccttgctcct gccgagaaag   3300
```

```
tatccatcat ggctgatgca atgcggcggc tgcatacgct tgatccggct acctgcccat   3360
tcgaccacca agcgaaacat cgcatcgagc gagcacgtac tcggatggaa gccggtcttg   3420
tcgatcagga tgatctggac gaagagcatc aggggctcgc gccagccgaa ctgttcgcca   3480
ggctcaaggc gcgcatgccc gacggcgagg atctcgtcgt gacccatggc gatgcctgct   3540
tgccgaatat catggtggaa aatggccgct tttctggatt catcgactgt ggccggctgg   3600
gtgtggcgga ccgctatcag gacatagcgt tggctacccg tgatattgct gaagagcttg   3660
gcggcgaatg ggctgaccgc ttcctcgtgc tttacggtat cgccgctccc gattcgcagc   3720
gcatcgcctt ctatcgcctt cttgacgagt tcttctgagc gggactctgg ggttcgaaat   3780
gaccgaccaa gcgacgccca acctgccatc acgagatttc gattccaccg ccgccttcta   3840
tgaaaggttg ggcttcggaa tcgttttccg ggacgccggc tggatgatcc tccagcgcgg   3900
ggatctcatg ctggagttct tcgcccaccc caacttgttt attgcagctt ataatggtta   3960
caaataaagc aatagcatca caaatttcac aaataaagca ttttttttcac tgcattctag   4020 ttgtggtttg tccaaactca tcaatgtatc ttatcatgtc tgtataccgt cgacctctag   4080
ctagagcttg gcgtaatcat ggtcatagct gtttcctgtg tgaaattgtt atccgctcac   4140
aattccacac aacatacgag ccggaagcat aaagtgtaaa gcctggggtg cctaatgagt   4200
gagctaactc acattaattg cgttgcgctc actgcccgct ttccagtcgg gaaacctgtc   4260
gtgccagctg cattaatgaa tcggccaacg cgcggggaga ggcggtttgc gtattgggcg   4320
ctcttccgct tcctcgctca ctgactcgct gcgctcggtc gttcggctgc ggcgagcggt   4380
atcagctcac tcaaaggcgg taatacggtt atccacagaa tcaggggata acgcaggaaa   4440
gaacatgtga gcaaaaggcc agcaaaaggc caggaaccgt aaaaaggccg cgttgctggc   4500 gttttttccat aggctccgcc cccctgacga gcatcacaaa aatcgacgct caagtcagag   4560
gtggcgaaac ccgacaggac tataaagata ccaggcgttt ccccctggaa gctccctcgt   4620
gcgctctcct gttccgaccc tgccgcttac cggatacctg tccgcctttc tcccttcggg   4680
aagcgtggcg ctttctcaat gctcacgctg taggtatctc agttcggtgt aggtcgttcg   4740
ctccaagctg ggctgtgtgc acgaaccccc cgttcagccc gaccgctgcg ccttatccgg   4800
taactatcgt cttgagtcca acccggtaag cacgacttat cgccactggc agcagccac   4860 tggtaacagg attagcagag cgaggtatgt aggcggtgct acagagttct tgaagtggtg   4920
gcctaactac ggctacacta aaggacagt atttggtatc tgcgctctgc tgaagccagt   4980
taccttcgga aaaagagttg gtagctcttg atccggcaaa caaaccaccg ctggtagcgg   5040
tggttttttt gtttgcaagc agcagattac gcgcagaaaa aaaggatctc aagaagatcc   5100
tttgatcttt tctacggggt ctgacgctca gtggaacgaa aactcacgtt aagggatttt   5160
ggtcatgaga ttatcaaaaa ggatcttcac ctagatcctt ttaaattaaa aatgaagttt   5220
taaatcaatc taaagtatat atgagtaaac ttggtctgac agttaccaat gcttaatcag   5280
tgaggcacct atctcagcga tctgtctatt tcgttcatcc atagttgcct gactccccgt   5340
cgtgtagata actacgatac gggagggctt accatctggc cccagtgctg caatgatacc   5400
gcgagaccca cgctcaccgg ctccagattt atcagcaata aaccagccag ccggaagggc   5460
cgagcgcaga agtggtcctg caactttatc cgcctccatc cagtctatta attgttgccg   5520
ggaagctaga gtaagtagtt cgccagttaa tagtttgcgc aacgttgttg ccattgctac   5580
aggcatcgtg gtgtcacgct cgtcgtttgg tatggcttca ttcagctccg gttcccaacg   5640
atcaaggcga gttacatgat cccccatgtt gtgcaaaaaa gcggttagct ccttcggtcc   5700
```

```
tccgatcgtt gtcagaagta agttggccgc agtgttatca ctcatggtta tggcagcact    5760
gcataattct cttactgtca tgccatccgt aagatgcttt tctgtgactg gtgagtactc    5820
aaccaagtca ttctgagaat agtgtatgcg gcgaccgagt tgctcttgcc cggcgtcaat    5880
acgggataat accgcgccac atagcagaac tttaaaagtg ctcatcattg gaaaacgttc    5940
ttcggggcga aaactctcaa ggatcttacc gctgttgaga tccagttcga tgtaacccac    6000
tcgtgcaccc aactgatctt cagcatcttt tactttcacc agcgtttctg ggtgagcaaa    6060
aacaggaagg caaaatgccg caaaaaaggg aataagggcg acacggaaat gttgaatact    6120
catactcttc cttttcaat attattgaag catttatcag ggttattgtc tcatgagcgg    6180
atacatattt gaatgtattt agaaaaataa acaaataggg gttccgcgca catttccccg    6240
aaaagtgcca cctgacgtc                                                 6259
```

<210> SEQ ID NO 54
<211> LENGTH: 245
<212> TYPE: PRT
<213> ORGANISM: Artificial Sequence
<220> FEATURE:
<223> OTHER INFORMATION: GFP amino acid sequence.

<400> SEQUENCE: 54

```
Ala Ser Lys Gly Glu Glu Leu Phe Thr Gly Val Val Pro Ile Leu Val
  1               5                  10                  15

Glu Leu Asp Gly Asp Val Asn Gly His Lys Phe Ser Val Ser Gly Glu
             20                  25                  30

Gly Glu Gly Asp Ala Thr Tyr Gly Lys Leu Thr Leu Lys Phe Ile Cys
         35                  40                  45

Thr Thr Gly Lys Leu Pro Val Pro Trp Pro Thr Leu Val Thr Thr Leu
     50                  55                  60

Cys Tyr Gly Val Gln Cys Phe Ser Arg Tyr Pro Asp His Met Lys Arg
 65                  70                  75                  80

His Asp Phe Phe Lys Ser Ala Met Pro Glu Gly Tyr Val Gln Glu Arg
                 85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Thr Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Asn Ile Asp
225                 230                 235                 240

Gly Gly Gly Gly Gly
                245
```

-continued

```
<210> SEQ ID NO 55
<211> LENGTH: 4
<212> TYPE: PRT
<213> ORGANISM: Artificial Sequence
<220> FEATURE:
<223> OTHER INFORMATION: G-spacer flexible spacer

<400> SEQUENCE: 55

Gly Gly Gly Gly
  1

<210> SEQ ID NO 56
<211> LENGTH: 5
<212> TYPE: PRT
<213> ORGANISM: Artificial Sequence
<220> FEATURE:
<223> OTHER INFORMATION: G-spacer flexible spacer

<400> SEQUENCE: 56

Gly Gly Gly Gly Ser
  1               5

<210> SEQ ID NO 57
<211> LENGTH: 4
<212> TYPE: PRT
<213> ORGANISM: Artificial Sequence
<220> FEATURE:
<223> OTHER INFORMATION: A-spacer flexible spacer

<400> SEQUENCE: 57

Ala Ala Ala Ala
  1

<210> SEQ ID NO 58
<211> LENGTH: 5
<212> TYPE: PRT
<213> ORGANISM: Artificial Sequence
<220> FEATURE:
<223> OTHER INFORMATION: A-spacer flexible spacer

<400> SEQUENCE: 58

Ala Ala Ala Ala Val
  1               5

<210> SEQ ID NO 59
<211> LENGTH: 821
<212> TYPE: PRT
<213> ORGANISM: Homo sapiens

<400> SEQUENCE: 59

Met Val Ser Trp Gly Arg Phe Ile Cys Leu Val Val Thr Met Ala
  1               5                  10                  15

Thr Leu Ser Leu Ala Arg Pro Ser Phe Ser Leu Val Glu Asp Thr Thr
                 20                  25                  30

Leu Glu Pro Glu Pro Pro Thr Lys Tyr Gln Ile Ser Gln Pro Glu
             35                  40                  45

Val Tyr Val Ala Ala Pro Gly Glu Ser Leu Glu Val Arg Cys Leu Leu
         50                  55                  60

Lys Asp Ala Ala Val Ile Ser Trp Thr Lys Asp Gly Val His Leu Gly
 65                  70                  75                  80

Pro Asn Asn Arg Thr Val Leu Ile Gly Glu Tyr Leu Gln Ile Lys Gly
                 85                  90                  95

Ala Thr Pro Arg Asp Ser Gly Leu Tyr Ala Cys Thr Ala Ser Arg Thr
            100                 105                 110
```

-continued

Val Asp Ser Glu Thr Trp Tyr Phe Met Val Asn Val Thr Asp Ala Ile
            115                 120                 125

Ser Ser Gly Asp Asp Glu Asp Thr Asp Gly Ala Glu Asp Phe Val
130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
                180                 185                 190

Lys Asn Gly Lys Glu Phe Lys Gln Glu His Arg Ile Gly Gly Tyr Lys
                195                 200                 205

Val Arg Asn Gln His Trp Ser Leu Ile Met Glu Ser Val Val Pro Ser
            210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
                260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
            290                 295                 300

Gly Leu Pro Tyr Leu Lys Val Leu Lys Ala Ala Gly Val Asn Thr Thr
305                 310                 315                 320

Asp Lys Glu Ile Glu Val Leu Tyr Ile Arg Asn Val Thr Phe Glu Asp
                325                 330                 335

Ala Gly Glu Tyr Thr Cys Leu Ala Gly Asn Ser Ile Gly Ile Ser Phe
                340                 345                 350

His Ser Ala Trp Leu Thr Val Leu Pro Ala Pro Gly Arg Glu Lys Glu
            355                 360                 365

Ile Thr Ala Ser Pro Asp Tyr Leu Glu Ile Ala Ile Tyr Cys Ile Gly
            370                 375                 380

Val Phe Leu Ile Ala Cys Met Val Val Thr Val Ile Leu Cys Arg Met
385                 390                 395                 400

Lys Asn Thr Thr Lys Lys Pro Asp Phe Ser Ser Gln Pro Ala Val His
                405                 410                 415

Lys Leu Thr Lys Arg Ile Pro Leu Arg Arg Gln Val Thr Val Ser Ala
                420                 425                 430

Glu Ser Ser Ser Ser Met Asn Ser Asn Thr Pro Leu Val Arg Ile Thr
            435                 440                 445

Thr Arg Leu Ser Ser Thr Ala Asp Thr Pro Met Leu Ala Gly Val Ser
            450                 455                 460

Glu Tyr Glu Leu Pro Glu Asp Pro Lys Trp Glu Phe Pro Arg Asp Lys
465                 470                 475                 480

Leu Thr Leu Gly Lys Pro Leu Gly Glu Gly Cys Phe Gly Gln Val Val
                485                 490                 495

Met Ala Glu Ala Val Gly Ile Asp Lys Asp Lys Pro Lys Glu Ala Val
                500                 505                 510

Thr Val Ala Val Lys Met Leu Lys Asp Asp Ala Thr Glu Lys Asp Leu
            515                 520                 525

Ser Asp Leu Val Ser Glu Met Glu Met Met Lys Met Ile Gly Lys His
            530                 535                 540

```
Lys Asn Ile Ile Asn Leu Leu Gly Ala Cys Thr Gln Asp Gly Pro Leu
545                 550                 555                 560

Tyr Val Ile Val Glu Tyr Ala Ser Lys Gly Asn Leu Arg Glu Tyr Leu
                565                 570                 575

Arg Ala Arg Arg Pro Gly Met Glu Tyr Ser Tyr Asp Ile Asn Arg
            580                 585                 590

Val Pro Glu Glu Gln Met Thr Phe Lys Asp Leu Val Ser Cys Thr Tyr
            595                 600                 605

Gln Leu Ala Arg Gly Met Glu Tyr Leu Ala Ser Gln Lys Cys Ile His
            610                 615                 620

Arg Asp Leu Ala Ala Arg Asn Val Leu Val Thr Glu Asn Asn Val Met
625                 630                 635                 640

Lys Ile Ala Asp Phe Gly Leu Ala Arg Asp Ile Asn Asn Ile Asp Tyr
                645                 650                 655

Tyr Lys Lys Thr Thr Asn Gly Arg Leu Pro Val Lys Trp Met Ala Pro
            660                 665                 670

Glu Ala Leu Phe Asp Arg Val Tyr Thr His Gln Ser Asp Val Trp Ser
            675                 680                 685

Phe Gly Val Leu Met Trp Glu Ile Phe Thr Leu Gly Gly Ser Pro Tyr
            690                 695                 700

Pro Gly Ile Pro Val Glu Glu Leu Phe Lys Leu Leu Lys Glu Gly His
705                 710                 715                 720

Arg Met Asp Lys Pro Ala Asn Cys Thr Asn Glu Leu Tyr Met Met Met
                725                 730                 735

Arg Asp Cys Trp His Ala Val Pro Ser Gln Arg Pro Thr Phe Lys Gln
                740                 745                 750

Leu Val Glu Asp Leu Asp Arg Ile Leu Thr Leu Thr Thr Asn Glu Glu
            755                 760                 765

Tyr Leu Asp Leu Ser Gln Pro Leu Glu Gln Tyr Ser Pro Ser Tyr Pro
            770                 775                 780

Asp Thr Arg Ser Ser Cys Ser Ser Gly Asp Asp Ser Val Phe Ser Pro
785                 790                 795                 800

Asp Pro Met Pro Tyr Glu Pro Cys Leu Pro Gln Tyr Pro His Ile Asn
                805                 810                 815

Gly Ser Val Lys Thr
            820

<210> SEQ ID NO 60
<211> LENGTH: 822
<212> TYPE: PRT
<213> ORGANISM: Homo sapiens

<400> SEQUENCE: 60

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
            50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95
```

```
Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Thr Asp Gly Ala Glu Asp Phe Val
        130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
            275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys His Ser Gly Ile Asn Ser Ser
305                 310                 315                 320

Asn Ala Glu Val Leu Ala Leu Phe Asn Val Thr Glu Ala Asp Ala Gly
                325                 330                 335

Glu Tyr Ile Cys Lys Val Ser Asn Tyr Ile Gly Gln Ala Asn Gln Ser
            340                 345                 350

Ala Trp Leu Thr Val Leu Pro Lys Gln Gln Ala Pro Gly Arg Glu Lys
            355                 360                 365

Glu Ile Thr Ala Ser Pro Asp Tyr Leu Glu Ile Ala Ile Tyr Cys Ile
            370                 375                 380

Gly Val Phe Leu Ile Ala Cys Met Val Val Thr Val Ile Leu Cys Arg
385                 390                 395                 400

Met Lys Asn Thr Thr Lys Lys Pro Asp Phe Ser Ser Gln Pro Ala Val
                405                 410                 415

His Lys Leu Thr Lys Arg Ile Pro Leu Arg Arg Gln Val Thr Val Ser
            420                 425                 430

Ala Glu Ser Ser Ser Ser Met Asn Ser Asn Thr Pro Leu Val Arg Ile
            435                 440                 445

Thr Thr Arg Leu Ser Ser Thr Ala Asp Thr Pro Met Leu Ala Gly Val
450                 455                 460

Ser Glu Tyr Glu Leu Pro Glu Asp Pro Lys Trp Glu Phe Pro Arg Asp
465                 470                 475                 480

Lys Leu Thr Leu Gly Lys Pro Leu Gly Glu Gly Cys Phe Gly Gln Val
                485                 490                 495

Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
```

```
                515                 520                 525
Leu Ser Asp Leu Val Ser Glu Met Glu Met Met Lys Met Ile Gly Lys
    530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
        595                 600                 605

Tyr Gln Leu Ala Arg Gly Met Glu Tyr Leu Ala Ser Gln Lys Cys Ile
    610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
        675                 680                 685

Ser Phe Gly Val Leu Met Trp Glu Ile Phe Thr Leu Gly Gly Ser Pro
    690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
        755                 760                 765

Glu Tyr Leu Asp Leu Ser Gln Pro Leu Glu Gln Tyr Ser Pro Ser Tyr
    770                 775                 780

Pro Asp Thr Arg Ser Ser Cys Ser Ser Gly Asp Asp Ser Val Phe Ser
785                 790                 795                 800

Pro Asp Pro Met Pro Tyr Glu Pro Cys Leu Pro Gln Tyr Pro His Ile
                805                 810                 815

Asn Gly Ser Val Lys Thr
            820

<210> SEQ ID NO 61
<211> LENGTH: 769
<212> TYPE: PRT
<213> ORGANISM: Homo sapiens

<400> SEQUENCE: 61

Met Val Ser Trp Gly Arg Phe Ile Cys Leu Val Val Val Thr Met Ala
  1               5                  10                  15

Thr Leu Ser Leu Ala Arg Pro Ser Phe Ser Leu Val Glu Asp Thr Thr
                20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
```

```
                65                  70                  75                  80
            Pro Asn Asn Arg Thr Val Leu Ile Gly Glu Tyr Leu Gln Ile Lys Gly
                            85                  90                  95

Ala Thr Pro Arg Asp Ser Gly Leu Tyr Ala Cys Thr Ala Ser Arg Thr
                        100                 105                 110

Val Asp Ser Glu Thr Trp Tyr Phe Met Val Asn Val Thr Asp Ala Ile
                        115                 120                 125

Ser Ser Gly Asp Asp Glu Asp Thr Asp Gly Ala Glu Asp Phe Val
                    130                 135                 140

Ser Glu Asn Ser Asn Asn Lys Arg Ala Pro Tyr Trp Thr Asn Thr Glu
            145                 150                 155                 160

Lys Met Glu Lys Arg Leu His Ala Val Pro Ala Ala Asn Thr Val Lys
                            165                 170                 175

Phe Arg Cys Pro Ala Gly Gly Asn Pro Met Pro Thr Met Arg Trp Leu
                        180                 185                 190

Lys Asn Gly Lys Glu Phe Lys Gln Glu His Arg Ile Gly Gly Tyr Lys
                        195                 200                 205

Val Arg Asn Gln His Trp Ser Leu Ile Met Glu Ser Val Val Pro Ser
                    210                 215                 220

Asp Lys Gly Asn Tyr Thr Cys Val Val Glu Asn Glu Tyr Gly Ser Ile
            225                 230                 235                 240

Asn His Thr Tyr His Leu Asp Val Val Glu Arg Ser Pro His Arg Pro
                            245                 250                 255

Ile Leu Gln Ala Gly Leu Pro Ala Asn Ala Ser Thr Val Val Gly Gly
                        260                 265                 270

Asp Val Glu Phe Val Cys Lys Val Tyr Ser Asp Ala Gln Pro His Ile
                        275                 280                 285

Gln Trp Ile Lys His Val Glu Lys Asn Gly Ser Lys Tyr Gly Pro Asp
                    290                 295                 300

Gly Leu Pro Tyr Leu Lys Val Leu Lys His Ser Gly Ile Asn Ser Ser
            305                 310                 315                 320

Asn Ala Glu Val Leu Ala Leu Phe Asn Val Thr Glu Ala Asp Ala Gly
                            325                 330                 335

Glu Tyr Ile Cys Lys Val Ser Asn Tyr Ile Gly Gln Ala Asn Gln Ser
                        340                 345                 350

Ala Trp Leu Thr Val Leu Pro Lys Gln Gln Ala Pro Gly Arg Glu Lys
                        355                 360                 365

Glu Ile Thr Ala Ser Pro Asp Tyr Leu Glu Ile Ala Ile Tyr Cys Ile
                    370                 375                 380

Gly Val Phe Leu Ile Ala Cys Met Val Val Thr Val Ile Leu Cys Arg
            385                 390                 395                 400

Met Lys Asn Thr Thr Lys Lys Pro Asp Phe Ser Ser Gln Pro Ala Val
                            405                 410                 415

His Lys Leu Thr Lys Arg Ile Pro Leu Arg Arg Gln Val Thr Val Ser
                        420                 425                 430

Ala Glu Ser Ser Ser Ser Met Asn Ser Asn Thr Pro Leu Val Arg Ile
                        435                 440                 445

Thr Thr Arg Leu Ser Ser Thr Ala Asp Thr Pro Met Leu Ala Gly Val
                    450                 455                 460

Ser Glu Tyr Glu Leu Pro Glu Asp Pro Lys Trp Glu Phe Pro Arg Asp
            465                 470                 475                 480

Lys Leu Thr Leu Gly Lys Pro Leu Gly Glu Gly Cys Phe Gly Gln Val
                            485                 490                 495
```

```
Val Met Ala Glu Ala Val Gly Ile Asp Lys Asp Lys Pro Lys Glu Ala
            500                 505                 510

Val Thr Val Ala Val Lys Met Leu Lys Asp Asp Ala Thr Glu Lys Asp
            515                 520                 525

Leu Ser Asp Leu Val Ser Glu Met Glu Met Met Lys Met Ile Gly Lys
            530                 535                 540

His Lys Asn Ile Ile Asn Leu Leu Gly Ala Cys Thr Gln Asp Gly Pro
545                 550                 555                 560

Leu Tyr Val Ile Val Glu Tyr Ala Ser Lys Gly Asn Leu Arg Glu Tyr
                565                 570                 575

Leu Arg Ala Arg Arg Pro Pro Gly Met Glu Tyr Ser Tyr Asp Ile Asn
            580                 585                 590

Arg Val Pro Glu Glu Gln Met Thr Phe Lys Asp Leu Val Ser Cys Thr
            595                 600                 605

Tyr Gln Leu Ala Arg Gly Met Glu Tyr Leu Ala Ser Gln Lys Cys Ile
            610                 615                 620

His Arg Asp Leu Ala Ala Arg Asn Val Leu Val Thr Glu Asn Asn Val
625                 630                 635                 640

Met Lys Ile Ala Asp Phe Gly Leu Ala Arg Asp Ile Asn Asn Ile Asp
                645                 650                 655

Tyr Tyr Lys Lys Thr Thr Asn Gly Arg Leu Pro Val Lys Trp Met Ala
            660                 665                 670

Pro Glu Ala Leu Phe Asp Arg Val Tyr Thr His Gln Ser Asp Val Trp
            675                 680                 685

Ser Phe Gly Val Leu Met Trp Glu Ile Phe Thr Leu Gly Gly Ser Pro
690                 695                 700

Tyr Pro Gly Ile Pro Val Glu Glu Leu Phe Lys Leu Leu Lys Glu Gly
705                 710                 715                 720

His Arg Met Asp Lys Pro Ala Asn Cys Thr Asn Glu Leu Tyr Met Met
                725                 730                 735

Met Arg Asp Cys Trp His Ala Val Pro Ser Gln Arg Pro Thr Phe Lys
            740                 745                 750

Gln Leu Val Glu Asp Leu Asp Arg Ile Leu Thr Leu Thr Thr Asn Glu
            755                 760                 765

Ile

<210> SEQ ID NO 62
<211> LENGTH: 709
<212> TYPE: PRT
<213> ORGANISM: Homo sapiens

<400> SEQUENCE: 62

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
        50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
```

-continued

```
                100                 105                 110
Val Asp Ser Glu Thr Trp Tyr Phe Met Val Asn Val Thr Asp Ala Ile
            115                 120                 125
Ser Ser Gly Asp Asp Glu Asp Thr Asp Gly Ala Glu Asp Phe Val
            130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
                180                 185                 190
Lys Asn Gly Lys Glu Phe Lys Gln Glu His Arg Ile Gly Gly Tyr Lys
                195                 200                 205
Val Arg Asn Gln His Trp Ser Leu Ile Met Glu Ser Val Val Pro Ser
            210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Ala Pro Gly Arg Glu Lys Glu
                245                 250                 255
Ile Thr Ala Ser Pro Asp Tyr Leu Glu Ile Ala Ile Tyr Cys Ile Gly
                260                 265                 270
Val Phe Leu Ile Ala Cys Met Val Val Thr Val Ile Leu Cys Arg Met
            275                 280                 285
Lys Asn Thr Thr Lys Lys Pro Asp Phe Ser Ser Gln Pro Ala Val His
            290                 295                 300
Lys Leu Thr Lys Arg Ile Pro Leu Arg Arg Gln Val Thr Val Ser Ala
305                 310                 315                 320
Glu Ser Ser Ser Ser Met Asn Ser Asn Thr Pro Leu Val Arg Ile Thr
                325                 330                 335
Thr Arg Leu Ser Ser Thr Ala Asp Thr Pro Met Leu Ala Gly Val Ser
                340                 345                 350
Glu Tyr Glu Leu Pro Glu Asp Pro Lys Trp Glu Phe Pro Arg Asp Lys
            355                 360                 365
Leu Thr Leu Gly Lys Pro Leu Gly Glu Gly Cys Phe Gly Gln Val Val
            370                 375                 380
Met Ala Glu Ala Val Gly Ile Asp Lys Asp Lys Pro Lys Glu Ala Val
385                 390                 395                 400
Thr Val Ala Val Lys Met Leu Lys Asp Asp Ala Thr Glu Lys Asp Leu
                405                 410                 415
Ser Asp Leu Val Ser Glu Met Glu Met Met Lys Met Ile Gly Lys His
                420                 425                 430
Lys Asn Ile Ile Asn Leu Leu Gly Ala Cys Thr Gln Asp Gly Pro Leu
            435                 440                 445
Tyr Val Ile Val Glu Tyr Ala Ser Lys Gly Asn Leu Arg Glu Tyr Leu
            450                 455                 460
Arg Ala Arg Arg Pro Pro Gly Met Glu Tyr Ser Tyr Asp Ile Asn Arg
465                 470                 475                 480
Val Pro Glu Glu Gln Met Thr Phe Lys Asp Leu Val Ser Cys Thr Tyr
                485                 490                 495
Gln Leu Ala Arg Gly Met Glu Tyr Leu Ala Ser Gln Lys Cys Ile His
                500                 505                 510
Arg Asp Leu Ala Ala Arg Asn Val Leu Val Thr Glu Asn Asn Val Met
            515                 520                 525
```

```
Lys Ile Ala Asp Phe Gly Leu Ala Arg Asp Ile Asn Asn Ile Asp Tyr
    530                 535                 540

Tyr Lys Lys Thr Thr Asn Gly Arg Leu Pro Val Lys Trp Met Ala Pro
545                 550                 555                 560

Glu Ala Leu Phe Asp Arg Val Tyr Thr His Gln Ser Asp Val Trp Ser
                565                 570                 575

Phe Gly Val Leu Met Trp Glu Ile Phe Thr Leu Gly Gly Ser Pro Tyr
            580                 585                 590

Pro Gly Ile Pro Val Glu Glu Leu Phe Lys Leu Leu Lys Glu Gly His
        595                 600                 605

Arg Met Asp Lys Pro Ala Asn Cys Thr Asn Glu Leu Tyr Met Met Met
    610                 615                 620

Arg Asp Cys Trp His Ala Val Pro Ser Gln Arg Pro Thr Phe Lys Gln
625                 630                 635                 640

Leu Val Glu Asp Leu Asp Arg Ile Leu Thr Leu Thr Thr Asn Glu Glu
                645                 650                 655

Tyr Leu Asp Leu Ser Gln Pro Leu Glu Gln Tyr Ser Pro Ser Tyr Pro
            660                 665                 670

Asp Thr Arg Ser Ser Cys Ser Ser Gly Asp Asp Ser Val Phe Ser Pro
        675                 680                 685

Asp Pro Met Pro Tyr Glu Pro Cys Leu Pro Gln Tyr Pro His Ile Asn
    690                 695                 700

Gly Ser Val Lys Thr
705

<210> SEQ ID NO 63
<211> LENGTH: 707
<212> TYPE: PRT
<213> ORGANISM: Homo sapiens

<400> SEQUENCE: 63

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Asp Thr
        35                  40                  45

Asp Gly Ala Glu Asp Phe Val Ser Glu Asn Ser Asn Asn Lys Arg Ala
    50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140

Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190
```

-continued

```
Ser Asp Ala Gln Pro His Ile Gln Trp Ile Lys His Val Glu Lys Asn
    195                 200                 205
Gly Ser Lys Tyr Gly Pro Asp Gly Leu Pro Tyr Leu Lys Val Leu Lys
210                 215                 220
Ala Ala Gly Val Asn Thr Thr Asp Lys Glu Ile Glu Val Leu Tyr Ile
225                 230                 235                 240
Arg Asn Val Thr Phe Glu Asp Ala Gly Glu Tyr Thr Cys Leu Ala Gly
                245                 250                 255
Asn Ser Ile Gly Ile Ser Phe His Ser Ala Trp Leu Thr Val Leu Pro
            260                 265                 270
Ala Pro Gly Arg Glu Lys Glu Ile Thr Ala Ser Pro Asp Tyr Leu Glu
        275                 280                 285
Ile Ala Ile Tyr Cys Ile Gly Val Phe Leu Ile Ala Cys Met Val Val
    290                 295                 300
Thr Val Ile Leu Cys Arg Met Lys Asn Thr Thr Lys Lys Pro Asp Phe
305                 310                 315                 320
Ser Ser Gln Pro Ala Val His Lys Leu Thr Lys Arg Ile Pro Leu Arg
                325                 330                 335
Arg Gln Val Thr Val Ser Ala Glu Ser Ser Ser Ser Met Asn Ser Asn
            340                 345                 350
Thr Pro Leu Val Arg Ile Thr Thr Arg Leu Ser Ser Thr Ala Asp Thr
        355                 360                 365
Pro Met Leu Ala Gly Val Ser Glu Tyr Glu Leu Pro Glu Asp Pro Lys
    370                 375                 380
Trp Glu Phe Pro Arg Asp Lys Leu Thr Leu Gly Lys Pro Leu Gly Glu
385                 390                 395                 400
Gly Cys Phe Gly Gln Val Val Met Ala Glu Ala Val Gly Ile Asp Lys
                405                 410                 415
Asp Lys Pro Lys Glu Ala Val Thr Val Ala Val Lys Met Leu Lys Asp
            420                 425                 430
Asp Ala Thr Glu Lys Asp Leu Ser Asp Leu Val Ser Glu Met Glu Met
        435                 440                 445
Met Lys Met Ile Gly Lys His Lys Asn Ile Ile Asn Leu Leu Gly Ala
    450                 455                 460
Cys Thr Gln Asp Gly Pro Leu Tyr Val Ile Val Glu Tyr Ala Ser Lys
465                 470                 475                 480
Gly Asn Leu Arg Glu Tyr Leu Arg Ala Arg Arg Pro Pro Gly Met Glu
                485                 490                 495
Tyr Ser Tyr Asp Ile Asn Arg Val Pro Glu Glu Gln Met Thr Phe Lys
            500                 505                 510
Asp Leu Val Ser Cys Thr Tyr Gln Leu Ala Arg Gly Met Glu Tyr Leu
        515                 520                 525
Ala Ser Gln Lys Cys Ile His Arg Asp Leu Ala Ala Arg Asn Val Leu
    530                 535                 540
Val Thr Glu Asn Asn Val Met Lys Ile Ala Asp Phe Gly Leu Ala Arg
545                 550                 555                 560
Asp Ile Asn Asn Ile Asp Tyr Tyr Lys Lys Thr Thr Asn Gly Arg Leu
                565                 570                 575
Pro Val Lys Trp Met Ala Pro Glu Ala Leu Phe Asp Arg Val Tyr Thr
            580                 585                 590
His Gln Ser Asp Val Trp Ser Phe Gly Val Leu Met Trp Glu Ile Phe
        595                 600                 605
Thr Leu Gly Gly Ser Pro Tyr Pro Gly Ile Pro Val Glu Glu Leu Phe
    610                 615                 620
```

```
Lys Leu Leu Lys Glu Gly His Arg Met Asp Lys Pro Ala Asn Cys Thr
625                 630                 635                 640

Asn Glu Leu Tyr Met Met Arg Asp Cys Trp His Ala Val Pro Ser
            645                 650                 655

Gln Arg Pro Thr Phe Lys Gln Leu Val Glu Asp Leu Asp Arg Ile Leu
                660                 665                 670

Thr Leu Thr Thr Asn Glu Glu Glu Lys Lys Val Ser Gly Ala Val Asp
            675                 680                 685

Cys His Lys Pro Pro Cys Asn Pro Ser His Leu Pro Cys Val Leu Ala
690                 695                 700

Val Asp Gln
705

<210> SEQ ID NO 64
<211> LENGTH: 706
<212> TYPE: PRT
<213> ORGANISM: Homo sapiens

<400> SEQUENCE: 64

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Gly Ala Pro Tyr Trp Thr Asn Thr Glu Lys Met Glu
        35                  40                  45

Lys Arg Leu His Ala Val Pro Ala Ala Asn Thr Val Lys Phe Arg Cys
50                  55                  60

Pro Ala Gly Gly Asn Pro Met Pro Thr Met Arg Trp Leu Lys Asn Gly
65                  70                  75                  80

Lys Glu Phe Lys Gln Glu His Arg Ile Gly Gly Tyr Lys Val Arg Asn
                85                  90                  95

Gln His Trp Ser Leu Ile Met Glu Ser Val Val Pro Ser Asp Lys Gly
            100                 105                 110

Asn Tyr Thr Cys Val Val Glu Asn Glu Tyr Gly Ser Ile Asn His Thr
        115                 120                 125

Tyr His Leu Asp Val Val Glu Arg Ser Pro His Arg Pro Ile Leu Gln
    130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
            180                 185                 190

Tyr Leu Lys Val Leu Lys Ala Ala Gly Val Asn Thr Thr Asp Lys Glu
        195                 200                 205

Ile Glu Val Leu Tyr Ile Arg Asn Val Thr Phe Glu Asp Ala Gly Glu
    210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
            260                 265                 270

Ile Ala Cys Met Val Val Thr Val Ile Leu Cys Arg Met Lys Asn Thr
        275                 280                 285
```

```
Thr Lys Lys Pro Asp Phe Ser Ser Gln Pro Ala Val His Lys Leu Thr
    290                 295                 300

Lys Arg Ile Pro Leu Arg Arg Gln Val Thr Val Ser Ala Glu Ser Ser
305                 310                 315                 320

Ser Ser Met Asn Ser Asn Thr Pro Leu Val Arg Ile Thr Thr Arg Leu
                325                 330                 335

Ser Ser Thr Ala Asp Thr Pro Met Leu Ala Gly Val Ser Glu Tyr Glu
            340                 345                 350

Leu Pro Glu Asp Pro Lys Trp Glu Phe Pro Arg Asp Lys Leu Thr Leu
            355                 360                 365

Gly Lys Pro Leu Gly Glu Gly Cys Phe Gly Gln Val Val Met Ala Glu
    370                 375                 380

Ala Val Gly Ile Asp Lys Asp Lys Pro Lys Glu Ala Val Thr Val Ala
385                 390                 395                 400

Val Lys Met Leu Lys Asp Asp Ala Thr Glu Lys Asp Leu Ser Asp Leu
                405                 410                 415

Val Ser Glu Met Glu Met Met Lys Met Ile Gly Lys His Lys Asn Ile
            420                 425                 430

Ile Asn Leu Leu Gly Ala Cys Thr Gln Asp Gly Pro Leu Tyr Val Ile
    435                 440                 445

Val Glu Tyr Ala Ser Lys Gly Asn Leu Arg Glu Tyr Leu Arg Ala Arg
450                 455                 460

Arg Pro Pro Gly Met Glu Tyr Ser Tyr Asp Ile Asn Arg Val Pro Glu
465                 470                 475                 480

Glu Gln Met Thr Phe Lys Asp Leu Val Ser Cys Thr Tyr Gln Leu Ala
                485                 490                 495

Arg Gly Met Glu Tyr Leu Ala Ser Gln Lys Cys Ile His Arg Asp Leu
            500                 505                 510

Ala Ala Arg Asn Val Leu Val Thr Glu Asn Asn Val Met Lys Ile Ala
            515                 520                 525

Asp Phe Gly Leu Ala Arg Asp Ile Asn Asn Ile Asp Tyr Tyr Lys Lys
    530                 535                 540

Thr Thr Asn Gly Arg Leu Pro Val Lys Trp Met Ala Pro Glu Ala Leu
545                 550                 555                 560

Phe Asp Arg Val Tyr Thr His Gln Ser Asp Val Trp Ser Phe Gly Val
                565                 570                 575

Leu Met Trp Glu Ile Phe Thr Leu Gly Gly Ser Pro Tyr Pro Gly Ile
            580                 585                 590

Pro Val Glu Glu Leu Phe Lys Leu Leu Lys Glu Gly His Arg Met Asp
            595                 600                 605

Lys Pro Ala Asn Cys Thr Asn Glu Leu Tyr Met Met Met Arg Asp Cys
    610                 615                 620

Trp His Ala Val Pro Ser Gln Arg Pro Thr Phe Lys Gln Leu Val Glu
625                 630                 635                 640

Asp Leu Asp Arg Ile Leu Thr Leu Thr Thr Asn Glu Glu Tyr Leu Asp
                645                 650                 655

Leu Ser Gln Pro Leu Glu Gln Tyr Ser Pro Ser Tyr Pro Asp Thr Arg
            660                 665                 670

Ser Ser Cys Ser Ser Gly Asp Asp Ser Val Phe Ser Pro Asp Pro Met
            675                 680                 685

Pro Tyr Glu Pro Cys Leu Pro Gln Tyr Pro His Ile Asn Gly Ser Val
    690                 695                 700

Lys Thr
```

-continued

705

<210> SEQ ID NO 65
<211> LENGTH: 705
<212> TYPE: PRT
<213> ORGANISM: Homo sapiens

<400> SEQUENCE: 65

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Ser Ala Glu Ser Ser Ser
305                 310                 315                 320

Ser Met Asn Ser Asn Thr Pro Leu Val Arg Ile Thr Thr Arg Leu Ser
                325                 330                 335

Ser Thr Ala Asp Thr Pro Met Leu Ala Gly Val Ser Glu Tyr Glu Leu
            340                 345                 350

Pro Glu Asp Pro Lys Trp Glu Phe Pro Arg Asp Lys Leu Thr Leu Gly
        355                 360                 365

Lys Pro Leu Gly Glu Gly Cys Phe Gly Gln Val Val Met Ala Glu Ala

```
                    370                 375                 380
Val Gly Ile Asp Lys Asp Lys Pro Lys Glu Ala Val Thr Val Ala Val
385                 390                 395                 400

Lys Met Leu Lys Asp Asp Ala Thr Glu Lys Asp Leu Ser Asp Leu Val
                    405                 410                 415

Ser Glu Met Glu Met Met Lys Met Ile Gly Lys His Lys Asn Ile Ile
                    420                 425                 430

Asn Leu Leu Gly Ala Cys Thr Gln Asp Gly Pro Leu Tyr Val Ile Val
                    435                 440                 445

Glu Tyr Ala Ser Lys Gly Asn Leu Arg Glu Tyr Leu Arg Ala Arg Arg
                    450                 455                 460

Pro Pro Gly Met Glu Tyr Ser Tyr Asp Ile Asn Arg Val Pro Glu Glu
465                 470                 475                 480

Gln Met Thr Phe Lys Asp Leu Val Ser Cys Thr Tyr Gln Leu Ala Arg
                    485                 490                 495

Gly Met Glu Tyr Leu Ala Ser Gln Lys Cys Ile His Arg Asp Leu Ala
                    500                 505                 510

Ala Arg Asn Val Leu Val Thr Glu Asn Asn Val Met Lys Ile Ala Asp
                    515                 520                 525

Phe Gly Leu Ala Arg Asp Ile Asn Asn Ile Asp Tyr Tyr Lys Lys Thr
530                 535                 540

Thr Asn Gly Arg Leu Pro Val Lys Trp Met Ala Pro Glu Ala Leu Phe
545                 550                 555                 560

Asp Arg Val Tyr Thr His Gln Ser Asp Val Trp Ser Phe Gly Val Leu
                    565                 570                 575

Met Trp Glu Ile Phe Thr Leu Gly Gly Ser Pro Tyr Pro Gly Ile Pro
                    580                 585                 590

Val Glu Glu Leu Phe Lys Leu Leu Lys Glu Gly His Arg Met Asp Lys
                    595                 600                 605

Pro Ala Asn Cys Thr Asn Glu Leu Tyr Met Met Met Arg Asp Cys Trp
                    610                 615                 620

His Ala Val Pro Ser Gln Arg Pro Thr Phe Lys Gln Leu Val Glu Asp
625                 630                 635                 640

Leu Asp Arg Ile Leu Thr Leu Thr Thr Asn Glu Glu Tyr Leu Asp Leu
                    645                 650                 655

Ser Gln Pro Leu Glu Gln Tyr Ser Pro Ser Tyr Pro Asp Thr Arg Ser
                    660                 665                 670

Ser Cys Ser Ser Gly Asp Asp Ser Val Phe Ser Pro Asp Pro Met Pro
                    675                 680                 685

Tyr Glu Pro Cys Leu Pro Gln Tyr Pro His Ile Asn Gly Ser Val Lys
                    690                 695                 700

Thr
705

<210> SEQ ID NO 66
<211> LENGTH: 704
<212> TYPE: PRT
<213> ORGANISM: Homo sapiens

<400> SEQUENCE: 66

Met Val Ser Trp Gly Arg Phe Ile Cys Leu Val Val Val Thr Met Ala
1               5                   10                  15

Thr Leu Ser Leu Ala Arg Pro Ser Phe Ser Leu Val Glu Asp Thr Thr
                    20                  25                  30

Leu Glu Pro Glu Gly Ala Pro Tyr Trp Thr Asn Thr Glu Lys Met Glu
```

```
              35                  40                  45
Lys Arg Leu His Ala Val Pro Ala Ala Asn Thr Val Lys Phe Arg Cys
 50                  55                  60

Pro Ala Gly Gly Asn Pro Met Pro Thr Met Arg Trp Leu Lys Asn Gly
 65                  70                  75                  80

Lys Glu Phe Lys Gln Glu His Arg Ile Gly Gly Tyr Lys Val Arg Asn
                 85                  90                  95

Gln His Trp Ser Leu Ile Met Glu Ser Val Val Pro Ser Asp Lys Gly
                100                 105                 110

Asn Tyr Thr Cys Val Val Glu Asn Glu Tyr Gly Ser Ile Asn His Thr
                115                 120                 125

Tyr His Leu Asp Val Val Glu Arg Ser Pro His Arg Pro Ile Leu Gln
130                 135                 140

Ala Gly Leu Pro Ala Asn Ala Ser Thr Val Val Gly Gly Asp Val Glu
145                 150                 155                 160

Phe Val Cys Lys Val Tyr Ser Asp Ala Gln Pro His Ile Gln Trp Ile
                165                 170                 175

Lys His Val Glu Lys Asn Gly Ser Lys Tyr Gly Pro Asp Gly Leu Pro
                180                 185                 190

Tyr Leu Lys Val Leu Lys Ala Ala Gly Val Asn Thr Thr Asp Lys Glu
                195                 200                 205

Ile Glu Val Leu Tyr Ile Arg Asn Val Thr Phe Glu Asp Ala Gly Glu
                210                 215                 220

Tyr Thr Cys Leu Ala Gly Asn Ser Ile Gly Ile Ser Phe His Ser Ala
225                 230                 235                 240

Trp Leu Thr Val Leu Pro Ala Pro Gly Arg Glu Lys Glu Ile Thr Ala
                245                 250                 255

Ser Pro Asp Tyr Leu Glu Ile Ala Ile Tyr Cys Ile Gly Val Phe Leu
                260                 265                 270

Ile Ala Cys Met Val Val Thr Val Ile Leu Cys Arg Met Lys Asn Thr
                275                 280                 285

Thr Lys Lys Pro Asp Phe Ser Ser Gln Pro Ala Val His Lys Leu Thr
                290                 295                 300

Lys Arg Ile Pro Leu Arg Arg Gln Val Ser Ala Glu Ser Ser Ser Ser
305                 310                 315                 320

Met Asn Ser Asn Thr Pro Leu Val Arg Ile Thr Thr Arg Leu Ser Ser
                325                 330                 335

Thr Ala Asp Thr Pro Met Leu Ala Gly Val Ser Glu Tyr Glu Leu Pro
                340                 345                 350

Glu Asp Pro Lys Trp Glu Phe Pro Arg Asp Lys Leu Thr Leu Gly Lys
                355                 360                 365

Pro Leu Gly Glu Gly Cys Phe Gly Gln Val Val Met Ala Glu Ala Val
370                 375                 380

Gly Ile Asp Lys Asp Lys Pro Lys Glu Ala Val Thr Val Ala Val Lys
385                 390                 395                 400

Met Leu Lys Asp Asp Ala Thr Glu Lys Asp Leu Ser Asp Leu Val Ser
                405                 410                 415

Glu Met Glu Met Met Lys Met Ile Gly Lys His Lys Asn Ile Ile Asn
                420                 425                 430

Leu Leu Gly Ala Cys Thr Gln Asp Gly Pro Leu Tyr Val Ile Val Glu
                435                 440                 445

Tyr Ala Ser Lys Gly Asn Leu Arg Glu Tyr Leu Arg Ala Arg Arg Pro
450                 455                 460
```

```
Pro Gly Met Glu Tyr Ser Tyr Asp Ile Asn Arg Val Pro Glu Glu Gln
465                 470                 475                 480

Met Thr Phe Lys Asp Leu Val Ser Cys Thr Tyr Gln Leu Ala Arg Gly
            485                 490                 495

Met Glu Tyr Leu Ala Ser Gln Lys Cys Ile His Arg Asp Leu Ala Ala
        500                 505                 510

Arg Asn Val Leu Val Thr Glu Asn Val Met Lys Ile Ala Asp Phe
    515                 520                 525

Gly Leu Ala Arg Asp Ile Asn Asn Ile Asp Tyr Tyr Lys Lys Thr Thr
        530                 535                 540

Asn Gly Arg Leu Pro Val Lys Trp Met Ala Pro Glu Ala Leu Phe Asp
545                 550                 555                 560

Arg Val Tyr Thr His Gln Ser Asp Val Trp Ser Phe Gly Val Leu Met
                565                 570                 575

Trp Glu Ile Phe Thr Leu Gly Gly Ser Pro Tyr Pro Gly Ile Pro Val
            580                 585                 590

Glu Glu Leu Phe Lys Leu Leu Lys Glu Gly His Arg Met Asp Lys Pro
        595                 600                 605

Ala Asn Cys Thr Asn Glu Leu Tyr Met Met Met Arg Asp Cys Trp His
610                 615                 620

Ala Val Pro Ser Gln Arg Pro Thr Phe Lys Gln Leu Val Glu Asp Leu
625                 630                 635                 640

Asp Arg Ile Leu Thr Leu Thr Thr Asn Glu Glu Tyr Leu Asp Leu Ser
                645                 650                 655

Gln Pro Leu Glu Gln Tyr Ser Pro Ser Tyr Pro Asp Thr Arg Ser Ser
            660                 665                 670

Cys Ser Ser Gly Asp Asp Ser Val Phe Ser Pro Asp Pro Met Pro Tyr
        675                 680                 685

Glu Pro Cys Leu Pro Gln Tyr Pro His Ile Asn Gly Ser Val Lys Thr
690                 695                 700

<210> SEQ ID NO 67
<211> LENGTH: 680
<212> TYPE: PRT
<213> ORGANISM: Homo sapiens

<400> SEQUENCE: 67

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Asp Ala Ile Ser Ser Gly Asp Asp Glu Asp Thr
        35                  40                  45

Asp Gly Ala Glu Asp Phe Val Ser Glu Asn Ser Asn Asn Lys Arg Ala
50                  55                  60

Pro Tyr Trp Thr Asn Thr Glu Lys Met Glu Lys Arg Leu His Ala Val
65                  70                  75                  80

Pro Ala Ala Asn Thr Val Lys Phe Arg Cys Pro Ala Gly Gly Asn Pro
                85                  90                  95

Met Pro Thr Met Arg Trp Leu Lys Asn Gly Lys Glu Phe Lys Gln Glu
            100                 105                 110

His Arg Ile Gly Gly Tyr Lys Val Arg Asn Gln His Trp Ser Leu Ile
        115                 120                 125

Met Glu Ser Val Val Pro Ser Asp Lys Gly Asn Tyr Thr Cys Val Val
    130                 135                 140
```

```
Glu Asn Glu Tyr Gly Ser Ile Asn His Thr Tyr His Leu Asp Val Val
145                 150                 155                 160

Glu Arg Ser Pro His Arg Pro Ile Leu Gln Ala Gly Leu Pro Ala Asn
                165                 170                 175

Ala Ser Thr Val Val Gly Gly Asp Val Glu Phe Val Cys Lys Val Tyr
            180                 185                 190

Ser Asp Ala Gln Pro His Ile Gln Trp Ile Lys His Val Glu Lys Asn
        195                 200                 205

Gly Ser Lys Tyr Gly Pro Asp Gly Leu Pro Tyr Leu Lys Val Leu Lys
    210                 215                 220

His Ser Gly Ile Asn Ser Asn Ala Glu Val Leu Ala Leu Phe Asn
225                 230                 235                 240

Val Thr Glu Ala Asp Ala Gly Glu Tyr Ile Cys Lys Val Ser Asn Tyr
                245                 250                 255

Ile Gly Gln Ala Asn Gln Ser Ala Trp Leu Thr Val Leu Pro Lys Gln
                260                 265                 270

Gln Ala Pro Gly Arg Glu Lys Glu Ile Thr Ala Ser Pro Asp Tyr Leu
            275                 280                 285

Glu Ile Ala Ile Tyr Cys Ile Gly Val Phe Leu Ile Ala Cys Met Val
290                 295                 300

Val Thr Val Ile Leu Cys Arg Met Lys Asn Thr Thr Lys Lys Pro Asp
305                 310                 315                 320

Phe Ser Ser Gln Pro Ala Val His Lys Leu Thr Lys Arg Ile Pro Leu
                325                 330                 335

Arg Arg Gln Val Thr Val Ser Ala Glu Ser Ser Ser Ser Met Asn Ser
                340                 345                 350

Asn Thr Pro Leu Val Arg Ile Thr Thr Arg Leu Ser Ser Thr Ala Asp
                355                 360                 365

Thr Pro Met Leu Ala Gly Val Ser Glu Tyr Glu Leu Pro Glu Asp Pro
            370                 375                 380

Lys Trp Glu Phe Pro Arg Asp Lys Leu Thr Leu Gly Lys Pro Leu Gly
385                 390                 395                 400

Glu Gly Cys Phe Gly Gln Val Val Met Ala Glu Ala Val Gly Ile Asp
                405                 410                 415

Lys Asp Lys Pro Lys Glu Ala Val Thr Val Ala Val Lys Met Leu Lys
                420                 425                 430

Asp Asp Ala Thr Glu Lys Asp Leu Ser Asp Leu Val Ser Glu Met Glu
            435                 440                 445

Met Met Lys Met Ile Gly Lys His Lys Asn Ile Ile Asn Leu Leu Gly
450                 455                 460

Ala Cys Thr Gln Asp Gly Pro Leu Tyr Val Ile Val Glu Tyr Ala Ser
465                 470                 475                 480

Lys Gly Asn Leu Arg Glu Tyr Leu Arg Ala Arg Arg Pro Pro Gly Met
                485                 490                 495

Glu Tyr Ser Tyr Asp Ile Asn Arg Val Pro Glu Glu Gln Met Thr Phe
            500                 505                 510

Lys Asp Leu Val Ser Cys Thr Tyr Gln Leu Ala Arg Gly Met Glu Tyr
        515                 520                 525

Leu Ala Ser Gln Lys Cys Ile His Arg Asp Leu Ala Ala Arg Asn Val
            530                 535                 540

Leu Val Thr Glu Asn Asn Val Met Lys Ile Ala Asp Phe Gly Leu Ala
545                 550                 555                 560

Arg Asp Ile Asn Asn Ile Asp Tyr Tyr Lys Lys Thr Thr Asn Gly Arg
                565                 570                 575
```

```
Leu Pro Val Lys Trp Met Ala Pro Glu Ala Leu Phe Asp Arg Val Tyr
            580                 585                 590

Thr His Gln Ser Asp Val Trp Ser Phe Gly Val Leu Met Trp Glu Ile
            595                 600                 605

Phe Thr Leu Gly Gly Ser Pro Tyr Pro Gly Ile Pro Val Glu Glu Leu
            610                 615                 620

Phe Lys Leu Leu Lys Glu Gly His Arg Met Asp Lys Pro Ala Asn Cys
625                 630                 635                 640

Thr Asn Glu Leu Tyr Met Met Met Arg Asp Cys Trp His Ala Val Pro
            645                 650                 655

Ser Gln Arg Pro Thr Phe Lys Gln Leu Val Glu Asp Leu Asp Arg Ile
            660                 665                 670

Leu Thr Leu Thr Thr Asn Glu Ile
            675                 680

<210> SEQ ID NO 68
<211> LENGTH: 396
<212> TYPE: PRT
<213> ORGANISM: Homo sapiens

<400> SEQUENCE: 68

Met Val Ser Trp Gly Arg Phe Ile Cys Leu Val Val Thr Met Ala
1               5                   10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
            35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
            115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Thr Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
            195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Glu Arg Ser Pro His Arg Pro
                245                 250                 255

Ile Leu Gln Ala Gly Leu Pro Ala Asn Ala Ser Thr Val Val Gly Gly
            260                 265                 270
```

-continued

```
Asp Val Glu Phe Val Cys Lys Val Tyr Ser Asp Ala Gln Pro His Ile
            275                 280                 285
Gln Trp Ile Lys His Val Glu Lys Asn Gly Ser Lys Tyr Gly Pro Asp
        290                 295                 300
Gly Leu Pro Tyr Leu Lys Val Leu Lys Ala Ala Gly Val Asn Thr Thr
305                 310                 315                 320
Asp Lys Glu Ile Glu Val Leu Tyr Ile Arg Asn Val Thr Phe Glu Asp
                325                 330                 335
Ala Gly Glu Tyr Thr Cys Leu Ala Gly Asn Ser Ile Gly Ile Ser Phe
            340                 345                 350
His Ser Ala Trp Leu Thr Val Leu Pro Gly Ile Tyr Cys Ser Phe Ser
        355                 360                 365
Leu Gly Phe Phe Pro Phe Ser Trp Leu Thr Ala Ile Lys Leu Thr Gln
370                 375                 380
Leu Leu Leu Ser Glu Met Ala Pro Phe Ile Leu Ala
                385                 390                 395

<210> SEQ ID NO 69
<211> LENGTH: 317
<212> TYPE: PRT
<213> ORGANISM: Homo sapiens

<400> SEQUENCE: 69

Met Val Ser Trp Gly Arg Phe Ile Cys Leu Val Val Thr Met Ala
1               5                   10                  15
Thr Leu Ser Leu Ala Arg Pro Ser Phe Ser Leu Val Glu Asp Thr Thr
            20                  25                  30
Leu Glu Pro Glu Glu Pro Pro Thr Lys Tyr Gln Ile Ser Gln Pro Glu
        35                  40                  45
Val Tyr Val Ala Ala Pro Gly Glu Ser Leu Glu Val Arg Cys Leu Leu
    50                  55                  60
Lys Asp Ala Ala Val Ile Ser Trp Thr Lys Asp Gly Val His Leu Gly
65                  70                  75                  80
Pro Asn Asn Arg Thr Val Leu Ile Gly Glu Tyr Leu Gln Ile Lys Gly
                85                  90                  95
Ala Thr Pro Arg Asp Ser Gly Leu Tyr Ala Cys Thr Ala Ser Arg Thr
            100                 105                 110
Val Asp Ser Glu Thr Trp Tyr Phe Met Val Asn Val Thr Asp Ala Ile
        115                 120                 125
Ser Ser Gly Asp Asp Glu Asp Asp Thr Asp Gly Ala Glu Asp Phe Val
130                 135                 140
Ser Glu Asn Ser Asn Asn Lys Arg Ala Pro Tyr Trp Thr Asn Thr Glu
145                 150                 155                 160
Lys Met Glu Lys Arg Leu His Ala Val Pro Ala Ala Asn Thr Val Lys
                165                 170                 175
Phe Arg Cys Pro Ala Gly Gly Asn Pro Met Pro Thr Met Arg Trp Leu
            180                 185                 190
Lys Asn Gly Lys Glu Phe Lys Gln Glu His Arg Ile Gly Gly Tyr Lys
        195                 200                 205
Val Arg Asn Gln His Trp Ser Leu Ile Met Glu Ser Val Val Pro Ser
    210                 215                 220
Asp Lys Gly Asn Tyr Thr Cys Val Val Glu Asn Glu Tyr Gly Ser Ile
225                 230                 235                 240
Asn His Thr Tyr His Leu Asp Val Val Glu Arg Ser Pro His Arg Pro
                245                 250                 255
```

```
Ile Leu Gln Ala Gly Leu Pro Ala Asn Ala Ser Thr Val Val Gly Gly
            260                 265                 270

Asp Val Glu Phe Val Cys Lys Val Tyr Ser Asp Ala Gln Pro His Ile
        275                 280                 285

Gln Trp Ile Lys His Val Glu Lys Asn Gly Ser Lys Tyr Gly Pro Asp
    290                 295                 300

Gly Leu Pro Tyr Leu Lys Val Leu Lys Val Arg Thr Phe
305                 310                 315

<210> SEQ ID NO 70
<211> LENGTH: 266
<212> TYPE: PRT
<213> ORGANISM: Homo sapiens

<400> SEQUENCE: 70

Met Val Ser Trp Gly Arg Phe Ile Cys Leu Val Val Thr Met Ala
 1               5                  10                  15

Thr Leu Ser Leu Ala Arg Pro Ser Phe Ser Leu Val Glu Asp Thr Thr
            20                  25                  30

Leu Glu Pro Glu Glu Pro Pro Thr Lys Tyr Gln Ile Ser Gln Pro Glu
        35                  40                  45

Val Tyr Val Ala Ala Pro Gly Glu Ser Leu Glu Val Arg Cys Leu Leu
    50                  55                  60

Lys Asp Ala Ala Val Ile Ser Trp Thr Lys Asp Gly Val His Leu Gly
65                  70                  75                  80

Pro Asn Asn Arg Thr Val Leu Ile Gly Glu Tyr Leu Gln Ile Lys Gly
                85                  90                  95

Ala Thr Pro Arg Asp Ser Gly Leu Tyr Ala Cys Thr Ala Ser Arg Thr
            100                 105                 110

Val Asp Ser Glu Thr Trp Tyr Phe Met Val Asn Val Thr Asp Ala Ile
        115                 120                 125

Ser Ser Gly Asp Asp Glu Asp Asp Thr Asp Gly Ala Glu Asp Phe Val
    130                 135                 140

Ser Glu Asn Ser Asn Asn Lys Arg Ala Pro Tyr Trp Thr Asn Thr Glu
145                 150                 155                 160

Lys Met Glu Lys Arg Leu His Ala Val Pro Ala Ala Asn Thr Val Lys
                165                 170                 175

Phe Arg Cys Pro Ala Gly Gly Asn Pro Met Pro Thr Met Arg Trp Leu
            180                 185                 190

Lys Asn Gly Lys Glu Phe Lys Gln Glu His Arg Ile Gly Gly Tyr Lys
        195                 200                 205

Val Arg Asn Gln His Trp Ser Leu Ile Met Glu Ser Val Val Pro Ser
    210                 215                 220

Asp Lys Gly Asn Tyr Thr Cys Val Val Glu Asn Glu Tyr Gly Ser Ile
225                 230                 235                 240

Asn His Thr Tyr His Leu Asp Val Val Gly Glu Ser Ala Ser Pro Arg
                245                 250                 255

Val Ala Ala Ala Tyr Gln Pro Ile Leu Ala
            260                 265

<210> SEQ ID NO 71
<211> LENGTH: 336
<212> TYPE: DNA
<213> ORGANISM: Mus musculus

<400> SEQUENCE: 71
```

```
caggtgaagc tgcaggagtc tggcgctgag ttggtgaaac ctggggcttc agtgaagata      60
tcctgcaagg cttctggcta catcttcact gaccatgctc ttcactgggt gaggcagaag     120
cctgaacagg gcctggaatg gattgggtat attttttccg gaaatggtaa tattgagtac     180
aatgagaagt tcaagggcaa ggccacactg actgcagaca atcctccag tactgcctac      240 atgcagctca acagcctgac atctggagat tctgcaatgt atttctgtaa aaagatggac     300
tactggggcc aagggaccac ggtcaccgtc tcctca                               336
```

\<210\> SEQ ID NO 72
\<211\> LENGTH: 112
\<212\> TYPE: PRT
\<213\> ORGANISM: Mus musculus

\<400\> SEQUENCE: 72

```
Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Ile Phe Thr Asp His
            20                  25                  30

Ala Leu His Trp Val Arg Gln Lys Pro Glu Gln Gly Leu Glu Trp Ile
        35                  40                  45

Gly Tyr Ile Phe Pro Gly Asn Gly Asn Ile Glu Tyr Asn Glu Lys Phe
    50                  55                  60

Lys Gly Lys Ala Thr Leu Thr Ala Asp Lys Ser Ser Thr Ala Tyr
65                  70                  75                  80

Met Gln Leu Asn Ser Leu Thr Ser Gly Asp Ser Ala Met Tyr Phe Cys
                85                  90                  95

Lys Lys Met Asp Tyr Trp Gly Gln Gly Thr Thr Val Thr Val Ser Ser
            100                 105                 110
```

\<210\> SEQ ID NO 73
\<211\> LENGTH: 336
\<212\> TYPE: DNA
\<213\> ORGANISM: Mus musculus

\<400\> SEQUENCE: 73

```
caggtgaagc tgcaggagtc tggcgctgag ttggtgaaac ctggggcttc agtgaagatc      60
tcctgcaagg cttctggtta caccttcact gaccattcta ttcactgggt gaagcagaag     120
cctggacagg gcctagaatg gattggatat cttttttccg gaaatggtaa ttttgaatat     180
aatgagaaat tcaagggcaa ggccacactg actgcagaca atcctccag cactgcctac      240 atgcacctca acagcctgac atctgaggat tctgcagtgt atttctgtaa aaagatggac     300
tactggggcc aagggaccac ggtcaccgtc tcctca                               336
```

\<210\> SEQ ID NO 74
\<211\> LENGTH: 112
\<212\> TYPE: PRT
\<213\> ORGANISM: Mus musculus

\<400\> SEQUENCE: 74

```
Gln Val Lys Leu Gln Glu Ser Gly Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ser Ile His Trp Val Lys Gln Lys Pro Gly Gln Gly Leu Glu Trp Ile
        35                  40                  45

Gly Tyr Leu Phe Pro Gly Asn Gly Asn Phe Glu Tyr Asn Glu Lys Phe
    50                  55                  60
```

Lys Gly Lys Ala Thr Leu Thr Ala Asp Lys Ser Ser Thr Ala Tyr
65                  70                  75                  80

Met His Leu Asn Ser Leu Thr Ser Glu Asp Ser Ala Val Tyr Phe Cys
                85                  90                  95

Lys Lys Met Asp Tyr Trp Gly Gln Gly Thr Thr Val Thr Val Ser Ser
            100                 105                 110

<210> SEQ ID NO 75
<211> LENGTH: 336
<212> TYPE: DNA
<213> ORGANISM: Mus musculus

<400> SEQUENCE: 75
caggttcagc tgcagcagtc cgacgctgag ttggtgaaac ctggggcttc agtgaagata      60
tcctgcaggg cttctggcta caccttcact gaccattcta ttcactgggt gaagcagcag     120
cctggccagg gcctggaatg gatcggatat attttccccg gaaatggaaa tattgaatac     180
aatgacaaat tcaagggcaa ggccacactg actcagaca aatcctccgg cactgcctac      240
atgcagctca acagcctgac atctgaggat tctgcagtgt atttctgtaa aaggatgggg    300
tactggggtc aaggaacctc agtcaccgtc tcctca                              336

<210> SEQ ID NO 76
<211> LENGTH: 112
<212> TYPE: PRT
<213> ORGANISM: Mus musculus

<400> SEQUENCE: 76

Gln Val Gln Leu Gln Gln Ser Asp Ala Glu Leu Val Lys Pro Gly Ala
1               5                   10                  15

Ser Val Lys Ile Ser Cys Arg Ala Ser Gly Tyr Thr Phe Thr Asp His
            20                  25                  30

Ser Ile His Trp Val Lys Gln Pro Gly Gln Gly Leu Glu Trp Ile
        35                  40                  45

Gly Tyr Ile Phe Pro Gly Asn Gly Asn Ile Glu Tyr Asn Asp Lys Phe
    50                  55                  60

Lys Gly Lys Ala Thr Leu Thr Ala Asp Lys Ser Ser Gly Thr Ala Tyr
65                  70                  75                  80

Met Gln Leu Asn Ser Leu Thr Ser Glu Asp Ser Ala Val Tyr Phe Cys
                85                  90                  95

Lys Arg Met Gly Tyr Trp Gly Gln Gly Thr Ser Val Thr Val Ser Ser
            100                 105                 110

<210> SEQ ID NO 77
<211> LENGTH: 336
<212> TYPE: DNA
<213> ORGANISM: Mus musculus

<400> SEQUENCE: 77
caggtcaagc tgcaggagtc tggcgctgag ttggtgaaac ctggggcttc agtgaagatc      60
tcctgcaagg cttctggcta caccttcact gaccattcta ttcactgggt gaagcagaag     120
cctggacagg gcctagaatg gattggatat cttttcccg gaaatggtaa ttttgagtac      180
aatgaaaaat tcaagggcaa ggccacactg actcagaca aatcctccag cactgtctac      240
atgtacctca acagcctgac atctgaggat tctgcagtgt atttctgtaa aaggatgggg    300 tactgggggcc aagggaccac ggtcaccgtc tcctca                             336

<210> SEQ ID NO 78
<211> LENGTH: 112
<212> TYPE: PRT
<213> ORGANISM: Mus musculus

<400> SEQUENCE: 78

```
Gln Val Lys Leu Gln Glu Ser Gly Ala Glu Leu Val Lys Pro Gly Ala
 1               5                  10                  15
Ser Val Lys Ile Ser Cys Lys Ala Ser Gly Tyr Thr Phe Thr Asp His
            20                  25                  30
Ser Ile His Trp Val Lys Gln Lys Pro Gly Gln Gly Leu Glu Trp Ile
        35                  40                  45
Gly Tyr Leu Phe Pro Gly Asn Gly Asn Phe Glu Tyr Asn Glu Lys Phe
    50                  55                  60
Lys Gly Lys Ala Thr Leu Thr Ala Asp Lys Ser Ser Thr Val Tyr
65                  70                  75                  80
Met Tyr Leu Asn Ser Leu Thr Ser Glu Asp Ser Ala Val Tyr Phe Cys
                85                  90                  95
Lys Arg Met Gly Tyr Trp Gly Gln Gly Thr Thr Val Thr Val Ser Ser
            100                 105                 110
```

<210> SEQ ID NO 79
<211> LENGTH: 336
<212> TYPE: DNA
<213> ORGANISM: Mus musculus

<400> SEQUENCE: 79

```
caggtcaagc tgcaggagtc tggacctgaa ctggtaaagc ctggggcttc agtgaagatg     60
tcctgcaagg cttctggata cacattcact aactatgtta tacactgggt gaagcaaaag    120
cctgggcagg gccttgagtg gattggatat attaatcctt acaatgatgg ctctaagtac    180
aatgagaagt tcaaaggcaa ggcctcactg acttcagaca atcctccag cacagcctac    240
atggagctca gcagcctgac ctctgaggac tctgcggtct attactgtgc aagaatggac    300
tactggggcc aagggaccac ggtcaccgtc tcctca                              336
```

<210> SEQ ID NO 80
<211> LENGTH: 112
<212> TYPE: PRT
<213> ORGANISM: Mus musculus

<400> SEQUENCE: 80

```
Gln Val Gln Leu Gln Glu Ser Gly Pro Glu Leu Val Lys Pro Gly Ala
 1               5                  10                  15
Ser Val Lys Met Ser Cys Lys Ala Ser Gly Tyr Thr Phe Thr Asn Tyr
            20                  25                  30
Val Ile His Trp Val Lys Gln Lys Pro Gly Gln Gly Leu Glu Trp Ile
        35                  40                  45
Gly Tyr Ile Asn Pro Tyr Asn Asp Gly Ser Lys Tyr Asn Glu Lys Phe
    50                  55                  60
Lys Gly Lys Ala Ser Leu Thr Ser Asp Lys Ser Ser Ser Thr Ala Tyr
65                  70                  75                  80
Met Glu Leu Ser Ser Leu Thr Ser Glu Asp Ser Ala Val Tyr Tyr Cys
                85                  90                  95
Ala Arg Met Asp Tyr Trp Gly Gln Gly Thr Thr Leu Thr Val Ser Ser
            100                 105                 110
```

<210> SEQ ID NO 81
<211> LENGTH: 336

```
<212> TYPE: DNA
<213> ORGANISM: Mus musculus

<400> SEQUENCE: 81
caggtcaagc tgcaggagtc tggacctgaa ctggtaaagc ctggggcttc agtgaagatg      60
tcctgcaagg cttctggata cacattcact aactatgtta tacactgggt gaagcaaaag    120
cctgggcagg gccttgagtg gattggatat attaatcctt acaatgatgg ctctaagtac    180
aatgagaagt tcaaaggcaa ggcctcactg acttcagaca atcctccag cacagcctac    240 atggagctca gcagcctgac ctctgaggac tctgcggtct attactgtgc aagaatgggg    300
tactggggcc aagggaccac ggtcaccgtc tcctca                              336

<210> SEQ ID NO 82
<211> LENGTH: 112
<212> TYPE: PRT
<213> ORGANISM: Mus musculus

<400> SEQUENCE: 82

Gln Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ser Lys Tyr Asn Glu Lys Phe
    50                  55                  60

Lys Gly Lys Ala Ser Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Met Gly Tyr Trp Gly Gln Gly Thr Thr Leu Thr Val Ser Ser
            100                 105                 110

<210> SEQ ID NO 83
<211> LENGTH: 342
<212> TYPE: DNA
<213> ORGANISM: Mus musculus

<400> SEQUENCE: 83
gatgttttga tgacccaaac tccactctcc ctgcctgtca gtcttggaga tcaagcctcc      60
atctcttgca gatctagtca gagcattgta catagtaatg aaacacccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tattactgct ttcaaggttc acatgttcct    300
cctacgttcg gtgctgggac caagctggag ctgaaacggg ct                      342

<210> SEQ ID NO 84
<211> LENGTH: 113
<212> TYPE: PRT
<213> ORGANISM: Mus musculus

<400> SEQUENCE: 84

Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
            20                  25                  30
```

Asn Gly Asn Thr Tyr Leu Glu Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser His Val Pro Pro Thr Phe Gly Ala Gly Thr Lys Leu Glu Leu Lys
                100                 105                 110

Arg

<210> SEQ ID NO 85
<211> LENGTH: 324
<212> TYPE: DNA
<213> ORGANISM: Mus musculus

<400> SEQUENCE: 85
gacatccaga tgactcagtc tccagcctcc ctatctgcat ctgtgggaga aactgtcacc      60
atcacatgtc gaacaactga aaatatttac agttatttg tatggtctca gcagagacag     120
ggaaaatctc ctcagctccg ggtctataat gcaaaatcct tagcagaagg tgtgccatca    180
agtttcaatg tcagtgtatc aggcacacag ttttctctga agatcaatag cctgcagcct    240
gaagattttg ggacttatca ctgtcaacac cattatggta ctccgtacac gttcggaggg    300
gggaccaggc tggaaataag acgg                                            324

<210> SEQ ID NO 86
<211> LENGTH: 108
<212> TYPE: PRT
<213> ORGANISM: Mus musculus

<400> SEQUENCE: 86

Asp Ile Gln Met Thr Gln Ser Pro Ala Ser Leu Ser Ala Ser Val Gly
 1               5                  10                  15

Glu Thr Val Thr Ile Thr Cys Arg Thr Thr Glu Asn Ile Tyr Ser Tyr
                 20                  25                  30

Phe Val Trp Ser Gln Gln Arg Gln Gly Lys Ser Pro Gln Leu Arg Val
         35                  40                  45

Tyr Asn Ala Lys Ser Leu Ala Glu Gly Val Pro Ser Ser Phe Asn Val
 50                  55                  60

Ser Val Ser Gly Thr Gln Phe Ser Leu Lys Ile Asn Ser Leu Gln Pro
 65                  70                  75                  80

Glu Asp Phe Gly Thr Tyr His Cys Gln His His Tyr Gly Thr Pro Tyr
                 85                  90                  95

Thr Phe Gly Gly Gly Thr Arg Leu Glu Ile Arg Arg
                100                 105

<210> SEQ ID NO 87
<211> LENGTH: 339
<212> TYPE: DNA
<213> ORGANISM: Mus musculus

<400> SEQUENCE: 87 gatgttttg atgacccaaac tccactcact ttgtcggtta ccattggaca accagcttcc      60 atctcttgc aagtccagtca gagcctctta tatactaatg aaaaacctta tttgacttgg     120 ttattccag aggccaggcca gtctccaaaa cgcctaatct atctggtgtc tgaattggac     180

```
tctggagtc cctgacaggtt cagtggcagt ggttcaggga cagatttcac actggaaatc    240 accagagtg gaggctgagga tttgggagtt tattactgct tgcagagtgc acattttcca    300 ttcacgttc ggctcgggcac caagctggaa atcaaacgg                            339
```

<210> SEQ ID NO 88
<211> LENGTH: 113
<212> TYPE: PRT
<213> ORGANISM: Mus musculus

<400> SEQUENCE: 88

```
Asp Val Leu Met Thr Gln Thr Pro Leu Thr Leu Ser Val Thr Ile Gly
  1               5                  10                  15

Gln Pro Ala Ser Ile Ser Cys Lys Ser Gln Ser Leu Leu Tyr Thr
             20                  25                  30

Asn Gly Lys Thr Tyr Leu Thr Trp Leu Phe Gln Arg Pro Gly Gln Ser
         35                  40                  45

Pro Lys Arg Leu Ile Tyr Leu Val Ser Glu Leu Asp Ser Gly Val Pro
     50                  55                  60

Asp Arg Phe Ser Gly Ser Gly Ser Gly Thr Asp Phe Thr Leu Glu Ile
 65                  70                  75                  80

Thr Arg Val Glu Ala Glu Asp Leu Gly Val Tyr Tyr Cys Leu Gln Ser
                 85                  90                  95

Ala His Phe Pro Phe Thr Phe Gly Ser Gly Thr Lys Leu Glu Ile Lys
            100                 105                 110

Arg
```

<210> SEQ ID NO 89
<211> LENGTH: 339
<212> TYPE: DNA
<213> ORGANISM: Mus musculus

<400> SEQUENCE: 89

```
gatgttgtga tgacccaaac tccactcact ctgtcggtga ccattggaca accagcgttc    60
atctcttgca gtccagtca gagcctcttt aacactaatg caaaaccta tttgacttgg    120 ttaattcaga ggccaggcca gtctccacag cgcctgatct atctggtgtc caaattggac    180
tctggcgtcc cggacaggtt cagtggcagt ggctcaggga cagatttcac actgaaaatc    240
agcagagtgg aggctgagga tctgggagtt tattactgcc tgcagagtag ccattttccg    300
tttacgttcg gctcgggcac caagctggaa atcaaacgg                            339
```

<210> SEQ ID NO 90
<211> LENGTH: 113
<212> TYPE: PRT
<213> ORGANISM: Mus musculus

<400> SEQUENCE: 90

```
Asp Val Val Met Thr Gln Thr Pro Leu Thr Leu Ser Val Thr Ile Gly
  1               5                  10                  15

Gln Pro Ala Ser Ile Ser Cys Lys Ser Gln Ser Leu Leu Asn Thr
             20                  25                  30

Asn Gly Lys Thr Tyr Leu Thr Trp Leu Ile Gln Arg Pro Gly Gln Ser
         35                  40                  45

Pro Gln Arg Leu Ile Tyr Leu Val Ser Lys Leu Asp Ser Gly Val Pro
     50                  55                  60

Asp Arg Phe Ser Gly Ser Gly Ser Gly Thr Asp Phe Thr Leu Lys Ile
 65                  70                  75                  80
```

```
Ser Arg Val Glu Ala Glu Asp Leu Gly Val Tyr Tyr Cys Leu Gln Ser
            85                  90                  95

Ser His Phe Pro Phe Thr Phe Gly Ser Gly Thr Lys Leu Glu Ile Lys
            100                 105                 110

Arg

<210> SEQ ID NO 91
<211> LENGTH: 327
<212> TYPE: DNA
<213> ORGANISM: Mus musculus

<400> SEQUENCE: 91
gatgttgtgc taactcagtc tcctgccacc ctgtctgtga ctccaggaga tagagtcagt    60
ctttcctgca gggccagcca aatattggc aactacctac actggtatca acagaaatca   120
catgagtctc caaggcttct catcaagtat gcttcccagt ccatctctgg atcccctcc   180 aggttcagtg gcagtggatc agtcacagat ttcactctca atatcaacag tgtggagact   240
gaagattttg gaatgtattt ctgtcaacag agtgacacct ggcctctcac gttcggtgct   300
gggaccaagc tggagctgaa acgggct                                      327

<210> SEQ ID NO 92
<211> LENGTH: 108
<212> TYPE: PRT
<213> ORGANISM: Mus musculus

<400> SEQUENCE: 92

Asp Val Val Leu Thr Gln Ser Pro Ala Thr Leu Ser Val Thr Pro Gly
 1               5                  10                  15

Asp Arg Val Ser Leu Ser Cys Arg Ala Ser Gln Asn Ile Gly Asn Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Val Thr Asp Phe Thr Leu Asn Ile Asn Ser Val Glu Thr
65                  70                  75                  80

Glu Asp Phe Gly Met Tyr Phe Cys Gln Gln Ser Asp Thr Trp Pro Leu
                85                  90                  95

Thr Phe Gly Ala Gly Thr Lys Leu Glu Leu Lys Arg
            100                 105

<210> SEQ ID NO 93
<211> LENGTH: 8
<212> TYPE: PRT
<213> ORGANISM: Mus musculus

<400> SEQUENCE: 93

Thr Phe Thr Asp His Ser Ile His
 1               5

<210> SEQ ID NO 94
<211> LENGTH: 8
<212> TYPE: PRT
<213> ORGANISM: Mus musculus

<400> SEQUENCE: 94

Thr Phe Thr Asn Tyr Val Ile His
 1               5
```

<210> SEQ ID NO 95
<211> LENGTH: 8
<212> TYPE: PRT
<213> ORGANISM: Mus musculus

<400> SEQUENCE: 95

Ile Phe Thr Asp His Ala Leu His
1               5

<210> SEQ ID NO 96
<211> LENGTH: 17
<212> TYPE: PRT
<213> ORGANISM: Mus musculus

<400> SEQUENCE: 96

Tyr Ile Phe Pro Gly Asn Gly Asn Ile Glu Tyr Asn Asp Lys Phe Lys
1               5                   10                  15

Gly

<210> SEQ ID NO 97
<211> LENGTH: 17
<212> TYPE: PRT
<213> ORGANISM: Mus musculus

<400> SEQUENCE: 97

Tyr Leu Phe Pro Gly Asn Gly Asn Phe Glu Tyr Asn Glu Lys Phe Lys
1               5                   10                  15

Gly

<210> SEQ ID NO 98
<211> LENGTH: 17
<212> TYPE: PRT
<213> ORGANISM: Mus musculus

<400> SEQUENCE: 98

Tyr Ile Asn Pro Tyr Asn Asp Gly Ser Lys Tyr Asn Glu Lys Phe Lys
1               5                   10                  15

Gly

<210> SEQ ID NO 99
<211> LENGTH: 17
<212> TYPE: PRT
<213> ORGANISM: Mus musculus

<400> SEQUENCE: 99

Tyr Ile Phe Pro Gly Asn Gly Asn Ile Glu Tyr Asn Glu Lys Phe Lys
1               5                   10                  15

Gly

<210> SEQ ID NO 100
<211> LENGTH: 5
<212> TYPE: PRT
<213> ORGANISM: Mus musculus

<400> SEQUENCE: 100

Lys Arg Met Gly Tyr
1               5

<210> SEQ ID NO 101
<211> LENGTH: 5
<212> TYPE: PRT
<213> ORGANISM: Mus musculus

<400> SEQUENCE: 101

Lys Lys Met Asp Tyr
1               5

<210> SEQ ID NO 102
<211> LENGTH: 5
<212> TYPE: PRT
<213> ORGANISM: Mus musculus

<400> SEQUENCE: 102

Ala Arg Met Asp Tyr
1               5

<210> SEQ ID NO 103
<211> LENGTH: 16
<212> TYPE: PRT
<213> ORGANISM: Mus musculus

<400> SEQUENCE: 103

Arg Ser Ser Gln Ser Ile Val His Ser Asn Gly Asn Thr Tyr Leu Glu
1               5                   10                  15

<210> SEQ ID NO 104
<211> LENGTH: 11
<212> TYPE: PRT
<213> ORGANISM: Mus musculus

<400> SEQUENCE: 104

Arg Thr Thr Glu Asn Ile Tyr Ser Tyr Phe Val
1               5                   10

<210> SEQ ID NO 105
<211> LENGTH: 16
<212> TYPE: PRT
<213> ORGANISM: Mus musculus

<400> SEQUENCE: 105

Lys Ser Ser Gln Ser Leu Leu Tyr Thr Asn Gly Lys Thr Tyr Leu Thr
1               5                   10                  15

<210> SEQ ID NO 106
<211> LENGTH: 16
<212> TYPE: PRT
<213> ORGANISM: Mus musculus

<400> SEQUENCE: 106

Lys Ser Ser Gln Ser Leu Leu Asn Thr Asn Gly Lys Thr Tyr Leu Thr
1               5                   10                  15

<210> SEQ ID NO 107
<211> LENGTH: 11
<212> TYPE: PRT
<213> ORGANISM: Mus musculus

<400> SEQUENCE: 107

Arg Ala Ser Gln Asn Ile Gly Asn Tyr Leu His
1               5                   10

<210> SEQ ID NO 108
<211> LENGTH: 7
<212> TYPE: PRT
<213> ORGANISM: Mus musculus

<400> SEQUENCE: 108

Lys Val Ser Asn Arg Phe Ser
1               5

```
<210> SEQ ID NO 109
<211> LENGTH: 7
<212> TYPE: PRT
<213> ORGANISM: Mus musculus

<400> SEQUENCE: 109

Asn Ala Lys Ser Leu Ala Glu
 1               5

<210> SEQ ID NO 110
<211> LENGTH: 7
<212> TYPE: PRT
<213> ORGANISM: Mus musculus

<400> SEQUENCE: 110

Leu Val Ser Glu Leu Asp Ser
 1               5

<210> SEQ ID NO 111
<211> LENGTH: 7
<212> TYPE: PRT
<213> ORGANISM: Mus musculus

<400> SEQUENCE: 111

Leu Val Ser Lys Leu Asp Ser
 1               5

<210> SEQ ID NO 112
<211> LENGTH: 7
<212> TYPE: PRT
<213> ORGANISM: Mus musculus

<400> SEQUENCE: 112

Tyr Ala Ser Gln Ser Ile Ser
 1               5

<210> SEQ ID NO 113
<211> LENGTH: 9
<212> TYPE: PRT
<213> ORGANISM: Mus musculus

<400> SEQUENCE: 113

Phe Gln Gly Ser His Val Pro Pro Thr
 1               5

<210> SEQ ID NO 114
<211> LENGTH: 9
<212> TYPE: PRT
<213> ORGANISM: Mus musculus

<400> SEQUENCE: 114

Gln His His Tyr Gly Thr Pro Tyr Thr
 1               5

<210> SEQ ID NO 115
<211> LENGTH: 9
<212> TYPE: PRT
<213> ORGANISM: Mus musculus

<400> SEQUENCE: 115

Leu Gln Ser Ala His Phe Pro Phe Thr
 1               5

<210> SEQ ID NO 116
```

```
<211> LENGTH: 9
<212> TYPE: PRT
<213> ORGANISM: Mus musculus

<400> SEQUENCE: 116

Leu Gln Ser Ser His Phe Pro Phe Thr
1               5

<210> SEQ ID NO 117
<211> LENGTH: 9
<212> TYPE: PRT
<213> ORGANISM: Mus musculus

<400> SEQUENCE: 117

Gln Gln Ser Asp Thr Trp Pro Leu Thr
1               5

<210> SEQ ID NO 118
<211> LENGTH: 5
<212> TYPE: PRT
<213> ORGANISM: Mus musculus

<400> SEQUENCE: 118

Asp His Ala Leu His
1               5

<210> SEQ ID NO 119
<211> LENGTH: 5
<212> TYPE: PRT
<213> ORGANISM: Mus musculus

<400> SEQUENCE: 119

Asp His Ser Ile His
1               5

<210> SEQ ID NO 120
<211> LENGTH: 5
<212> TYPE: PRT
<213> ORGANISM: Mus musculus

<400> SEQUENCE: 120

Asn Tyr Val Ile His
1               5

<210> SEQ ID NO 121
<211> LENGTH: 9
<212> TYPE: PRT
<213> ORGANISM: Mus musculus

<400> SEQUENCE: 121

Ile Phe Pro Gly Asn Gly Asn Ile Glu
1               5

<210> SEQ ID NO 122
<211> LENGTH: 9
<212> TYPE: PRT
<213> ORGANISM: Mus musculus

<400> SEQUENCE: 122

Leu Phe Pro Gly Asn Gly Asn Phe Glu
1               5

<210> SEQ ID NO 123
<211> LENGTH: 9
<212> TYPE: PRT
<213> ORGANISM: Mus musculus
```

<400> SEQUENCE: 123

Ile Asn Pro Tyr Asn Asp Gly Ser Lys
1               5

<210> SEQ ID NO 124
<211> LENGTH: 11
<212> TYPE: PRT
<213> ORGANISM: Mus musculus

<400> SEQUENCE: 124

His Leu Ala Asn Thr Tyr Tyr Tyr Phe Asp Tyr
1               5                   10

<210> SEQ ID NO 125
<211> LENGTH: 5
<212> TYPE: PRT
<213> ORGANISM: Mus musculus

<400> SEQUENCE: 125

Ser Asn Gly Asn Thr
1               5

<210> SEQ ID NO 126
<211> LENGTH: 5
<212> TYPE: PRT
<213> ORGANISM: Mus musculus

<400> SEQUENCE: 126

Glu Asn Ile Tyr Ser
1               5

<210> SEQ ID NO 127
<211> LENGTH: 5
<212> TYPE: PRT
<213> ORGANISM: Mus musculus

<400> SEQUENCE: 127

Thr Ser Gly Tyr Ser
1               5

<210> SEQ ID NO 128
<211> LENGTH: 5
<212> TYPE: PRT
<213> ORGANISM: Mus musculus

<400> SEQUENCE: 128

Gln Asp Ile Lys Ser
1               5

<210> SEQ ID NO 129
<211> LENGTH: 5
<212> TYPE: PRT
<213> ORGANISM: Mus musculus

<400> SEQUENCE: 129

Gln Asn Ile Gly Asn
1               5

<210> SEQ ID NO 130
<211> LENGTH: 4654
<212> TYPE: DNA
<213> ORGANISM: Homo sapiens

<400> SEQUENCE: 130

```
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtccttcct tcctctcgtt ccccaaatcc gagggcagcc     300
cgcgggcgtc atgcccgcgc tcctccgcag cctgggtac gcgtgaagcc cgggaggctt      360
ggcgccggcg aagacccaag gaccactctt ctgcgtttgg agttgctccc cgcaaccccg     420
ggctcgtcgc tttctccatc ccgacccacg cggggcgcgg gacaacaca ggtcgcggag      480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atggggtgca cttggggccc aacaatagga     900
cagtgcttat tggggagtac ttgcagataa agggcgccac gcctagagac tccgcctct      960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
gtgagaacag taacaacaag agagcaccat actggaccaa cacagaaaag atggaaaagc    1140
ggctccatgc tgtgcctgcg gccaacactg tcaagtttcg ctgcccagcc gggggggaacc   1200
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga atgaatacgg gtccatcaat cacacgtacc    1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaaggccg ccggtgttaa caccacggac aaagagattg    1620
aggttctcta tattcggaat gtaactttg aggacgctgg ggaatatacg tgcttggcgg     1680
gtaattctat tgggatatcc tttcactctg catggttgac agttctgcca gcgcctggaa    1740
gagaaaagga gattacagct tccccagact acctggagat agccatttac tgcatagggg    1800
tcttcttaat cgcctgtatg gtggtaacag tcatcctgtg ccgaatgaag aacacgacca    1860
agaagccaga cttcagcagc cagccggctg tgcacaagct gaccaaacgt atcccctgc     1920
ggagacaggt aacagtttcg gctgagtcca gctcctccat gaactccaac accccgctgg    1980
tgaggataac aacacgcctc tcttcaacgg cagacacccc catgctggca ggggtctccg    2040
agtatgaact tccagaggac ccaaaatggg agtttccaag agataagctg acactgggca    2100
agcccctggg agaaggttgc tttgggcaag tggtcatggc ggaagcagtg ggaattgaca    2160
aagcaagcc caaggaggcg gtcaccgtgg ccgtgaagat gttgaaagat gatgccacag    2220
agaaagacct ttctgatctg gtgtcagaga tggagatgat gaagatgatt gggaaacaca   2280
agaatatcat aaatcttctt ggagcctgca cacaggatgg gcctctctat gtcatagttg    2340
agtatgcctc taaaggcaac ctccgagaat acctccgagc ccgagggcca cccgggatgg    2400
```

```
agtactccta tgacattaac cgtgttcctg aggagcagat gaccttcaag gacttggtgt    2460
catgcaccta ccagctggcc agaggcatgg agtacttggc ttcccaaaaa tgtattcatc    2520
gagatttagc agccagaaat gttttggtaa cagaaaacaa tgtgatgaaa atagcagact    2580
ttggactcgc cagagatatc aacaatatag actattacaa aaagaccacc aatgggcggc    2640
ttccagtcaa gtggatggct ccagaagccc tgtttgatag agtatacact catcagagtg    2700
atgtctggtc cttcggggtg ttaatgtggg agatcttcac tttaggggc tcgccctacc     2760
cagggattcc cgtggaggaa cttttaagc tgctgaagga aggacacaga atggataagc     2820
cagccaactg caccaacgaa ctgtacatga tgatgaggga ctgttggcat gcagtgccct    2880
cccagagacc aacgttcaag cagttggtag aagacttgga tcgaattctc actctcacaa    2940
ccaatgagga atacttggac ctcagccaac ctctcgaaca gtattcacct agttaccctg    3000
acacaagaag ttcttgttct tcaggagatg attctgtttt ttctccagac cccatgcctt    3060
acgaaccatg ccttcctcag tatccacaca taaacggcag tgttaaaaca tgaatgactg    3120
tgtctgcctg tccccaaaca ggacagcact gggaacctag ctacactgag cagggagacc    3180
atgcctccca gagcttgttg tctccacttg tatatatgga tcagaggagt aaataattgg    3240
aaaagtaatc agcatatgtg taaagattta tacagttgaa aacttgtaat cttccccagg    3300
aggagaagaa ggtttctgga gcagtggact gccacaagcc accatgtaac ccctctcacc    3360
tgccgtgcgt actggctgtg gaccagtagg actcaaggtg gacgtgcgtt ctgccttcct    3420
tgttaatttt gtaataattg gagaagattt atgtcagcac acacttacag agcacaaatg    3480
cagtatatag gtgctggatg tatgtaaata tattcaaatt atgtataaat atatattata    3540
tatttacaag gagttatttt ttgtattgat tttaaatgga tgtcccaatg cacctagaaa    3600
attggtctct cttttttttaa tagctatttg ctaaatgctg ttcttacaca taatttctta    3660
attttcaccg agcagaggtg gaaaaatact tttgctttca gggaaaatgg tataacgtta    3720
atttattaat aaaattggtaa tatacaaaac aattaatcat ttatagtttt ttttgtaatt    3780
taagtggcat ttctatgcag gcagcacagc agactagtta atctattgct tggacttaac    3840
tagttatcag atccttttgaa aagagaatat ttacaatata tgactaattt ggggaaaatg    3900
aagttttgat ttatttgtgt ttaaatgctg ctgtcagacg attgttctta gacctcctaa    3960
atgccccata ttaaaagaac tcattcatag gaaggtgttt cattttggtg tgcaaccctg    4020
tcattacgtc aacgcaacgt ctaactggac ttcccaagat aaatggtacc agcgtcctct    4080
taaaagatgc cttaatccat tccttgagga cagaccttag ttgaaatgat agcagaatgt    4140
gcttctctct ggcagctggc cttctgcttc tgagttgcac attaatcaga ttagcctgta    4200
ttctcttcag tgaattttga taatggcttc cagactcttt ggcgttggag acgcctgtta    4260
ggatcttcaa gtcccatcat agaaaattga acacagagt tgttctgctg atagttttgg     4320
ggatacgtcc atcttttaa gggattgctt tcatctaatt ctggcaggac ctcaccaaaa     4380
gatccagcct catacctaca tcagacaaaa tatcgccgtt gttccttctg tactaaagta    4440
ttgtgttttg ctttggaaac acccactcac tttgcaatag ccgtgcaaga tgaatgcaga    4500
ttacactgat cttatgtgtt acaaaattgg agaaagtatt taataaaacc tgttaatttt    4560
tatactgaca ataaaaatgt ttctacagat attaatgtta acaagacaaa ataaatgtca    4620
cgcaacttat ttttttaata aaaaaaaaaa aaaa                                4654
```

<210> SEQ ID NO 131
<211> LENGTH: 4657
<212> TYPE: DNA

<213> ORGANISM: Homo sapiens

<400> SEQUENCE: 131

```
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctggcccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg gacaacaca ggtcgcggag      480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atggggtgca cttggggccc aacaatagga     900
cagtgcttat tggggagtac ttgcagataa agggcgccac gcctagagac tccggcctct     960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
gtgagaacag taacaacaag agagcaccat actggaccaa cacagaaaag atggaaaagc    1140
ggctccatgc tgtgcctgcg gccaacactg tcaagtttcg ctgcccagcc gggggggaacc   1200
caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga atgaatacgg gtccatcaat cacacgtacc    1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaagcact cgggataaa tagttccaat gcagaagtgc     1620
tggctctgtt caatgtgacc gaggcggatg ctggggaata tatatgtaag gtctccaatt    1680
atataggca ggccaaccag tctgcctggc tcactgtcct gccaaaacag caagcgcctg      1740
gaagagaaaa ggagattaca gcttccccag actacctgga gatagccatt tactgcatag    1800
gggtcttctt aatcgcctgt atggtggtaa cagtcatcct gtgccgaatg aagaacacga    1860
ccaagaagcc agacttcagc agccagccgg ctgtgcacaa gctgaccaaa cgtatccccc    1920
tgcgagaca ggtaacagtt tcggctgagt ccagctcctc catgaactcc aacacccgc      1980
tggtgaggat aacaacacgc ctctcttcaa cggcagacac cccatgctg gcagggtct      2040
ccgagtatga acttcagag gacccaaaat gggagtttcc aagagataag ctgcacactgg    2100
gcaagcccct gggagaaggt tgctttgggc aagtggtcat ggcggaagca gtgggaattg    2160
acaaagacaa gccaaggag gcggtcaccg tggccgtgaa gatgttgaaa gatgatgcca     2220
cagagaaaga cctttctgat ctggtgtcag agatggagat gatgaagatg attgggaaac    2280
```

```
acaagaatat cataaatctt cttggagcct gcacacagga tgggcctctc tatgtcatag     2340
ttgagtatgc ctctaaaggc aacctccgag aatacctccg agcccggagg ccacccggga     2400
tggagtactc ctatgacatt aaccgtgttc ctgaggagca gatgaccttc aaggacttgg     2460
tgtcatgcac ctaccagctg gccagaggca tggagtactt ggcttcccaa aaatgtattc     2520
atcgagattt agcagccaga aatgttttgg taacagaaaa caatgtgatg aaaatagcag     2580
actttggact cgccagagat atcaacaata tagactatta caaaaagacc accaatgggc     2640
ggcttccagt caagtggatg gctccagaag ccctgtttga tagagtatac actcatcaga     2700
gtgatgtctg gtccttcggg gtgttaatgt gggagatctt cactttaggg ggctcgccct     2760
acccagggat tcccgtggag gaactttta agctgctgaa ggaaggacac agaatggata     2820
agccagccaa ctgcaccaac gaactgtaca tgatgatgag ggactgttgg catgcagtgc     2880
cctcccagag accaacgttc aagcagttgg tagaagactt ggatcgaatt ctcactctca     2940
caaccaatga ggaatacttg gacctcagcc aacctctcga acagtattca cctagttacc     3000
ctgacacaag aagttcttgt tcttcaggag atgattctgt ttttctcca gaccccatgc     3060 cttacgaacc atgccttcct cagtatccac acataaacgg cagtgttaaa acatgaatga     3120
ctgtgtctgc ctgtccccaa acaggacagc actgggaacc tagctacact gagcagggag     3180
accatgcctc ccagagcttg ttgtctccac ttgtatatat ggatcagagg agtaaataat     3240
tggaaaagta atcagcatat gtgtaaagat ttatacagtt gaaaacttgt aatcttcccc     3300
aggaggagaa gaaggtttct ggagcagtgg actgccacaa gccaccatgt aaccctctc     3360 acctgccgtg cgtactggct gtggaccagt aggactcaag gtggacgtgc gttctgcctt     3420
ccttgttaat tttgtaataa ttggagaaga tttatgtcag cacacactta cagagcacaa     3480
atgcagtata taggtgctgg atgtatgtaa atatattcaa attatgtata aatatatatt     3540
atatatttac aaggagttat tttttgtatt gattttaaat ggatgtccca atgcacctag     3600
aaaattggtc tctctttttt taatagctat ttgctaaatg ctgttcttac acataatttc     3660
ttaattttca ccgagcagag gtggaaaaat acttttgctt tcagggaaaa tggtataacg     3720
ttaatttatt aataaattgg taatatacaa acaattaat catttatagt ttttttttgta     3780 atttaagtgg catttctatg caggcagcac agcagactag ttaatctatt gcttggactt     3840
aactagttat cagatccttt gaaaagagaa tatttacaat atatgactaa tttgggggaaa     3900 atgaagtttt gatttatttg tgtttaaatg ctgctgtcag acgattgttc ttagacctcc     3960
taaatgcccc atattaaaag aactcattca taggaaggtg tttcattttg gtgtgcaacc     4020
ctgtcattac gtcaacgcaa cgtctaactg gacttcccaa gataaatggt accagcgtcc     4080
tcttaaaaga tgccttaatc cattccttga ggacagacct tagttgaaat gatagcagaa     4140
tgtgcttctc tctggcagct ggccttctgc ttctgagttg cacattaatc agattagcct     4200
gtattctctt cagtgaattt tgataatggc ttccagactc tttggcgttg gagacgcctg     4260
ttaggatctt caagtcccat catagaaaat tgaaacacag agttgttctg ctgatagttt     4320
tggggatacg tccatctttt taagggattg ctttcatcta attctggcag gacctccacca     4380 aaagatccag cctcatacct acatcagaca aaatatcgcc gttgttcctt ctgtactaaa     4440
gtattgtgtt ttgctttgga aacacccact cactttgcaa tagccgtgca agatgaatgc     4500
agattacact gatcttatgt gttacaaaat tggagaaagt atttaataaa acctgttaat     4560
ttttatactg acaataaaaa tgtttctaca gatattaatg ttaacaagac aaaataaatg     4620
tcacgcaact tattttttta ataaaaaaaa aaaaaaa                              4657
```

<210> SEQ ID NO 132
<211> LENGTH: 2781
<212> TYPE: DNA
<213> ORGANISM: Homo sapiens

<400> SEQUENCE: 132

| | | | | | |
|---|---|---|---|---|---|
| tgactgcagc | agcagcggca | gcgcctcggt | tcctgagccc | accgcaggct | gaaggcattg | 60 |
| cgcgtagtcc | atgcccgtag | aggaagtgtg | cagatgggat | taacgtccac | atggagatat | 120 |
| ggaagaggac | cggggattgg | taccgtaacc | atggtcagct | ggggtcgttt | catctgcctg | 180 |
| gtcgtggtca | ccatggcaac | cttgtccctg | gcccggccct | ccttcagttt | agttgaggat | 240 |
| accacattag | agccagaaga | gccaccaacc | aaataccaaa | tctctcaacc | agaagtgtac | 300 |
| gtggctgcgc | caggggagtc | gctagaggtg | cgctgcctgt | tgaaagatgc | cgccgtgatc | 360 |
| agttggacta | aggatggggt | gcacttgggg | cccaacaata | ggacagtgct | tattggggag | 420 |
| tacttgcaga | taaagggcgc | cacgcctaga | gactccggcc | tctatgcttg | tactgccagt | 480 |
| aggactgtag | acagtgaaac | ttggtacttc | atggtgaatg | tcacagatgc | catctcatcc | 540 |
| ggagatgatg | aggatgacac | cgatggtgcg | gaagattttg | tcagtgagaa | cagtaacaac | 600 |
| aagagagcac | catactggac | caacacagaa | aagatggaaa | agcggctcca | tgctgtgcct | 660 |
| gcggccaaca | ctgtcaagtt | tcgctgccca | gccgggggga | acccaatgcc | aaccatgcgg | 720 |
| tggctgaaaa | acgggaagga | gtttaagcag | gagcatcgca | ttggaggcta | caaggtacga | 780 |
| aaccagcact | ggagcctcat | tatggaaagt | gtggtcccat | ctgacaaggg | aaattatacc | 840 |
| tgtgtagtgg | agaatgaata | cgggtccatc | aatcacacgt | accacctgga | tgttgtggag | 900 |
| cgatcgcctc | accggcccat | cctccaagcc | ggactgccgg | caaatgcctc | cacagtggtc | 960 |
| ggaggagacg | tagagtttgt | ctgcaaggtt | tacagtgatg | cccagcccca | catccagtgg | 1020 |
| atcaagcacg | tggaaaagaa | cggcagtaaa | tacgggcccg | acgggctgcc | ctacctcaag | 1080 |
| gttctcaagc | actcggggat | aaatagttcc | aatgcagaag | tgctggctct | gttcaatgtg | 1140 |
| accgaggcgg | atgctgggga | atatatatgt | aaggtctcca | attatatagg | gcaggccaac | 1200 |
| cagtctgcct | ggctcactgt | cctgccaaaa | cagcaagcgc | ctggaagaga | aaggagatt | 1260 |
| acagcttccc | cagactacct | ggagatagcc | atttactgca | tagggtgtct | tcttaatcgcc | 1320 |
| tgtatggtgg | taacagtcat | cctgtgccga | atgaagaaca | cgaccaagaa | gccagacttc | 1380 |
| agcagccagc | cggctgtgca | caagctgacc | aaacgtatcc | ccctgcggag | acaggtaaca | 1440 |
| gtttcggctg | agtccagctc | ctccatgaac | tccaacaccc | cgctggtgag | gataacaaca | 1500 |
| cgcctctctt | caacggcaga | cacccccatg | ctggcagggg | tctccgagta | tgaacttcca | 1560 |
| gaggacccaa | aatgggagtt | tccaagagat | aagctgacac | tggcaagcc | cctgggagaa | 1620 |
| ggttgctttg | gcaagtggt | catggcggaa | gcagtgggaa | ttgacaaaga | caagcccaag | 1680 |
| gaggcggtca | ccgtggccgt | gaagatgttg | aaagatgatg | ccacagagaa | agaccttctct | 1740 |
| gatctggtgt | cagagatgga | gatgatgaag | atgattggga | aacacaagaa | tatcataaat | 1800 |
| cttcttggag | cctgcacaca | ggatgggcct | ctctatgtca | tagttgagta | tgcctctaaa | 1860 |
| ggcaacctcc | gagaatacct | ccgagcccgg | aggccacccg | ggatggagta | ctcctatgac | 1920 |
| attaaccgtg | ttcctgagga | gcagatgacc | ttcaaggact | tggtgtcatg | cacctaccag | 1980 |
| ctggccagag | gcatggagta | cttggcttcc | caaaaatgta | ttcatcgaga | tttagcagcc | 2040 |
| agaaatgttt | tggtaacaga | aaacaatgtg | atgaaaatag | cagactttgg | actcgccaga | 2100 |
| gatatcaaca | atatagacta | ttacaaaaag | accaccaatg | ggcggcttcc | agtcaagtgg | 2160 |

-continued

| | |
|---|---|
| atggctccag aagccctgtt tgatagagta tacactcatc agagtgatgt ctggtccttc | 2220 |
| ggggtgttaa tgtgggagat cttcacttta gggggctcgc cctacccagg gattcccgtg | 2280 |
| gaggaacttt ttaagctgct gaaggaagga cacagaatgg ataagccagc caactgcacc | 2340 |
| aacgaactgt acatgatgat gagggactgt tggcatgcag tgccctccca gagaccaacg | 2400 |
| ttcaagcagt tggtagaaga cttggatcga attctcactc tcacaaccaa tgagatctga | 2460 |
| aagtttatgg cttcattgag aaactgggaa agttggtca ggcgcagtgg ctcatgcctg | 2520 |
| taatcccagc actttgggag gccgaggcag gcggatcatg aggtcaggag ttccagacca | 2580 |
| gcctggccaa catggtgaaa ccctgtctct actaaagata caaaaaatta gccgggcgtg | 2640 |
| ttggtgtgca cctgtaatcc cagctactcc gggaggctga ggcaggagag tcacttgaac | 2700 |
| cggggaggcg gaggttgcag tgagccgaga tcatgccatt gcattccagc cttggcgaca | 2760 |
| gagcgagact ccgtctcaaa a | 2781 |

<210> SEQ ID NO 133
<211> LENGTH: 3821
<212> TYPE: DNA
<213> ORGANISM: Homo sapiens

<400> SEQUENCE: 133

| | |
|---|---|
| tgactgcagc agcagcggca gcgcctcggt tcctgagccc accgcaggct gaaggcattg | 60 |
| cgcgtagtcc atgcccgtag aggaagtgtg cagatgggat taacgtccac atggagatat | 120 |
| ggaagaggac cggggattgg taccgtaacc atggtcagct ggggtcgttt catctgcctg | 180 |
| gtcgtggtca ccatggcaac cttgtccctg gcccggccct ccttcagttt agttgaggat | 240 |
| accacattag agccagaaga gccaccaacc aaataccaaa tctctcaacc agaagtgtac | 300 |
| gtggctgcgc caggggagtc gctagaggtg cgctgcctgt tgaaagatgc cgccgtgatc | 360 |
| agttggacta aggatggggt gcacttgggg cccaacaata ggacagtgct tattggggag | 420 |
| tacttgcaga taaagggcgc cacgcctaga gactccggcc tctatgcttg tactgccagt | 480 |
| aggactgtag acagtgaaac ttggtacttc atggtgaatg tcacagatgc catctcatcc | 540 |
| ggagatgatg aggatgacac cgatggtgcg gaagattttg tcagtgagaa cagtaacaac | 600 |
| aagagagcac catactggac caacacagaa aagatggaaa agcggctcca tgctgtgcct | 660 |
| gcggccaaca ctgtcaagtt tcgctgccca gccgggggga acccaatgcc aaccatgcgg | 720 |
| tggctgaaaa acgggaagga gtttaagcag gagcatcgca ttggaggcta caaggtacga | 780 |
| aaccagcact ggagcctcat tatggaaagt gtggtcccat ctgacaaggg aaattatacc | 840 |
| tgtgtagtgg agaatgaata cgggtccatc aatcacacgt accacctgga tgttgtggcg | 900 |
| cctgaaagag aaaaggagat tacagcttcc ccagactacc tggagatagc catttactgc | 960 |
| atagggtct tcttaatcgc ctgtatggtg gtaacagtca tcctgtgccg aatgaagaac | 1020 |
| acgaccaaga gccagactt cagcagccag ccggctgtgc acaagctgac caaacgtatc | 1080 |
| ccctgcgga gacaggtaac agtttcggct gagtccagct cctccatgaa ctccaacacc | 1140 |
| ccgctggtga gataacaac acgcctctct tcaacggcag acacccccat gctggcaggg | 1200 |
| gtctccgagt atgaacttcc agaggaccca aaatgggagt tccaagaga taagctgaca | 1260 |
| ctgggcaagc cctgggaga aggttgcttt gggcaagtgg tcatggcgga agcagtggga | 1320 |
| attgacaaag acaagcccaa ggaggcggtc accgtggccg tgaagatgtt gaaagatgat | 1380 |
| gccacagaga aagaccttc tgatctggtg tcagagatgg agatgatgaa gatgattggg | 1440 |
| aaacacaaga atatcataaa tcttcttgga gcctgcacac aggatgggcc tctctatgtc | 1500 |

```
atagttgagt atgcctctaa aggcaacctc cgagaatacc tccgagcccg gaggccaccc    1560
gggatggagt actcctatga cattaaccgt gttcctgagg agcagatgac cttcaaggac    1620
ttggtgtcat gcacctacca gctggccaga ggcatggagt acttggcttc ccaaaaatgt    1680
attcatcgag atttagcagc cagaaatgtt ttggtaacag aaaacaatgt gatgaaaata    1740
gcagactttg gactcgccag agatatcaac aatatagact attacaaaaa gaccaccaat    1800
gggcggcttc cagtcaagtg gatggctcca gaagccctgt tgatagagt atacactcat     1860 cagagtgatg tctggtcctt cggggtgtta atgtgggaga tcttcacttt aggggctcg     1920 ccctacccag ggattcccgt ggaggaactt tttaagctgc tgaaggaagg acacagaatg    1980
gataagccag ccaactgcac caacgaactg tacatgatga tgagggactg ttggcatgca    2040
gtgccctccc agagaccaac gttcaagcag ttggtagaag acttggatcg aattctcact    2100
ctcacaacca atgaggaata cttggacctc agccaacctc tcgaacagta ttcacctagt    2160
taccctgaca caagaagttc ttgttcttca ggagatgatt ctgttttttc tccagacccc    2220
atgccttacg aaccatgcct tcctcagtat ccacacataa acggcagtgt taaaacatga    2280
atgactgtgt ctgcctgtcc ccaaacagga cagcactggg aacctagcta cactgagcag    2340
ggagaccatg cctcccagag cttgttgtct ccacttgtat atatggatca gaggagtaaa    2400
taattggaaa agtaatcagc atatgtgtaa agatttatac agttgaaaac ttgtaatctt    2460
ccccaggagg agaagaaggt ttctggagca gtggactgcc acaagccacc atgtaacccc    2520
tctcacctgc cgtgcgtact ggctgtggac cagtaggact caaggtggac gtgcgttctg    2580
ccttccttgt taattttgta ataattggag aagatttatg tcagcacaca cttacagagc    2640
acaaatgcag tatataggtg ctggatgtat gtaaatatat tcaaattatg tataaatata    2700
tattatatat ttacaaggag ttatttttg tattgatttt aaatggatgt cccaatgcac    2760
ctagaaaatt ggtctctctt tttttaatag ctatttgcta aatgctgttc ttacacataa    2820
tttcttaatt ttcaccgagc agaggtggaa aaatactttt gctttcaggg aaaatggtat    2880
aacgttaatt tattaataaa ttggtaatat acaaaacaat taatcattta tagttttttt    2940
tgtaatttaa gtggcatttc tatgcaggca gcacagcaga ctagttaatc tattgcttgg    3000
acttaactag ttatcagatc ctttgaaaag agaatattta caatatatga ctaatttggg    3060
gaaaatgaag ttttgattta tttgtgttta aatgctgctg tcagacgatt gttcttagac    3120
ctcctaaatg ccccatatta aaagaactca ttcataggaa ggtgtttcat tttggtgtgc    3180
aaccctgtca ttacgtcaac gcaacgtcta actggacttc ccaagataaa tggtaccagc    3240
gtcctcttaa aagatgcctt aatccattcc ttgaggacag accttagttg aaatgatagc    3300
agaatgtgct tctctctggc agctggcctt ctgcttctga gttgcacatt aatcagatta    3360
gcctgtattc tcttcagtga attttgataa tggcttccag actctttggc gttggagacg    3420
cctgttagga tcttcaagtc ccatcataga aaattgaaac acagagttgt tctgctgata    3480
gttttgggga tacgtccatc ttttaaggg attgctttca tctaattctg gcaggacctc    3540
accaaaagat ccagcctcat acctacatca gacaaaatat cgccgttgtt ccttctgtac    3600
taaagtattg tgttttgctt tggaaacacc cactcacttt gcaatagccg tgcaagatga    3660
atgcagatta cactgatctt atgtgttaca aaattggaga aagtatttaa taaaacctgt    3720
taatttttat actgacaata aaaatgtttc tacagatatt aatgttaaca agacaaaata    3780
aatgtcacgc aacttatttt tttaataaaa aaaaaaaaa a                         3821
```

<210> SEQ ID NO 134

<211> LENGTH: 3708
<212> TYPE: DNA
<213> ORGANISM: Homo sapiens

<400> SEQUENCE: 134

```
aatttgttga ggaatttccc cctagccttg accccttgac agctcccgct cctactcagt     60
gctggggaga agtagggagg ccttaagcga agagatgggt ctgcactttg gaggagccgg    120
acactgttga ctttcctgat gtgaaatcta cccaggaaca aaacaccagt gactgcagca    180
gcagcggcag cgcctcggtt cctgagccca ccgcaggctg aaggcattgc gcgtagtcca    240
tgcccgtaga ggaagtgtgc agatgggatt aacgtccaca tggagatatg aagaggacc    300
ggggattggt accgtaacca tggtcagctg gggtcgtttc atctgcctgg tcgtggtcac    360
catggcaacc ttgtccctgg cccggccctc cttcagttta gttgaggata ccacattaga    420
gccagaagat gccatctcat ccggagatga tgaggatgac accgatggtg cggaagattt    480
tgtcagtgag aacagtaaca acaagagagc accatactgg accaacacag aaaagatgga    540
aaagcggctc catgctgtgc ctgcggccaa cactgtcaag tttcgctgcc cagccggggg    600
gaacccaatg ccaaccatgc ggtggctgaa aaacgggaag gagtttaagc aggagcatcg    660
cattggaggc tacaaggtac gaaaccagca ctggagcctc attatggaaa gtgtggtccc    720
atctgacaag ggaaattata cctgtgtagt ggagaatgaa tacgggtcca tcaatcacac    780
gtaccacctg gatgttgtgg agcgatcgcc tcaccggccc atcctccaag ccggactgcc    840
ggcaaatgcc tccacagtgg tcggaggaga cgtagagttt gtctgcaagg tttacagtga    900
tgcccagccc cacatccagt ggatcaagca cgtggaaaag aacggcagta aatacggggcc    960
cgacgggctg ccctacctca aggttctcaa ggccgccggt gttaacacca cggacaaaga   1020
gattgaggtt ctctatattc ggaatgtaac ttttgaggac gctggggaat atacgtgctt   1080
ggcgggtaat tctattggga tatcctttca ctctgcatgg ttgacagttc tgccagcgcc   1140
tggaagagaa aaggagatta cagcttcccc agactacctg gagatagcca tttactgcat   1200
aggggtcttc ttaatcgcct gtatggtggt aacagtcatc ctgtgccgaa tgaagaacac   1260
gaccaagaag ccagacttca gcagccagcc ggctgtgcac aagctgacca aacgtatccc   1320
cctgcggaga caggtaacag tttcggctga gtccagctcc tccatgaact ccaacacccc   1380
gctggtgagg ataacaacac gcctctcttc aacggcagac cccccatgc tggcaggggt   1440
ctccgagtat gaacttccag aggacccaaa atgggagttt ccaagagata agctgacact   1500
gggcaagccc ctgggagaag gttgctttgg gcaagtggtc atggcggaag cagtgggaat   1560
tgacaaagac aagcccaagg aggcggtcac cgtggccgtg aagatgttga aagatgatgc   1620
cacagagaaa gacctttctg atctggtgtc agagatggag atgatgaaga tgattgggaa   1680
acacaagaat atcataaatc ttcttggagc ctgcacacag gatgggcctc tctatgtcat   1740
agttgagtat gcctctaaag gcaacctccg agaatacctc cgagcccgga ggccaccgg   1800
gatggagtac tcctatgaca ttaaccgtgt tcctgaggag cagatgacct tcaaggactt   1860
ggtgtcatgc acctaccagc tggccagagg catggagtac ttggcttccc aaaaatgtat   1920
tcatcgagat ttagcagcca gaaatgtttt ggtaacagaa acaatgtga tgaaaatagc   1980
agactttgga ctcgccagag atatcaacaa tatagactat tacaaaaaga ccaccaatgg   2040
gcggcttcca gtcaagtgga tggctccaga agccctgttt gatagagtat acactcatca   2100
gagtgatgtc tggtccttcg gggtgttaat gtgggagatc ttcactttag ggggctcgcc   2160
ctacccaggg attcccgtgg aggaactttt taagctgctg aaggaaggac acagaatgga   2220
```

| | |
|---|---|
| taagccagcc aactgcacca acgaactgta catgatgatg agggactgtt ggcatgcagt | 2280 |
| gccctcccag agaccaacgt tcaagcagtt ggtagaagac ttggatcgaa ttctcactct | 2340 |
| cacaaccaat gaggaggaga agaaggtttc tggagcagtg gactgccaca agccaccatg | 2400 |
| taaccctct cacctgccgt gcgtactggc tgtggaccag taggactcaa ggtggacgtg | 2460 |
| cgttctgcct tccttgttaa ttttgtaata attggagaag atttatgtca gcacacactt | 2520 |
| acagagcaca aatgcagtat ataggtgctg gatgtatgta aatatattca aattatgtat | 2580 |
| aaatatatat tatatattta caaggagtta ttttttgtat tgattttaaa tggatgtccc | 2640 |
| aatgcaccta gaaaattggt ctctcttttt ttaatagcta tttgctaaat gctgttctta | 2700 |
| cacataattt cttaattttc accgagcaga ggtggaaaaa tacttttgct ttcagggaaa | 2760 |
| atggtataac gttaatttat taataaattg gtaatataca aaacaattaa tcatttatag | 2820 |
| ttttttttgt aatttaagtg gcatttctat gcaggcagca cagcagacta gttaatctat | 2880 |
| tgcttggact taactagtta tcagatcctt tgaaaagaga atatttacaa tatatgacta | 2940 |
| atttggggaa aatgaagttt tgatttattt gtgtttaaat gctgctgtca gacgattgtt | 3000 |
| cttagacctc ctaaatgccc catattaaaa gaactcattc ataggaaggt gtttcatttt | 3060 |
| ggtgtgcaac cctgtcatta cgtcaacgca acgtctaact ggacttccca agataaatgg | 3120 |
| taccagcgtc ctcttaaaag atgccttaat ccattccttg aggacagacc ttagttgaaa | 3180 |
| tgatagcaga atgtgcttct ctctggcagc tggccttctg cttctgagtt gcacattaat | 3240 |
| cagattagcc tgtattctct tcagtgaatt ttgataatgg cttccagact ctttggcgtt | 3300 |
| ggagacgcct gttaggatct tcaagtccca tcatagaaaa ttgaaacaca gagttgttct | 3360 |
| gctgatagtt tgggatac gtccatcttt taagggatt gctttcatct aattctggca | 3420 |
| ggacctcacc aaaagatcca gcctcatacc tacatcagac aaaatatcgc cgttgttcct | 3480 |
| tctgtactaa agtattgtgt tttgctttgg aaacacccac tcactttgca atagccgtgc | 3540 |
| aagatgaatg cagattacac tgatcttatg tgttacaaaa ttggagaaag tatttaataa | 3600 |
| aacctgttaa ttttttatact gacaataaaa atgtttctac agatattaat gttaacaaga | 3660 |
| caaaataaat gtcacgcaac ttatttttttt aataaaaaaa aaaaaaaa | 3708 |

<210> SEQ ID NO 135
<211> LENGTH: 4103
<212> TYPE: DNA
<213> ORGANISM: Homo sapiens

<400> SEQUENCE: 135

| | |
|---|---|
| gagcacacat tgcctcactg aagtggctgc acgtatctga gtcctgtagc tactgtttta | 60 |
| tctctgtttc ttaaaagtat gcttttaaaa agattagcct cacacatttc tgtggaccgg | 120 |
| tctggtggta tcacctggga ctctgaggtg aggatggaag gatttagcag ataatgaaaa | 180 |
| agaactctgt ttgcgcacat ttgagaggct gaaaaatggt tttatcccac ttgggctgga | 240 |
| gtgatttggc attggggaag attccctgac tcgccaatct cttttccttta gtgactgcag | 300 |
| cagcagcgga agcgcctcgg ttcctgagcc caccgcaggc tgaaggcatt gcgcgtagtc | 360 |
| catgcccgta gaggaagtgt gcagatggga ttaacgtcca catggagata tggaagagga | 420 |
| ccggggattg gtaccgtaac catggtcagc tgggtcgtt tcatctgcct ggtcgtggtc | 480 |
| accatggcaa ccttgtccct ggcccggccc tccttcagtt tagttgagga taccacatta | 540 |
| gagccagaag gagcaccata ctggaccaac acagaaaaga tggaaaagcg gctccatgct | 600 |
| gtgcctgcgg ccaacactgt caagtttcgc tgcccagccg gggggaaccc aatgccaacc | 660 |

-continued

```
atgcggtggc tgaaaaacgg gaaggagttt aagcaggagc atcgcattgg aggctacaag    720
gtacgaaacc agcactggag cctcattatg gaaagtgtgg tcccatctga caagggaaat    780
tatacctgtg tagtggagaa tgaatacggg tccatcaatc acacgtacca cctggatgtt    840
gtggagcgat cgcctcaccg gcccatcctc caagccggac tgccggcaaa tgcctccaca    900
gtggtcggag gagacgtaga gtttgtctgc aaggtttaca gtgatgccca gccccacatc    960
cagtggatca agcacgtgga aaagaacggc agtaaatacg ggcccgacgg gctgccctac   1020
ctcaaggttc tcaaggccgc cggtgttaac accacggaca agagattga ggttctctat    1080 attcggaatg taacttttga ggacgctggg gaatatacgt gcttggcggg taattctatt   1140
gggatatcct ttcactctgc atggttgaca gttctgccag cgcctggaag agaaaaggag   1200
attacagctt ccccagacta cctggagata gccatttact gcatagggt cttcttaatc    1260 gcctgtatgg tggtaacagt catcctgtgc cgaatgaaga acacgaccaa gaagccagac   1320
ttcagcagcc agccggctgt gcacaagctg accaaacgta tccccctgcg agacaggta    1380 acagtttcgg ctgagtccag ctcctccatg aactccaaca ccccgctggt gaggataaca   1440
acacgcctct cttcaacggc agacaccccc atgctggcag gggtctccga gtatgaactt   1500
ccagaggacc caaaatggga gtttccaaga gataagctga cactgggcaa gcccctggga   1560
gaaggttgct ttgggcaagt ggtcatggcg gaagcagtgg gaattgacaa agacaagccc   1620
aaggaggcgg tcaccgtggc cgtgaagatg ttgaaagatg atgccacaga gaaagacctt   1680
tctgatctgg tgtcagagat ggagatgatg aagatgattg ggaaacacaa gaatatcata   1740
aatcttcttg gagcctgcac acaggatggg cctctctatg tcatagttga gtatgcctct   1800
aaaggcaacc tccgagaata cctccgagcc cggaggccac ccgggatgga gtactcctat   1860
gacattaacc gtgttcctga ggagcagatg accttcaagg acttggtgtc atgcacctac   1920
cagctggcca gaggcatgga gtacttggct tcccaaaaat gtattcatcg agatttagca   1980
gccagaaatg ttttggtaac agaaaacaat gtgatgaaaa tagcagactt tggactcgcc   2040
agagatatca acaatataga ctattacaaa aagaccacca tgggcggct tccagtcaag   2100 tggatggctc cagaagccct gtttgataga gtatacactc atcagagtga tgtctggtcc   2160
ttcggggtgt taatgtggga gatcttcact ttagggggct cgccctaccc agggattccc   2220
gtggaggaac tttttaagct gctgaaggaa ggacacagaa tggataagcc agccaactgc   2280
accaacgaac tgtacatgat gatgagggac tgttggcatg cagtgccctc ccagagacca   2340
acgttcaagc agttggtaga agacttggat cgaattctca ctctcacaac caatgaggaa   2400
tacttggacc tcagccaacc tctcgaacag tattcaccta gttaccctga cacaagaagt   2460
tcttgttctt caggagatga ttctgttttt tctccagacc ccatgcctta cgaaccatgc   2520
cttcctcagt atccacacat aaacggcagt gttaaaacat gaatgactgt gtctgcctgt   2580
ccccaaacag gacagcactg gaacctagc tacactgagc agggagacca tgcctcccag   2640
agcttgttgt ctccacttgt atatatggat cagaggagta ataattggaa aaagtaatca   2700
gcatatgtgt aaagatttat acagttgaaa acttgtaatc ttccccagga ggagaagaag   2760
gtttctggag cagtggactg ccacaagcca ccatgtaacc cctctcacct gccgtgcgta   2820
ctggctgtgg accagtagga ctcaaggtgg acgtgcgttc tgccttcctt gttaattttg   2880
taataattgg agaagattta tgtcagcaca cacttacaga gcacaaatgc agtatatagg   2940
tgctggatgt atgtaaatat attcaaatta tgtataaata tatattatat atttacaagg   3000
agttattttt tgtattgatt ttaaatggat gtcccaatgc acctagaaaa ttggtctctc   3060
```

```
tttttttaat agctatttgc taaatgctgt tcttacacat aatttcttaa ttttcaccga    3120
gcagaggtgg aaaaatactt ttgctttcag ggaaaatggt ataacgttaa tttattaata    3180
aattggtaat atacaaaaca attaatcatt tatagttttt tttgtaattt aagtggcatt    3240
tctatgcagg cagcacagca gactagttaa tctattgctt ggacttaact agttatcaga    3300
tcctttgaaa agagaatatt tacaatatat gactaatttg gggaaaatga agttttgatt    3360
tatttgtgtt taaatgctgc tgtcagacga ttgttcttag acctcctaaa tgccccatat    3420
taaaagaact cattcatagg aaggtgtttc attttggtgt gcaaccctgt cattacgtca    3480
acgcaacgtc taactggact tcccaagata aatggtacca gcgtcctctt aaaagatgcc    3540
ttaatccatt ccttgaggac agaccttagt tgaaatgata gcagaatgtg cttctctctg    3600
gcagctggcc ttctgcttct gagttgcaca ttaatcagat tagcctgtat tctcttcagt    3660
gaattttgat aatggcttcc agactctttg gcgttggaga cgcctgttag gatcttcaag    3720
tcccatcata gaaaattgaa acacagagtt gttctgctga tagttttggg gatacgtcca    3780
tctttttaag ggattgcttt catctaattc tggcaggacc tcaccaaaag atccagcctc    3840
atacctacat cagacaaaat atcgccgttg ttccttctgt actaaagtat tgtgttttgc    3900
tttggaaaca cccactcact ttgcaatagc cgtgcaagat gaatgcagat tacactgatc    3960
ttatgtgtta caaaattgga gaaagtattt aataaaacct gttaattttt atactgacaa    4020
taaaaatgtt tctacagata ttaatgttaa caagacaaaa taaatgtcac gcaacttatt    4080
tttttaataa aaaaaaaaaa aaa                                           4103

<210> SEQ ID NO 136
<211> LENGTH: 4306
<212> TYPE: DNA
<213> ORGANISM: Homo sapiens

<400> SEQUENCE: 136
ggcggcggct ggaggagagc gcggtggaga gccgagcggg cgggcggcgg gtgcggagcg      60
ggcgagggag cgcgcgcggc cgccacaaag ctcgggcgcc gcggggctgc atgcggcgta     120
cctgccccgg cgcggcgact gctctccggg ctggcggggg ccggccgcga gccccggggg     180
ccccgaggcc gcagcttgcc tgcgcgctct gagccttcgc aactcgcgag caaagtttgg     240
tggaggcaac gccaagcctg agtcctttct tcctctcgtt ccccaaatcc gagggcagcc     300
cgcgggcgtc atgcccgcgc tcctccgcag cctggggtac gcgtgaagcc cgggaggctt     360
ggcgccggcg aagacccaag gaccactctt ctgcgtttgg agttgctccc cgcaaccccg     420
ggctcgtcgc tttctccatc ccgacccacg cggggcgcgg ggacaacaca ggtcgcggag     480
gagcgttgcc attcaagtga ctgcagcagc agcggcagcg cctcggttcc tgagcccacc     540
gcaggctgaa ggcattgcgc gtagtccatg cccgtagagg aagtgtgcag atgggattaa     600
cgtccacatg gagatatgga agaggaccgg ggattggtac cgtaaccatg gtcagctggg     660
gtcgtttcat ctgcctggtc gtggtcacca tggcaacctt gtccctggcc cggccctcct     720
tcagtttagt tgaggatacc acattagagc cagaagagcc accaaccaaa taccaaatct     780
ctcaaccaga agtgtacgtg gctgcgccag gggagtcgct agaggtgcgc tgcctgttga     840
aagatgccgc cgtgatcagt tggactaagg atgggtgca cttggggccc aacaatagga     900
cagtgcttat tggggagtac ttgcagataa agggcgccac gcctagagac tccggcctct     960
atgcttgtac tgccagtagg actgtagaca gtgaaacttg gtacttcatg gtgaatgtca    1020
cagatgccat ctcatccgga gatgatgagg atgacaccga tggtgcggaa gattttgtca    1080
```

```
gtgagaacag taacaacaag agagcaccat actggaccaa cacagaaaag atggaaaagc    1140
ggctccatgc tgtgcctgcg gccaacactg tcaagtttcg ctgcccagcc gggggggaacc   1200 caatgccaac catgcggtgg ctgaaaaacg ggaaggagtt taagcaggag catcgcattg    1260
gaggctacaa ggtacgaaac cagcactgga gcctcattat ggaaagtgtg gtcccatctg    1320
acaagggaaa ttatacctgt gtagtggaga atgaatacgg gtccatcaat cacacgtacc    1380
acctggatgt tgtggagcga tcgcctcacc ggcccatcct ccaagccgga ctgccggcaa    1440
atgcctccac agtggtcgga ggagacgtag agtttgtctg caaggtttac agtgatgccc    1500
agccccacat ccagtggatc aagcacgtgg aaaagaacgg cagtaaatac gggcccgacg    1560
ggctgcccta cctcaaggtt ctcaaggttt cggctgagtc cagctcctcc atgaactcca    1620
acaccccgct ggtgaggata caacacgcc tctcttcaac ggcagacacc cccatgctgg     1680
caggggtctc cgagtatgaa cttccagagg acccaaaatg ggagtttcca agagataagc    1740
tgacactggg caagcccctg ggagaaggtt gctttgggca agtggtcatg gcggaagcag    1800
tgggaattga caaagacaag cccaaggagg cggtcaccgt ggccgtgaag atgttgaaag    1860
atgatgccac agaaaagac ctttctgatc tggtgtcaga gatggagatg atgaagatga     1920
ttgggaaaca caagaatatc ataaatcttc ttggagcctg cacacaggat gggcctctct    1980
atgtcatagt tgagtatgcc tctaaaggca acctccgaga atacctccga gcccggaggc    2040
cacccgggat ggagtactcc tatgacatta accgtgttcc tgaggagcag atgaccttca    2100
aggacttggt gtcatgcacc taccagctgg ccagaggcat ggagtacttg gcttcccaaa    2160
aatgtattca tcgagattta gcagccagaa atgttttggt aacagaaaac aatgtgatga    2220
aaatagcaga cttggactc gccagagata tcaacaatat agactattac aaaaagacca    2280
ccaatgggcg gcttccagtc aagtggatgg ctccagaagc cctgtttgat agagtataca    2340
ctcatcagag tgatgtctgg tccttcgggg tgttaatgtg ggagatcttc actttagggg    2400
gctcgcccta cccagggatt cccgtggagg aacttttttaa gctgctgaag gaaggacaca    2460
gaatggataa gccagccaac tgcaccaacg aactgtacat gatgatgagg gactgttggc    2520
atgcagtgcc ctcccagaga ccaacgttca agcagttggt agaagacttg gatcgaattc    2580
tcactctcac aaccaatgag gaatacttgg acctcagcca acctctcgaa cagtattcac    2640
ctagttaccc tgcacacaaga agttcttgtt cttcaggaga tgattctgtt ttttctccag    2700
accccatgcc ttacgaacca tgccttcctc agtatccaca cataaacggc agtgttaaaa    2760
catgaatgac tgtgtctgcc tgtccccaaa caggacagca ctgggaacct agctacactg    2820
agcagggaga ccatgcctcc cagagcttgt tgtctccact tgtatatatg gatcagagga    2880
gtaaataatt ggaaaagtaa tcagcatatg tgtaaagatt tatacagttg aaaacttgta    2940
atcttcccca ggaggagaag aaggtttctg gagcagtgga ctgccacaag ccaccatgta    3000
acccctctca cctgccgtgc gtactggctg tggaccagta ggactcaagg tggacgtgcg    3060
ttctgccttc cttgttaatt ttgtaataat tggagaagat ttatgtcagc acacacttac    3120
agagcacaaa tgcagtatat aggtgctgga tgtatgtaaa tatattcaaa ttatgtataa    3180
atatatatta tatatttaca aggagttatt ttttgtattg attttaaatg gatgtcccaa    3240
tgcacctaga aaattggtct ctcttttttt aatagctatt tgctaaatgc tgttcttaca    3300
cataatttct taattttcac cgagcagagg tggaaaaata cttttgcttt cagggaaaat    3360
ggtataacgt taatttatta ataaattggt aatatacaaa acaattaatc atttatagtt    3420
ttttttgtaa tttaagtggc atttctatgc aggcagcaca gcagactagt taatctattg    3480
```

```
cttggactta actagttatc agatcctttg aaaagagaat atttacaata tatgactaat     3540
ttggggaaaa tgaagttttg atttatttgt gtttaaatgc tgctgtcaga cgattgttct     3600
tagacctcct aaatgcccca tattaaaaga actcattcat aggaaggtgt ttcattttgg     3660
tgtgcaaccc tgtcattacg tcaacgcaac gtctaactgg acttcccaag ataaatggta     3720
ccagcgtcct cttaaaagat gccttaatcc attccttgag acagaccttt agttgaaatg     3780
atagcagaat gtgcttctct ctggcagctg gccttctgct tctgagttgc acattaatca     3840
gattagcctg tattctcttc agtgaatttt gataatggct tccagactct ttggcgttgg     3900
agacgcctgt taggatcttc aagtcccatc atagaaaatt gaaacacaga gttgttctgc     3960
tgatagtttt ggggatacgt ccatcttttt aagggattgc tttcatctaa ttctggcagg     4020
acctcaccaa aagatccagc ctcataccta catcagacaa aatatcgccg ttgttccttc     4080
tgtactaaag tattgtgttt tgctttggaa acacccactc actttgcaat agccgtgcaa     4140
gatgaatgca gattacactg atcttatgtg ttacaaaatt ggagaaagta tttaataaaa     4200
cctgttaatt tttatactga caataaaaat gtttctacag atattaatgt taacaagaca     4260
aaataaatgt cacgcaactt attttttttaa taaaaaaaaa aaaaaa                   4306

<210> SEQ ID NO 137
<211> LENGTH: 4303
<212> TYPE: DNA
<213> ORGANISM: Homo sapiens

<400> SEQUENCE: 137
ggcggcggct ggaggagagc gcggtggaga gccgagcggg cgggcggcgg gtgcggagcg       60
ggcgagggag cgcgcgcggc cgccacaaag ctcgggcgcc gcggggctgc atgcggcgta      120 cctgcccgg cgcggcgact gctctccggg ctggcggggg ccggccgcga gccccggggg      180
ccccgaggcc gcagcttgcc tgcgcgctct gagccttcgc aactcgcgag caaagttttgg     240 tggaggcaac gccaagcctg agtcctttct tcctctcgtt ccccaaatcc gagggcagcc      300
cgcgggcgtc atgcccgcgc tcctccgcag cctggggtac gcgtgaagcc cgggaggctt      360
ggcgccggcg aagacccaag gaccactctt ctgcgtttgg agttgctccc cgcaaccccg      420
ggctcgtcgc tttctccatc ccgacccacg cggggcgcgg ggacaacaca ggtcgcggag      480
gagcgttgcc attcaagtga ctgcagcagc agcggcagcg cctcggttcc tgagcccacc      540
gcaggctgaa ggcattgcgc gtagtccatg cccgtagagg aagtgtgcag atgggattaa      600
cgtccacatg gagatatgga agaggaccgg ggattggtac cgtaaccatg gtcagctggg      660
gtcgtttcat ctgcctggtc gtggtcacca tggcaacctt gtccctggcc cggccctcct      720
tcagtttagt tgaggatacc acattagagc cagaaggagc accatactgg accaacacag      780
aaaagatgga aaagcggctc catgctgtgc ctgcggccaa cactgtcaag tttcgctgcc      840
cagccggggg gaacccaatg ccaaccatgc ggtggctgaa aaacgggaag agtttaagc      900 aggagcatcg cattggaggc tacaaggtac gaaaccagca ctggagcctc attatggaaa      960
gtgtggtccc atctgacaag ggaaattata cctgtgtagt ggagaatgaa tacgggtcca     1020
tcaatcacac gtaccacctg gatgttgtgg agcgatcgcc tcaccggccc atcctccaag     1080
ccggactgcc ggcaaatgcc tccacagtgg tcggaggaga cgtagagttt gtctgcaagg     1140
tttacagtga tgcccagccc cacatccagt ggatcaagca cgtggaaaag aacggcagta     1200
aatacgggcc cgacggcctg ccctacctca aggttctcaa ggccgccggt gttaacacca     1260
cggacaaaga gattgaggtt ctctatattc ggaatgtaac ttttgaggac gctggggaat     1320
```

```
atacgtgctt ggcgggtaat tctattggga tatcctttca ctctgcatgg ttgacagttc    1380
tgccagcgcc tggaagagaa aaggagatta cagcttcccc agactacctg agatagcca     1440
tttactgcat aggggtcttc ttaatcgcct gtatggtggt aacagtcatc ctgtgccgaa    1500
tgaagaacac gaccaagaag ccagacttca gcagccagcc ggctgtgcac aagctgacca    1560
aacgtatccc cctgcggaga caggtttcgg ctgagtccag ctcctccatg aactccaaca    1620
ccccgctggt gaggataaca acacgcctct cttcaacggc agacaccccc atgctggcag    1680
gggtctccga gtatgaactt ccagaggacc caaaatggga gtttccaaga gataagctga    1740
cactgggcaa gcccctggga gaaggttgct tgggcaagt ggtcatggcg gaagcagtgg     1800
gaattgacaa agacaagccc aaggaggcgg tcaccgtggc cgtgaagatg ttgaaagatg    1860
atgccacaga gaaagacctt tctgatctgg tgtcagagat ggagatgatg aagatgattg    1920
ggaaacacaa gaatatcata atcttcttg gagcctgcac acaggatggg cctctctatg     1980
tcatagttga gtatgcctct aaaggcaacc tccgagaata cctccgagcc cggaggccac    2040
ccgggatgga gtactcctat gacattaacc gtgttcctga ggagcagatg accttcaagg    2100
acttggtgtc atgcacctac cagctggcca gaggcatgga gtacttggct tcccaaaaat    2160
gtattcatcg agatttagca gccagaaatg ttttggtaac agaaaacaat gtgatgaaaa    2220
tagcagactt tggactcgcc agagatatca acaatataga ctattacaaa aagaccacca    2280
atgggcggct tccagtcaag tggatggctc cagaagccct gtttgataga gtatacactc    2340
atcagagtga tgtctggtcc ttcggggtgt aatgtgggga gatcttcact ttagggggct    2400
cgccctaccc agggattccc gtggaggaac tttttaagct gctgaaggaa ggacacagaa    2460
tggataagcc agccaactgc accaacgaac tgtacatgat gatgagggac tgttggcatg    2520
cagtgccctc ccagagacca acgttcaagc agttggtaga agacttggat cgaattctca    2580
ctctcacaac caatgaggaa tacttggacc tcagccaacc tctcgaacag tattcaccta    2640
gttaccctga cacaagaagt tcttgttctt caggagatga ttctgttttt tctccagacc    2700
ccatgcctta cgaaccatgc cttcctcagt atccacacat aaacggcagt gttaaaacat    2760
gaatgactgt gtctgcctgt ccccaaacag gacagcactg gaacctagc tacactgagc     2820
agggagacca tgcctcccag agcttgttgt ctccacttgt atatatggat cagaggagta    2880
aataattgga aaagtaatca gcatatgtgt aaagatttat acagttgaaa acttgtaatc    2940
ttccccagga ggagaagaag gtttctggag cagtggactg ccacaagcca ccatgtaacc    3000
cctctcacct gccgtgcgta ctggctgtgg accagtagga ctcaaggtgg acgtgcgttc    3060
tgccttcctt gttaattttg taataattgg agaagattta tgtcagcaca cacttacaga    3120
gcacaaatgc agtatatagg tgctggatgt atgtaaatat attcaaatta tgtataaata    3180
tatattatat atttacaagg agttattttt tgtattgatt ttaaatggat gtcccaatgc    3240
acctagaaaa ttggtctctc ttttttttaat agctatttgc taaatgctgt tcttacacat    3300
aatttcttaa ttttcaccga gcagaggtgg aaaaatactt ttgctttcag ggaaaatggt    3360
ataacgttaa tttattaata aattggtaat atacaaaaca attaatcatt tatagttttt    3420
tttgtaattt aagtggcatt tctatgcagg cagcacagca gactagttaa tctattgctt    3480
ggacttaact agttatcaga tccttttgaaa agagaatatt tacaatatat gactaatttg    3540
gggaaaatga agttttgatt tatttgtgtt taaatgctgc tgtcagacga ttgttcttag    3600
acctcctaaa tgccccatat taaaagaact cattcatagg aaggtgtttc attttggtgt    3660
gcaaccctgt cattacgtca acgcaacgtc taactggact tcccaagata aatggtacca    3720
```

```
gcgtcctctt aaaagatgcc ttaatccatt ccttgaggac agaccttagt tgaaatgata     3780
gcagaatgtg cttctctctg gcagctggcc ttctgcttct gagttgcaca ttaatcagat     3840
tagcctgtat tctcttcagt gaattttgat aatggcttcc agactctttg gcgttggaga     3900
cgcctgttag gatcttcaag tcccatcata gaaaattgaa acacagagtt gttctgctga     3960
tagttttggg gatacgtcca tcttttttaag ggattgcttt catctaattc tggcaggacc     4020
tcaccaaaag atccagcctc atacctacat cagacaaaat atcgccgttg ttccttctgt     4080
actaaagtat tgtgttttgc tttggaaaca cccactcact ttgcaatagc cgtgcaagat     4140
gaatgcagat tacactgatc ttatgtgtta caaaattgga gaaagtattt aataaaaacct     4200 gttaattttt atactgacaa taaaaatgtt tctacagata ttaatgttaa caagacaaaa     4260
taaatgtcac gcaacttatt tttttaataa aaaaaaaaaa aaa                      4303
```

<210> SEQ ID NO 138
<211> LENGTH: 3011
<212> TYPE: DNA
<213> ORGANISM: Homo sapiens

<400> SEQUENCE: 138

```
ggcggcggct ggaggagagc gcggtggaga gccgagcggg cgggcggcgg gtgcggagcg       60
ggcgagggag cgcgcgcggc cgccacaaag ctcgggcgcc gcggggctgc atgcggcgta      120
cctggcccgg cgcggcgact gctctccggg ctggcggggg ccggccgcga gccccggggg      180
ccccgaggcc gcagcttgcc tgcgcgctct gagccttcgc aactcgcgag caaagtttgg      240
tggaggcaac gccaagcctg agtcctttct tcctctcgtt ccccaaatcc gagggcagcc      300
cgcgggcgtc atgcccgcgc tcctccgcag cctggggtac gcgtgaagcc cgggaggctt      360
ggcgccggcg aagacccaag gaccactctt ctgcgtttgg agttgctccc cgcaaccccg      420
ggctcgtcgc tttctccatc ccgacccacg cggggcgcgg ggacaacaca ggtcgcggag      480
gagcgttgcc attcaagtga ctgcagcagc agcggcagcg cctcggttcc tgagcccacc      540
gcaggctgaa ggcattgcgc gtagtccatg cccgtagagg aagtgtgcag atgggattaa      600
cgtccacatg gagatatgga agaggaccgg ggattggtac cgtaaccatg gtcagctggg      660
gtcgtttcat ctgcctggtc gtggtcacca tggcaacctt gtccctggcc cggccctcct      720
tcagtttagt tgaggatacc acattagagc cagaagatgc catctcatcc ggagatgatg      780
aggatgacac cgatggtgcg gaagattttg tcagtgagaa cagtaacaac aagagagcac      840
catactggac caacacagaa aagatggaaa agcggctcca tgctgtgcct gcggccaaca      900
ctgtcaagtt tcgctgccca gccgggggga acccaatgcc aaccatgcgg tggctgaaaa      960
acgggaagga gtttaagcag gagcatcgca ttggaggcta caaggtacga aaccagcact     1020
ggagcctcat tatggaaagt gtggtcccat ctgacaaggg aaattatacc tgtgtagtgg     1080
agaatgaata cggttccatc aatcacacgt accaacctgga tgttgtggag cgatcgcctc     1140
accggcccat cctccaagcc ggactgccgg caaatgcctc cacagtggtc ggaggagacg     1200
tagagtttgt ctgcaaggtt tacagtgatg cccagcccca catccagtgg atcaagcacg     1260
tggaaaagaa cggcagtaaa tacgggcccg acggctgcc ctacctcaag gttctcaagc     1320
actcggggat aaatagttcc aatgcagaag tgctggctct gttcaatgtg accgaggcgg     1380
atgctgggga atatatatgt aaggtctcca attatatagg gcaggccaac cagtctgcct     1440
ggctcactgt cctgccaaaa cagcaagcgc tggaagaga aaaggagatt acagcttccc     1500
cagactacct ggagatagcc atttactgca taggggtctt cttaatcgcc tgtatggtgg     1560
```

```
taacagtcat cctgtgccga atgaagaaca cgaccaagaa gccagacttc agcagccagc    1620
cggctgtgca caagctgacc aaacgtatcc ccctgcggag acaggtaaca gtttcggctg    1680
agtccagctc ctccatgaac tccaacaccc cgctggtgag gataacaaca cgcctctctt    1740
caacggcaga caccccatg ctggcagggg tctccgagta tgaacttcca gaggacccaa     1800
aatgggagtt ccaagagat aagctgacac tgggcaagcc cctgggagaa ggttgctttg     1860
ggcaagtggt catggcggaa gcagtgggaa ttgacaaaga caagcccaag gaggcggtca    1920
ccgtggccgt gaagatgttg aaagatgatg ccacagagaa agaccttct gatctggtgt     1980 cagagatgga gatgatgaag atgattggga aacacaagaa tatcataaat cttcttggag    2040
cctgcacaca ggatgggcct ctctatgtca tagttgagta tgcctctaaa ggcaacctcc    2100
gagaatacct ccgagcccgg aggccacccg ggatggagta ctcctatgac attaaccgtg    2160
ttcctgagga gcagatgacc ttcaaggact tggtgtcatg cacctaccag ctggccagag    2220
gcatggagta cttggcttcc caaaaatgta ttcatcgaga tttagcagcc agaaatgttt    2280
tggtaacaga aaacaatgtg atgaaaatag cagactttgg actcgccaga gatatcaaca    2340
atatagacta ttacaaaaag accaccaatg ggcggcttcc agtcaagtgg atggctccag    2400
aagccctgtt tgatagagta tacactcatc agagtgatgt ctggtccttc ggggtgttaa    2460
tgtgggagat cttcactta gggggctcgc cctacccagg gattcccgtg gaggaacttt     2520
ttaagctgct gaaggaagga cacagaatgg ataagccagc caactgcacc aacgaactgt    2580
acatgatgat gagggactgt tggcatgcag tgccctccca gagaccaacg ttcaagcagt    2640
tggtagaaga cttggatcga attctcactc tcacaaccaa tgagatctga agtttatgg     2700 cttcattgag aaactgggaa aagttggtca ggcgcagtgg ctcatgcctg taatcccagc    2760
actttgggag gccgaggcag gcggatcatg aggtcaggag ttccagacca gcctggccaa    2820
catggtgaaa ccctgtctct actaaagata caaaaaatta gccgggcgtg ttggtgtgca    2880
cctgtaatcc cagctactcc gggaggctga ggcaggagaa tcacttgaac cggggaggcg    2940
gaggttgcag tgagccgaga tcatgccatt gcattccagc cttggcgaca gagcgagact    3000
ccgtctcaaa a                                                         3011
```

<210> SEQ ID NO 139
<211> LENGTH: 4286
<212> TYPE: DNA
<213> ORGANISM: Homo sapiens

<400> SEQUENCE: 139

```
gtcgcgggca gctggcgccg cgcggtcctg ctctgccggt cgcacggacg caccggcggg     60
ccgccggccg gagggacggg gcgggagctg ggcccgcgga cagcgagccg gagcgggagc    120
cgcgcgtagc gagccgggct ccggcgctcg ccagtctccc gagcggcgcc cgcctcccgc    180
cggtgcccgc gccgggccgt gggggcagc atgcccgcgc gcgctgcctg aggacgccgc     240
ggcccccgcc cccgccatgg gcgcccctgc ctgcgccctc gcgctctgcg tggccgtggc    300
catcgtggcc ggcgcctcct cggagtcctt ggggacggag cagcgcgtcg tggggcgagc    360
ggcagaagtc ccgggcccag agccggcca gcaggagcag ttggtcttcg gcagcgggga    420
tgctgtggag ctgagctgtc cccgccggg ggtggtccc atgggcccca ctgtctgggt      480
caaggatggc acagggctgg tgccctcgga gcgtgtcctg gtggggcccc agcggctgca    540
ggtgctgaat gcctcccacg aggactccgg ggcctacagc tgccgcagc ggctcacgca     600 gcgcgtactg tgccacttca gtgtgcgggt gacagacgct ccatcctcgg gagatgacga    660
```

-continued

| | |
|---|---|
| agacggggag gacgaggctg aggacacagg tgtggacaca ggggcccctt actggacacg | 720 |
| gcccgagcgg atggacaaga agctgctggc cgtgccggcc gccaacaccg tccgcttccg | 780 |
| ctgcccagcc gctggcaacc ccactccctc catctcctgg ctgaagaacg gcagggagtt | 840 |
| ccgcggcgag caccgcattg gaggcatcaa gctgcggcat cagcagtgga gcctggtcat | 900 |
| ggaaagcgtg gtgccctcgg accgcggcaa ctacacctgc gtcgtggaga caagtttgg | 960 |
| cagcatccgg cagacgtaca cgctggacgt gctggagcgc tccccgcacc ggcccatcct | 1020 |
| gcaggcgggg ctgccggcca accagacggc ggtgctgggc agcgacgtgg agttccactg | 1080 |
| caaggtgtac agtgacgcac agccccacat ccagtggctc aagcacgtgg aggtgaatgg | 1140 |
| cagcaaggtg ggcccggacg gcacaccta cgttaccgtg ctcaagacgg cgggcgctaa | 1200 |
| caccaccgac aaggagctag aggttctctc cttgcacaac gtcacctttg aggacgccgg | 1260 |
| ggagtacacc tgcctggcgg gcaattctat tgggttttct catcactctg cgtggctggt | 1320 |
| ggtgctgcca gccgaggagg agctggtgga ggctgacgag gcgggcagtg tgtatgcagg | 1380 |
| catcctcagc tacggggtgg gcttcttcct gttcatcctg gtggtggcgg ctgtgacgct | 1440 |
| ctgccgcctg cgcagccccc ccaagaaagg cctgggctcc cccaccgtgc acaagatctc | 1500 |
| ccgcttcccg ctcaagcgac aggtgtccct ggagtccaac gcgtccatga gctccaacac | 1560 |
| accactggtg cgcatcgcaa ggctgtcctc aggggagggc cccacgctgg ccaatgtctc | 1620 |
| cgagctcgag ctgcctgccg accccaaatg ggagctgtct cgggcccggc tgaccctggg | 1680 |
| caagccccctt ggggagggct gcttcggcca ggtggtcatg gcggaggcca tcggcattga | 1740 |
| caaggaccgg gccgccaagc ctgtcaccgt agccgtgaag atgctgaaag acgatgccac | 1800 |
| tgacaaggac ctgtcggacc tggtgtctga gatggagatg atgaagatga tcggaaaaca | 1860 |
| caaaaacatc atcaacctgc tgggcgcctg cacgcagggc gggcccctgt acgtgctggt | 1920 |
| ggagtacgcg gccaagggta acctgcggga gttttctgcgg gcgcggcggc ccccgggcct | 1980 |
| ggactactcc ttcgacacct gcaagccgcc cgaggagcag ctcaccttca aggacctggt | 2040 |
| gtcctgtgcc taccaggtgg cccgggggcat ggagtacttg gcctcccaga agtgcatcca | 2100 |
| cagggacctg gctgcccgca atgtgctggt gaccgaggac aacgtgatga agatcgcaga | 2160 |
| cttcgggctg gcccgggacg tgcacaacct cgactactac aagaagacga ccaacggccg | 2220 |
| gctgccgtg aagtggatgg cgcctgaggc cttgtttgac cgagtctaca ctcaccagag | 2280 |
| tgacgtctgg tcctttgggg tcctgctctg ggagatcttc acgctggggg gctcccgta | 2340 |
| ccccggcatc cctgtggagg agctcttcaa gctgctgaag gagggccacc gcatggacaa | 2400 |
| gcccgccaac tgcacacacg acctgtacat gatcatgcgg gagtgctggc atgccgcgcc | 2460 |
| ctcccagagg cccaccttca gcagctggt ggaggacctg gaccgtgtcc ttaccgtgac | 2520 |
| gtccaccgac gagtacctgg acctgtcggc gcctttcgag cagtactccc cgggtggcca | 2580 |
| ggacaccccc agctccagct cctcagggga cgactccgtg tttgcccacg acctgctgcc | 2640 |
| cccggcccca cccagcagtg ggggctcgcg gacgtgaagg gccactggtc cccaacaatg | 2700 |
| tgaggggtcc ctagcagccc accctgctgc tggtgcacag ccactccccg gcatgagact | 2760 |
| cagtgcagat ggagagacag ctacacagag ctttggtctg tgtgtgtgtg tgtgcgtgtg | 2820 |
| tgtgtgtgtg tgtgcacatc cgcgtgtgcc tgtgtgcgtg cgcatcttgc ctccaggtgc | 2880 |
| agaggtaccc tgggtgtccc cgctgctgtg caacggtctc ctgactggtg ctgcagcacc | 2940 |
| gagggggcctt tgttctgggg ggacccagtg cagaatgtaa gtgggcccac ccggtgggac | 3000 |
| ccccgtgggg cagggagctg ggcccgacat ggctccggcc tctgcctttg caccacggga | 3060 |

| | |
|---|---|
| catcacaggg tgggcctcgg cccctcccac acccaaagct gagcctgcag ggaagcccca | 3120 |
| catgtccagc accttgtgcc tggggtgtta gtggcaccgc ctccccacct ccaggctttc | 3180 |
| ccacttccca ccctgcccct cagagactga aattacgggt acctgaagat gggagccttt | 3240 |
| acctttatg caaaaggttt attccggaaa ctagtgtaca tttctataaa tagatgctgt | 3300 |
| gtatatggta tatatacata tatatatata acatatatgg aagaggaaaa ggctggtaca | 3360 |
| acggaggcct cgcaccctgg gggcacagga ggcaggcatg ccctgggcg gggcgtgggg | 3420 |
| gggcgtggag ggaggcccca gggggtctca cccatgcaag cagaggacca gggccttttc | 3480 |
| tggcaccgca gttttgtttt aaaactggac ctgtatattt gtaaagctat ttatgggccc | 3540 |
| ctggcactct tgttcccaca ccccaacact tccagcattt agctggccac atggcggaga | 3600 |
| gttttaattt ttaacttatt gacaaccgag aaggtttatc cgccgatag agggacggcc | 3660 |
| aagaatgtac gtccagcctg ccccggagct ggaggatccc ctccaagcct aaaaggttgt | 3720 |
| taatagttgg aggtgattcc agtgaagata tttatttcc tttgtccttt ttcaggagaa | 3780 |
| ttagatttct ataggatttt tctttaggag atttatttttt tggacttcaa agcaagctgg | 3840 |
| tattttcata caaattcttc taattgctgt gtgtcccagg cagggagacg gtttccaggg | 3900 |
| aggggccggc cctgtgtgca ggttccgatg ttattagatg ttacaagttt atatatatct | 3960 |
| atatatataa tttattgagt ttttacaaga tgtatttgtt gtagacttaa cacttcttac | 4020 |
| gcaatgcttc tagagtttta tagcctggac tgctaccttt caaagcttgg agggaagccg | 4080 |
| tgaattcagt tggttcgttc tgtactgtta ctgggccctg agtctgggca gctgtccctt | 4140 |
| gcttgcctgc agggccatgg ctcagggtgg tctcttcttg gggcccagtg catggtggcc | 4200 |
| agaggtgtca cccaaaccgg caggtgcgat tttgttaacc cagcgacgaa ctttccgaaa | 4260 |
| aataaagaca cctggttgct aacctg | 4286 |

<210> SEQ ID NO 140
<211> LENGTH: 3950
<212> TYPE: DNA
<213> ORGANISM: Homo sapiens

<400> SEQUENCE: 140

| | |
|---|---|
| gtcgcgggca gctggcgccg cgcggtcctg ctctgccggt cgcacggacg caccggcggg | 60 |
| ccgccggccg gagggacggg gcgggagctg ggcccgcgga cagcgagccg gagcgggagc | 120 |
| cgcgcgtagc gagccgggct ccggcgctcg ccagtctccc gagcggcgcc cgcctcccgc | 180 |
| cggtgcccgc gccgggccgt gggggggcagc atgcccgcgc gcgctgcctg aggacgccgc | 240 |
| ggccccccgcc cccgccatgg gcgcccctgc ctgcgccctc gcgctctgcg tggccgtggc | 300 |
| catcgtggcc ggcgcctcct cggagtcctt ggggacggag cagcgcgtcg tggggcgagc | 360 |
| ggcagaagtc ccgggcccag agcccggcca gcaggagcag ttggtcttcg gcagcgggga | 420 |
| tgctgtggag ctgagctgtc cccgcccggg ggtggtccc atgggcccca ctgtctgggt | 480 |
| caaggatggc acagggctgg tgccctcgga gcgtgtcctg gtggggcccc agcggctgca | 540 |
| ggtgctgaat gcctcccacg aggactccgg ggcctacagc tgccgcagc ggctcacgca | 600 |
| gcgcgtactg tgccacttca gtgtgcgggt gacagacgct ccatcctcgg gagatgacga | 660 |
| agacggggag gacgaggctg aggacacagg tgtggacaca ggggccccctt actgggacacg | 720 |
| gcccgagcgg atggacaaga agctgctggc cgtgccggcc gccaacaccg tccgcttccg | 780 |
| ctgcccagcc gctggcaacc ccactccctc catctcctgg ctgaagaacg cagggagtt | 840 |
| ccgcggcgag caccgcattg gaggcatcaa gctgcgcat cagcagtgga gcctggtcat | 900 |

-continued

```
ggaaagcgtg gtgccctcgg accgcggcaa ctacacctgc gtcgtggaga acaagtttgg      960
cagcatccgg cagacgtaca cgctggacgt gctggagcgc tccccgcacc ggcccatcct     1020
gcaggcgggg ctgccggcca accagacggc ggtgctgggc agcgacgtgg agttccactg     1080
caaggtgtac agtgacgcac agccccacat ccagtggctc aagcacgtgg aggtgaatgg     1140
cagcaaggtg ggcccggacg gcacaccctg cgttaccgtg ctcaaggtgt ccctggagtc     1200
caacgcgtcc atgagctcca acacaccact ggtgcgcatc gcaaggctgt cctcagggga     1260
gggccccacg ctggccaatg tctccgagct cgagctgcct gccgacccca aatgggagct     1320
gtctcgggcc cggctgaccc tgggcaagcc ccttggggag ggctgcttcg gccaggtggt     1380
catggcggag gccatcggca ttgacaagga ccgggccgcc aagcctgtca ccgtagccgt     1440
gaagatgctg aaagacgatg ccactgacaa ggacctgtcg gacctggtgt ctgagatgga     1500
gatgatgaag atgatcggga acacaaaaaa catcatcaac ctgctgggcg cctgcacgca     1560
gggcgggccc ctgtacgtgc tggtggagta cgccggcaag ggtaacctgc gggagtttct     1620
gcgggcgcgg cggccccogg gcctggacta ctccttcgac acctgcaagc cgcccgagga     1680
gcagctcacc ttcaaggacc tggtgtcctg tgcctaccag gtggcccggg gcatggagta     1740
cttggcctcc cagaagtgca tccacaggga cctggctgcc cgcaatgtgc tggtgaccga     1800
ggacaacgtg atgaagatcg cagacttcgg gctggcccgg gacgtgcaca acctcgacta     1860
ctacaagaag acgaccaacg gccggctgcc cgtgaagtgg atggcgcctg aggccttgtt     1920
tgaccgagtc tacactcacc agagtgacgt ctggtccttt ggggtcctgc tctgggagat     1980
cttcacgctg gggggctccc cgtacccogg catccctgtg gaggagctct tcaagctgct     2040
gaaggagggc caccgcatgg acaagcccgc caactgcaca cacgacctgt acatgatcat     2100
gcgggagtgc tggcatgccg cgccctccca gaggcccacc ttcaagcagc tggtggagga     2160
cctggaccgt gtccttaccg tgacgtccac cgacgagtac ctggacctgt cggcgccttt     2220
cgagcagtac tccccggggtg ccaggacac ccccagctcc agctcctcag ggacgactc     2280
cgtgttgcc cacgacctgc tgcccccggc cccacccagc agtggggct cgcggacgtg     2340
aagggccact ggtccccaac aatgtgaggg gtccctagca gcccaccctg ctgctggtgc     2400
acagccactc cccggcatga gactcagtgc agatggagag acagctacac agagctttgg     2460
tctgtgtgtg tgtgtgtgcg tgtgtgtgtg tgtgtgtgca catccgcgtg tgcctgtgtg     2520
cgtgcgcatc ttgcctccag gtgcagaggt accctgggtg tccccgctgc tgtgcaacgg     2580
tctcctgact ggtgctgcag caccgagggg cctttgttct ggggggaccc agtgcagaat     2640
gtaagtgggc ccaccggtg ggaccccgt ggggcaggga gctgggcccg acatggctcc     2700
ggcctctgcc tttgcaccac gggacatcac agggtgggcc tcggcccctc ccacacccaa     2760
agctgagcct gcaggggaagc cccacatgtc cagcaccttg tgcctggggt gttagtggca     2820
ccgcctcccc acctccaggc tttcccactt cccaccctgc ccctcagaga ctgaaattac     2880
gggtacctga agatgggagc ctttaccttt tatgcaaaag gtttattccg gaaactagtg     2940
tacatttcta taaatagatg ctgtgtatat ggtatatata catatatata taacatat       3000
atggaagagg aaaaggctgg tacaacggag gcctgcgacc ctggggcac aggaggcagg     3060
catggccctg ggcggggcgt ggggggggcgt ggagggaggc cccaggggt ctcacccatg      3120
caagcagagg accagggcct tttctggcac cgcagttttg ttttaaaact ggacctgtat     3180
atttgtaaag ctatttatgg gccctggca ctcttgttcc cacaccccaa cacttccagc      3240
atttagctgg ccacatggcg gagagtttta atttttaact tattgacaac cgagaaggtt     3300
```

| | |
|---|---|
| tatcccgccg atagagggac ggccaagaat gtacgtccag cctgccccgg agctggagga | 3360 |
| tcccctccaa gcctaaaagg ttgttaatag ttggaggtga ttccagtgaa gatattttat | 3420 |
| ttcctttgtc cttttcagg agaattagat ttctatagga tttttcttta ggagatttat | 3480 |
| tttttggact tcaaagcaag ctggtatttt catacaaatt cttctaattg ctgtgtgtcc | 3540 |
| caggcaggga gacggtttcc agggagggc cggccctgtg tgcaggttcc gatgttatta | 3600 |
| gatgttacaa gtttatatat atctatatat ataatttatt gagtttttac aagatgtatt | 3660 |
| tgttgtagac ttaacacttc ttacgcaatg cttctagagt tttatagcct ggactgctac | 3720 |
| cttttcaaagc ttggagggaa gccgtgaatt cagttggttc gttctgtact gttactgggc | 3780 |
| cctgagtctg ggcagctgtc ccttgcttgc ctgcagggcc atggctcagg tggtctctt | 3840 |
| cttgggccc agtgcatggt ggccagaggt gtcacccaaa ccggcaggtg cgattttgtt | 3900 |
| aacccagcga cgaactttcc gaaaaataaa gacacctggt tgctaacctg | 3950 |

<210> SEQ ID NO 141
<211> LENGTH: 2085
<212> TYPE: DNA
<213> ORGANISM: Homo sapiens

<400> SEQUENCE: 141

| | |
|---|---|
| atgggcgccc ctgcctgcgc cctcgcgctc tgcgtggccg tggccatcgt ggccggcgcc | 60 |
| tcctcggagt ccttggggac ggagcagcgc gtcgtggggc gagcggcaga agtcccgggc | 120 |
| ccagagcccg gccagcagga gcagttggtc ttcggcagcg gggatgctgt ggagctgagc | 180 |
| tgtccccgc ccggggtgg tcccatgggg cccactgtct gggtcaagga tggcacaggg | 240 |
| ctggtgccct cggagcgtgt cctggtgggg cccagcggc tgcaggtgct gaatgcctcc | 300 |
| cacgaggact ccggggccta cagctgccgg cagcggctca cgcagcgcgt actgtgccac | 360 |
| ttcagtgtgc gggtgacaga cgctccatcc tcgggagatg acgaagacgg ggaggacgag | 420 |
| gctgaggaca caggtgtgga cacaggggcc ccttactgga cacggcccga gcggatggac | 480 |
| aagaagctgc tggccgtgcc ggccgccaac accgtccgct tccgctgccc agccgctggc | 540 |
| aaccccactc cctccatctc ctggctgaag aacggcaggg agttccgcgg cgagcaccgc | 600 |
| attggaggca tcaagctgcg gcatcagcag tggagcctgg tcatggaaag cgtggtgccc | 660 |
| tcggaccgcg gcaactacac ctgcgtcgtg gagaacaagt ttggcagcat ccggcagacg | 720 |
| tacacgctgg acgtgctgga gcgctccccg caccggccca tcctgcaggc ggggctgccg | 780 |
| gccaaccaga cggcggtgct gggcagcgac gtggagttcc actgcaaggt gtacagtgac | 840 |
| gcacagcccc acatccagtg gctcaagcac gtggaggtga acggcagcaa ggtgggcccg | 900 |
| gacggcacac cctacgttac cgtgctcaag gtgtccctgg agtccaacgc gtccatgagc | 960 |
| tccaacacac cactggtgcg catcgcaagg ctgtcctcag ggagggccc cacgctggcc | 1020 |
| aatgtctccg agctcgagct gcctgccgac cccaaatggg agctgtctcg ggcccggctg | 1080 |
| accctgggca agcccctgg ggagggctgc ttcggccagg tggtcatggc ggaggccatc | 1140 |
| ggcattgaca ggaccggc cgccaagcct gtcaccgtag ccgtgaagat gctgaaagac | 1200 |
| gatgccactg acaaggacct gtcggacctg gtgtctgaga tggagatgat gaagatgatc | 1260 |
| gggaaacaca aaaacatcat caacctgctg ggcgcctgca cgcagggcgg gcccctgtac | 1320 |
| gtgctggtgg agtacgcggc caagggtaac ctgcgggagt ttctgcgggc gcggcggccc | 1380 |
| ccgggcctgg actactcctt cgacacctgc aagccgcccg aggagcagct cacccttcaag | 1440 |
| gacctggtgt cctgtgccta ccaggtggcc cggggcatgg agtacttggc ctcccagaag | 1500 |

| | |
|---|---|
| tgcatccaca gggacctggc tgcccgcaat gtgctggtga ccgaggacaa cgtgatgaag | 1560 |
| atcgcagact tcgggctggc ccgggacgtg cacaacctcg actactacaa gaagacaacc | 1620 |
| aacggccggc tgcccgtgaa gtggatggcg cctgaggcct tgtttgaccg agtctacact | 1680 |
| caccagagtg acgtctggtc ctttggggtc ctgctctggg agatcttcac gctgggggc | 1740 |
| tccccgtacc ccggcatccc tgtggaggag ctcttcaagc tgctgaagga gggccaccgc | 1800 |
| atggacaagc ccgccaactg cacacacgac ctgtacatga tcatgcggga gtgctggcat | 1860 |
| gccgcgccct cccagaggcc caccttcaag cagctggtgg aggacctgga ccgtgtcctt | 1920 |
| accgtgacgt ccaccgacga gtacctggac ctgtcggcgc ctttcgagca gtactccccg | 1980 |
| ggtggccagg acaccccag ctccagctcc tcaggggacg actccgtgtt tgcccacgac | 2040 |
| ctgctgcccc cggccccacc cagcagtggg ggctcgcgga cgtga | 2085 |

<210> SEQ ID NO 142
<211> LENGTH: 4431
<212> TYPE: DNA
<213> ORGANISM: Homo sapiens

<400> SEQUENCE: 142

| | |
|---|---|
| aggcggggct ggagtggtgg aagggggtg gcaggtctgc attgccgctt ccctggtgcc | 60 |
| gggagcagtc gccgctgccg cctccgcccg cggccgggac cccgtcctc gcccgggact | 120 |
| ccttacccgg ggaacctaga ccaggtctcc agaggcttgt ggaagagaag caggcgaccc | 180 |
| ttcctgagtt atcctggctt agcctcccaa tctggctccc cttcccttc ccattcccct | 240 |
| gctcccctg tcccttcccc atccacccaa ctgaactggg tataggtcaa agctcctctc | 300 |
| tttccttttc cttcctaggc actcattggc taggacctgt ttgctctttt ttttgtgccc | 360 |
| agagatactg gaacacgctt catctaagta actgtgggga ggggtctttt tgactctaca | 420 |
| agtccttgag caaaaagctg aaaaagaagc aggaggtgga gaagacccag tgaagtgccc | 480 |
| caagccccat catggaagag ggcttccgag accgggcagc tttcatccgt ggggccaaag | 540 |
| acattgctaa ggaagtcaaa aagcatgcgg ccaagaaggt ggtgaagggc ctggacagag | 600 |
| tccaggacga atattcccga agatcgtact cccgctttga ggaggaggat gatgatgatg | 660 |
| acttccctgc tcccagtgat ggttattacc gaggagaagg gacccaggat gaggaggaag | 720 |
| gtggtgcatc cagtgatgct actgagggcc atgacgagga tgatgagatc tatgaagggg | 780 |
| aatatcaggg cattccccgg gcagagtctg ggggcaaagg cgagcggatg gcagatgggg | 840 |
| cgcccctggc tggagtaagg gggggcttga gtgatgggga gggtccccct ggggccgggg | 900 |
| gggaggcaca acgacggaaa gaacgagaag aactggccca acagtatgaa gccatcctac | 960 |
| gggagtgtgg ccacgccgc ttccagtgga cactgtattt tgtgcttggt ctggcgctga | 1020 |
| tggctgacgg tgtggaggtc tttgtggtgg gcttcgtgct gcccagcgct gagaaagaca | 1080 |
| tgtgcctgtc cgactccaac aaaggcatgc taggcctcat cgtctacctg gcatgatgg | 1140 |
| tgggagcctt cctctgggga ggtctggctg accggctggg tcggaggcag tgtctgctca | 1200 |
| tctcgctctc agtcaacagc gtcttcgcct tcttctcatc ttttgtccag ggttacggca | 1260 |
| cttttcctctt ctgccgccta ctttctgggg ttgggattgg agggtccatc cccattgtct | 1320 |
| tctcctatt ctccgagttt ctggcccagg agaaacgagg ggagcatttg agctggctct | 1380 |
| gcatgttttg gatgattggt ggcgtgtacg cagctgctat ggcctgggcc atcatccccc | 1440 |
| actatgggtg gagttttcag atgggttctg cctaccagtt ccacagctgg agggtcttcg | 1500 |
| tcctcgtctg cgcctttcct tctgtgtttg ccattggggc tctgaccacg cagcctgaga | 1560 |

```
gcccccgttt cttcctagag aatggaaagc atgatgaggc ctggatggtg ctgaagcagg    1620
tccatgatac caacatgcga gccaaaggac atcctgagcg agtgttctca gtaacccaca    1680
ttaagacgat tcatcaggag gatgaattga ttgagatcca gtcggacaca gggacctggt    1740
accagcgctg gggggtccgg gccttgagcc taggggggca ggtttggggg aattttctct    1800
cctgttttgg tcccgaatat cggcgcatca ctctgatgat gatgggtgtg tggttcacca    1860
tgtcattcag ctactatggc ctgaccgtct ggtttcctga catgatccgc catctccagg    1920
cagtggacta cgcatcccgc accaaagtgt tccccgggga gcgcgtagag catgtaactt    1980
ttaacttcac gttggagaat cagatccacc gaggcgggca gtacttcaat gacaagttca    2040
ttgggctgcg gctcaagtca gtgtcctttg aggattccct gtttgaagag tgttattttg    2100
aggatgtcac atccagcaac acgttttccc gcaactgcac attcatcaac actgtgttct    2160
ataacactga cctgttcgag tacaagtttg tgaacagccg tctgataaac agtacattcc    2220
tgcacaacaa ggagggctgc ccgctagacg tgacagggac gggcgaaggt gcctacatgg    2280
tatactttgt gagcttcctg gggacactgg cagtgcttcc tgggaatatc gtgtctgccc    2340
tgctcatgga caagatcggc aggctcagaa tgcttgctgg ctccagcgtg atgtcctgtg    2400
tctcctgctt cttcctgtct tttgggaaca gtgagtcggc catgatcgct ctgctctgcc    2460
tttttggcgg ggtcagcatt gcatcctgga atgcgctgga cgtgttgact gttgaactct    2520
accccctcaga caagaggacc acagcttttg gcttcctgaa tgccctgtgt aagctggcag    2580
ctgtgctggg gatcagcatc ttcacatcct tcgtgggaat caccaaggct gcacccatcc    2640
tctttgcctc agctgcccft gcccttggca gctctctggc cctgaagctg cctgagaccc    2700
ggggcaggt gctgcagtga agggtctct agggctttgg gattggcagg cacactgtga    2760
gaccaacaac tccttccttc ccctccctgc cctgccatcc tgacctccag agccctcact    2820
ccccactccc cgtgtttggt gtcttagctg tgtgtgcgtg tgcgtgtgca tgtgtgtaaa    2880
cccgtgggc agggactaca gggaaggctc cttcatccca gttttgagat gaagctgtac    2940
tccccatttc ccactgccct tgactttgca caagagaagg ctgagcccca tccttctccc    3000
cctgttagag aggggccctt gcttccctgt tccaggggtt ccagaatagg cttcctgcct    3060
tccccatcat tccctctgcc taggccctgg tgaaaccaca ggtatgcaat tatgctaggg    3120
gctgggctc tggtgtagac catggaccaa agaacttct tagagtctga agagtgggcc    3180
tcgggtgccc tctcacatct cctgttggat gctgggggag aagcaataaa cctcagccct    3240
ctggcctcca ctttcctctc aatttgggct gcaaatatga agcctgaatt ttatgaaatt    3300
agctttctga ttcttattta ttaatagatt aagttctgag gcagctccgc aggactgtgt    3360
gtgaatgtgt atgtatactt acatatgtgt gtgcatgtgc catggggcgg ggggtatcac    3420
tatactgtcc tcaaatataa gccaagggta atttcagcgg atgcacacac aaccctgcct    3480
cccacagttc ctcccctaat ctggtttctg tgttgagcct gggatggagg agccctaggc    3540
cagcctggga taagagtccc acagtctagg gagatctgag ggcatccgac aaggcccatc    3600
tccttccctc ctcaagaagc agaggcctcc tctggagtga gaggctccac ccactacagc    3660
acaggcggga atagcacagc tgccctccca tgctccctac ctgtcccctc acagggaggg    3720
gagcagggga gggaaagaaa ccaggcatct ggtcaaacca gcagatcaaa aagcacaaag    3780
agctggggca gaggcaggaa gcagggccc tcctggcagc tcctctgagt ggggagaggt    3840
tgggcagtga gtgagggacc cctaatgcag ggactagaag cctcagtttc cccattttac    3900
ccttccacac aatagcctct gtaggttagg ctgccccatc ccaccctact ctgtgtggct    3960
```

| | | | |
|---|---|---|---|
| gctttctttg | gtgccctccc | ctcacccac tgtagctgtg acgtgttgta gtttttagat | 4020 |
| gtttgtaaaa | tgtttaaaaa | aatgttaaaa ggaaaaaagt gaaaataaca aaaagaaaa | 4080 |
| tcaaaattca | ccttcgtcat | gctgcgtcca gtgccccaac cctgtggtca ctctccccat | 4140 |
| tttgtaacac | tgtaccaggt | ggtgactgtt taactctttg gtgtctgtgc tcaaaagact | 4200 |
| gccttctcca | gtgcccagtg | tatgagtgtg tgccctgtgc ccttgtccct cactccccac | 4260 |
| atgctggacg | tagccctctt | cctcgcaccc ctgggaggga cccatccatc tcccttgctc | 4320 |
| tcctggggaa | ccctaaaccc | aactctgttg atgtgaaaaa tgcagtgaaa aatattgacg | 4380 |
| aaaaataaaa | cggaaacaaa | tcctcaaaat acaaaaaaaa aaaaaaaaaa a | 4431 |

<210> SEQ ID NO 143
<211> LENGTH: 5311
<212> TYPE: DNA
<213> ORGANISM: Homo sapiens

<400> SEQUENCE: 143

| | | | |
|---|---|---|---|
| agcataacct | tcggtggcag | gacaaatcag gccagcacgc agtctgccaa gtcctgctcg | 60 |
| ctccctgtca | agaaaaacag | ctggatccat ttctaatcaa cacttcccaa cgcaacactt | 120 |
| ctgagtctct | gaaggagacc | agagcttgaa actttccaga cttccaacag acatcgagtg | 180 |
| caaaaggata | tttaggttgt | cttttgcacaa atctggttga tttgagagat aaaggggggg | 240 |
| ggaaccagtg | tgactttcac | ctaagaagtc acatgaacat atttcacatt tgaactacat | 300 |
| aatgaatgat | ggttattgaa | atagcccaaa cctctaccac agagcgaggg atatagctca | 360 |
| aggggcaacc | aggcagtcgc | agaaccaagg aatggatgac tacaagtatc aggacaatta | 420 |
| tgggggctat | gctcccagtg | atggctatta ccgcggcaat gagtccaacc cagaagaaga | 480 |
| tgcacagagt | gatgtcaccg | aaggccatga tgaggaagac gagatctatg agggcgagta | 540 |
| ccagggtatc | cctcacccag | atgatgtcaa ggccaagcag gccaagatgg cgccctccag | 600 |
| aatgacagc | cttcggggcc | agacagacct gatggctgag aggctggaag atgaggagca | 660 |
| gttggcccac | cagtacgaga | ccatcatgga tgagtgtggc catggccgct tccagtggat | 720 |
| cctcttttc | gtcttgggtt | tggccctgat ggccgatggg gtggaagtgt tcgtggtgag | 780 |
| ttttgccctg | cccagtgcag | agaaggacat gtgtctgtcc agttccaaaa aggaatgct | 840 |
| agggatgata | gtctacttgg | gaatgatggc gggcgccttc atcctgggag gcctggctga | 900 |
| taagctggga | aggaagcgag | tcctcagcat gtctctggcc gtcaatgcct ccttcgcctc | 960 |
| cctctcttcc | ttcgtgcagg | gatatggagc cttcctcttc tgccgactca tctcaggcat | 1020 |
| cggtattggg | ggtgctctac | cgattgtttt tgcctatttt tctgaattct tgtctcggga | 1080 |
| gaagcgagga | gaacacctca | gttggctggg catcttctgg atgactgggg gcctgtacgc | 1140 |
| atctgccatg | gcctggagca | tcatcccaca ctatggctgg ggcttcagca tggggaccaa | 1200 |
| ttaccacttc | catagctgga | gagtgttttgt catcgtctgt gctctgccct gcaccgtgtc | 1260 |
| catggtggcc | ctgaagttca | tgccagagag cccaaggttt ctgctagaga tgggcaaaca | 1320 |
| tgatgaagcc | tggatgattc | tcaagcaagt ccatgacacc aacatgagag ctaagggggac | 1380 |
| cccagagaaa | gtgttcacgg | tttccaacat caaaactccc aagcaaatgg atgaattcat | 1440 |
| tgagatccaa | agttcaacag | gaacctggta ccagcgctgg ctggtcagat tcaagaccat | 1500 |
| tttcaagcag | gtctgggata | tgcccctgta ctgtgtgatg gggcctaca gaatgaatac | 1560 |
| actgattctg | gccgtggttt | ggtttgccat ggcattcagt tactatggac tgacagtttg | 1620 |
| gtttcctgat | atgatccgct | attttcaaga tgaagaatac aagtctaaaa tgaaggtgtt | 1680 |

```
tttggtgag catgtgtacg gcgccacaat caacttcacg atggaaaatc agatccacca    1740
acatgggaaa cttgtgaatg ataagttcac aagaatgtac tttaaacatg tactctttga    1800
ggacacattc tttgacgagt gctattttga agacgtaaca tcaacagata cctacttcaa    1860
aaattgtacc attgaatcaa ccatctttta caacacagac ctctacgagc acaagttcat    1920
caactgtcgg tttatcaact ccaccttcct ggagcagaag agggctgcc  acatggactt    1980 ggagcaagat aatgacttcc tgatttacct cgtcagcttc ctgggcagcc tgtctgtctt    2040
acccgggaac atcatttctg ccctgctcat ggatagaatt ggaaggctca agatgattgg    2100
tggctccatg ctaatctctg cagtctgctg cttcttcctg ttttttggca acagtgagtc    2160
tgcaatgatc ggctggcagt gcctgttctg tgggacaagc attgcagcct ggaatgctct    2220
ggatgtgatc acagtggagc tgtatcccac caaccagaga gcaacagcct tcggcattct    2280
caatggatta tgcaaatttg gcgccatcct gggaaacacc atctttgctt cttttgttgg    2340
gataaccaaa gtggtcccca tccttctggc tgctgcttct ctggttgggg gtggcctgat    2400
tgcccttcga ctgccagaga ctcgagaaca ggtcctgatg tgaacaacct atgggaaaag    2460
gaaaggtcga gagaatcttg tccaggacac tgaaatgcat ccacacttcc tgcctatcac    2520
ggtccggagg acaccttgga tagcacggga ggagaagttg actttgtgac ccctagttta    2580
ggacccactt cagctgtcaa tatgtttgta actcaggtga ctgatttggg ggtgccctga    2640
gccaccctta gaatcacaga gctgcgtgtt aacttcaag  tcttcccagt ccaaggcagg    2700
gagaggattc tccagtgagt gcacacacta tgcgaggagc aagcatttct ctaagtcaag    2760
tgcaaggact taacttgcgt ttgaaaagga attagagggt cagaaacacc caggttcctc    2820
cagaaagctc cttggagccc aacaacttaa caaatcaact tggctggaag ttagagtcat    2880
tatatgaaga ttgggcttga agtatatatt tttgcattta aaagtatcac ctatcatatt    2940
ttccactcga aaattgacat agtagcattg aggatactct gatctagaaa gccaagtatt    3000
tgagcaacat ctatagagat ctactttct  cctatgtctc ctaggctttc catgataatt    3060
aggtaataca tttaagaagg atatttattt ctgttttgct ctattcaaag aaacggaatg    3120
ggatagttat tctgtaaact aagtttgtat ataactttat ttgggtttaa tttccacaac    3180
tggtatctgc aaatattgcc agcatttag  ccatattttg ggagaacttg gtgtttgagg    3240
tcccaggaaa tgaggtctga tcaaatgaaa tgcaagcaca atttcttaca gcctttaac     3300 tttctgttgg gaggatgaat taacaaactc acattgtgca gtctgcttaa tccaggcact    3360 tttcttttgtg caggtgtagt gagtagttac ttctctccct tacacagatg acttgtgaaa    3420
ctcaagctca ccatcttcag tgctggcatt ttactttgcc actacccaaa aacaatgtga    3480
gatgtgttca gtgcctctg  gtactctttg caggcaagaa tcaaacaaca tggggactga    3540
gggaaggatg gggaagtgta gccacagttc ttccaaatgt aaatacttt  tgtttgttct    3600 agtggtaaaa tgcaaatgca atccatattt gttaggatgg tcaggtctca tgagaaatct    3660
atgctatgtg tccagagctt ttgaaacaga gtccattgga gtgggagtta gggagtgtag    3720
tggatgccaa atatgttttt cttcagtgct taagagaact gtttcctgaa gtccagcttt    3780
gaacataaac aggggtgtgg gttggggggag gagcttagga caaacctctc tgatgaaggt    3840
cagcaataga ctgaagtctt gactgcatgg aagaggaaaa acatcagaac tgtctgacaa    3900 tggagggggac agtgagctac gcacaactgc cagcggaggt gaacttgcac ctgcccaggc    3960
cggatgaaca tcagcctgca agaactagtt gtttgagttg atttgcagtg ctctcaatgg    4020
gcaagtgcca cattttccct ggcagagatc tccaaaaatt taaaacagaa taataatggc    4080
```

```
tatatcgagt gttttctcag tattggagaa atgcttaggt cctatgatag cttcgggaca    4140
tctttctgta attttcctca attaacgggt tggtaggggaa aaatcttatg acacctttcc    4200
accgtcgatt tgagatcagt tttaatggtt aaaatgttta ctctccttct gtcaaccctc    4260 accttttttat ttacaccccct cccttttttt ctgtacaggg agagaagaca tattgactct    4320
gactggacac cctgattcct ccaaatatat ataccactgt gtattaatct ttctctcagt    4380
gttttatagg agtactaaca tttattgctc tgtcaataat gaaaggctcg atgtaatata    4440
gctgtaattt actttccata tgaatacagt ggctaggttc ataaaagaga attgtgtgag    4500
tctgggatta ccacatctaa aacattattc tttaatggga taatacaatt cattgagcag    4560
ctaccactta aaaaacttgc aggacagtta gagcctgcat ttctagttaa gatggatctt    4620
gtaaatttaa aattggatta acattggagt gctggggtgg ctgcaataat ttgggggcta    4680
actccatttg gtttccaaga tctcacttct gcattatctt tatggctctt taaaccagcc    4740
acctagccaa tcaagggcaa ttcccatctc atccatcact caggtctttg taaagggtgc    4800
agccaagctc tgcagacttt tgcaggattg tctagcctga gtaccgggct acttcttaaa    4860
tgccgtcact cctgctgaga taaatgcgtc tttaaaaata gtctctgtgg caggtcactg    4920
ggggacaatg tacagcattc tggccatcca cttcttttc acttcatgtt ctaccccaag    4980
agactcccga tgtcggctgt ggagggttaa agggatgagg cttttccttttg tttagcaaat    5040 ctgttcacag ttcttgatga tgtattttat gatgcccagc ttggaaatag ttgctttcca    5100
tagtctcaac tgtattgtgt catctcctga tgctgatttt tgatcttttg ttttattaaa    5160
aataattagt gaaagaggtg tgcctatctg tgaagtttgt agtacatcat cctgaggtca    5220
tgtaacaagt aaaccccaac ccagcgttcc ctcctacgtt gtgttagttc attaaaacta    5280
aataataaaa ataactgtaa gaaaacctta a                                    5311

<210> SEQ ID NO 144
<211> LENGTH: 2362
<212> TYPE: DNA
<213> ORGANISM: Homo sapiens

<400> SEQUENCE: 144
cactcagggc aagggtgtcc gacggctgga gcgttctgtt ttgaacccaa agtggatgat      60
gctgtcagag ctgaactact gaaaggaggc tgtgaaaatt tcccatcttc tcattggcca     120
tcagttgaga taagatggaa gactcttaca aggataggac ttcactgatg aagggtgcca     180
aggacattgc cagagaggtg aagaaacaaa cagtaaagaa ggtgaatcaa gctgtggacc     240
gagcccagga tgaatacacc cagaggtcct acagtcggtt ccaagatgaa gaagatgatg     300
atgactacta cccggctgga gaaacctata tggtgaggc caacgatgac gaaggctcaa     360
gtgaagccac tgaggggcat gatgaagatg atgagatcta tgagggggag tatcagggca     420
tccccagtat gaaccaagcg aaggacagca tcgtgtcagt ggggcagccc aagggcgatg     480
agtacaagga ccgacgggag ctggaatcag aaaggagagc tgacgaggaa gagttagccc     540
agcagtatga gctgataatc caagaatgcg gtcatggtcg ttttcagtgg gccctttttct     600 tcgtcctggg catggctctt atggcagacg tgtagaggt gtttgtcgtt ggcttcgtgt     660
tacccagtgc tgagacagac ctctgcatcc caaattcagg atctggatgg ctaggcagca     720
tagtgtacct cgggatgatg gtgggggcgt tcttctgggg aggactggca gacaaagtgg     780
gaaggaaaca gtctcttctg atttgcatgt ctgtcaacgg attctttgcc ttcctttctt     840
catttgtcca aggttatggc ttctttctct tctgtcgctt actttctgga ttcgggattg     900
```

```
gaggagccat acccactgtg ttctcgtact ttgctgaagt cctggcccgg gaaaagcggg      960
gcgaacactt gagctggctc tgcatgttct ggatgatcgg tggcatctac gcctctgcca     1020
tggcctgggc catcatcccg cactacgggt ggagcttcag catgggatcg gcctaccagt     1080
ttcacagttg gcgtgtgttt gtcatcgtct gtgcactccc ctgtgtctcc tccgtggtgg     1140
ccctcacatt catgcctgaa agcccacgat tcttgttgga ggttggaaaa catgatgaag     1200
cttggatgat tctgaagtta attcatgaca ccaacatgag agcccggggt cagcctgaga     1260
aggtcttcac ggtaaacaaa ataaaaactc ctaaacaaat agatgagctg attgaaattg     1320
agagtgacac aggaacatgg tataggaggt gttttgttcg gatccgcacc gagctgtacg     1380
gaatttggtt gacttttatg agatgtttca actacccagt cagggataat acaataaagc     1440
ttacaattgt ttggttcacc ctgtcctttg ggtactatgg attatccgtt tggttccctg     1500
atgtcattaa acctctgcag tccgatgaat atgcattgct aaccagaaat gtggagagag     1560
ataaatatgc aaatttcact attaacttta caatggaaaa tcagattcat actggaatgg     1620
aatacgacaa tggcagattc atagggggtca agttcaaatc tgtaactttc aaagactctg     1680
```

```
tttttaagtc ctgcacctttt gaggatgtaa cttcagtgaa cacctacttc aagaactgca     1740
catttattga cactgttttt gacaacacag attttgagcc atataaattc attgacagtg     1800
aatttaaaaa ctgctcgttt tttcacaaca agacgggatg tcagattacc tttgatgatg     1860
actatagtgc ctactggatt tattttgtca actttctggg gacattggca gtattgccag     1920
ggaacattgt gtctgctctg ctgatggaca gaattgggcg cttaacaatg ctaggtggct     1980
ctatggtgct ttcggggatc agctgtttct tcctttggtt cggcaccagt gaatccatga     2040
tgataggcat gctgtgtctg tacaatggat tgaccatctc agcctggaac tctcttgacg     2100
tggtcactgt ggaactgtac cccacagacc ggagggcaac aggctttggc ttcttaaatg     2160
cgctatgcaa ggcagcagcc gtcctgggaa acttaatatt tggctctctg gtcagcatca     2220
ccaaatcaat cccatcctg ctggcttcta ctgtgctcgt gtgtgagga ctcgttgggc     2280 tgtgcctgcc tgacacacga acccaggttc tgatgtaatg ggaaaaaaag ccatccttcc     2340
tgcgtttctt cctcctgccc tg                                              2362
```

<210> SEQ ID NO 145
<211> LENGTH: 2053
<212> TYPE: DNA
<213> ORGANISM: Homo sapiens

<400> SEQUENCE: 145

```
catctttgat gagggcagag ctcacgttgc attgaagacg aaacctcggg gaggtcaggc       60
gctgtctttc cttccctccc tgctcggcgg ctccaccaca gttgcaacct gcagaggccc      120
ggagaacaca accctcccga gaagcccagg tccagagcca aacccgtcac tgaccccccca     180 gcccaggcgc ccagccactc cccaccgcta ccatggccga agacgcagac atgcgcaatg      240
agctggagga gatgcagcga agggctgacc agttggctga tgagtcgctg aaaagcaccc      300
gtcgtatgct gcaactggtt gaagagagta aagatgctgg tatcaggact ttggttatgt      360
tggatgaaca aggagaacaa ctcgatcgtg tcgaagaagg catgaaccat atcaaccaag      420
acatgaagga ggctgagaaa aatttaaaag atttagggaa atgctgtggc cttttcatat      480
gtccttgtaa caagcttaaa tcaagtgatg cttacaaaaa agcctggggc aataatcagg      540
acggagtggt ggccagccag cctgctcgtg tagtggacga acgggagcag atggccatca      600
gtggcggctt catccgcagg gtaacaaatg atgcccgaga aaatgaaatg gatgaaaacc      660
```

| | |
|---|---|
| tagagcaggt gagcggcatc atcgggaacc tccgtcacat ggccctggat atgggcaatg | 720 |
| agatcgatac acagaatcgc cagatcgaca ggatcatgga aaggctgat tccaacaaaa | 780 |
| ccagaattga tgaggccaac caacgtgcaa caaagatgct gggaagtggt taagtgtgcc | 840 |
| cacccgtgtt ctcctccaaa tgctgtcggg caagatagcc ccttcatgct tttctcatgg | 900 |
| tattatctag taggtctgca cacataacac acatcagtcc accccattg tgaatgttgt | 960 |
| cctgtgtcat ctgtcagctt cccaacaata ctttgtgtct tttgttctct cttggtctct | 1020 |
| ttctttccaa aggttgtaca tagtggtcat ttggtggctc taactccttg atgtcttgag | 1080 |
| tttcatttt cattttctct cctcggtggc atttgctgaa taacaacaat ttaggaatgc | 1140 |
| tcaatgtgct gttgattctt tcaatccaca gtattgttct tgtaaaactg tgacattcca | 1200 |
| cagagttact gccacggtcc tttgagtgtc aggctctgaa tctctcaaaa tgtgccgtct | 1260 |
| ttggttcctc atggctgtta tctgtcttta tgatttcatg attagacaat gtggaattac | 1320 |
| ataacaggca ttgcactaaa agtgatgtga tttatgcatt tatgcatgag aactaaatag | 1380 |
| atttttagat tcctacttaa acaaaaactt tccatgacag tagcatactg atgagacaac | 1440 |
| acacacacac acaaaacaac agcaacaaca acagaacaac aacaaagcat gctcagtatt | 1500 |
| gagacactgt caagattaag ttataccagc aaaagtgcag tagtgtcact ttttcctgt | 1560 |
| caatatatag agacttctaa atcataatca tccttttta aaaaaagaa ttttaaaaaa | 1620 |
| gatggatttg acacactcac catttaatca tttccagcaa aatatatgtt tggctgaaat | 1680 |
| tatgtcaaat ggatgtaata tagggtttgt ttgctgcttt tgatggctac gttttggaga | 1740 |
| gagcaatctt gctgtgaaac agtgtggatg taaattttat aaggctgact cttactaacc | 1800 |
| accatttccc ctgtggtttg ttatcagtac aattctttgt tgcttaatct agagctatgc | 1860 |
| acaccaaatt gctgagatgt ttagtagctg ataaagaaac cttttaaaaa aataatataa | 1920 |
| atgaatgaaa tataaactgt gagataaata tcattatagc atgtaatatt aaattcctcc | 1980 |
| tgtctcctct gtcagtttgt gaagtgattg acattttgta gctagtttaa aattattaaa | 2040 |
| aattatagac tcc | 2053 |

<210> SEQ ID NO 146
<211> LENGTH: 2053
<212> TYPE: DNA
<213> ORGANISM: Homo sapiens

<400> SEQUENCE: 146

| | |
|---|---|
| catctttgat gagggcagag ctcacgttgc attgaagacg aaacctcggg gaggtcaggc | 60 |
| gctgtctttc cttccctccc tgctcggcgg ctccaccaca gttgcaacct gcagaggccc | 120 |
| ggagaacaca accctcccga gaagcccagg tccagagcca aacccgtcac tgaccccca | 180 |
| gcccaggcgc ccagccactc cccaccgcta ccatggccga agacgcagac atgcgcaatg | 240 |
| agctggagga gatgcagcga agggctgacc agttggctga tgagtcgctg gaaagcaccc | 300 |
| gtcgtatgct gcaactggtt gaagagagta agatgctgg tatcaggact ttggttatgt | 360 |
| tggatgaaca aggagaacaa ctggaacgca ttgaggaagg gatggaccaa atcaataagg | 420 |
| acatgaaaga agcagaaaag aatttgacgg acctaggaaa attctgcggg ctttgtgtgt | 480 |
| gtccctgtaa caagcttaaa tcaagtgatg cttacaaaaa agcctgggc aataatcagg | 540 |
| acggagtggt ggccagccag cctgctcgtg tagtggacga acgggagcag atggccatca | 600 |
| gtggcggctt catccgcagg gtaacaaatg atgcccgaga aaatgaaatg gatgaaaacc | 660 |
| tagagcaggt gagcggcatc atcgggaacc tccgtcacat ggccctggat atgggcaatg | 720 |

-continued

```
agatcgatac acagaatcgc cagatcgaca ggatcatgga gaaggctgat ccaacaaaa      780 ccagaattga tgaggccaac caacgtgcaa caaagatgct gggaagtggt taagtgtgcc     840
cacccgtgtt ctcctccaaa tgctgtcggg caagatagct ccttcatgct tttctcatgg    900
tattatctag taggtctgca cacataacac acatcagtcc accccattg tgaatgttgt     960 cctgtgtcat ctgtcagctt cccaacaata ctttgtgtct tttgttctct cttggtctct    1020
ttctttccaa aggttgtaca tagtggtcat tggtggctc taactccttg atgtcttgag     1080
tttcattttt cattttctct cctcggtggc atttgctgaa taacaacaat ttaggaatgc    1140
tcaatgtgct gttgattctt tcaatccaca gtattgttct tgtaaaactg tgacattcca    1200
cagagttact gccacggtcc tttgagtgtc aggctctgaa tctctcaaaa tgtgccgtct    1260
ttggttcctc atggctgtta tctgtcttta tgatttcatg attagacaat gtggaattac    1320
ataacaggca ttgcactaaa agtgatgtga tttatgcatt tatgcatgag aactaaatag    1380 attttagat tcctacttaa acaaaaactt tccatgacag tagcatactg atgagacaac     1440
acacacacac acaaaacaac agcaacaaca acagaacaac aacaaagcat gctcagtatt    1500
gagacactgt caagattaag ttataccagc aaaagtgcag tagtgtcact tttttcctgt    1560
caatatatag agacttctaa atcataatca tccttttta aaaaaagaa ttttaaaaaa      1620 gatggatttg acacactcac catttaatca tttccagcaa aatatatgtt tggctgaaat    1680
tatgtcaaat ggatgtaata tagggttgt ttgctgcttt tgatggctac gttttggaga    1740
gagcaatctt gctgtgaaac agtgtggatg taaattttat aaggctgact cttactaacc    1800
accatttccc ctgtggtttg ttatcagtac aattctttgt tgcttaatct agagctatgc    1860
acaccaaatt gctgagatgt ttagtagctg ataaagaaac cttttaaaaa ataatataa     1920 atgaatgaaa tataaactgt gagataaata tcattatagc atgtaatatt aaattcctcc    1980
tgtctcctct gtcagtttgt gaagtgattg acattttgta gctagtttaa aattattaaa    2040
aattatagac tcc                                                        2053
```

<210> SEQ ID NO 147
<211> LENGTH: 5
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 147

Asp Glu Ala Asn Gln
 1               5

<210> SEQ ID NO 148
<211> LENGTH: 6
<212> TYPE: PRT
<213> ORGANISM: Artificial Sequence
<220> FEATURE:
<223> OTHER INFORMATION: SNAP-25 antigen having a free carboxyl-
      terminus at the P1 residue of the scissile bond of the BoNT/A
      cleavage site

<400> SEQUENCE: 148

Ile Asp Glu Ala Asn Gln
 1               5

<210> SEQ ID NO 149
<211> LENGTH: 360
<212> TYPE: DNA

```
<213> ORGANISM: Mus musculus

<400> SEQUENCE: 149
caggtgaagc tgcaggagtc tggacctgaa ctggtaaagc ctggggcttc agtgaagatg      60
tcctgcaagg cttctggata cacattcact aactatgtta tacactgggt gaagcaaaag     120
cctgggcagg gccttgagtg gattggatat attaatcctt acaatgatgg ctctaagtac     180
aatgagaagt tcaaaggcaa ggcctcactg acttcagaca aatcctccag cacagcctac     240
atggagctca gcagcctgac ctctgaggac tctgcggtct attactgtgc aagacatctc     300
gctaatacct actactactt tgactactgg ggccaaggca ccactctcac agtctcctca     360

<210> SEQ ID NO 150
<211> LENGTH: 120
<212> TYPE: PRT
<213> ORGANISM: Mus musculus

<400> SEQUENCE: 150

Gln Val Gln Leu Gln Glu Ser Gly Pro Glu Leu Val Lys Pro Gly Ala
 1               5                  10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Trp Ile
        35                  40                  45

Gly Tyr Ile Asn Pro Tyr Asn Asp Gly Ser Lys Tyr Asn Glu Lys Phe
    50                  55                  60

Lys Gly Lys Ala Ser Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg His Leu Ala Asn Thr Tyr Tyr Tyr Phe Asp Tyr Trp Gly Gln
            100                 105                 110

Gly Thr Thr Leu Thr Val Ser Ser
        115                 120

<210> SEQ ID NO 151
<211> LENGTH: 5
<212> TYPE: PRT
<213> ORGANISM: Mus musculus

<400> SEQUENCE: 151

Ala Arg Met Gly Tyr
 1               5

<210> SEQ ID NO 152
<211> LENGTH: 13
<212> TYPE: PRT
<213> ORGANISM: Mus musculus

<400> SEQUENCE: 152

Ala Arg His Leu Ala Asn Thr Tyr Tyr Tyr Phe Asp Tyr
 1               5                  10
```

What is claimed is:

1. An established single cell derived clonal cell line from a parental SiMa cell line DSMZ ACC 164 comprising cells susceptible to intoxication by botulinum toxin type A (BoNT/A), wherein the cells exhibit at least a 1.5-fold increase in mRNA expression levels after differentiation in the genes CD9, ENC1, Gβγ, GNAI1, GNG11, GNG12, GPSM2, ITGA6, JNK, KCNJ4, MSN, MYRIP, NXPH1, STK17A, TRAF4, TSPAN, TSPAN4 and VAV3 relative to the mRNA expression levels of each of these genes in cells from a 2D6 derived from the parental SiMa cell line DSMZ ACC 164; and, wherein the cells exhibit at least a 1.5-fold decrease in mRNA expression levels after differentiation in the genes CNGA3, HIST1H3E and PTGS1 as compared to the mRNA expression levels of each of these genes in cells from the 2D6 cell line; and, wherein the clonal cell line comprises cells susceptible to BoNT/A intoxication by about 100 pM or less of a BoNT/A.

2. The established clonal cell line of claim 1, wherein the cells exhibit at least a 2.0-fold difference in gene expression levels of at least one gene as compared to the expression levels of the gene in cells from the 2D6 cell line.

3. The established clonal cell line of claim 1, wherein the cells exhibit at least a 3.0-fold difference in gene expression levels of at least one gene as compared to the expression levels of the gene in cells from the 2D6 cell line.

4. The established clonal cell line of claim 1, wherein the cells exhibit at least a 4.0-fold difference in gene expression levels of at least one gene as compared to the expression levels of the gene in cells from the 2D6 cell line.

5. The established clonal cell line of claim 1, wherein the cell from an established clonal cell line exhibits about 100 pM or less of a BoNT/A intoxication for at least 5 or more cell passages.

* * * * *